US011820792B2

(12) United States Patent
Hajitou et al.

(10) Patent No.: US 11,820,792 B2
(45) Date of Patent: Nov. 21, 2023

(54) CANCER TREATMENT

(71) Applicant: Imperial College Innovations Limited, London (GB)

(72) Inventors: Amin Hajitou, London (GB); Keittisak Suwan, London (GB); Mariam Albahrani, London (GB); Sajee Waramit, London (GB)

(73) Assignee: Imperial College Innovations Limited, London (GB)

( * ) Notice: Subject to any disclaimer, the term of this patent is extended or adjusted under 35 U.S.C. 154(b) by 967 days.

(21) Appl. No.: 16/607,653

(22) PCT Filed: Apr. 24, 2018

(86) PCT No.: PCT/GB2018/051070
§ 371 (c)(1),
(2) Date: Oct. 23, 2019

(87) PCT Pub. No.: WO2018/197859
PCT Pub. Date: Nov. 1, 2018

(65) Prior Publication Data
US 2020/0239535 A1    Jul. 30, 2020

(30) Foreign Application Priority Data

Apr. 24, 2017 (GB) ..................................... 1706451

(51) Int. Cl.
| A61K 48/00 | (2006.01) |
| A61K 35/76 | (2015.01) |
| A61K 38/20 | (2006.01) |
| C12N 7/01 | (2006.01) |
| C12N 15/11 | (2006.01) |
| C12N 15/19 | (2006.01) |
| C12N 15/86 | (2006.01) |
| C07K 14/525 | (2006.01) |
| C07K 14/54 | (2006.01) |
| C12N 7/00 | (2006.01) |
| A61K 38/00 | (2006.01) |
| A61K 33/243 | (2019.01) |

(52) U.S. Cl.
CPC ........ *C07K 14/525* (2013.01); *C07K 14/5406* (2013.01); *C07K 14/5434* (2013.01); *C12N 7/00* (2013.01); *C12N 15/111* (2013.01); *C12N 15/86* (2013.01); *A61K 33/243* (2019.01); *A61K 38/00* (2013.01); *C07K 2319/02* (2013.01); *C12N 2750/14143* (2013.01); *C12N 2750/14152* (2013.01); *C12N 2750/14171* (2013.01); *C12N 2800/202* (2013.01); *C12N 2800/24* (2013.01); *C12N 2800/50* (2013.01); *C12N 2810/405* (2013.01); *C12N 2820/60* (2013.01)

(58) Field of Classification Search
None
See application file for complete search history.

(56) References Cited

U.S. PATENT DOCUMENTS

| 10,471,138 | B2 | 11/2019 | Hajitou et al. | |
| 10,799,542 | B2 | 10/2020 | Hajitou et al. | |
| 11,603,540 | B2 | 3/2023 | Hajitou et al. | |
| 2007/0128728 | A1 | 6/2007 | Bradbury | |
| 2013/0195800 | A1* | 8/2013 | Roeth | A61P 19/02 435/320.1 |
| 2016/0114032 | A1 | 4/2016 | Hajitou et al. | |
| 2017/0008969 | A1* | 1/2017 | Towner | C12Q 1/6886 |
| 2017/0340684 | A1 | 11/2017 | Hajitou et al. | |
| 2018/0320200 | A1 | 11/2018 | Hajitou et al. | |
| 2019/0062394 | A1* | 2/2019 | Yarlagadda | C07K 14/5434 |
| 2019/0083610 | A1 | 3/2019 | Hajitou et al. | |

FOREIGN PATENT DOCUMENTS

| WO | 9209690 A2 | 6/1992 |
| WO | 2005019435 A2 | 3/2005 |
| WO | 2007067818 A2 | 6/2007 |
| WO | 2007118245 A2 | 10/2007 |
| WO | 2014184528 A1 | 11/2014 |
| WO | 2014184529 A1 | 11/2014 |
| WO | 2017077275 A1 | 5/2017 |
| WO | 2018197859 A1 | 11/2018 |

OTHER PUBLICATIONS

Cloning Vector pUC119, 2014, Mo Bi Tec, pp. 1-3.*
Larocca et al. Receptor-Targeted Gene Delivery Using Multivalent Phagemid Particles, Molecular Therapy, 2001 pp. 476-484.*
Sunderland et al, Phage-Enabled Nanomedicine: From Probes to Therapeutics in Precision Medicine, Angew Chem Int Ed Engl. 2017, pp. 1-57.*
Berraondo et al, Cytokines in clinical cancer immunotherapy. British Journal of Cancer (2019) pp. 6-15.*
Rallis et al, Cytokine-based Cancer Immunotherapy: Challenges and Opportunities for IL-10, Anticancer Research 41: (2021), 3247-3252.*
Shen et al., Anti-cancer therapy with TNFα and IFNγ: A comprehensive review, Cell Proliferation, 2017, pp. 1-11.*

(Continued)

*Primary Examiner* — Maria Marvich
(74) *Attorney, Agent, or Firm* — Linda B. Huber; Nixon Peabody LLP

(57) ABSTRACT

The present invention provides phagemid vectors and associated phagemid particles for cancer treatment, and in particular, to the use of novel phagemid particles and associated expression systems for the treatment, prevention, amelioration, or management of cancer. In particular, the invention relates to the use of phagemid particles and expression systems for the delivery of transgenes encoding cytokines, for the treatment, prevention, amelioration, or management of cancer. The invention also extends to the use of phagemid particles and expression systems for the delivery of transgenes, and for the combination of such treatment with the use of adoptively transferred T cells, for the treatment, prevention, amelioration, or management of cancer.

14 Claims, 75 Drawing Sheets

Specification includes a Sequence Listing.

(56) References Cited

OTHER PUBLICATIONS

Jafari et al, Phage Particles as Vaccine Delivery Vehicles: Concepts, Applications and Prospects, Asian Pacific Journal of Cancer Prevention, vol. 16, 2015 pp. 8019-8029.*
Hajitou et al., Design and construction of targeted AAVP vectors for mammalian cell transductions, Nature Protocols, 2007, vol. 2(3), pp. 523-531.
Albahrani et al., Selective Cytokine Gene Therapy for the Treatment of Paediatric Brain Cancer, 2017, Human Gene Therapy, vol. 28(8), p. 037, 1 page.
Carl H. June, Adoptive T Cell Therapy for Cancer in the Clinic, 2007, The Journal of Clinical Investigation, vol. 117 (6), pp. 1466-1476.
Jiang et al., Development of Efficient RNA Interference System Using EGF-Displaying Phagemid Particles, 2008, Acta Pharmacol. Sin., vol. 29(4), pp. 437-442.
Li et al., Cell-Targeted Phagemid Particles Preparation Using *Escherichia coli* Bearing Ligand-pIII Encoding Helper Phage Genome, 2006, BioTechniques, vol. 41, pp. 706-707.
Lund et al., Pseudovirions as Vehicles for the Delivery of siRNA, 2010, Pharm. Research, vol. 27(3), pp. 400-420.
Redeker et al., Improving Adoptive T Cell Therapy: The Particular Role of T Cell Costimulation, Cytokines, and Post-Transfer Vaccination, 2016, Frontiers in Immunology, vol. 7(345), 8 Pages.

\* cited by examiner

Comparing AAVP and PAAV

| | Next-generation PAAV vectors |
|---|---|
| Relative genome size | c. 6000 bases (42% of AAVP) |
| Relative virus size | ~50% shorter than AAVP |
| Production yield | up to 100,000X current AAVP yields |
| Payloads per particle | Multiple (AAVP can only carry 1 payload) |
| Biodistribution | *Potentially better* |

AAVP (c.14Kb)    PAAV (6Kb)

*Phagemid/Adeno-associated Virion (PAAV)*

Figure 8

```
tattctcactccgcttGTGATTGTAGGGGGATTGTTTTGTgaaactgttgaaagtt
ataagagtgaggcgaACACTAACATCCCCCTAACAAAACACTTTgacaactttcaa
 15              20         25         30
  Y  S  H  S  A  C  D  C  R  G  D  C  F  C  E  T  V  E  S
                |_____RGD4C Targeting Peptide_____|
                                                |____M13 gene III____
```

Purification (centrifugation + filtration)

PAAV ready for in vitro or in vivo transduction

Figure 23
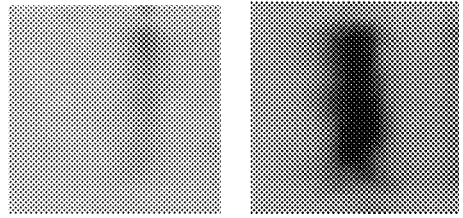
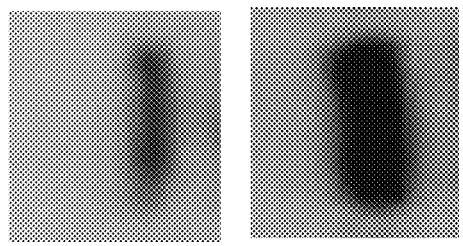
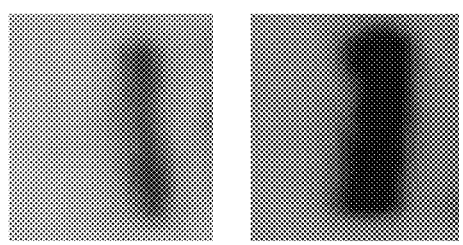

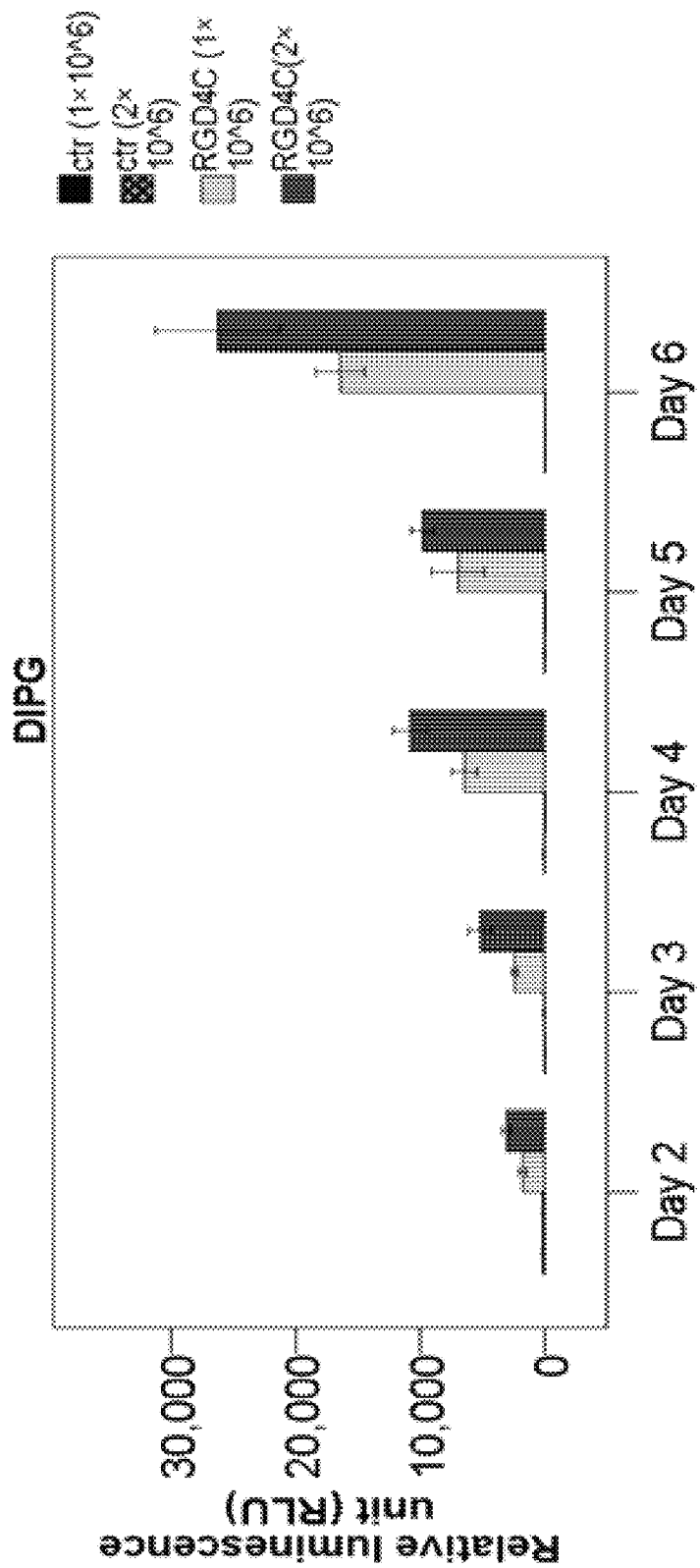

Figure 28 (cont)
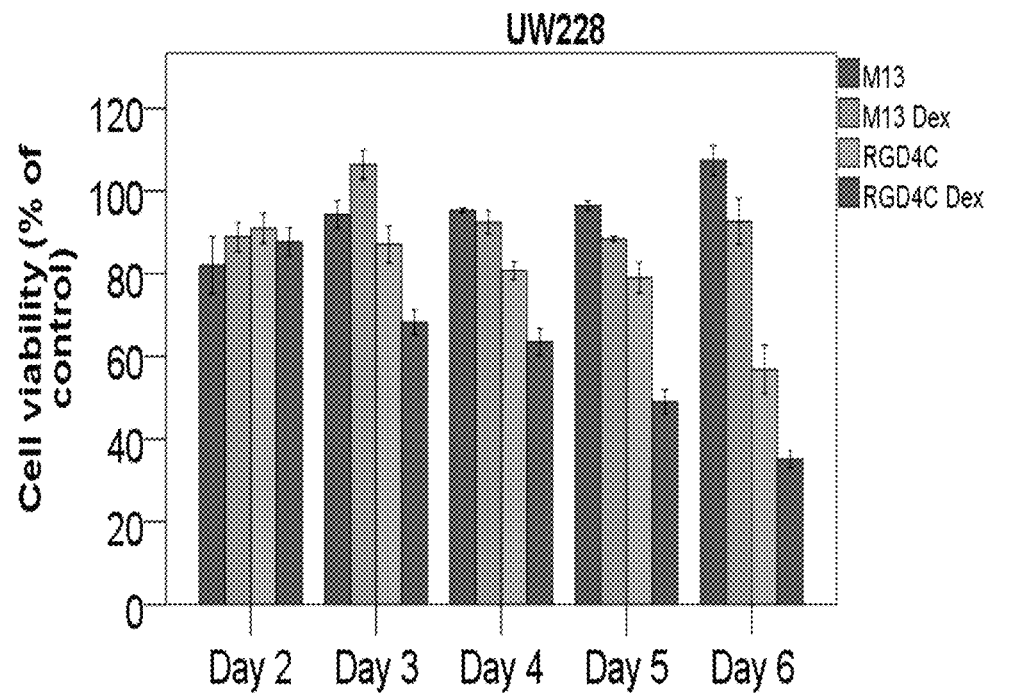
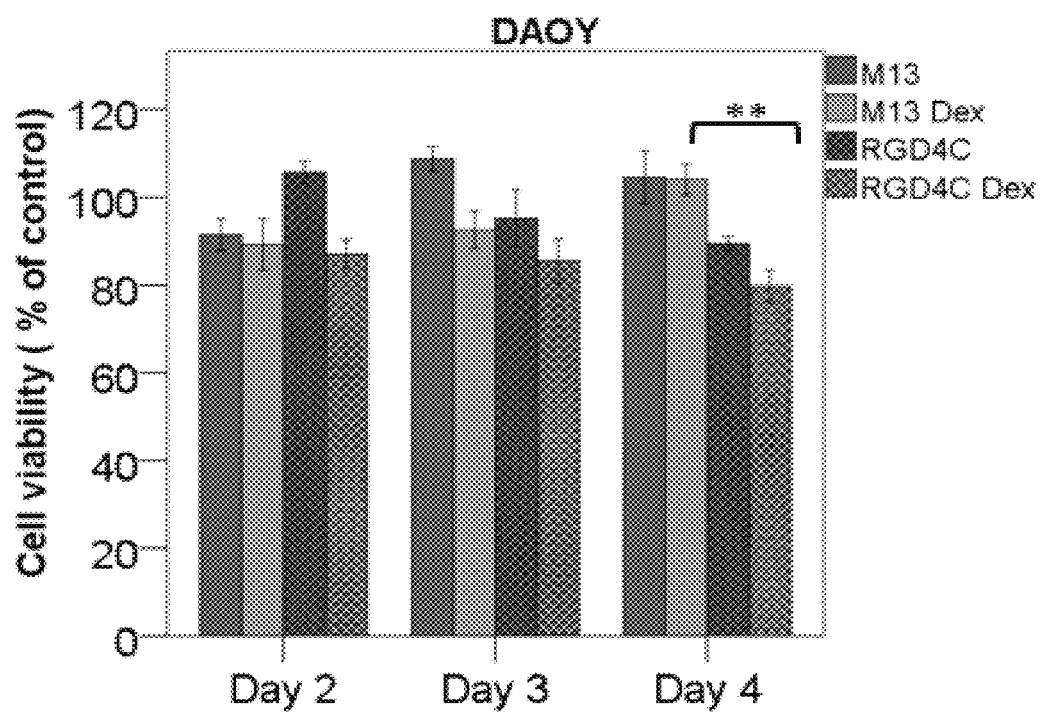

Figure 36
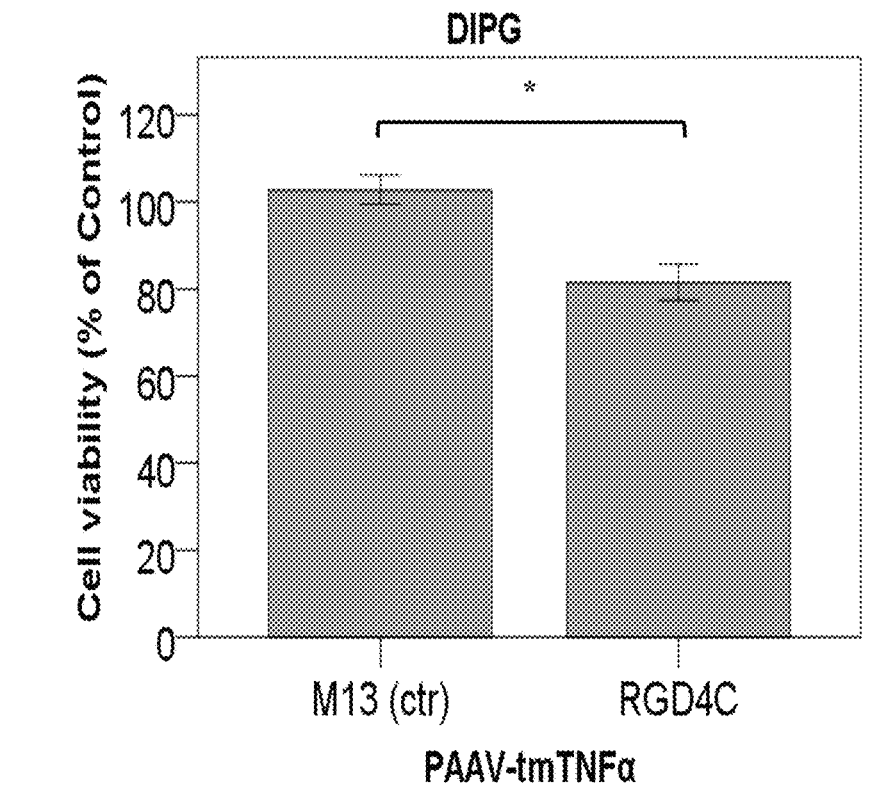
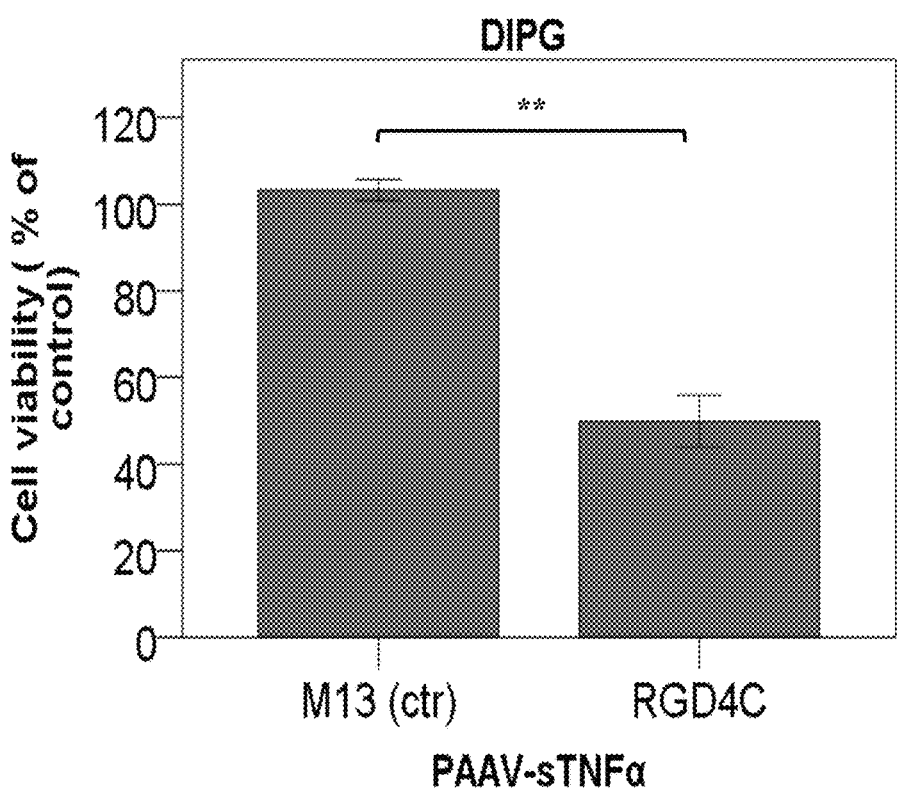

Figure 38
A.
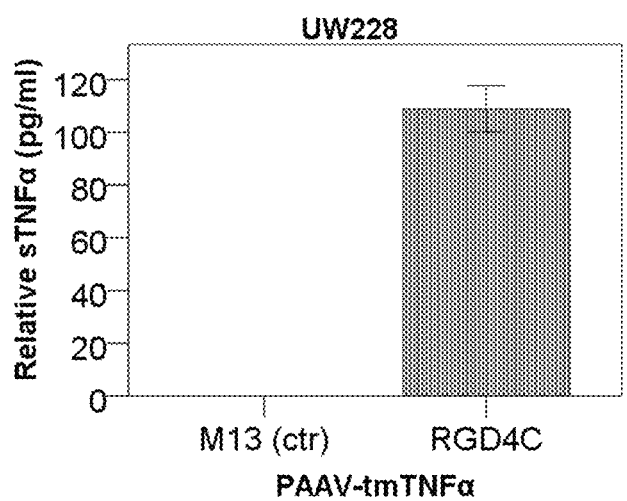
B.
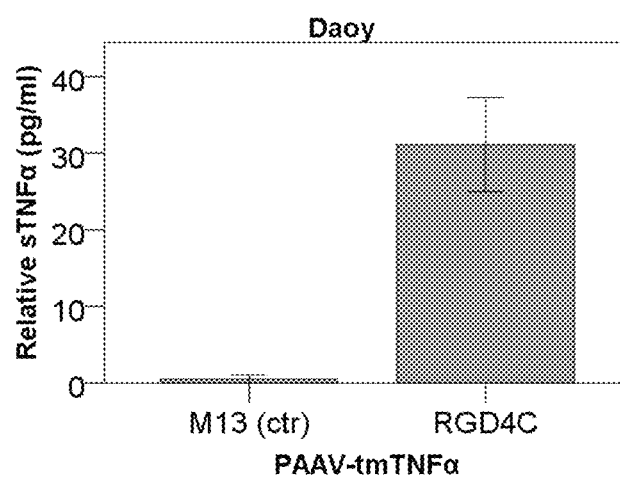

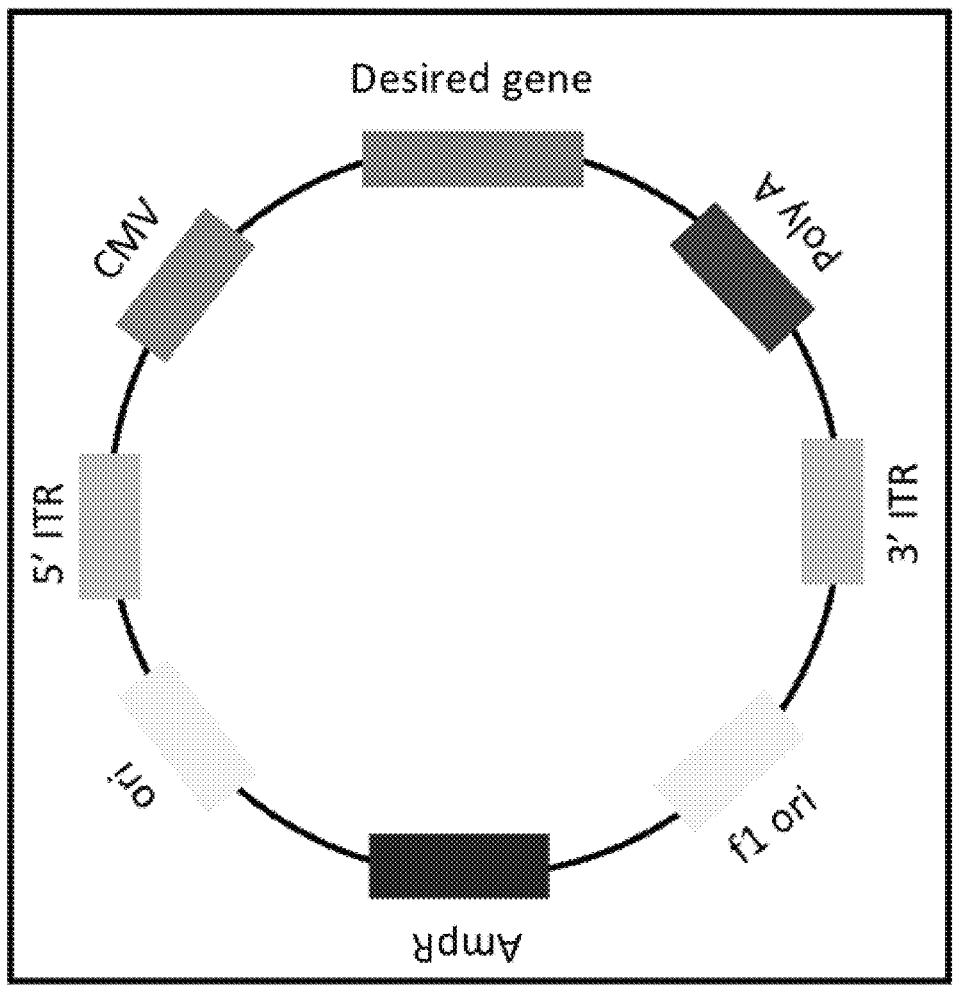
Figure 43
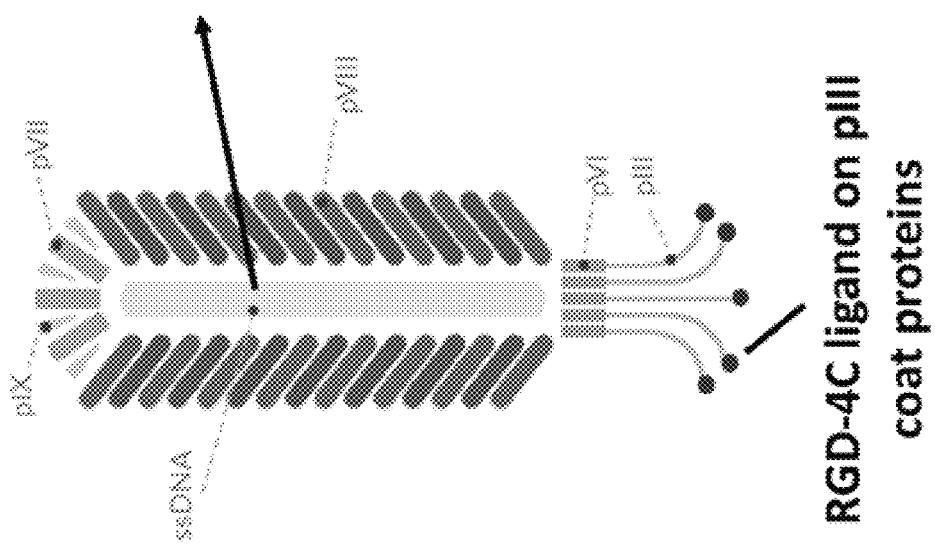

Figure 46 continued
Amplified hTRAIL EcoRI SalI
921 bp
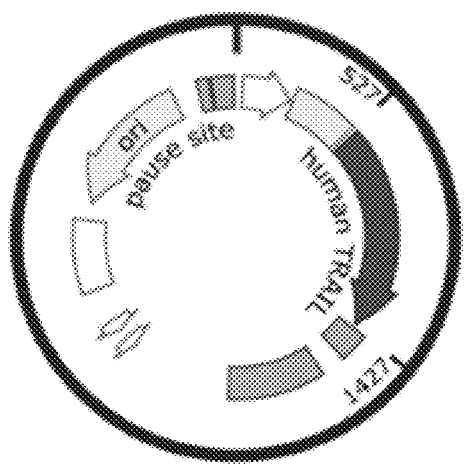
pUNO1-hTRAIL
4026 bp

SEQUENCE LISTING

```
<160> NUMBER OF SEQ ID NOS: 27

<210> SEQ ID NO 1
<211> LENGTH: 456
<212> TYPE: DNA
<213> ORGANISM: Escherichia coli

<400> SEQUENCE: 1
acgcgccctg tagcggcgca ttaagcgcgg cgggtgtggt ggttacgcgc agcgtgaccg       60
ctacacttgc cagcgcccta gcgcccgctc ctttcgcttt cttccttcc tttctcgcca      120
```

```
cgttcgccgg ctttccccgt caagctctaa atcgggggct ccctttaggg ttccgattta    180
gtgctttacg gcacctcgac cccaaaaaac ttgatttggg tgatggttca cgtagtgggc    240
catcgccctg atagacggtt tttcgccctt tgacgttgga gtccacgttc tttaatagtg    300
gactcttgtt ccaaactgga acaacactca accctatctc gggctattct tttgatttat    360
aagggatttt gccgatttcg gcctattggt taaaaatga gctgatttaa caaaaattta    420
acgcgaattt taacaaaata ttaacgttta caattt                             456

<210> SEQ ID NO 2
<211> LENGTH: 589
<212> TYPE: DNA
<213> ORGANISM: Unknown
<220> FEATURE:
<223> OTHER INFORMATION: DNA sequence of a pUC ori
      (origin of replication)

<400> SEQUENCE: 2
ttgagatcct ttttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgtcct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttttgtgat gctcgtcagg ggggcggagc ctatggaaa              589

<210> SEQ ID NO 3
<211> LENGTH: 663
<212> TYPE: DNA
<213> ORGANISM: Unknown
<220> FEATURE:
<223> OTHER INFORMATION: A DNA sequence of a promoter of a
      Cytomegalovirus

<400> SEQUENCE: 3
acgcgtggag ctagttatta atagtaatca attacggggt cattagttca tagcccatat     60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta acaactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tcc                                                                 663
```

```
<210> SEQ ID NO 4
<211> LENGTH: 479
<212> TYPE: DNA
<213> ORGANISM: Unknown
<220> FEATURE:
<223> OTHER INFORMATION: The DNA sequence of one embodiment of a nucleic
      acid for encoding a polyA tail

<400> SEQUENCE: 4
acgggtggca tccctgtgac ccctccccag tgcctctcct ggccctggaa gttgccactc     60
cagtgcccac cagccttgtc ctaataaaat taagttgcat cattttgtct gactaggtgt    120
ccttctataa tattatgggg tggagggggg tggtatggag caaggggcaa gttgggaaga    180
caacctgtag ggcctgcggg gtctattggg aaccaagctg gagtgcagtg gcacaatctt    240
ggctcactgc aatctccgcc tcctgggttc aagcgattct cctgcctcag cctcccgagt    300
tgttgggatt ccaggcatgc atgaccaggc tcagctaatt tttgtttttt tggtagagac    360
ggggtttcac catattggcc aggctggtct ccaactccta atctcaggtg atctacccac    420
cttggcctcc caaattgctg ggattacagg cgtgaaccac tgctcccttc cctgtcctt     479

<210> SEQ ID NO 5
<211> LENGTH: 130
<212> TYPE: DNA
<213> ORGANISM: Unknown
<220> FEATURE:
<223> OTHER INFORMATION: The DNA sequence of one (left) embodiment of an
      Inverted Terminal Repeat sequences (ITR)

<400> SEQUENCE: 5
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct                                                           130

<210> SEQ ID NO 6
<211> LENGTH: 141
<212> TYPE: DNA
<213> ORGANISM: Unknown
<220> FEATURE:
<223> OTHER INFORMATION: The DNA sequence of one (right) embodiment of
      an Inverted Terminal Repeat sequences (ITR)

<400> SEQUENCE: 6
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcctgcag g                                              141

<210> SEQ ID NO 7
<211> LENGTH: 9
<212> TYPE: PRT
<213> ORGANISM: Unknown
<220> FEATURE:
<223> OTHER INFORMATION: The amino acid sequence of a RGD4C targeting
      peptide

<400> SEQUENCE: 7

Cys Asp Cys Arg Gly Asp Cys Phe Cys
1               5

<210> SEQ ID NO 8
<211> LENGTH: 378
<212> TYPE: DNA
```

<213> ORGANISM: Unknown
<220> FEATURE:
<223> OTHER INFORMATION: The nucleic acid sequence of one embodiment of the grp78 promoter.

<400> SEQUENCE: 8

| | | | | | |
|---|---|---|---|---|---|
| cccgggggcc | caacgtgagg | ggaggacctg | gacggttacc | ggcggaaacg | gtttccaggt | 60 |
| gagaggtcac | ccgagggaca | ggcagctgct | caaccaatag | gaccagctct | cagggcggat | 120 |
| gctgcctctc | attggcggcc | gttaagaatg | accagtagcc | aatgagtcgg | ctgggggcg | 180 |
| cgtaccagtg | acgtgagttg | cggaggaggc | cgcttcgaat | cggcagcggc | cagcttggtg | 240 |
| gcatgaacca | accagcggcc | tccaacgagt | agcgagttca | ccaatcggag | gcctccacga | 300 |
| cggggctgcg | ggaggatat | ataagccgag | tcggcgaccg | gcgcgctcga | tactggctgt | 360 |
| gactacactg | acttggac | | | | | 378 |

<210> SEQ ID NO 9
<211> LENGTH: 2876
<212> TYPE: DNA
<213> ORGANISM: Unknown
<220> FEATURE:
<223> OTHER INFORMATION: The nucleic acid sequence of one embodiment of a first vector (i.e. phagemid particle's genome)
<220> FEATURE:
<221> NAME/KEY: misc_feature
<222> LOCATION: (138)..(139)
<223> OTHER INFORMATION: A transgene is present between positions 138 and 139

<400> SEQUENCE: 9

| | | | | | |
|---|---|---|---|---|---|
| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgcag | gaacccctag | tgatggagtt | ggccactccc | tctctgcgcg | 180 |
| ctcgctcgct | cactgaggcc | gggcgaccaa | aggtcgcccg | acgcccgggc | tttgcccggg | 240 |
| cggcctcagt | gagcgagcga | gcgcgcagct | gcctgcaggg | gcgcctgatg | cggtattttc | 300 |
| tccttacgca | tctgtgcggt | atttcacacc | gcatacgtca | aagcaaccat | agtacgcgcc | 360 |
| ctgtagcggc | gcattaagcg | cggcgggtgt | ggtggttacg | cgcagcgtga | ccgctacact | 420 |
| tgccagcgcc | ctagcgcccg | ctcctttcgc | tttcttccct | tcctttctcg | ccacgttcgc | 480 |
| cggctttccc | cgtcaagctc | taaatcgggg | gctcccttta | gggttccgat | ttagtgcttt | 540 |
| acggcacctc | gaccccaaaa | aacttgattt | gggtgatggt | tcacgtagtg | ggccatcgcc | 600 |
| ctgatagacg | gtttttcgcc | ctttgacgtt | ggagtccacg | ttctttaata | gtggactctt | 660 |
| gttccaaact | ggaacaacac | tcaaccctat | ctcgggctat | tcttttgatt | tataagggat | 720 |
| tttgccgatt | tcggcctatt | ggttaaaaaa | tgagctgatt | taacaaaaat | ttaacgcgaa | 780 |
| ttttaacaaa | atattaacgt | ttacaatttt | atggtgcact | ctcagtacaa | tctgctctga | 840 |
| tgccgcatag | ttaagccagc | cccgacaccc | gccaacaccc | gctgacgcgc | cctgacgggc | 900 |
| ttgtctgctc | ccggcatccg | cttacagaca | agctgtgacc | gtctccggga | gctgcatgtg | 960 |
| tcagaggttt | tcaccgtcat | caccgaaacg | cgcgagacga | aagggcctcg | tgatacgcct | 1020 |
| attttttatag | gttaatgtca | tgataataat | ggtttcttag | acgtcaggtg | gcacttttcg | 1080 |
| gggaaatgtg | cgcggaaccc | ctatttgttt | atttttctaa | atacattcaa | atatgtatcc | 1140 |
| gctcatgaga | caataaccct | gataaatgct | tcaataatat | tgaaaaagga | agagtatgag | 1200 |
| tattcaacat | ttccgtgtcg | cccttattcc | cttttttgcg | gcattttgcc | ttcctgtttt | 1260 |

```
tgctcaccca gaaacgctgg tgaaagtaaa agatgctgaa gatcagttgg gtgcacgagt    1320
gggttacatc gaactggatc tcaacagcgg taagatcctt gagagttttc gccccgaaga    1380
acgttttcca atgatgagca cttttaaagt tctgctatgt ggcgcggtat tatcccgtat    1440
tgacgccggg caagagcaac tcggtcgccg catacactat tctcagaatg acttggttga    1500
gtactcacca gtcacagaaa agcatcttac ggatggcatg acagtaagag aattatgcag    1560
tgctgccata accatgagtg ataacactgc ggccaactta cttctgacaa cgatcggagg    1620
accgaaggag ctaaccgctt ttttgcacaa catgggggat catgtaactc gccttgatcg    1680
ttgggaaccg gagctgaatg aagccatacc aaacgacgag cgtgacacca cgatgcctgt    1740
agcaatggca acaacgttgc gcaaactatt aactggcgaa ctacttactc tagcttcccg    1800
gcaacaatta atagactgga tggaggcgga taaagttgca ggaccacttc tgcgctcggc    1860
ccttccggct ggctggttta ttgctgataa atctggagcc ggtgagcgtg ggtctcgcgg    1920
tatcattgca gcactggggc cagatggtaa gccctcccgt atcgtagtta tctacacgac    1980
ggggagtcag gcaactatgg atgaacgaaa tagacagatc gctgagatag gtgcctcact    2040
gattaagcat tggtaactgt cagaccaagt ttactcatat atactttaga ttgatttaaa    2100
acttcatttt taatttaaaa ggatctaggt gaagatcctt tttgataatc tcatgaccaa    2160
aatcccttaa cgtgagtttt cgttccactg agcgtcagac cccgtagaaa agatcaaagg    2220
atcttcttga tccttttttt tctgcgcgt aatctgctgc ttgcaaacaa aaaaaccacc    2280
gctaccagcg gtggtttgtt tgccggatca agagctacca actctttttc cgaaggtaac    2340
tggcttcagc agagcgcaga taccaaatac tgtccttcta gtgtagccgt agttaggcca    2400
ccacttcaag aactctgtag caccgcctac atacctcgct ctgctaatcc tgttaccagt    2460
ggctgctgcc agtggcgata gtcgtgtct taccgggttg gactcaagac gatagttacc    2520
ggataaggcg cagcggtcgg gctgaacggg gggttcgtgc acacagccca gcttggagcg    2580
aacgacctac accgaactga gatacctaca gcgtgagcta tgagaaagcg ccacgcttcc    2640
cgaagggaga aaggcggaca ggtatccggt aagcggcagg gtcggaacag gagagcgcac    2700
gagggagctt ccagggggaa acgcctggta tctttatagt cctgtcgggt ttcgccacct    2760
ctgacttgag cgtcgatttt tgtgatgctc gtcaggggg cggagcctat ggaaaaacgc    2820
cagcaacgcg gcctttttac ggttcctggc cttttgctgg ccttttgctc acatgt        2876
```

<210> SEQ ID NO 10
<211> LENGTH: 8696
<212> TYPE: DNA
<213> ORGANISM: Unknown
<220> FEATURE:
<223> OTHER INFORMATION: The nucleic acid sequence of the preferred
      embodiment of a second vector (helper phage with RGD sequence)

<400> SEQUENCE: 10

```
aacgctacta ctattagtag aattgatgcc acctttttcag ctcgcgcccc aaatgaaaat      60
atagctaaac aggttattga ccatttgcga aatgtatcta atggtcaaac taaatctact     120
cgttcgcaga attgggaatc aactgttaca tggaatgaaa cttccagaca ccgtacttta     180
gttgcatatt taaaacatgt tgagctacag caccagattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tcttttttgat gcaatccgct ttgcttctga ctataatagt     420
```

```
cagggtaaag acctgatttt tgatttatgg tcattctcgt tttctgaact gtttaaagca    480
tttgagggg  attcaatgaa tatttatgac gattccgcag tattggacgc tatccagtct    540
aaacatttta ctattacccc ctctggcaaa acttcttttg caaaagcctc tcgctatttt    600
ggttttatc  gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggaga  ttttcaacgt gaaaaaatta ttattcgcaa ttcctttagt tgttcctttc   1620
tattctcact ccgcttgtga ttgtaggggg gattgttttt gtgaaactgt tgaaagttgt   1680
ttagcaaaac cccatacaga aaattcattt actaacgtct ggaaagacga caaaacttta   1740
gatcgttacg ctaactatga gggttgtctg tggaatgcta caggcgttgt agtttgtact   1800
ggtgacgaaa ctcagtgtta cggtacatgg gttcctattg gcttgctat  ccctgaaaat   1860
gagggtggtg gctctgaggg tggcggttct gagggtggcg gttctgaggg tggcggtact   1920
aaacctcctg agtacggtga tacacctatt ccgggctata cttatatcaa ccctctcgac   1980
ggcacttatc cgcctggtac tgagcaaaac cccgctaatc ctaatccttc tcttgaggag   2040
tctcagcctc ttaatacttt catgtttcag aataataggt tccgaaatag caggggca    2100
ttaactgttt atacgggcac tgttactcaa ggcactgacc ccgttaaaac ttattaccag   2160
tacactcctg tatcatcaaa agccatgtat gacgcttact ggaacggtaa attcagagac   2220
tgcgcttttcc attctggctt taatgaggat ccattcgttt gtgaatatca aggccaatcg   2280
tctgacctgc ctcaacctcc tgtcaatgct ggcggcggct ctggtggtgg ttctggtggc   2340
ggctctgagg gtggtggctc tgagggtggc ggttctgagg gtggcggctc tgagggaggc   2400
ggttccggtg gtggctctgg ttccggtgat tttgattatg aaaagatggc aaacgctaat   2460
aagggggcta tgaccgaaaa tgccgatgaa aacgcgctac agtctgacgc taaaggcaaa   2520
cttgattctg tcgctactga ttacggtgct gctatcgatg gtttcattgg tgacgtttcc   2580
ggccttgcta atggtaatgg tgctactggt gattttgctg gctctaattc ccaaatggct   2640
caagtcggtg acggtgataa ttcacctttaa tgaataatt tccgtcaata tttaccttcc   2700
ctccctcaat cggttgaatg tcgccctttt gtctttagcg ctggtaaacc atatgaattt   2760
tctattgatt gtgacaaaat aaacttattc cgtggtgtct ttgcgtttct tttatatgtt   2820
```

```
gccacctttta tgtatgtatt ttctacgttt gctaacatac tgcgtaataa ggagtcttaa    2880
tcatgccagt tcttttgggt attccgttat tattgcgttt cctcggtttc cttctggtaa    2940
ctttgttcgg ctatctgctt acttttctta aaagggctt cggtaagata gctattgcta    3000
tttcattgtt tcttgctctt attattgggc ttaactcaat tcttgtgggt tatctctctg    3060
atattagcgc tcaattaccc tctgactttg ttcagggtgt tcagttaatt ctcccgtcta    3120
atgcgcttcc ctgtttttat gttattctct ctgtaaaggc tgctattttc attttgacg    3180 ttaaacaaaa aatcgtttct tatttggatt gggataaata atatggctgt ttattttgta    3240
actggcaaat taggctctgg aaagacgctc gttagcgttg gtaagattca ggataaaatt    3300
gtagctgggt gcaaaatagc aactaatctt gatttaaggc ttcaaaacct cccgcaagtc    3360
gggaggttcg ctaaaacgcc tcgcgttctt agaataccgg ataagccttc tatatctgat    3420
ttgcttgcta ttgggcgcgg taatgattcc tacgatgaaa ataaaaacgg cttgcttgtt    3480
ctcgatgagt gcggtacttg gtttaatacc cgttcttgga atgataagga agacagccg    3540 attattgatt ggtttctaca tgctcgtaaa ttaggatggg atattatttt tcttgttcag    3600
gacttatcta ttgttgataa acaggcgcgt tctgcattag ctgaacatgt tgtttattgt    3660
cgtcgtctgg acagaattac tttacctttt gtcggtactt tatattctct tattactggc    3720
tcgaaaatgc ctctgcctaa attacatgtt ggcgttgtta aatatggcga ttctcaatta    3780
agccctactg ttgagcgttg gctttatact ggtaagaatt tgtataacgc atatgatact    3840
aaacaggctt tttctagtaa ttatgattcc ggtgtttatt cttatttaac gccttattta    3900
tcacacggtc ggtatttcaa accattaaat ttaggtcaga agatgaaatt aactaaaata    3960
tatttgaaaa agttttctcg cgttctttgt cttgcgattg gatttgcatc agcatttaca    4020
tatagttata taacccaacc taagccggag gttaaaaagg tagtctctca gacctatgat    4080
tttgataaat tcactattga ctcttctcag cgtcttaatc taagctatcg ctatgttttc    4140
aaggattcta agggaaaatt aattaatagc gacgatttac agaagcaagg ttattcactc    4200
acatatattg atttatgtac tgtttccatt aaaaaaggta attcaaatga aattgttaaa    4260
tgtaattaat tttgttttct tgatgtttgt ttcatcatct tcttttgctc aggtaattga    4320
aatgaataat tcgcctctgc gcgattttgt aacttggtat tcaaagcaat caggcgaatc    4380
cgttattgtt tctcccgatg taaaaggtac tgttactgta tattcatctg acgttaaacc    4440
tgaaaatcta cgcaatttct ttatttctgt tttacgtgct aataattttg atatggttgg    4500
ttcaattcct tccataattc agaagtataa tccaaacaat caggattata ttgatgaatt    4560
gccatcatct gataatcagg aatatgatga taattccgct ccttctggtg gtttctttgt    4620
tccgcaaaat gataatgtta ctcaaacttt taaaattaat aacgttcggg caaaggattt    4680
aatacgagtt gtcgaattgt ttgtaaagtc taatacttct aaatcctcaa atgtattatc    4740
tattgacggc tctaatctat tagttgttag tgcacctaaa gatattttag ataaccttcc    4800
tcaattcctt tctactgttg atttgccaac tgaccagata ttgattgagg gtttgatatt    4860
tgaggttcag caaggtgatg ctttagattt ttcatttgct gctggctctc agcgtggcac    4920
tgttgcaggc ggtgttaata ctgaccgcct cacctctgtt ttatcttctg ctggtggttc    4980
gttcggtatt tttaatggcg atgttttagg ctatcagtt cgcgcattaa agactaatag    5040
ccattcaaaa atattgtctg tgccacgtat tcttacgctt tcaggtcaga agggttctat    5100
ctctgttggc cagaatgtcc cttttattac tggtcgtgtg actggtgaat ctgccaatgt    5160
```

-continued

| | | | | |
|---|---|---|---|---|
| aaataatcca | tttcagacga | ttgagcgtca | aaatgtaggt | atttccatga gcgttttcc | 5220 |
| tgttgcaatg | gctggcggta | atattgttct | ggatattacc | agcaaggccg atagtttgag | 5280 |
| ttcttctact | caggcaagtg | atgttattac | taatcaaaga | agtattgcta caacggttaa | 5340 |
| tttgcgtgat | ggacagactc | ttttactcgg | tggcctcact | gattataaaa acacttctca | 5400 |
| agattctggc | gtaccgttcc | tgtctaaaat | ccctttaatc | ggcctcctgt ttagctcccg | 5460 |
| ctctgattcc | aacgaggaaa | gcacgttata | cgtgctcgtc | aaagcaacca tagtacgcgc | 5520 |
| cctgtagcgg | cgcattaagc | gcggcgggtg | tggtggttac | gcgcagcgtg accgctacac | 5580 |
| ttgccagcgc | cctagcgccc | gctcctttcg | ctttcttccc | ttcctttctc gccacgttcg | 5640 |
| ccggctttcc | ccgtcaagct | ctaaatcggg | ggctcccttt | agggttccga tttagtgctt | 5700 |
| tacggcacct | cgaccccaaa | aaacttgatt | tgggtgatgg | ttcacgtagt gggccatcgc | 5760 |
| cctgatagac | ggtttttcgc | cctttgacgt | tggagtccac | gttctttaat agtggactct | 5820 |
| tgttccaaac | tggaacaaca | ctcaaccta | tctcgggacg | gatcgcttca tgtggcagga | 5880 |
| gaaaaaaggc | tgcaccggtg | cgtcagcaga | atatgtgata | caggatatat tccgcttcct | 5940 |
| cgctcactga | ctcgctacgc | tcggtcgttc | gactgcggcg | agcggaaatg gcttacgaac | 6000 |
| ggggcggaga | tttcctggaa | gatgccagga | agatacttaa | cagggaagtg agagggccgc | 6060 |
| ggcaaagccg | ttttccata | ggctccgccc | ccctgacaag | catcacgaaa tctgacgctc | 6120 |
| aaatcagtgg | tggcgaaacc | cgacaggact | ataaagatac | caggcgtttc ccctggcgg | 6180 |
| ctccctcgtg | cgctctcctg | ttcctgcctt | tcggtttacc | ggtgtcattc cgctgttatg | 6240 |
| gccgcgtttg | tctcattcca | cgcctgacac | tcagttccgg | gtaggcagtt cgctccaagc | 6300 |
| tggactgtat | gcacgaaccc | cccgttcagt | ccgaccgctg | cgccttatcc ggtaactatc | 6360 |
| gtcttgagtc | caacccggaa | agacatgcaa | aagcaccact | ggcagcagcc actggtaatt | 6420 |
| gatttagagg | agttagtctt | gaagtcatgc | gccggttaag | gctaaactga aggacaagt | 6480 |
| tttggtgact | gcgctcctcc | aagccagtta | cctcggttca | aagagttggt agctcagaga | 6540 |
| accttcgaaa | aaccgccctg | caaggcggtt | ttttcgtttt | cagagcaaga gattacgcgc | 6600 |
| agaccaaaac | gatctcaaga | agatcatctt | attaaggggt | ctgacgctca gtggaacgaa | 6660 |
| aactcacgtt | aagggatttt | ggtcatgaga | ttatcaaaaa | ggatcttcac ctagatcctt | 6720 |
| ttaaattaaa | aatgaagttt | taaatcaatc | taaagtatat | atgagtaaac ttggtctgac | 6780 |
| agttaccaat | gcttaatcag | tgaggcacct | atctcagcga | tctgtctatt tcgttcatcc | 6840 |
| atagttgcct | gactccccgt | cgtgtagata | actacgatac | gggagggctt accatctggc | 6900 |
| cccagtgctg | caatgatacc | gcgagaccca | cgctcaccgg | ctccagattt atcagcaata | 6960 |
| aaccagccag | ccgattcgag | ctcgccccgg | ggatcgacca | gttggtgatt ttgaacttt | 7020 |
| gctttgccac | ggaacggtct | gcgttgtcgg | gaagatgcgt | gatctgatcc ttcaactcag | 7080 |
| caaaagttcg | atttattcaa | caaagccgcc | gtcccgtcaa | gtcagcgtaa tgctctgcca | 7140 |
| gtgttacaac | caattaacca | attctgatta | gaaaaactca | tcgagcatca aatgaaactg | 7200 |
| caatttattc | atatcaggat | tatcaatacc | atattttga | aaaagccgtt tctgtaatga | 7260 |
| aggagaaaac | tcaccgaggc | agttccatag | gatggcaaga | tcctggtatc ggtctgcgat | 7320 |
| tccgactcgt | ccaacatcaa | tacaacctat | taatttcccc | tcgtcaaaaa taaggttatc | 7380 |
| aagtgagaaa | tcaccatgag | tgacgactga | atccggtgag | aatggcaaaa gcttatgcat | 7440 |
| ttctttccag | acttgttcaa | caggccagcc | attacgctcg | tcatcaaaat cactcgcatc | 7500 |
| aaccaaaccg | ttattcattc | gtgattgcgc | ctgagcgaga | cgaaatacgc gatcgctgtt | 7560 |

```
aaaaggacaa ttacaaacag gaatcgaatg caaccggcgc aggaacactg ccagcgcatc    7620
aacaatattt tcacctgaat caggatattc ttctaatacc tggaatgctg ttttcccggg    7680
gatcgcagtg gtgagtaacc atgcatcatc aggagtacgg ataaaatgct tgatggtcgg    7740
aagaggcata aattccgtca gccagtttag tctgaccatc tcatctgtaa catcattggc    7800
aacgctacct ttgccatgtt tcagaaacaa ctctggcgca tcgggcttcc catacaatcg    7860
atagattgtc gcacctgatt gcccgacatt atcgcgagcc catttatacc catataaatc    7920
agcatccatg ttggaattta atcgcggcct cgagcaagac gtttcccgtt gaatatggct    7980
cataacaccc cttgtattac tgtttatgta agcagacagt tttattgttc atgatgatat    8040
atttttatct tgtgcaatgt aacatcagag attttgagac acaacgtggc tttcccccc    8100 cccccctgca ggtctcgggc tattcttttg atttataagg gattttgccg atttcggcct    8160
attggttaaa aaatgagctg atttaacaaa aatttaacgc gaattttaac aaaatattaa    8220
cgtttacaat ttaaatattt gcttatacaa tcttcctgtt tttggggctt ttctgattat    8280
caaccggggt acatatgatt gacatgctag ttttacgatt accgttcatc gattctcttg    8340
tttgctccag actctcaggc aatgacctga tagcctttgt agacctctca aaaatagcta    8400
ccctctccgg catgaattta tcagctagaa cggttgaata tcatattgat ggtgatttga    8460
ctgtctccgg cctttctcac cttttgaat ctttacctac acattactca ggcattgcat    8520
ttaaaatata tgagggttct aaaaattttt atccttgcgt tgaaataaag gcttctcccg    8580
caaaagtatt acagggtcat aatgtttttg gtacaaccga tttagcttta tgctctgagg    8640
ctttattgct taattttgct aattctttgc cttgcctgta tgatttattg gatgtt       8696
```

<210> SEQ ID NO 11
<211> LENGTH: 8669
<212> TYPE: DNA
<213> ORGANISM: Unknown
<220> FEATURE:
<223> OTHER INFORMATION: The nucleic acid sequence of a preferred second
      vector (helper phage without RGD sequence)

<400> SEQUENCE: 11

```
aacgctacta ctattagtag aattgatgcc accttttcag ctcgcgcccc aaatgaaaat     60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaaacatgt tgagctcag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540 aaacattta ctattacccc ctctggcaaa acttcttttg caaaagcctc tcgctatttt    600 ggttttatc gtcgtctggt aaacgagggt tatgatagtt tgctcttac tatgcctcgt    660 aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
```

```
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaattat   1140 caggcgatga tacaaatctc cgttgtactt tgtttcgcgc ttggtataat cgctggggt    1200 caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctccttt ggagcctttt    1560 tttttggaga ttttcaacgt gaaaaaatta ttattcgcaa ttcctttagt tgttcctttc   1620
tattctcact ccgctgaaac tgttgaaagt tgtttagcaa accccatac agaaaattca    1680 tttactaacg tctggaaaga cgacaaaact ttagatcgtt acgctaacta tgagggttgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg acccccgttaa aacttattac cagtacactc ctgtatcatc aaaagccatg   2160
tatgacgctt actggaacgg taaattcaga gactgcgctt tccattctgg ctttaatgag   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggg ctatgaccga aaatgccgat    2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg tgacggtga taattcacct    2640 ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttactttc    2940 ttaaaaaggg cttcggtaag atagctattg ctatttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcatttttg acgttaaaca aaaaatcgtt tcttatttgg   3180
attgggataa ataatatggc tgtttatttt gtaactggca aattaggctc tggaaagacg   3240
```

```
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta cttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg ctttttctag taattatgat    3840
tccggtgttt attcttattt aacgccttat ttatcacacg gtcggtattt caaaccatta    3900
aatttaggtc agaagatgaa attaactaaa atatatttga aaagttttc tcgcgttctt    3960
tgtcttgcga ttggatttgc atcagcattt acatatagtt atataaccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gttctcccg atgtaaaagg    4380
tactgttact gtatattcat ctgacgttaa acctgaaaat ctacgcaatt tctttatttc    4440
tgttttacgt gctaataatt ttgatatggt tggttcaatt ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgcacct aaagatattt tagataacct tcctcaattc ctttctactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt attttttaatg gcgatgtttt    4980
agggctatca gttcgcgcat taaagactaa tagccattca aaaatattgt ctgtgccacg    5040
tattcttacg ctttcaggtc agaagggttc tatctctgtt ggccagaatg tccctttat    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact    5340
cggtggcctc actgattata aaaacacttc tcaagattct ggcgtaccgt tcctgtctaa    5400
aatccctta atcggcctcc tgtttagctc ccgctctgat tccaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
```

```
gggggctccc tttagggttc cgatttagtg cttttacggca cctcgacccc aaaaaacttg    5700
atttgggtga tggttcacgt agtgggccat cgccctgata cacggttttt cgcccttttga   5760 cgttggagtc cacgttcttt aatagtggac tcttgttcca aactggaaca acactcaacc    5820
ctatctcggg acggatcgct tcatgtggca ggagaaaaaa ggctgcaccg gtgcgtcagc    5880
agaatatgtg atacaggata tattccgctt cctcgctcac tgactcgcta cgctcggtcg    5940
ttcgactgcg gcgagcggaa atggcttacg aacggggcgg agatttcctg gaagatgcca    6000
ggaagatact taacagggaa gtgagagggc cgcggcaaag ccgttttttcc ataggctccg    6060 cccccctgac aagcatcacg aaatctgacg ctcaaatcag tggtggcgaa acccgacagg    6120
actataaaga taccaggcgt ttccccctgg cggctccctc gtgcgctctc ctgttcctgc    6180
ctttcggttt accggtgtca ttccgctgtt atggccgcgt ttgtctcatt ccacgcctga    6240
cactcagttc cgggtaggca gttcgctcca agctggactg tatgcacgaa ccccccgttc    6300
agtccgaccg ctgcgcctta tccggtaact atcgtcttga gtccaacccg gaaagacatg    6360
caaaagcacc actggcagca gccactggta attgatttag aggagttagt cttgaagtca    6420
tgcgccggtt aaggctaaac tgaaaggaca gttttggtg actgcgctcc tccaagccag     6480
ttacctcggt tcaaagagtt ggtagctcag agaaccttcg aaaaaccgcc ctgcaaggcg    6540
gttttttcgt tttcagagca agagattacg cgcagaccaa aacgatctca agaagatcat    6600
cttattaagg ggtctgacgc tcagtggaac gaaaactcac gttaagggat tttggtcatg    6660
agattatcaa aaaggatctt cacctagatc cttttaaatt aaaaatgaag ttttaaatca    6720
atctaaagta tatatgagta aacttggtct gacagttacc aatgcttaat cagtgaggca    6780
cctatctcag cgatctgtct atttcgttca tccatagttg cctgactccc cgtcgtgtag    6840
ataactacga tacgggaggg cttaccatct ggccccagtg ctgcaatgat accgcgagac    6900
ccacgctcac cggctccaga tttatcagca ataaaccagc cagccgattc gagctcgccc    6960
cggggatcga ccagttggtg attttgaact tttgctttgc cacggaacgg tctgcgttgt    7020
cgggaagatg cgtgatctga tccttcaact cagcaaaagt tcgatttatt caacaaagcc    7080
gccgtcccgt caagtcagcg taatgctctg ccagtgttac aaccaattaa ccaattctga    7140
ttagaaaaac tcatcgagca tcaaatgaaa ctgcaattta ttcatatcag gattatcaat    7200
accatatttt tgaaaaagcc gtttctgtaa tgaaggagaa aactcaccga gcagttccat    7260
taggatggca agatcctggt atcggtctgc gattccgact cgtccaacat caatacaacc    7320
tattaatttc cctcgtcaa aaataaggtt atcaagtgag aaatcaccat gagtgacgac    7380
tgaatccggt gagaatggca aaagcttatg catttctttc cagacttgtt caacaggcca    7440
gccattacgc tcgtcatcaa aatcactcgc atcaaccaaa ccgttattca ttcgtgattg    7500
cgcctgagcg agacgaaata cgcgatcgct gttaaaagga caattacaaa caggaatcga    7560
atgcaaccgg cgcaggaaca ctgccagcgc atcaacaata ttttcacctg aatcaggata    7620
ttcttctaat acctggaatg ctgttttccc ggggatcgca gtggtgagta accatgcatc    7680
atcaggagta cggataaaat gcttgatggt cggaagaggc ataaattccg tcagccagtt    7740
tagtctgacc atctcatctg taacatcatt ggcaacgcta cctttgccat gtttcagaaa    7800
caactctggc gcatcgggct tcccatacaa tcgatagatt gtcgcacctg attgcccgac    7860
attatcgcga gcccatttat acccatataa atcagcatcc atgttggaat ttaatcgcgg    7920
cctcgagcaa gacgtttccc gttgaatatg gctcataaca ccccttgtat tactgtttat    7980
```

-continued

```
gtaagcagac agtttttattg ttcatgatga tatattttta tcttgtgcaa tgtaacatca    8040 gagatttttga gacacaacgt ggctttcccc cccccccct gcaggtctcg ggctattctt    8100
ttgatttata agggattttg ccgatttcgg cctattggtt aaaaaatgag ctgatttaac    8160
aaaaatttaa cgcgaatttt aacaaaatat taacgtttac aatttaaata tttgcttata    8220
caatcttcct gttttttgggg cttttctgat tatcaaccgg ggtacatatg attgacatgc    8280
tagttttacg attaccgttc atcgattctc ttgtttgctc cagactctca ggcaatgacc    8340
tgatagcctt tgtagacctc tcaaaaatag ctaccctctc cggcatgaat ttatcagcta    8400
gaacggttga atatcatatt gatggtgatt tgactgtctc cggcctttct caccctttttg   8460 aatctttacc tacacattac tcaggcattg catttaaaat atatgagggt tctaaaaatt    8520
tttatccttg cgttgaaata aaggcttctc ccgcaaaagt attacagggt cataatgttt    8580
ttggtacaac cgatttagct ttatgctctg aggctttatt gcttaatttt gctaattctt    8640
tgccttgcct gtatgattta ttggatgtt                                       8669
```

<210> SEQ ID NO 12
<211> LENGTH: 233
<212> TYPE: PRT
<213> ORGANISM: Homo sapiens

<400> SEQUENCE: 12

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 13

<211> LENGTH: 702
<212> TYPE: DNA
<213> ORGANISM: Homo sapiens

<400> SEQUENCE: 13

```
atgagcactg aaagcatgat ccgggacgtg gagctggccg aggaggcgct ccccaagaag      60
acagggggc cccagggctc caggcggtgc ttgttcctca gcctcttctc cttcctgatc     120
gtggcaggcg ccaccacgct cttctgcctg ctgcactttg gagtgatcgg cccccagagg    180
gaagagttcc ccagggacct ctctctaatc agccctctgg cccaggcagt cagatcatct    240
tctcgaaccc cgagtgacaa gcctgtagcc catgttgtag caaaccctca agctgagggg    300
cagctccagt ggctgaaccg ccgggccaat gccctcctgg ccaatggcgt ggagctgaga    360
gataaccagc tggtggtgcc atcagagggc ctgtacctca tctactccca ggtcctcttc    420
aagggccaag gctgcccctc cacccatgtg ctcctcaccc acaccatcag ccgcatcgcc    480
gtctcctacc agaccaaggt caacctcctc tctgccatca gagcccctg ccagagggag     540
accccagagg gggctgaggc caagccctgg tatgagccca tctatctggg aggggtcttc    600
cagctggaga agggtgaccg actcagcgct gagatcaatc ggcccgacta tctcgacttt    660
gccgagtctg ggcaggtcta ctttgggatc attgccctgt ga                       702
```

<210> SEQ ID NO 14
<211> LENGTH: 921
<212> TYPE: DNA
<213> ORGANISM: Homo sapiens

<400> SEQUENCE: 14

```
atggctctcc cagtgactgc cctactgctt cccctagcgc ttctcctgca tgcaaccgcc      60
cctccagccc acggagtgac cagcgcccct gacacccggc tgctcctgg aagcacagct     120
ccacctgccc acggcgttac ctctgcacca gatactaggc ctgctccagg ctccatcgag    180
gtgatgtacc cccccccta cctggacaac gagaagagca acggcaccat catccacgtg    240
aagggcaagc acctgtgccc cagcccctg ttccccggcc ccagcaagcc cttctgggtg     300
ctggtggtgg tgggcggcgt gctggcctgc tacagcctgc tggtgaccgt ggccttcatc    360
atcttctggg tgcggagcaa gaggagaaag cgcagcggtt ccggcgaggg ccggggcagc    420
ctgctgacct gcggcgacgt ggaggagaac cccggcccta tgggcctgac agccagctt    480
ctgccccccc tgttcttcct gctggcctgc gccggcaact tcgtgcacgg ccacaagtgc    540
gacatcaccc tgcaggagat catcaagacc ctgaacagcc tgaccgagca aagaccctg     600
tgcaccgagc tgaccgtgac cgacatcttc gccgccagca gaacaccac cgagaaggag    660
accttctgcc gggccgccac cgtgctgcgg cagttctaca gccaccacga gaaggacacc    720
cggtgcctgg gcgccaccgc ccagcagttc acccggcaca gcaactgat ccggttcctg     780
aagcggctgg accggaacct gtggggcctg ccggcctga acagttgccc cgtgaaggag     840
gccaaccaga gcaccctgga gaacttcctg gagcggctga gaccatcat gcgggagaag    900
tacagcaagt gcagcagcta g                                              921
```

<210> SEQ ID NO 15
<211> LENGTH: 825
<212> TYPE: DNA
<213> ORGANISM: Homo sapiens

<400> SEQUENCE: 15

```
atggctctcc cagtgactgc cctactgctt cccctagcgc ttctcctgca tgcaaccgcc      60
```

```
cctccagccc acggagtgac cagcgcccct gacacccggc ctgctcctgg aagcacagct    120
ccacctgccc acggcgttac ctctgcacca gatactaggc ctgctccagg ctcccccaac    180
aagggcagcg gcacaaccag cggaaccacc aggctgttga gcggccacac ctgcttcacc    240
ctgacaggcc tgctgggcac cctggtgaca atgggcctgc tgaccaggag aaagcgcagc    300
ggttccggcg agggccgggg cagcctgctg acctgcggcg acgtggagga aaccccggc     360 cctatgggcc tgaccagcca gcttctgccc cccctgttct tcctgctggc ctgcgccggc    420
aacttcgtgc acggccacaa gtgcgacatc accctgcagg agatcatcaa gaccctgaac    480
agcctgaccg agcagaagac cctgtgcacc gagctgaccg tgaccgacat cttcgccgcc    540
agcaagaaca ccaccgagaa ggagaccttc tgccgggccg ccaccgtgct gcggcagttc    600
tacagccacc acgagaagga cacccggtgc ctgggcgcca ccgcccagca gttccaccgg    660
cacaagcaac tgatccggtt cctgaagcgg ctggaccgga acctgtgggg cctggccggc    720
ctgaacagtt gccccgtgaa ggaggccaac cagagcaccc tggagaactt cctggagcgg    780
ctgaagacca tcatgcggga gaagtacagc aagtgcagca gctag                   825

<210> SEQ ID NO 16
<211> LENGTH: 2253
<212> TYPE: DNA
<213> ORGANISM: Homo sapiens

<400> SEQUENCE: 16
atgtggaacc tgctgcacga gactgacagc gccgtggcaa ccgcacggag accccggtgg    60
ctgtgcgctg gcgcactggt gctggccggc gggttctttc tgctggggtt cctgtttgga   120
tggtttatca aaagctccaa cgaggccacc aatattacac ctaagcacaa tatgaaagca   180
ttcctggatg aactgaaggc cgagaacatc aagaaattcc tgtacaactt tactcagatt   240
ccacatctgg ctggcaccga gcagaacttt cagctggcaa acagatccca gagccagtgg   300
aaggaattcg gctggactcc gtggagctg ccccactacg atgtcctgct gagttatcca    360
aataagacac atcccaacta tatctcaatc attaacgaag acggaaatga gatttcaac    420 acttcactgt ttgaaccccc tccacccggc tacgagaacg tgagcgacat cgtccctcca    480
ttctcagcct ttagcccaca gggaatgcct gaggggatc tggtgtacgt caattatgct    540
cgcaccgaag acttctttaa gctggagcga gatatgaaaa tcaactgtag cggcaagatc    600
gtgattgcca gatacggcaa agtgtttcgc gggaataagg tcaaaaacgc tcagctggcc    660
ggggctaagg gagtgattct gtactctgac cccgctgatt atttcgcacc tggagtgaag    720
agttatccag acggatggaa tctgccagga ggaggagtgc agcgaggaaa catcctgaac    780
ctgaatgggg ccggagatcc tctgaccccca ggatacccccg ccaacgaata cgcttatagg    840
cgaggaattg cagaggcagt gggactgcct tccatcccag tccaccccat ggctactat     900 gacgcccaga gctgctgga gaaaatggga ggctctgctc cccctgattc tagttggaga    960
ggcagtctga aggtgcctta caatgtcggc ccagggttca gggaacttt ttcaactcag    1020 aaggtgaaaa tgcacatcca tagcactaat gaagtgacca ggatctataa cgtcattgga   1080
actctgcgag gcgccgtgga gcctgacaga tacgtcattc tggggggaca ccgcgactcc    1140
tgggtgtttg gcgggatcga tccacagtct ggcgccgctg tggtccatga aattgtgcgg   1200
tctttcggca cactgaagaa agagggggtgg agacccgac ggactatcct gtttgcaagt   1260
tgggatgccg aggaattcgg cctgctgggg agtacagaat gggccgagga aaattcacgg   1320
```

-continued

```
ctgctgcagg agagagggt ggcttacatc aatgcagact caagcattga aggaaactat    1380
acactgcggg tggattgcac tccctgatg tacagcctgg tccacaacct gaccaaggag    1440
ctgaaatccc ctgacgaggg attcgaaggc aaaagcctgt atgaatcctg acaaagaaa    1500 agtccatcac ccgagtttag cggaatgcct cgaatctcta agctgggaag tggcaatgat    1560
ttcgaagtgt tctttcagag actggggatt gcctccggaa gagctaggta caccaaaaat    1620
tgggagacaa acaagttctc cggctaccca ctgtatcaca gcgtgtacga gacttatgaa    1680
ctggtcgaga aattctacga ccccatgttt aagtatcatc tgaccgtggc acaggtcagg    1740
ggaggcatgg tgtttgagct ggccaattcc atcgtcctgc cattcgactg tagagattat    1800
gctgtggtcc tgaggaagta cgcagacaaa atctatagca tttccatgaa acatccccag    1860
gagatgaaga cctactctgt gagtttcgat tccctgtttt ctgccgtcaa aaacttcaca    1920
gaaatcgcta gtaagttttc agagcgcctg caggacttcg ataagtctaa tcccattgtg    1980
ctgaggatga tgaacgacca gctgatgttc ctggaacgcg cctttatcga ccctctgggg    2040
ctgcctgatc gccccttcta ccgacacgtg atctacgcac cttcctctca taacaagtac    2100
gccggagagt cttttccagg catctatgac gctctgttcg atattgaatc aaaggtcgat    2160
cccagcaaag catggggcga ggtcaagaga cagatctacg tggcagcctt caccgtccag    2220
gctgcagccg aaacactgag cgaggtggcc tga                                2253
```

<210> SEQ ID NO 17
<211> LENGTH: 1255
<212> TYPE: PRT
<213> ORGANISM: Homo sapiens

<400> SEQUENCE: 17

```
Met Thr Pro Gly Thr Gln Ser Pro Phe Phe Leu Leu Leu Leu Thr
1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205
```

```
Gly Ser Thr Ala Pro Pro Ala His Gly Val Thr Ser Ala Pro Asp Thr
            210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
                275                 280                 285

Gly Ser Thr Ala Pro Pro Ala His Gly Val Thr Ser Ala Pro Asp Thr
            290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
                355                 360                 365

Gly Ser Thr Ala Pro Pro Ala His Gly Val Thr Ser Ala Pro Asp Thr
            370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
                435                 440                 445

Gly Ser Thr Ala Pro Pro Ala His Gly Val Thr Ser Ala Pro Asp Thr
            450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
                515                 520                 525

Gly Ser Thr Ala Pro Pro Ala His Gly Val Thr Ser Ala Pro Asp Thr
            530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
                595                 600                 605

Gly Ser Thr Ala Pro Pro Ala His Gly Val Thr Ser Ala Pro Asp Thr
            610                 615                 620

Arg Pro Ala Pro Gly Ser Thr Ala Pro Pro Ala His Gly Val Thr Ser
```

```
                    625                 630                 635                 640
Ala Pro Asp Thr Arg Pro Ala Pro Gly Ser Thr Ala Pro Pro Ala His
                    645                 650                 655
Gly Val Thr Ser Ala Pro Asp Thr Arg Pro Ala Pro Gly Ser Thr Ala
                    660                 665                 670
Pro Pro Ala His Gly Val Thr Ser Ala Pro Asp Thr Arg Pro Ala Pro
                    675                 680                 685
Gly Ser Thr Ala Pro Pro Ala His Gly Val Thr Ser Ala Pro Asp Thr
                    690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                    725                 730                 735
Gly Val Thr Ser Ala Pro Asp Thr Arg Pro Ala Pro Gly Ser Thr Ala
                    740                 745                 750
Pro Pro Ala His Gly Val Thr Ser Ala Pro Asp Thr Arg Pro Ala Pro
                    755                 760                 765
Gly Ser Thr Ala Pro Pro Ala His Gly Val Thr Ser Ala Pro Asp Thr
                    770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                    805                 810                 815
Gly Val Thr Ser Ala Pro Asp Thr Arg Pro Ala Pro Gly Ser Thr Ala
                    820                 825                 830
Pro Pro Ala His Gly Val Thr Ser Ala Pro Asp Thr Arg Pro Ala Pro
                    835                 840                 845
Gly Ser Thr Ala Pro Pro Ala His Gly Val Thr Ser Ala Pro Asp Thr
                    850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
                    885                 890                 895
Gly Val Thr Ser Ala Pro Asp Thr Arg Pro Ala Pro Gly Ser Thr Ala
                    900                 905                 910
Pro Pro Ala His Gly Val Thr Ser Ala Pro Asp Thr Arg Pro Ala Pro
                    915                 920                 925
Gly Ser Thr Ala Pro Pro Ala His Gly Val Thr Ser Ala Pro Asp Asn
                    930                 935                 940
Arg Pro Ala Leu Gly Ser Thr Ala Pro Pro Val His Asn Val Thr Ser
945                 950                 955                 960
Ala Ser Gly Ser Ala Ser Gly Ser Ala Ser Thr Leu Val His Asn Gly
                    965                 970                 975
Thr Ser Ala Arg Ala Thr Thr Thr Pro Ala Ser Lys Ser Thr Pro Phe
                    980                 985                 990
Ser Ile Pro Ser His His Ser Asp Thr Pro Thr Thr Leu Ala Ser His
                    995                 1000                1005
Ser Thr Lys Thr Asp Ala Ser Ser Thr His His Ser Ser Val Pro
                    1010                1015                1020
Pro Leu Thr Ser Ser Asn His Ser Thr Ser Pro Gln Leu Ser Thr
                    1025                1030                1035
Gly Val Ser Phe Phe Phe Leu Ser Phe His Ile Ser Asn Leu Gln
                    1040                1045                1050
```

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 18
<211> LENGTH: 157
<212> TYPE: PRT
<213> ORGANISM: Homo sapiens

<400> SEQUENCE: 18

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu

<210> SEQ ID NO 19
<211> LENGTH: 474
<212> TYPE: DNA
<213> ORGANISM: Homo sapiens

<400> SEQUENCE: 19

```
gtcagatcat cttctcgaac cccgagtgac aagcctgtag cccatgttgt agcaaaccct    60
caagctgagg ggcagctcca gtggctgaac cgccgggcca atgccctcct ggccaatggc   120
gtggagctga gagataacca gctggtggtg ccatcagagg gcctgtacct catctactcc   180
caggtcctct tcaagggcca aggctgcccc tccacccatg tgctcctcac ccacaccatc   240
agccgcatcg ccgtctccta ccagaccaag gtcaacctcc tctctgccat caagagcccc   300
tgccagaggg agaccccaga gggggctgag gccaagccct ggtatgagcc catctatctg   360
ggagggtct tccagctgga aagggtgac cgactcagcg ctgagatcaa tcggcccgac   420
tatctcgact ttgccgagtc tgggcaggtc tactttggga tcattgccct gtga        474
```

<210> SEQ ID NO 20
<211> LENGTH: 20
<212> TYPE: PRT
<213> ORGANISM: Homo sapiens

<400> SEQUENCE: 20

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 21
<211> LENGTH: 60
<212> TYPE: DNA
<213> ORGANISM: Homo sapiens

<400> SEQUENCE: 21

```
atgtacagaa tgcaactcct gtcttgtatt gcactaagtc tcgcacttgt cacaaacagt    60
```

<210> SEQ ID NO 22
<211> LENGTH: 179
<212> TYPE: PRT
<213> ORGANISM: Homo sapiens

<400> SEQUENCE: 22

```
Met Tyr Arg Met Gln Leu Leu Ser Cys Ile Ala Leu Ser Leu Ala Leu
1               5                   10                  15

Val Thr Asn Ser Glu Ser Val Arg Ser Ser Arg Thr Pro Ser Asp
            20                  25                  30

Lys Pro Val Ala His Val Val Ala Asn Pro Gln Ala Glu Gly Gln Leu
        35                  40                  45

Gln Trp Leu Asn Arg Arg Ala Asn Ala Leu Leu Ala Asn Gly Val Glu
    50                  55                  60

Leu Arg Asp Asn Gln Leu Val Val Pro Ser Glu Gly Leu Tyr Leu Ile
65                  70                  75                  80

Tyr Ser Gln Val Leu Phe Lys Gly Gln Gly Cys Pro Ser Thr His Val
                85                  90                  95

Leu Leu Thr His Thr Ile Ser Arg Ile Ala Val Ser Tyr Gln Thr Lys
            100                 105                 110
```

```
Val Asn Leu Leu Ser Ala Ile Lys Ser Pro Cys Gln Arg Glu Thr Pro
            115                 120                 125

Glu Gly Ala Glu Ala Lys Pro Trp Tyr Glu Pro Ile Tyr Leu Gly Gly
        130                 135                 140

Val Phe Gln Leu Glu Lys Gly Asp Arg Leu Ser Ala Glu Ile Asn Arg
145                 150                 155                 160

Pro Asp Tyr Leu Asp Phe Ala Glu Ser Gly Gln Val Tyr Phe Gly Ile
            165                 170                 175

Ile Ala Leu

<210> SEQ ID NO 23
<211> LENGTH: 540
<212> TYPE: DNA
<213> ORGANISM: Homo sapiens

<400> SEQUENCE: 23
atgtacagaa tgcaactcct gtcttgtatt gcactaagtc tcgcacttgt cacaaacagt      60
gaattcgtca gatcatcttc tcgaaccccg agtgacaagc ctgtagccca tgttgtagca     120
aaccctcaag ctgaggggca gctccagtgg ctgaaccgcc gggccaatgc cctcctggcc     180
aatggcgtgg agctgagaga taaccagctg gtggtgccat cagagggcct gtacctcatc     240
tactcccagg tcctcttcaa gggccaaggc tgcccctcca ccatgtgct cctcacccac      300 accatcagcc gcatcgccgt ctcctaccag accaaggtca acctcctctc tgccatcaag     360
agcccctgcc agagggagac cccagagggg gctgaggcca gccctggta tgagcccatc      420 tatctgggag ggtcttcca gctggagaag ggtgaccgac tcagcgctga gatcaatcgg      480
cccgactatc tcgactttgc cgagtctggg caggtctact ttgggatcat tgccctgtga     540

<210> SEQ ID NO 24
<211> LENGTH: 28
<212> TYPE: DNA
<213> ORGANISM: Homo sapiens

<400> SEQUENCE: 24
gagtgaattc gctgtgaccg gcgcctac                                         28

<210> SEQ ID NO 25
<211> LENGTH: 35
<212> TYPE: DNA
<213> ORGANISM: Homo sapiens

<400> SEQUENCE: 25
gctcgtcgac tcatgtctgg ccagctagct tagcc                                 35

<210> SEQ ID NO 26
<211> LENGTH: 58
<212> TYPE: DNA
<213> ORGANISM: Artificial Sequence
<220> FEATURE:
<223> OTHER INFORMATION: A nucleic acid sequence comprising a section
      of a genome of a helper phage comprising a RGD4C targeting peptide
      in a pIII minor coat protein

<400> SEQUENCE: 26
tattctcact ccgcttgtga ttgtaggggg gattgttttt gtgaaactgt tgaaagtt        58

<210> SEQ ID NO 27
<211> LENGTH: 19
<212> TYPE: PRT
<213> ORGANISM: Artificial Sequence
```

```
<220> FEATURE:
<223> OTHER INFORMATION: An amino acid sequence comprising a section of
      a genome of a helper phage comprising a RGD4C targeting peptide in
      a pIII minor coat protein

<400> SEQUENCE: 27

Tyr Ser His Ser Ala Cys Asp Cys Arg Gly Asp Cys Phe Cys Glu Thr
1               5                   10                  15

Val Glu Ser
```

CANCER TREATMENT

CROSS-REFERENCE TO RELATED APPLICATIONS

This application is a National Phase of International Application No. PCT/GB2018/051070 filed Apr. 24, 2018, currently pending, which designated the U.S. and that International Application was published under PCT Article 21(2) in English. This application also includes a claim of priority under 35 U.S.C. § 119(a) and § 365(b) to British patent application No. GB 1706451.0 filed Apr. 24, 2017, the entirety of which is hereby incorporated by reference.

The present invention relates to cancer treatment, and in particular, to the use of novel phagemid particles and associated expression systems for the treatment, prevention, amelioration, or management of cancer. In particular, the invention relates to the use of phagemid particles and expression systems for the delivery of transgenes encoding cytokines, for the treatment, prevention, amelioration, or management of cancer. The invention also extends to the use of phagemid particles and expression systems for the delivery of transgenes, and for the combination of such treatment with the use of adoptively transferred T cells, for the treatment, prevention, amelioration, or to management of cancer.

Paediatric high-grade gliomas are a heterogeneous group of tumours that accounts for 15%-20% of all paediatric central nervous system (CNS) tumours in children. Tumours can originate from any site within the CNS. When arising from the brainstem, specifically the pons, they are referred to as DIPG. Diagnosis is based on imaging and histological appearance. Despite many clinical trials, prognosis remains poor with 2-year survival rates being less than 10%, making it one of the major causes of brain cancer-related deaths in children. Given its location, the tumour is inoperable and conventional fractionated radiation remains the mainstay treatment to provide temporary benefit, with no other treatment showing any efficacy over conventional radiotherapy. Poor response to conventional treatment in DIPG therefore warrants innovative treatment approaches.

In recent years, efforts have been focused on researching gene therapy as a biological mechanism-based technique to specifically target tumour cells and cause anti-tumour activity. Gene therapy has traditionally been conceived for the treatment of congenital diseases, but has increasingly been used in cancer treatment to improve efficiencies of co-administered treatments such as chemotherapy and radiotherapy, and directly induce death in tumour cells. Considering the many side effects that arise from conventional cancer treatments lacking discrimination between healthy and tumour tissue, delivery of therapeutic genes via targeted vectors offer more specificity and safety.

Various cytokine genes are suitable for use in cancer immune-gene therapy such as interleukins (IL-4, IL-12 and IL-15) and the Tumour Necrosis factor Alpha (TNFα) and TNF-related apoptosis-inducing ligand (TRAIL). TRAIL, a member of the TNF family, induces apoptosis in various cancer cell lines, with high tolerance and minimal toxicity to normal tissue. Both local and systemic injection of TRAIL protein exerts antitumor effects on human tumour xenografts in mice. However, the rapid clearance of TRAIL following systemic administration and large dose required to achieve tumour regression have limited the TRAIL effectiveness in patients. The presently disclosed particles are ideal and cost-effective for the efficient delivery and sustained expression of the TRAIL gene in cancer. IL-4 was efficacious in the induction of antitumour effect, in mouse models of cancer. Moreover, a phase I clinical trial was initiated to determine the safety and tolerability of IL-4 in recurrent human malignant glioma when injected intratumorally by convection enhanced delivery (CED). No histological evidence of neurotoxicity to normal brain was identified in any patient and no drug-related systemic toxicity was evident in any treated patients. Six of nine patients showed glioma necrosis, and one remained disease free for >18 months after the procedure. Yet, again, the large protein dose and cost required to achieve efficacy, and the invasiveness of intracranial delivery places important limitations.

During the past two decades, IL-12 has emerged as one of the most potent cytokines in mediating antitumor activity in a variety of preclinical models. Through pleiotropic effects on different immune cells that form the tumour microenvironment, IL-12 establishes a link between innate and adaptive immunity that involves different immune effector cells and cytokines depending on the type of tumour or the affected tissue. Although IL-12 has no direct effect on tumour cells, it improves activation of cytotoxic T and NK effector cells which mediates tumour lysis. IL-12, moreover, improves the Th1 cell response, induces a panel of cytokines including IFN-γ, and exhibits antiangiogenesis. In mice, local intratumoral adenoviral vector delivery of IL-12 gene was completed safely, significantly prolonged animal survival and induced dramatic regression of tumour size.

Recently, intracranial injection of recombinant rAAV vector encoding the IL-12 was used for brain tumour gene therapy in a rat model, and resulted in antitumour effects associated with increased induction of activated microglia cells. Finally, The TNFα displays powerful anti-tumour cell effects, directly by apoptosis or indirectly by immunomodulatory activity; it also targets and destroys tumour neovascularization.

Interleukin 15 participates in the development of important immune antitumor mechanisms. It activates CD8+ T cells, natural killer (NK) cells, NK T cells, and can promote the formation of antitumor antibodies. IL-15 can also protect T effector cells from the action of T regulatory cells and reverse tolerance to tumour associated antigens.

The advantages of IL-15 in tumour immunotherapy result from its unique ability to activate important mechanisms of antitumor immunity, including development and activity of both NK cells and CD8+ T cells, and promoting a persistent immune response through its action on memory T cells. What is more, IL-15 is less toxic and less effective in inducing Treg cell activity, as compared with IL-2, and in certain circumstances it can even protect human effector T cells from the action of Treg cells. IL-15 is at the top of the National Cancer Institute's list of agents with the greatest potential use in tumor immunotherapy, and the first clinical study of recombinant human IL-15 in adults with refractory metastatic melanoma and metastatic renal cell cancer is currently recruiting patients (http://clinicaltrials.gov/ct2/show/NCT01021059).

Survival of colon carcinoma-bearing mice has been significantly improved by treatment with IL-15 and was further improved by programmed death ligand1 (PD-L1) blockade. Still, the greatest therapeutic effects have been achieved with combination modality treatment based on application of IL-15 and blockade of both PD-L1 and cytotoxic T-lymphocyte antigen 4 (CTLA-4).

Unfortunately, in spite of high expectations, while IL-15 shows efficacy in treatment of metastatic malignancy its lack of in vivo biochemical stability is a key limiting issue. The systemic rhIL-15 cytokine in clinical trials has a very short plasma half-life (<1 h) and rapid renal clearance, which easily results in impedance of efficacy. Furthermore, systemic administration of rhIL15 has the potential to cause toxic side effects, including the induction of autoimmunity.

Delivery of IL-15 directly into the tumour instead of systemic administration would be ideal to decrease toxicity and increase efficacy. However, direct injection into the tumour mass or incorporation of IL-15 as a transgene in adoptive cell transfer is difficult to implement. The presence of multiple metastatic sites or excessive growth and potential leukemic transformation of transduced cells may in fact limit therapeutic relevance.

Another solution to lengthen the time window of IL-15 bioavailability was found in gene therapy approaches. The advantages of gene therapy include loco-regional production, ability to generate fusion constructs and versatility for combination strategies. Unfortunately, systemic delivery using eukaryotic viruses has had limited success due to undesired uptake by the liver and reticulo endothelial system, insertional mutagenesis, immunogenicity arising from reactions with the complement system or pre-existing antibodies, and broad tropism for mammalian cells. Viral tropism may be modified by the addition of tissue-specific ligands to viral capsid proteins to mediate a ligand-receptor interaction on the target tissue. However, addition of these ligands to eukaryotic viruses can alter the structure of the viral capsid, which can reduce efficacy and diminish targeting properties of the peptides themselves.

Thus, while the cytokines described above are suitable for use in cancer immune-therapy, the majority of clinical trials involving cytokines fail to show sustained antitumor responses because of the lack of tumour selectivity resulting in systemic toxicity.

There is, therefore, a need for improved methods for delivery of cytokines in immune-oncotherapy.

In a first aspect, there is provided a recombinant phagemid particle for expressing a transgene in a target tumour cell transduced with the particle, for use in a method for treating, preventing, or ameliorating cancer, wherein the phagemid particle comprises at least one transgene expression cassette comprising a nucleic acid sequence encoding one or more cytokine, and comprises a genome which lacks at least 50% of its bacteriophage genome, and wherein the method comprises delivering the nucleic acid sequence to at least adjacent to the tumour cell, such that one or more cytokine is expressed.

In a preferred embodiment, the transgene expression cassette may encode a cytokine which may have the effect of apoptosis induction in the tumour cell, alternation of the tumour cell to promote endogenous anti-tumour responses, alternation of the tumour cell to facilitate other therapies, or alternation of the tumour microenvironment to facilitate therapy.

In a particular preferred embodiment, the cytokine may be IL-4, IL-12, IL-15, TNFα, TRAIL, IFN-γ, or any combination thereof. Preferably, the cytokine is IL-15, Preferably, the cytokine is IL-4. Preferably, the cytokine is IL-12. Preferably, the cytokine is TRAIL. Preferably, the cytokine is IFN-γ. In one preferred embodiment, the cytokine is not TNFα.

However, in another preferred embodiment, the cytokine is TNFα. Preferably, the cytokine is a hybrid TNFα comprising a non-endogenous signal peptide configured to increase expression and/or secretion of TNFα. Preferably, the signal peptide is a cytokine signal peptide other than that of TNFα. For example, the signal peptide is preferably the IL-2 signal peptide.

Thus, in one embodiment the transmembrane domain of TNFα is replaced with a cytokine signal peptide other than that of TNFα, preferably the IL-2 signal peptide. In another embodiment, a signal peptide different to any other cytokine of the invention, preferably the IL-2 signal peptide, is combined with any other cytokine of the invention, such that the expression and/or secretion of the resulting hybrid cytokine is increased. In particular, the hybrid cytokine may be any one of a hybrid IL-4, IL-12, IL-15, TRAIL or IFN-γ.

The hybrid IL-2-TNFα sequence relates to replacement of the transmembrane domain of TNFα, leaving the sequence encoding the secreted form of TNFα, with the signal peptide of IL-2, such that a hybrid TNFα produced that displays greater expression and/or secretion.

The skilled person would understand that "signal peptide sequence" can relate to an N-terminal sequence that functions to direct the translocation of a protein to the cellular membrane, and regulates secretion of the protein.

In particular, the skilled person would understand that "non-endogenous signal peptide sequence" can relate to a cytokine signal peptide, such as an interleukin, that is different to that of the cytokine being expressed.

The skilled person would understand that "hybrid cytokine" can relate to a cytokine that comprises a non-endogenous signal peptide sequence.

In one embodiment, the full length TNFα comprising the transmembrane domain has the amino acid sequence provided herein as SEQ ID No: 12, as follows:

[SEQ ID No: 12]
```
5' MSTESMIRDVELAEEALPKKTGGPQGSRRCLVLSLFSFLIVAGATTL

FCLLHFGVIGPQREEFPRDLSLISPLAQAVRSSSRTPSDKPVAHVVANPQ

AEGQLQWLNRRANALLANGVELRDNQLVVPSEGLYLIYSQVLFKGQGCPS

TVHLLTHTISRIAVSYQTKVNLLSAIKSPCQRETPEGAEAKPWYEPIYLG

GVFQLEKGDRLSAEINRPDYLDFAESGQVYFGIIAL 3'
```

The nucleic acid sequence encoding full length TNFα comprising the transmembrane domain may be represented herein, as follows:

[SEQ ID No: 13]
```
5' ATGAGCACTGAAAGCATGATCCGGGACGTGGAGCTGGCCGAGGAGGC

GCTCCCCAAGAAGACAGGGGGGCCCCAGGGCTCCAGGCGGTGCTTGTTCC

TCAGCCTCTTCTCCTTCCTGATCGTGGCAGGCGCCACCACGCTCTTCTGC

CTGCTGCACTTTGGAGTGATCGGCCCCCAGAGGGAAGAGTTCCCCAGGGA

CCTCTCTCTAATCAGCCCTCTGGCCCAGGCAGTCAGATCATCTTCTCGAA

CCCCGAGTGACAAGCCTGTAGCCCATGTTGTAGCAAACCCTCAAGCTGAG

GGGCAGCTCCAGTGGCTGAACCGCCGGGCCAATGCCCTCCTGGCCAATGG

CGTGGAGCTGAGAGATAACCAGCTGGTGGTGCCATCAGAGGGCCTGTACC

TCATCTACTCCCAGGTCCTCTTCAAGGGCCAAGGCTGCCCCTCCACCCAT

GTGCTCCTCACCCACACCATCAGCCGCATCGCCGTCTCCTACCAGACCAA

GGTCAACCTCCTCTCTGCCATCAAGAGCCCCTGCCAGAGGGAGACCCCAG

AGGGGGCTGAGGCCAAGCCCTGGTATGAGCCCATCTATCTGGGAGGGGTC

TTCCAGCTGGAGAAGGGTGACCGACTCAGCGCTGAGATCAATCGGCCCGA

CTATCTCGACTTTGCCGAGTCTGGGCAGGTCTACTTTGGGATCATTGCCC

TGTGA 3'
```

In one embodiment, the secreted form of TNFα has the amino acid sequence provided herein as SEQ ID No: 18, as follows:

[SEQ ID No: 18]
VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

In one embodiment, the nucleic acid sequence encoding the secreted form of TNFα may be represented herein, as follows:

[SEQ ID No: 19]
5' GTCAGATCATCTTCTCGAACCCCGAGTGACAAGCCTGTAGCCCATGT

TGTAGCAAACCCTCAAGCTGAGGGGCAGCTCCAGTGGCTGAACCGCCGGG

CCAATGCCCTCCTGGCCAATGGCGTGGAGCTGAGAGATAACCAGCTGGTG

GTGCCATCAGAGGGCCTGTACCTCATCTACTCCCAGGTCCTCTTCAAGGG

CCAAGGCTGCCCCTCCACCCATGTGCTCCTCACCCACACCATCAGCCGCA

TCGCCGTCTCCTACCAGACCAAGGTCAACCTCCTCTCTGCCATCAAGAGC

CCCTGCCAGAGGGAGACCCCAGAGGGGCTGAGGCCAAGCCCTGGTATGA

GCCCATCTATCTGGGAGGGTCTTCCAGCTGGAGAAGGGTGACCGACTCA

GCGCTGAGATCAATCGGCCCGACTATCTCGACTTTGCCGAGTCTGGGCAG

GTCTACTTTGGGATCATTGCCCTGTGA 3'

In one embodiment, the IL-2 signal peptide has the amino acid sequence provided herein as SEQ ID No: 20, as follows:

[SEQ ID No: 20]
MYRMQLLSCIALSLALVTNS

In one embodiment, the nucleic acid sequence encoding the IL-2 signal peptide may be represented herein as SEQ ID No: 21, as follows:

[SEQ ID No: 21]
5' ATGTACAGAATGCAACTCCTGTCTTGTATTGCACTAAGTCTCGCACT

TGTCACAAACAGT 3'

Accordingly, in one embodiment, the hybrid IL-2-TNFα has the amino acid sequence provided herein as SEQ ID No 22, as follows:

[SEQ ID No: 22]
MYRMQLLSCIALSLALVTNSESVRSSSRTPSDKPVAHVVANPQAEGQLQW

LNRRANALLANGVELRDNQLVVPSEGLYLIYSQVLFKGQGCPSTHVLLTH

TISRIAVSYQTKVNLLSAIKSPCQRETPEGAEAKPWYEPIYLGGVFQLEK

GDRLSAEINRPDYLDFAESGQVYFGIIAL

Accordingly, in one embodiment, the nucleic acid sequence encoding hybrid IL-2-TNFα may be represented herein as SEQ ID No: 23, as follows:

[SEQ ID No: 23]
5' ATGTACAGAATGCAACTCCTGTCTTGTATTGCACTAAGTCTCGCACT

TGTCACAAACAGTGAATTCGTCAGATCATCTTCTCGAACCCCGAGTGACA

AGCCTGTAGCCCATGTTGTAGCAAACCCTCAAGCTGAGGGGCAGCTCCAG

TGGCTGAACCGCCGGGCCAATGCCCTCCTGGCCAATGGCGTGGAGCTGAG

AGATAACCAGCTGGTGGTGCCATCAGAGGGCCTGTACCTCATCTACTCCC

AGGTCCTCTTCAAGGGCCAAGGCTGCCCCTCCACCCATGTGCTCCTCACC

CACACCATCAGCCGCATCGCCGTCTCCTACCAGACCAAGGTCAACCTCCT

CTCTGCCATCAAGAGCCCCTGCCAGAGGGAGACCCCAGAGGGGCTGAGG

CCAAGCCCTGGTATGAGCCCATCTATCTGGGAGGGGTCTTCCAGCTGGAG

AAGGGTGACCGACTCAGCGCTGAGATCAATCGGCCCGACTATCTCGACTT

TGCCGAGTCTGGGCAGGTCTACTTTGGGATCATTGCCCTGTGA 3'

Thus, in one embodiment, the one or more cytokine comprises an amino acid sequence of any one of SEQ ID Nos: 12, 18, 20 and 22 or a fragment or variant thereof.

Preferably, the one or more cytokine comprises an amino acid sequence as substantially set out in SEQ ID No: 22 or a fragment or variant thereof.

Thus, in one embodiment, the nucleic acid sequence encoding the one or more cytokine comprises any one of SEQ ID Nos: 13, 19, 21, and 23 or a fragment or variant thereof.

Preferably, the nucleic acid sequence encoding the one or more cytokine comprises SEQ ID No: 23 or a fragment or variant thereof.

In a second aspect, there is provided a method of treating, preventing, or ameliorating cancer in a subject, the method comprising administering, to a subject in need of such treatment, a therapeutically effective amount of the recombinant phagemid particle according to the first aspect.

The method of the second aspect may be used for the management of cancer in a subject.

In an embodiment, the recombinant phagemid particle is for use in treating, preventing or ameliorating paediatric brain tumours. In other embodiments, the recombinant phagemid particle is for use in treating, preventing or ameliorating diffuse intrinsic pontine glioma (DIPG) or medulloblastoma.

In a third aspect, there is provided a system for producing a recombinant phagemid particle from a prokaryotic host, the system comprising:—
  (i) a first vector configured to persist inside a prokaryotic host, and comprising at least one transgene expression cassette comprising a nucleic acid sequence encoding one or more cytokine, and a packaging signal for enabling replication of the vector into single-stranded DNA; and
  (ii) a second vector comprising nucleic acid encoding structural proteins required for packaging the single-stranded DNA, resulting in the formation and extrusion of a recombinant phagemid particle from the prokaryotic host.

In a fourth aspect, there is provided a method for producing a recombinant phagemid particle from a prokaryotic host, the method comprising:—
  (i) introducing, into a prokaryotic host cell, a first vector configured to persist inside the prokaryotic host, and comprising at least one transgene expression cassette comprising a nucleic acid sequence encoding one or more cytokine, and a packaging signal for enabling replication of the vector into single-stranded DNA;
(ii) introducing, into the host, a helper phage comprising nucleic acid encoding bacteriophage structural proteins; and
(iii) culturing the host under conditions which result in the single-stranded DNA being packaged by the structural proteins to form and extrude a recombinant phagemid particle from the prokaryotic host.

In a fifth aspect, there is provided a method for producing a recombinant phagemid particle from a prokaryotic host, the method comprising:—
(i) introducing into a prokaryotic host cell: (a) a first vector configured to persist inside the prokaryotic host, and comprising at least one transgene expression cassette comprising a nucleic acid sequence encoding one or more cytokine, and a packaging signal for enabling replication of the vector into single-stranded DNA, and (b) a second vector comprising nucleic acid encoding structural proteins required for packaging the single-stranded DNA; and
(ii) culturing the host under conditions which result in the single-stranded DNA being packaged by the structural proteins to form and extrude a recombinant phagemid particle from the prokaryotic host.

In a sixth aspect of the invention, there is provided a pharmaceutical composition comprising the recombinant phagemid viral particle produced by the system according to the third aspect, or produced by the methods of the fourth or fifth aspect, and a pharmaceutically acceptable vehicle.

The invention also provides, in a seventh aspect, a process for making the pharmaceutical composition according to the sixth aspect, the process comprising contacting a therapeutically effective amount of the recombinant phagemid particle produced by the system according to the third aspect, or produced by the methods of the fourth or fifth aspect, and a pharmaceutically acceptable vehicle.

In another aspect of the invention there is provided a recombinant phagemid particle for expressing a transgene in a target tumour cell transduced with the particle, wherein the phagemid particle comprises at least one transgene expression cassette comprising a nucleic acid sequence encoding one or more cytokine, and comprises a genome which lacks at least 50% of its bacteriophage genome, and wherein, in use, the particle is configured to deliver the nucleic acid sequence to at least adjacent to the tumour cell, such that one or more cytokine is expressed, and wherein the cytokine is any one of IL-4, IL-12, IL-15, TRAIL, IFN-γ, hybrid TNFα or any combination thereof.

Preferably, the cytokine is IL-15, Preferably, the cytokine is IL-4. Preferably, the cytokine is IL-12. Preferably, the cytokine is TRAIL. Preferably, the cytokine is IFN-γ.

Preferably, the cytokine is a hybrid TNFα comprising a non-endogenous signal peptide configured to increase expression and/or secretion of TNFα. Preferably, the signal peptide is a cytokine signal peptide other than that of TNFα. For example, the signal peptide is preferably the IL-2 signal peptide.

In another embodiment, a signal peptide different to any other cytokine of the invention, preferably the IL-2 signal peptide, is combined with any other cytokine of the invention, such that the expression and/or secretion of the resulting hybrid cytokine is increased. In particular, the hybrid cytokine may be any one of a hybrid IL-4, IL-12, IL-15, TRAIL or IFN-γ.

In a preferred embodiment, the transgene expression cassette may encode a cytokine which may have the effect of apoptosis induction in the tumour cell, alternation of the tumour cell to promote endogenous anti-tumour responses, alternation of the tumour cell to facilitate other therapies, or alternation of the tumour microenvironment to facilitate therapy In a further aspect, there is provided a recombinant phagemid particle for expressing a transgene in a target tumour cell transduced with the particle, wherein the phagemid particle comprises at least one transgene expression cassette comprising a nucleic acid sequence encoding one or more cytokine, and comprises a genome which lacks at least 50% of its bacteriophage genome, and wherein, in use, the particle is configured to deliver the nucleic acid sequence to at least adjacent to the tumour cell, such that one or more cytokine is expressed, and wherein the cytokine is any one of IL-4, IL-12, IL-15, TRAIL, IFN-γ, hybrid TNFα or any combination thereof, for use in therapy or diagnosis.

Preferably, the cytokine is IL-15, Preferably, the cytokine is IL-4. Preferably, the cytokine is IL-12. Preferably, the cytokine is TRAIL. Preferably, the cytokine is IFN-γ.

Preferably, the cytokine is a hybrid TNFα comprising a non-endogenous signal peptide configured to increase expression and/or secretion of TNFα. Preferably, the signal peptide is a cytokine signal peptide other than that of TNFα. For example, the signal peptide is preferably the IL-2 signal peptide.

In another embodiment, a signal peptide different to any other cytokine of the invention, preferably the IL-2 signal peptide, is combined with any other cytokine of the invention, such that the expression and/or secretion of the resulting hybrid cytokine is increased. In particular, the hybrid cytokine may be any one of a hybrid IL-4, IL-12, IL-15, TRAIL or IFN-γ.

There is, also a need for improved methods for treating cancer, for use with adoptive transfer therapy, such as CAR T cell therapy. The inventors have shown in the Examples that it is possible to use the particles described herein for decorating or labelling tumour cells with antigens which are recognisable by CAR T cells, and the like.

Thus, according to an eighth aspect of the invention, there is provided a recombinant phagemid particle for expressing at least one antigen in a target tumour cell transduced with the particle, the phagemid particle comprising at least one transgene expression cassette comprising a nucleic acid sequence encoding one or more antigen that is recognised by one or more adoptively transferred T cell, and comprising a genome which lacks at least 50% of its bacteriophage genome, and wherein, in use, the particle is configured to deliver the nucleic acid sequence to at least adjacent to the target tumour cell, such that the one or more antigen is expressed, and recognised by one or more adoptively transferred T cell.

In a ninth aspect, there is provided the recombinant phagemid particle according to the eighth aspect, for use in therapy or diagnosis.

In a tenth aspect, there is provided the recombinant phagemid particle according to the eighth aspect, for use in treating, preventing or ameliorating cancer.

Advantageously, using the particles of the present invention to target the delivery and expression of cytokines and antigens to tumour cells results in greater tumour killing efficacies, and reduced off target effects that are associated with conventional therapies. The inventors have developed novel vectors and systems (a so-called "hybrid phagemid viral vector system") that are particularly advantageous for the delivery of antigens or cytokines to tumour cells. There is provided a so-called phagemid particle being referred to as Phagemid/Adeno-associated Virion (i.e. PAAV). Another name used by the inventors for the novel vectors they have created is "phasmid". Provided herein is a bacteriophage guided cytokine therapy. Also provided herein is a bacteriophage-guided CAR T cell therapy.

Unlike the prior art AAVP genome (*Nature protocols* 2, 523-531 (2007); *Cell* 125, 385-398 (2006)), which consists of a rAAV cassette inserted into the filamentous phage genome, the PAAV genome of the invention does not contain any structural bacteriophage (phage) genes, and so a prokaryotic helper phage virus is required to facilitate vector assembly in the host. This is advantageous as AAVP still has certain inherent limitations of bacteriophage and thus leaves room for significant improvement of AAVP or phage vectors in general. For instance, AAVP are a hybrid between two virus species (i.e. bacteriophage and AAV), AAVP vectors contain the genome of both the eukaryotic and prokaryotic viruses. Despite being essential for AAVP viral reproduction, the prokaryotic genome is functionally or therapeutically irrelevant. Inclusion of the phage viral genome thus deleteriously affects vector efficiency and the production method, and ultimately leads to AAVP's relatively low gene transduction efficacy when compared to mammalian viruses.

Advantageously, re-engineering hybrid viral vectors (e.g. AAV or lentivirus) into the phagemid particle according to the eighth or any above aspect, substantially lacking the phage genome from which the particle is derived, dramatically enhances the functional properties of the resultant vector (i.e. the phagemid particle). Altering the viral expression system to a phagemid-based system according to the invention expands the possibility of applying phagemid viral vectors in a much broader context. By eliminating at least 50% of the bacteriophage genome, which constitutes over 50% of the genome size, from the particle's genome, the resultant particle size of the phagemid particle is dramatically reduced.

The term "phagemid particle" can refer to a hybrid phagemid genome encapsulated by phage-derived coat proteins. The hybrid phagemid genome is a "phagemid genome" (i.e. a genetic construct containing two origins of replication—one from bacteriophage (e.g. F1), and one from bacteria (e.g. pUC1)). In one embodiment, the phagemid genome may contain an incorporated "recombinant transgene cassette from AAV" (rAAV), and is therefore a hybrid and not a conventional phagemid genome with a normal (i.e. generic, non-viral) recombinant transgene expression cassette. The phagemid particle can refer to the hybrid phagemid genome (i.e. the invention) that has been encapsulated by phage proteins derived from a trans-acting agent (such as a helper phage).

While allowing additional capacities to incorporate very large or multiple transgene cassettes, these smaller phagemid particles also display added advantages in enhanced gene transfer, production yield, biodistribution and evasion from eukaryotic cellular barriers. Another significant advantage of using the phagemid particle of the invention is that they have the ability to accommodate extremely large and numerous transgene cassettes or gene inserts, such as genes of the three plasmids used for recombinant virus (e.g. rAAV or lentivirus) production by transfection, as described hereinafter. Hence, by combining the genetic components for viral production in a single or multiple phagemid vector(s), an efficient commercial-scale virus-producing gene delivery system has been designed. Preferably, therefore, the particle comprises multiple transgene cassettes.

In an embodiment, the recombinant phagemid particle is for use in treating a subject that has not been exposed to the delivered one or more antigen, for example by prior vaccination.

In one embodiment, the phagemid particle is preferably configured to deliver the transgene expression cassette to a cell that is adjacent to the target tumour cell, such that the nucleic acid sequence is expressed, thereby producing the or each antigen or cytokine, the antigen can then associate with, or become attached to, the target the tumour cell.

However, in a preferred embodiment, the phagemid particle is configured to deliver the transgene expression cassette to the target tumour cell. Preferably, the or each antigen is a peptide or protein which is expressed on the cell surface of the target tumour cell. Preferably, the or each antigen is a peptide or protein that, when expressed by the tumour cell, would be accessible to a CAR T cell. The peptide or protein may be such that, when expressed by the tumour cell, it is present as a folded peptide protein at or on the cell-surface.

In an eleventh aspect of the invention, there is provided a recombinant phagemid particle for expressing at least one antigen in a target tumour cell transduced with the particle, the phagemid particle comprising at least one transgene expression cassette comprising a nucleic acid sequence encoding one or more cytokine, and comprising a genome which lacks at least 50% of its bacteriophage genome, and wherein, in use, the particle is configured to deliver the nucleic acid sequence to at least adjacent to the target tumour cell, such that the one or more cytokine is expressed.

In a twelfth aspect, there is provided the recombinant phagemid particle according to the eleventh aspect, for use in therapy or diagnosis.

In a thirteenth aspect, there is provided the recombinant phagemid particle according to the eleventh aspect, for use in treating, preventing or ameliorating cancer.

In a fourteenth aspect, there is provided a method of treating, preventing, or ameliorating cancer in a subject, the method comprising administering, to a subject in need of such treatment, a therapeutically effective amount of the recombinant phagemid particle according to the eleventh aspect.

In a fifteenth aspect, there is provided use of a helper phage comprising nucleic acid encoding viral vector structural proteins to produce the recombinant phagemid particle according to the eleventh aspect from a prokaryotic host.

In a sixteenth aspect, there is provided a recombinant phagemid viral particle according to the eleventh aspect, produced by the system according to the third aspect, produced by the methods of the fourth or fifth aspect, or produced according to the use of the fifteenth aspect, wherein the recombinant phagemid particle is for production of a recombinant viral vector comprising or derived from the viral genome within the genome of the phagemid particle, wherein the recombinant viral vector is used for delivering the nucleic acid sequence encoding one or more antigen, to at least adjacent to the tumour cell, such that one or more cytokine is expressed.

In a seventeenth aspect, there is provided a recombinant vector comprising rAAV, rep-cap, adenohelper genes, and a nucleic acid sequence encoding one or more antigen or cytokine, for use in the treatment, prevention, or amelioration of cancer.

In an eighteenth aspect, there is provided a recombinant phagemid particle comprising the vector of the seventeenth aspect, for use in a method for the treatment, prevention, or amelioration of cancer.

The or each antigen may be a known target for existing CAR T cells suitable for use in humans. For example, the or each antigen may be selected from a group consisting of: MUC1; PSMA; CD19; CD20; estrogen-related receptor beta type 2 (ErRB2); or any combination thereof. The or each antigen may be MUC1 or PSMA.

In one embodiment, a nucleic acid sequence encoding the suitable antigen (e.g. MUC1.CD28.IL4) may be represented herein, as follows:

[SEQ ID NO: 14]
ATGGCTCTCCCAGTGACTGCCCTACTGCTTCCCCTAGCGCTTCTCCTGC
ATGCAACCGCCCCTCCAGCCCACGGAGTGACCAGCGCCCCTGACACCCG
GCCTGCTCCTGGAAGCACAGCTCCACCTGCCCACGGCGTTACCTCTGCA
CCAGATACTAGGCCTGCTCCAGGCTCCATCGAGGTGATGTACCCCCCCC
CCTACCTGGACAACGAGAAGAGCAACGGCACCATCATCCACGTGAAGGG
CAAGCACCTGTGCCCCAGCCCCCTGTTCCCCGGCCCCAGCAAGCCCTTC
TGGGTGCTGGTGGTGGTGGGCGGCGTGCTGGCCTGCTACAGCCTGCTGG
TGACCGTGGCCTTCATCATCTTCTGGGTGCGGAGCAAGAGGAGAAAGCG
CAGCGGTTCCGGCGAGGGCCGGGGCAGCCTGCTGACCTGCGGCGACGTG
GAGGAGAACCCCGGCCCTATGGGCCTGACCAGCCAGCTTCTGCCCCCCC
TGTTCTTCCTGCTGGCCTGCGCCGGCAACTTCGTGCACGCCACAAGTG
CGACATCACCCTGCAGGAGATCATCAAGACCCTGAACAGCCTGACCGAG
CAGAAGACCCTGTGCACCGAGCTGACCGTGACCGACATCTTCGCCGCCA
GCAAGAACACCACCGAGAAGGAGACCTTCTGCCGGGCCGCCACCGTGCT
GCGGCAGTTCTACAGCCACCACGAGAAGGACACCCGGTGCCTGGGCGCC
ACCGCCCAGCAGTTCCACCGGCACAAGCAACTGATCCGGTTCCTGAAGC
GGCTGGACCGGAACCTGTGGGGCCTGGCCGGCCTGAACAGTTGCCCCGT
GAAGGAGGCCAACCAGAGCACCCTGGAGAACTTCCTGGAGCGGCTGAAG
ACCATCATGCGGGAGAAGTACAGCAAGTGCAGCAGCTAG

In another embodiment, a nucleic acid sequence encoding the antigen (e.g. MUC1.GPI.IL4) may be represented herein, as follows:

[SEQ ID NO: 15]
ATGGCTCTCCCAGTGACTGCCCTACTGCTTCCCCTAGCGCTTCTCCTGC
ATGCAACCGCCCCTCCAGCCCACGGAGTGACCAGCGCCCCTGACACCCG
GCCTGCTCCTGGAAGCACAGCTCCACCTGCCCACGGCGTTACCTCTGCA
CCAGATACTAGGCCTGCTCCAGGCTCCCCCAACAAGGGCAGCGGCACAA
CCAGCGGAACCACCAGGCTGTTGAGCGGCCACACCTGCTTCACCCTGAC
AGGCCTGCTGGGCACCCTGGTGACAATGGGCCTGCTGACCAGGAGAAAG
CGCAGCGGTTCCGGCGAGGGCCGGGGCAGCCTGCTGACCTGCGGCGACG
TGGAGGAGAACCCCGGCCCTATGGGCCTGACCAGCCAGCTTCTGCCCCC
CCTGTTCTTCCTGCTGGCCTGCGCCGGCAACTTCGTGCACGCCACAAG
TGCGACATCACCCTGCAGGAGATCATCAAGACCCTGAACAGCCTGACCG
AGCAGAAGACCCTGTGCACCGAGCTGACCGTGACCGACATCTTCGCCGC
CAGCAAGAACACCACCGAGAAGGAGACCTTCTGCCGGGCCGCCACCGTG
CTGCGGCAGTTCTACAGCCACCACGAGAAGGACACCCGGTGCCTGGGCG
CCACCGCCCAGCAGTTCCACCGGCACAAGCAACTGATCCGGTTCCTGAA
GCGGCTGGACCGGAACCTGTGGGGCCTGGCCGGCCTGAACAGTTGCCCC
GTGAAGGAGGCCAACCAGAGCACCCTGGAGAACTTCCTGGAGCGGCTGA
AGACCATCATGCGGGAGAAGTACAGCAAGTGCAGCAGCTAG

In yet another embodiment, a nucleic acid sequence encoding the antigen (e.g. PSMA) may be represented herein, as follows:

[SEQ ID NO: 16]
ATGTGGAACCTGCTGCACGAGACTGACAGCGCCGTGGCAACCGCACGGA
GACCCCGGTGGCTGTGCGCTGGCGCACTGGTGCTGGCCGGCGGGTTCTT
TCTGCTGGGGTTCCTGTTTGGATGGTTTATCAAAAGCTCCAACGAGGCC
ACCAATATTACACCTAAGCACAATATGAAAGCATTCCTGGATGAACTGA
AGGCCGAGAACATCAAGAAATTCCTGTACAACTTTACTCAGATTCCACA
TCTGGCTGGCACCGAGCAGAACTTTCAGCTGGCAAAACAGATCCAGAGC
CAGTGGAAGGAATTCGGGCTGGACTCCGTGGAGCTGGCCCACTACGATG
TCCTGCTGAGTTATCCAAATAAGACACATCCCAACTATATCTCAATCAT
TAACGAAGACGGAAATGAGATTTTCAACACTTCACTGTTTGAACCCCCT
CCACCCGGCTACGAGAACGTGAGCGACATCGTCCCTCCATTCTCAGCCT
TTAGCCCACAGGGAATGCCTGAGGGGATCTGGTGTACGTCAATTATGC
TCGCACCGAAGACTTCTTTAAGCTGGAGCGAGATATGAAAATCAACTGT
AGCGGCAAGATCGTGATTGCCAGATACGGCAAAGTGTTTCGCGGGAATA
AGGTCAAAAACGCTCAGCTGGCCGGGGCTAAGGGAGTGATTCTGTACTC
TGACCCCGCTGATTATTTCGCACCTGGAGTGAAGAGTTATCCAGACGGA
TGGAATCTGCCAGGAGGAGGAGTGCAGCGAGGAAACATCCTGAACCTGA
ATGGGGCCGGAGATCCTCTGACCCCAGGATACCCCGCCAACGAATACGC
TTATAGGCGAGGAATTGCAGAGGCAGTGGGACTGCCTTCCATCCCAGTC
CACCCCATTGGCTACTATGACGCCCAGAAGCTGCTGGAGAAAATGGGAG
GCTCTGCTCCCCCTGATTCTAGTTGGAGAGGCAGTCTGAAGGTGCCTTA
CAATGTCGGCCCAGGGTTCACAGGGAACTTTTCAACTCAGAAGGTGAAA
ATGCACATCCATAGCACTAATGAAGTGACCAGGATCTATAACGTCATTG
GAACTCTGCGAGGCGCCGTGGAGCCTGACAGATACGTCATTCTGGGGGG
ACACCGCGACTCCTGGGTGTTTGGCGGGATCGATCCACAGTCTGGCGCC
GCTGTGGTCCATGAAATTGTGCGGTCTTTCGGCACACTGAAGAAAGAGG
GGTGGAGACCCCGACGGACTATCCTGTTTGCAAGTTGGGATGCCGAGGA
ATTCGGCCTGCTGGGGAGTACAGAATGGGCCGAGGAAAATTCACGGCTG
CTGCAGGAGAGAGGGGTGGCTTACATCAATGCAGACTCAAGCATTGAAG
GAAACTATACACTGCGGGTGGATTGCACTCCCCTGATGTACAGCCTGGT
CCACAACCTGACCAAGGAGCTGAAATCCCCTGACGAGGGATTCGAAGGC
AAAAGCCTGTATGAATCCTGGACAAAGAAAAGTCCATCACCCGAGTTTA
GCGGAATGCCTCGAATCTCTAAGCTGGGAAGTGGCAATGATTTCGAAGT

```
GTTCTTTCAGAGACTGGGGATTGCCTCCGGAAGAGCTAGGTACACCAAA

AATTGGGAGACAAACAAGTTCTCCGGCTACCCACTGTATCACAGCGTGT

ACGAGACTTATGAACTGGTCGAGAAATTCTACGACCCCATGTTTAAGTA

TCATCTGACCGTGGCACAGGTCAGGGGAGGCATGGTGTTTGAGCTGGCC

AATTCCATCGTCCTGCCATTCGACTGTAGAGATTATGCTGTGGTCCTGA

GGAAGTACGCAGACAAAATCTATAGCATTTCCATGAAACATCCCCAGGA

GATGAAGACCTACTCTGTGAGTTTCGATTCCCTGTTTTCTGCCGTCAAA

AACTTCACAGAAATCGCTAGTAAGTTTTCAGAGCGCCTGCAGGACTTCG

ATAAGTCTAATCCCATTGTGCTGAGGATGATGAACGACCAGCTGATGTT

CCTGGAACGCGCCTTTATCGACCCTCTGGGGCTGCCTGATCGCCCCTTC

TACCGACACGTGATCTACGCACCTTCCTCTCATAACAAGTACGCCGGAG

AGTCTTTTCCAGGCATCTATGACGCTCTGTTCGATATTGAATCAAAGGT

CGATCCCAGCAAAGCATGGGCGAGGTCAAGAGACAGATCTACGTGGCA

GCCTTCACCGTCCAGGCTGCAGCCGAAACACTGAGCGAGGTGGCCTGA
```

Thus, preferably the transgene comprises a nucleic acid sequence substantially as set out in any one of SEQ ID No: 14-16, or a fragment or variant thereof.

In yet another embodiment, the antigen may comprise or be derived from an amino acid sequence (e.g. MUC1, Genbank accession number: P15941), substantially as set out in SEQ ID No: 17, or a fragment or variant thereof:

```
                                              [SEQ ID NO: 17]
mtpgtqspff lllltvltv vtgsghasst pggeketsat qrssvpsste knavsmtssv lsshspgsgs sttqgqdvtl apatepasgs aatwgqdvts vpvtrpalgs ttppandvts apdnkpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdtrpapgs tappahgvts apdnrpalgs tappvhnvts asgsasgsas tlvhngtsar atttpaskst pfsipshhsd tpttlashst ktdassthhs svppltssnh stspqlstgv sffflsfhis nlqfnssled pstdyyqelq rdisemflqi ykqggflgls nikfrpgsvv vqltlafreg tinvhdvetq fnqykteaas rynltisdvs vsdvpfpfsa qsgagvpgwg iallvlvcvl valaivylia lavcqcrrkn ygqldifpar dtyhpmseyp tyhthgryvp psstdrspye kvsagnggss lsytnpavaa tsanl
```

In some embodiments, one antigen type or species, or cytokine is delivered to at least adjacent to the target tumour cell. In other embodiments, two or more antigen types or species, or cytokine are delivered to at least adjacent to the tumour cell. The two or more antigens or cytokines may be delivered by the same recombinant phagemid particle, or they may be delivered separately by two or more recombinant phagemid particles.

In one embodiment, the or each antigen may be a self-antigen to which a CAR T cell has been developed. A self antigen may be considered to be an antigen expressed by non-tumour tissues of the subject, and such antigens have been utilised as targets for CAR T cells and are suitable for use with the present invention.

In a preferred embodiment, however, the or each antigen may be a wholly non-self antigen to which a CAR T cell has been developed. A non-self antigen may include neo-antigens that are newly expressed by tumours, and these neo-antigens have also been utilised as targets for CAR T cells and are also suitable for use with the present invention. A non-self antigen may include foreign antigens, not expressed by any tissues of the subject, to which a CAR T cell has been developed. Such foreign antigens may be advantageous because the therapy may result in fewer "off-target" effects caused by targeting of non-tumour tissues expressing the target antigen.

In an embodiment, the or each antigen may be derived from the dengue virus or derived from yellow fever virus.

In a preferred embodiment, the recombinant phagemid particle is for use in a method that further comprises the use of adoptively transferred T cells. The adoptively transferred T cells may be specific for the or each antigen introduced by the recombinant phagemid particle into the target tumour cell. Preferably, more than one type of T cell is adoptively transferred. Preferably, the more than one type of T cell is specific for the same antigen or for different antigens.

Preferably, the adoptively transferred T cell which recognises the one or more antigen expressed at least adjacent to the target tumour cell is selected from a group consisting of a chimeric antigen receptor (CAR) T cell; a T cell receptor (TCR) transgenic T cell; and a tumour infiltrating lymphocyte (TIL). The TCR transgenic T cell may be specific for an epitope associated with the or each introduced antigen. The TIL may originate from a tissue known to contain lymphocytes with a specificity to a known antigen.

Most preferably, however, the adoptively transferred T cell is a chimeric antigen receptor (CAR) T cell. The CAR T cell may be specific for the or each antigen introduced by the recombinant phagemid particle into the tumour cell.

In a most preferred embodiment, the recombinant phagemid particle is for use in a method that comprises the specific targeting of tumour cells by the recombinant phagemid particle and subsequent delivery to a tumour cell of one or more sequence encoding one or more antigen or cytokine for expression by the tumour cell, and in relation to the antigen, the transfer of CAR T cells with a specificity for the one or more delivered antigen, and subsequent cytotoxic activity against the tumour cells for the treatment, prevention, or amelioration of cancer.

In an embodiment, the CAR T cell may be a dual specificity CAR T cell, which may have specificity for one or more antigen delivered by one or more recombinant phagemid particle. For instance, a single type or species of recombinant phagemid particle may deliver two or more antigens for recognition by a single type of dual-specificity CAR T cell.

Preferably, the phagemid particle comprises a virion. One preferred embodiment of the genome of the recombinant phagemid particle is illustrated on FIG. 3, with preferred components being shown on FIGS. 4-6.

Preferably, the genome of the recombinant phagemid particle comprises a packaging signal for enabling replication of the phagemid genome into single-stranded DNA, which can subsequently be packaged into the phagemid particle inside a prokaryotic host. The packaging signal may preferably comprise an origin of replication. For example, the origin of replication preferably comprises an F1 ori, more preferably from an F1 bacteriophage. The DNA sequence of one embodiment of the F1 ori is represented herein as SEQ ID No: 1, as follows:

```
                                            [SEQ ID NO: 1]
ACGCGCCCTGTAGCGGCGCATTAAGCGCGGCGGGTGTGGTGGTTACGCG

CAGCGTGACCGCTACACTTGCCAGCGCCCTAGCGCCCGCTCCTTTCGCT

TTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCT

CGACCCCAAAAAACTTGATTTGGGTGATGGTTCACGTAGTGGGCCATCG

CCCTGATAGACGGTTTTTCGCCCTTTGACGTTGGAGTCCACGTTCTTTA

ATAGTGGACTCTTGTTCCAAACTGGAACAACACTCAACCCTATCTCGGG

CTATTCTTTTGATTTATAAGGGATTTTGCCGATTTCGGCCTATTGGTTA

AAAAATGAGCTGATTTAACAAAAATTTAACGCGAATTTTAACAAAATAT

TAACGTTTACAATTT
```

Preferably, the genome of the recombinant phagemid particle comprises an origin of replication for enabling replication of double-stranded vector inside a prokaryotic host. Preferably, the origin of replication enables high copy number replication of the vector inside the host. Preferably, the origin of replication comprises a pUC ori. The DNA sequence of one embodiment of the pUC ori is represented herein as SEQ ID No: 2, as follows:

```
                                            [SEQ ID NO: 2]
TTGAGATCCTTTTTTTCTGCGCGTAATCTGCTGCTTGCAAACAAAAAAA

CCACCGCTACCAGCGGTGGTTTGTTTGCCGGATCAAGAGCTACCAACTC

TTTTTCCGAAGGTAACTGGCTTCAGCAGAGCGCAGATACCAAATACTGT

CCTTCTAGTGTAGCCGTAGTTAGGCCACCACTTCAAGAACTCTGTAGCA

CCGCCTACATACCTCGCTCTGCTAATCCTGTTACCAGTGGCTGCTGCCA

GTGGCGATAAGTCGTGTCTTACCGGGTTGGACTCAAGACGATAGTTACC

GGATAAGGCGCAGCGGTCGGGCTGAACGGGGGGTTCGTGCACACAGCCC

AGCTTGGAGCGAACGACCTACACCGAACTGAGATACCTACAGCGTGAGC

TATGAGAAAGCGCCACGCTTCCCGAAGGGAGAAAGGCGGACAGGTATCC

GGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGAC

TTGAGCGTCGATTTTTGTGATGCTCGTCAGGGGGCGGAGCCTATGGAA
A
```

Alternatively, in another embodiment, the phagemid particle may be designed such that it integrates into the genome of a host cell. In this case, nucleic acid sequences, which favour targeted integration (e.g. by homologous recombination) of the particle's genome are envisaged. Hence, the genome of the recombinant phagemid particle may comprise one or more DNA sequence, which favours targeted integration into a host genome.

In another embodiment, preferably the phagemid particle may be used as a recombinant vector for the delivery of the transgene to a tissue specific target (e.g. tumour tissue), irrespective of whether the vector is administered systemically or locally to a subject in vivo.

Preferably, the at least one transgene expression cassette comprises a viral transgene expression cassette, more preferably a mammalian viral transgene expression cassette.

For example, the at least one transgene expression cassette may, in one preferred embodiment, comprise a lentivirus transgene expression cassette. The at least one transgene expression cassette is preferably an adeno-associated virus (AAV) transgene expression cassette.

The transgene expression cassette may comprise any nucleic acid encoding the or each antigen or cytokine, which is expressed in the target tumour cell or tissue. In one embodiment of the invention, the nucleic acid may be DNA, which may be genomic DNA or cDNA. Non-naturally occurring cDNA may be preferred in some embodiments. In another embodiment, the nucleic acid may be RNA, such as antisense RNA or shRNA.

As shown in the illustrative Example 7, the phagemid may be used to deliver a gene to tumour cells. In this example, down-regulation of mTOR expression in tumour cells (e.g. medulloblastoma cells) may be achieved with treatment with RGD4C-phagemid carrying a sequence encoding the mTOR/shRNA (RGD4C-mTOR/shRNA). Example 7 provides another illustrative example of the use of the phagemid to deliver genes to tumour cells. As shown in Example 7, RGD4C-phagemid can successfully deliver TNFα to DIPG (diffuse intrinsic pontine glioma) in a selective manner, resulting in apoptosis induction. Therefore, the RGD4C-phagemid has therapeutic potential for use in targeted therapy against DIPG using cytokines However, it will be appreciated that the type of tumour cell, which is targeted by the recombinant phagemid particle depends on the type of cell-targeting ligand, which may be expressed on the surface of the particle. Cell-targeting ligands are discussed below.

The transgene expression cassette may comprise one or more functional elements required for expression of the nucleic acid in the target tumour cell. For example, preferably the transgene expression cassette comprises a promoter, such as the CMV promoter. The DNA sequence of one embodiment of the CMV promoter is represented herein as SEQ ID No: 3, as follows:

[SEQ ID NO: 3]
ACGCGTGGAGCTAGTTATTAATAGTAATCAATTACGGGGTCATTAGTTC

ATAGCCCATATATGGAGTTCCGCGTTACATAACTTACGGTAAATGGCCC

GCCTGGCTGACCGCCCAACGACCCCCGCCCATTGACGTCAATAATGACG

TATGTTCCCATAGTAACGTCAATAGGGACTTTCCATTGACGTCAATGGG

TGGAGTATTTACGGTAAACTGCCCACTTGGCAGTACATCAAGTGTATCA

TATGCCAAGTACGCCCCCTATTGACGTCAATGACGGTAAATGGCCCGCC

TGGCATTATGCCCAGTACATGACCTTATGGGACTTTCCTACTTGGCAGT

ACATCTACGTATTAGTCATCGCTATTACCATGGTGATGCGGTTTTGGCA

GTACATCAATGGGCGTGGATAGCGGTTTGACTCACGGGGATTTCCAAGT

CTCCACCCCATTGACGTCAATGGGAGTTTGTTTTGCACCAAAATCAACG

GGACTTTCCAAAATGTCGTAACAACTCCGCCCCATTGACGCAAATGGGC

GGTAGGCGTGTACGGTGGGAGGTCTATATAAGCAGAGCTCGTTTAGTGA

ACCGTCAGATCGCCTGGAGACGCCATCCACGCTGTTTTGACCTCCATAG

AAGACACCGGGACCGATCCAGCCTCC

In another preferred embodiment, the transgene expression cassette comprises a promoter which is only active in the target tumour cell. The promoter may therefore be tumour-activated and/or temozolomide-induced.

In an embodiment, the promoter may be multidrug resistant promoter (MDR), which is highly active in cancer cells. This promoter can be activated by cancer drugs to produce the P-gp and ABC transporter to efflux the drug out from the cell. This promoter may be used for gene therapy in combination with cancer drugs.

In another embodiment, the promoter may be human telomerase reverse transcriptase (hTERT) promoter. This promoter is exclusively active in tumour cells, but not in normal proliferating cells. Hence, this promoter can be used as a tumour-specific promoter.

In preferred embodiment, the transgene expression cassette comprises a grp78 promoter. The nucleic acid sequence of one embodiment of the grp78 promoter is represented herein as SEQ ID No: 8, as follows:

[SEQ ID NO: 8]
CCCGGGGGCCCAACGTGAGGGGAGGACCTGGACGGTTACCGGCGAAAC

GGTTTCCAGGTGAGAGGTCACCCGAGGGACAGGCAGCTGCTCAACCAAT

AGGACCAGCTCTCAGGGCGGATGCTGCCTCTCATTGGCGGCCGTTAAGA

ATGACCAGTAGCCAATGAGTCGGCTGGGGGGCGCGTACCAGTGACGTGA

GTTGCGGAGGAGGCCGCTTCGAATCGGCAGCGGCCAGCTTGGTGGCATG

AACCAACCAGCGGCCTCCAACGAGTAGCGAGTTCACCAATCGGAGGCCT

CCACGACGGGGCTGCGGGGAGGATATATAAGCCGAGTCGGCGACCGGCG

CGCTCGATACTGGCTGTGACTACACTGACTTGGAC

Preferably, the transgene expression cassette comprises nucleic acid for encoding a polyA tail attachable to the or each expressed antigen or cytokine. The DNA sequence of one embodiment of the nucleic acid for encoding a polyA tail is represented herein as SEQ ID No: 4, as follows:

[SEQ ID NO: 4]
ACGGGTGGCATCCCTGTGACCCCTCCCCAGTGCCTCTCCTGGCCCTGGA

AGTTGCCACTCCAGTGCCCACCAGCCTTGTCCTAATAAAATTAAGTTGC

ATCATTTTGTCTGACTAGGTGTCCTTCTATAATATTATGGGGTGGAGGG

GGGTGGTATGGAGCAAGGGGCAAGTTGGGAAGACAACCTGTAGGGCCTG

CGGGGTCTATTGGGAACCAAGCTGGAGTGCAGTGGCACAATCTTGGCTC

ACTGCAATCTCCGCCTCCTGGGTTCAAGCGATTCTCCTGCCTCAGCCTC

CCGAGTTGTTGGGATTCCAGGCATGCATGACCAGGCTCAGCTAATTTTT

GTTTTTTTGGTAGAGACGGGGTTTCACCATATTGGCCAGGCTGGTCTCC

AACTCCTAATCTCAGGTGATCTACCCACCTTGGCCTCCCAAATTGCTGG

GATTACAGGCGTGAACCACTGCTCCCTTCCCTGTCCTT

Preferably, the transgene expression cassette comprises left and/or right Inverted Terminal Repeat sequences (ITRs). An ITR can be specific to an AAV or Long Terminal Repeats Sequences (LTRs) specific to a lentivirus serotype, and can be any sequence, so long as it forms a hairpin loop in its secondary structure. For example, the AAV serotype may be AAV1-9, but is preferably AAV1, AAV2, AAV5, AAV6 or AAV8. The DNA sequence of one embodiment (left ITR from a commercially available AAV plasmid) of the ITR is represented herein as SEQ ID No: 5, as follows:

[SEQ ID NO: 5]
CCTGCAGGCAGCTGCGCGCTCGCTCGCTCACTGAGGCCGCCCGGGCGTC

GGGCGACCTTTGGTCGCCCGGCCTCAGTGAGCGAGCGAGCGCGCAGAGA

GGGAGTGGCCAACTCCATCACTAGGGGTTCCT

The DNA sequence of another embodiment (right ITR from a commercially available AAV plasmid) of the ITR is represented herein as SEQ ID No: 6, as follows:

[SEQ ID NO: 6]
AGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCC

CGGGCGGCCTCAGTGAGCGAGCGAGCGCGCAGCTGCCTGCAGG

Preferably, the genome of the recombinant phagemid particle comprises a selection marker, which will depend on the host cell in which the vector is harboured, for example for conferring ampicillin resistance in a host cell, preferably a bacterium. The marker provides selection pressure during production of the phagemid particle in the host cell.

Preferably, the recombinant phagemid particle comprises one or more capsid minor coat protein. The recombinant phagemid particle may comprise a pIII capsid minor coat protein that is configured to display a cell-targeting ligand for enabling delivery of the particle to the target tumour cell. Preferably, the recombinant phagemid particle comprises one or more capsid major coat protein. The recombinant phagemid particle may comprise at least one pVIII capsid major coat protein that is configured to display a foreign peptide thereon.

The recombinant phagemid particle may comprise a modification of the capsid structure, for example by treatment, or chemical or biochemical conjugation. Examples of suitable modifications may include cross-linking peptide residues on to the phagemid particle. In another embodiment, the recombinant phagemid particle may comprise one or functional peptide attached to the capsid thereof. For example, a functional peptide may comprise a nuclear translocation signal. The phagemid particle may therefore be multifunctional, and use features disclosed in WO 2014/184528.

In another embodiment, the recombinant phagemid particle may be combined with a cationic polymer to form a complex having a net positive charge, as described in WO 2014/184529. The cationic polymer may be selected from a group consisting of: chitosan; poly-D-lysine (PDL); diethylaminoethyl (DEAE); diethylaminoethyl-dextran (DEAE-.DEX); polyethyleneimine (PEI); polybrene; protamine sulphate; and a cationic lipid. Preferably, the cationic lipid is selected from the group consisting of Fugene®, Lipofectamine®, and DOTAP (N-[1-(2,3-Dioleoyloxy)propyl]-N,N,N-trimethylammonium methyl-sulfate). Preferably, the cationic polymer comprises DEAE, more preferably DEAE.DEX.

Preferably, the phagemid particle comprises a genome which substantially lacks the phage genome from which the particle is derived. Preferably, the genome of the recombinant phagemid particle lacks at least 60%, more preferably at least 70%, and even more preferably at least 80% of the bacteriophage genome from which it is derived. More preferably, the genome of the recombinant phagemid particle lacks at least 90%, more preferably at least 95%, and even more preferably at least 99% of the bacteriophage genome from which it is derived. Preferably, the genome of the recombinant phagemid particle lacks all of the bacteriophage genome from which it is derived. As discussed above, however, the genome of the phagemid viral particle may, in some embodiments, comprise the bacteriophage origin of replication for enabling replication of the particle into single-stranded DNA, i.e. F1 bacteriophage ori.

Preferably, the phagemid particle comprises a genome which has a relative genome size of less than 14 Kb. The relative genome size may be less than about 13 Kb, less than about 12 Kb, less than about 11 Kb, less than about 10 Kb, less than about 9 Kb, less than about 8 Kb, or less than about 7 Kb. The relative genome size may be between 3 Kb and 9 Kb, 4 Kb and 8 Kb, 5 Kb and 7 Kb, or preferably approximately 6 Kb.

Preferably, the phagemid particle lacks bacteriophage structural genes in its genome required for the formation, packaging or extrusion of the particle from a prokaryotic host. Such structural genes encode the capsid proteins etc. Preferably, the phagemid particle comprises a genome which lacks a gene encoding a minor or major coat protein from which the particle is derived. Preferably, the phagemid particle comprises a genome which lacks a pIII capsid minor coat protein, or which lacks a pVIII capsid major coat protein. Most preferably, the phagemid particle comprises a genome which lacks both a pIII capsid minor coat protein, and a pVIII capsid major coat protein.

Thus, the recombinant phagemid particle preferably comprises a replication-deficient, virus-like-particle or virion constructed from, and displaying, the structural components, including but not limited to proteins and other conjugated compounds, derived from a bacteriophage, despite the genome of the particle not containing the structural genes of a bacteriophage from which it is derived.

Accordingly, given that the genome of the recombinant phagemid particle of the eighth or any above aspect lacks the derivative phage genome, including the structural genes, an alternative system is required in order to provide the necessary structural (i.e. capsid) genes that are required to package the recombinant phagemid genome in a bacteriophage capsid to produce the particle of the invention. Accordingly, the inventors have devised a novel system for producing the particles of the eight or any above aspect, involving the use of a separate so-called "helper virus" vector. In effect, therefore, the particle of the eighth or any above aspect is a hybrid phagemid vector, which includes components of a phagemid and a eukaryotic virus.

Hence, in a nineteenth aspect, there is provided a system for producing a recombinant phagemid particle from a prokaryotic host, the system comprising:—
(i) a first vector configured to persist inside a prokaryotic host, and comprising at least one transgene expression cassette comprising a nucleic acid sequence encoding one or more cytokine, or one or more antigen that is recognised by one or more adoptively transferred T cell, and a packaging signal for enabling replication of the vector into single-stranded DNA; and
(ii) a second vector comprising nucleic acid encoding structural proteins required for packaging the single-stranded DNA, resulting in the formation and extrusion of a recombinant phagemid particle from the prokaryotic host.

Advantageously, separating the reproductive elements of the phagemid particle into the first "therapeutic" vector carrying the transgene encoding the or each antigen recognised by the or each adoptively transferred T cell or cytokine, and the second separate "helper" vector carrying the viral structural genes substantially decreases the genome/vector size, and thereby significantly increases transgene capacity. The phagemid particle is used therapeutically (e.g. in CAR-T cell therapy) and the increased transgene capacity is a particularly useful advantage for gene therapy applications of the new system. Consequently, this results in an enhanced production yield, gene transduction efficiency and flexibility of the vector system for other applications.

The novelty of the system of the nineteenth aspect is its ability to package the genome of eukaryotic viruses (such as AAV or lentivirus), which is provided by the first vector, into a prokaryotic virus capsid (i.e. bacteriophage), which is provided by the second vector. Thus, while the prior art system (i.e. AAVP) is a chimera of two genomes, the system of the nineteenth aspect (i.e. PAAV) is a chimera between prokaryotic viral phenotypes and a eukaryotic viral genotype.

The antigen may be any as disclosed herein. In a preferred embodiment, the or each antigen is a peptide or protein which is expressed on the cell surface of the target tumour cell. Preferably, the or each antigen is a peptide or protein that, when expressed by the tumour cell, would be accessible to a CAR T cell. The peptide or protein may be such that, when expressed by the tumour cell, it is present as a folded peptide protein at or on the cell-surface. The or each antigen may be a known target for existing CAR T cells suitable for use in humans. For example, the or each antigen may be selected from a group consisting of: MUC1; PSMA; CD19; CD20; estrogen-related receptor beta type 2 (ErRB2); or any combination thereof. In an embodiment, the or each antigen may be dengue virus or yellow fever vaccine antigens.

Preferably, the system of the nineteenth aspect is used to produce the recombinant phagemid particle of the eighth aspect. Preferably, the first vector therefore comprises the genome of the recombinant phagemid particle. The packaging signal of the first vector may preferably comprise an origin or replication. Preferably, the origin of replication in the first vector comprises an F1 ori, more preferably from an F1 bacteriophage.

Preferably, the first vector comprises a second origin of replication for enabling replication of double-stranded vector inside a prokaryotic host. Preferably, the origin of replication enables high copy number replication of the vector inside the host. Preferably, the origin of replication comprises a pUC ori. Alternatively, the first vector may comprise one or more DNA sequence, which favours targeted integration into a host genome, thus removing the requirement for any origin of replication.

The transgene expression cassette comprises a viral transgene expression cassette, more preferably a mammalian viral transgene expression cassette. For example, the at least one transgene expression cassette may comprise a lentivirus transgene expression cassette or a AAV transgene expression cassette. An AAV transgene expression cassette is preferred.

One preferred example of the second vector is illustrated in FIG. 7, with preferred components being shown in FIG. 8. The second vector or "helper phage" is preferably a bacteriophage engineered specifically for rescuing the phagemid particles carrying the first vector (i.e. the phagemid particle's genome) from prokaryotic hosts, an embodiment of which is shown in FIG. 3. The second vector (i.e. the helper phage) is therefore provided to lend its proteins and polypeptides to the first vector (i.e. the phagemid particle's genome), or any other DNA entity that contains a functional packaging signal and/or a single stranded origin or replication. The second vector is most preferably replication-defective. Preferably, the second vector comprises a disrupted packaging signal, which significantly deters its ability to package itself into phage particles. Preferably, the second vector comprises a disrupted origin of replication. In one embodiment, the disrupted origin of replication is a medium copy number origin, such as p15a. In another embodiment, the disrupted origin of replication is a low copy number origin, such as a pMB1. Preferably, the first vector (i.e. the phagemid particle's genome) is configured to outcompete with the second vector (i.e. the helper phage) in both replication and packaging.

The genome of the second vector may be engineered to give the resultant recombinant phagemid particle targeting properties (or multifunctional properties as described in WO 2014/184528). Hence, it provides the structural capsid proteins for phagemid particle assembly. Preferably, the second vector comprises nucleic acid encoding one or more capsid minor coat proteins, or one or more capsid major coat proteins. All capsid proteins may either be wild type or recombinant, present in single or multiple copies, and modified to display chimeric or synthetic peptides. This includes the display of antigens of other viruses for peptide vaccine delivery or as an adjuvant in the case that a DNA vaccine (delivered by the phagemid particle of the eighth aspect) is desired.

In one example, therefore, the second vector may comprise a first nucleic acid sequence encoding a pIII minor coat protein that is configured to display a cell-targeting ligand for enabling delivery of the recombinant phagemid particle to the target cell (e.g. a tumour). Therefore, it may be desired to induce a 9-amino acid mutation in the pIII minor coat protein of the recombinant phagemid particle in order to confer its specificity to tumour cells and angiogenic tumour-associated endothelial cells that express $\alpha_v\beta_3$ and $\alpha_v\beta_5$ integrins. Thus, the genome of the second vector may comprise the RGD4C targeting peptide (CDCRGDCFC—SEQ ID No: 7).

In another example, the second vector may comprise a second nucleic acid sequence encoding at least one pVIII capsid major coat protein that is configured to display a foreign peptide thereon. Thus, it may be desired to induce a mutation in the wild pVIII major coat protein of the recombinant phagemid particle in order to display a short peptide, for example less than 10 amino acids long. The short peptide may be a targeting moiety and/or have inherent biological/chemical functionality in vivo or in vitro. For example, immune stimulation in vivo via antigen display, wherein the peptide displayed on the pVIII coat protein may be processed through the exogenous pathway and presented on the MHC II of the target cell, thus presenting another target for adoptively transferred T cells. Alternatively, the at least one pVIII major coat protein might have binding functionality, for instance to nanoparticles (e.g. gold) in vitro via displaying a gold-binding peptide.

The first vector may be a member of the Retroviridae family, or of the Orthoretrovirinae Sub-family. The first vector may be a member of the Lentivirus genus. Preferably, the first vector is a member of the Parvoviridae family or sub-family. Preferably, the first vector is a member of the Dependoparvovirus, or adeno-associated virus species.

Once the first vector (i.e. the phagemid particle's genome) and the second vector (i.e. the Helper phage) have been constructed, they are used together to produce, in a prokaryotic host, the recombinant phagemid particle of the eighth or any above aspect. It will be appreciated that the packaging signal (e.g. the origin of replication) of the first vector, which is for enabling replication of the phagemid genome into single-stranded DNA, functions to signal the second vector (i.e. the helper phage) structural proteins to package the phagemid genome (i.e. they work together in trans in the host) to create the particle used in the eighth or any above aspect.

In one preferred embodiment, the first vector (phagemid particle genome) comprises a nucleic acid sequence substantially as set out in SEQ ID No: 9, or a fragment or variant thereof, wherein SEQ ID No: 9 is represented as follows, wherein "N" is a transgene:

[SEQ ID No: 9]
```
CCTGCAGGCAGCTGCGCGCTCGCTCGCTCACTGAGGCCGCCCGGGCGTC

GGGCGACCTTTGGTCGCCCGGCCTCAGTGAGCGAGCGAGCGCGCAGAGA

GGGAGTGGCCAACTCCATCACTAGGGGTTCCTGCGGCCGCNAGGAACCC

CTAGTGATGGAGTTGGCCACTCCCTCTCTGCGCGCTCGCTCGCTCACTG

AGGCCGGGCGACCAAAGGTCGCCCGACGCCCGGGCTTTGCCCGGGCGGC

CTCAGTGAGCGAGCGAGCGCGCAGCTGCCTGCAGGGGCGCCTGATGCGG

TATTTTCTCCTTACGCATCTGTGCGGTATTTCACACCGCATACGTCAAA

GCAACCATAGTACGCGCCCTGTAGCGGCGCATTAAGCGCGGCGGGTGTG

GTGGTTACGCGCAGCGTGACCGCTACACTTGCCAGCGCCCTAGCGCCCG

CTCCTTTCGCTTTCTTCCCTTCCTTTCTCGCCACGTTCGCCGGCTTTCC

CCGTCAAGCTCTAAATCGGGGGCTCCCTTTAGGGTTCCGATTTAGTGCT

TTACGGCACCTCGACCCCAAAAAACTTGATTTGGGTGATGGTTCACGTA

GTGGGCCATCGCCCTGATAGACGGTTTTTCGCCCTTTGACGTTGGAGTC
```

-continued

```
CACGTTCTTTAATAGTGGACTCTTGTTCCAAACTGGAACAACACTCAAC

CCTATCTCGGGCTATTCTTTTGATTTATAAGGGATTTTGCCGATTTCGG

CCTATTGGTTAAAAAATGAGCTGATTTAACAAAAATTTAACGCGAATTT

TAACAAAATATTAACGTTTACAATTTTATGGTGCACTCTCAGTACAATC

TGCTCTGATGCCGCATAGTTAAGCCAGCCCCGACACCCGCCAACACCCG

CTGACGCGCCCTGACGGGCTTGTCTGCTCCCGGCATCCGCTTACAGACA

AGCTGTGACCGTCTCCGGGAGCTGCATGTGTCAGAGGTTTTCACCGTCA

TCACCGAAACGCGCGAGACGAAAGGGCCTCGTGATACGCCTATTTTTAT

AGGTTAATGTCATGATAATAATGGTTTCTTAGACGTCAGGTGGCACTTT

TCGGGGAAATGTGCGCGGAACCCCTATTTGTTTATTTTTCTAAATACAT

TCAAATATGTATCCGCTCATGAGACAATAACCCTGATAAATGCTTCAAT

AATATTGAAAAAGGAAGAGTATGAGTATTCAACATTTCCGTGTCGCCCT

TATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGG

GTTACATCGAACTGGATCTCAACAGCGGTAAGATCCTTGAGAGTTTTCG

CCCCGAAGAACGTTTTCCAATGATGAGCACTTTTAAAGTTCTGCTATGT

GGCGCGGTATTATCCCGTATTGACGCCGGGCAAGAGCAACTCGGTCGCC

GCATACACTATTCTCAGAATGACTTGGTTGAGTACTCACCAGTCACAGA

AAAGCATCTTACGGATGGCATGACAGTAAGAGAATTATGCAGTGCTGCC

ATAACCATGAGTGATAACACTGCGGCCAACTTACTTCTGACAACGATCG

GAGGACCGAAGGAGCTAACCGCTTTTTGCACAACATGGGGGATCATGT

AACTCGCCTTGATCGTTGGGAACCGGAGCTGAATGAAGCCATACCAAAC

GACGAGCGTGACACCACGATGCCTGTAGCAATGGCAACAACGTTGCGCA

AACTATTAACTGGCGAACTACTTACTCTAGCTTCCCGGCAACAATTAAT

AGACTGGATGGAGGCGGATAAAGTTGCAGGACCACTTCTGCGCTCGGCC

CTTCCGGCTGGCTGGTTTATTGCTGATAAATCTGGAGCCGGTGAGCGTG

GGTCTCGCGGTATCATTGCAGCACTGGGGCCAGATGGTAAGCCCTCCCG

TATCGTAGTTATCTACACGACGGGGAGTCAGGCAACTATGGATGAACGA

AATAGACAGATCGCTGAGATAGGTGCCTCACTGATTAAGCATTGGTAAC

TGTCAGACCAAGTTTACTCATATATACTTTAGATTGATTTAAAACTTCA

TTTTTAATTTAAAAGGATCTAGGTGAAGATCCTTTTTGATAATCTCATG

ACCAAAATCCCTTAACGTGAGTTTTCGTTCCACTGAGCGTCAGACCCCG

TAGAAAAGATCAAAGGATCTTCTTGAGATCCTTTTTTTCTGCGCGTAAT

CTGCTGCTTGCAAACAAAAAAACCACCGCTACCAGCGGTGGTTTGTTTG

CCGGATCAAGAGCTACCAACTCTTTTTCCGAAGGTAACTGGCTTCAGCA

GAGCGCAGATACCAAATACTGTCCTTCTAGTGTAGCCGTAGTTAGGCCA

CCACTTCAAGAACTCTGTAGCACCGCCTACATACCTCGCTCTGCTAATC

CTGTTACCAGTGGCTGCTGCCAGTGGCGATAAGTCGTGTCTTACCGGGT

TGGACTCAAGACGATAGTTACCGGATAAGGCGCAGCGGTCGGGCTGAAC

GGGGGGTTCGTGCACACAGCCCAGCTTGGAGCGAACGACCTACACCGAA

CTGAGATACCTACAGCGTGAGCTATGAGAAAGCGCCACGCTTCCCGAAG

GGAGAAAGGCGGACAGGTATCCGGTAAGCGGCAGGGTCGGAACAGGAGA

GCGCACGAGGGAGCTTCCAGGGGGAAACGCCTGGTATCTTTATAGTCCT

GTCGGGTTTCGCCACCTCTGACTTGAGCGTCGATTTTTGTGATGCTCGT

CAGGGGGGCGGAGCCTATGGAAAAACGCCAGCAACGCGGCCTTTTTACG

GTTCCTGGCCTTTTGCTGGCCTTTTGCTCACATGT
```

In one preferred embodiment, the second vector (helper phage with RGD sequence) comprises a nucleic acid sequence substantially as set out in SEQ ID No: 10, or a fragment or variant thereof, wherein SEQ ID No: to is represented as follows:

[SEQ ID No: 10]
```
AACGCTACTACTATTAGTAGAATTGATGCCACCTTTTCAGCTCGCGCCC

CAAATGAAAATATAGCTAAACAGGTTATTGACCATTTGCGAAATGTATC

TAATGGTCAAACTAAATCTACTCGTTCGCAGAATTGGGAATCAACTGTT

ACATGGAATGAAACTTCCAGACACCGTACTTTAGTTGCATATTTAAAAC

ATGTTGAGCTACAGCACCAGATTCAGCAATTAAGCTCTAAGCCATCCGC

AAAAATGACCTCTTATCAAAAGGAGCAATTAAAGGTACTCTCTAATCCT

GACCTGTTGGAGTTTGCTTCCGGTCTGGTTCGCTTTGAAGCTCGAATTA

AAACGCGATATTTGAAGTCTTTCGGGCTTCCTCTTAATCTTTTTGATGC

AATCCGCTTTGCTTCTGACTATAATAGTCAGGGTAAAGACCTGATTTTT

GATTTATGGTCATTCTCGTTTTCTGAACTGTTTAAAGCATTTGAGGGGG

ATTCAATGAATATTTATGACGATTCCGCAGTATTGGACGCTATCCAGTC

TAAACATTTTACTATTACCCCCTCTGGCAAAACTTCTTTTGCAAAAGCC

TCTCGCTATTTTGGTTTTTATCGTCGTCTGGTAAACGAGGGTTATGATA

GTGTTGCTCTTACTATGCCTCGTAATTCCTTTTGGCGTTATGTATCTGC

ATTAGTTGAATGTGGTATTCCTAAATCTCAACTGATGAATCTTTCTACC

TGTAATAATGTTGTTCCGTTAGTTCGTTTTATTAACGTAGATTTTTCTT

CCCAACGTCCTGACTGGTATAATGAGCCAGTTCTTAAAATCGCATAAGG

TAATTCACAATGATTAAAGTTGAAATTAAACCATCTCAAGCCCAATTTA

CTACTCGTTCTGGTGTTTCTCGTCAGGGCAAGCCTTATTCACTGAATGA

GCAGCTTTGTTACGTTGATTTGGGTAATGAATATCCGGTTCTTGTCAAG

ATTACTCTTGATGAAGGTCAGCCAGCCTATGCGCCTGGTCTGTACACCG

TTCATCTGTCCTCTTTCAAAGTTGGTCAGTTCGGTTCCCTTATGATTGA

CCGTCTGCGCCTCGTTCCGGCTAAGTAACATGGAGCAGGTCGCGGATTT

CGACACAATTTATCAGGCGATGATACAAATCTCCGTTGTACTTTGTTTC

GCGCTTGGTATAATCGCTGGGGGTCAAAGATGAGTGTTTTAGTGTATTC

TTTCGCCTCTTTCGTTTTAGGTTGGTGCCTTCGTAGTGGCATTACGTAT

TTTACCCGTTTAATGGAAACTTCCTCATGAAAAAGTCTTTAGTCCTCAA

AGCCTCTGTAGCCGTTGCTACCCTCGTTCCGATGCTGTCTTTCGCTGCT

GAGGGTGACGATCCCGCAAAAGCGGCCTTTAACTCCCTGCAAGCCTCAG

CGACCGAATATATCGGTTATGCGTGGGCGATGGTTGTTGTCATTGTCGG
```

CGCAACTATCGGTATCAAGCTGTTTAAGAAATTCACCTCGAAAGCAAGC
TGATAAACCGATACAATTAAAGGCTCCTTTTGGAGCCTTTTTTTTTGGA
GATTTTCAACGTGAAAAAATTATTATTCGCAATTCCTTTAGTTGTTCCT
TTCTATTCTCACTCCGCTTGTGATTGTAGGGGGGATTGTTTTTGTGAAA
CTGTTGAAAGTTGTTTAGCAAAACCCCATACAGAAAATTCATTTACTAA
CGTCTGGAAAGACGACAAAACTTTAGATCGTTACGCTAACTATGAGGGT
TGTCTGTGGAATGCTACAGGCGTTGTAGTTTGTACTGGTGACGAAACTC
AGTGTTACGGTACATGGGTTCCTATTGGGCTTGCTATCCCTGAAAATGA
GGGTGGTGGCTCTGAGGGTGGCGGTTCTGAGGGTGGCGGTTCTGAGGGT
GGCGGTACTAAACCTCCTGAGTACGGTGATACACCTATTCCGGGCTATA
CTTATATCAACCCTCTCGACGGCACTTATCCGCCTGGTACTGAGCAAAA
CCCCGCTAATCCTAATCCTTCTCTTGAGGAGTCTCAGCCTCTTAATACT
TTCATGTTTCAGAATAATAGGTTCCGAAATAGGCAGGGGGCATTAACTG
TTTATACGGGCACTGTTACTCAAGGCACTGACCCCGTTAAAACTTATTA
CCAGTACACTCCTGTATCATCAAAAGCCATGTATGACGCTTACTGGAAC
GGTAAATTCAGAGACTGCGCTTTCCATTCTGGCTTTAATGAGGATCCAT
TCGTTTGTGAATATCAAGGCCAATCGTCTGACCTGCCTCAACCTCCTGT
CAATGCTGGCGGCGGCTCTGGTGGTGGTTCTGGTGGCGGCTCTGAGGGT
GGTGGCTCTGAGGGTGGCGGTTCTGAGGGTGGCGGCTCTGAGGGAGGCG
GTTCCGGTGGTGGCTCTGGTTCCGGTGATTTTGATTATGAAAAGATGGC
AAACGCTAATAAGGGGGCTATGACCGAAAATGCCGATGAAAACGCGCTA
CAGTCTGACGCTAAAGGCAAACTTGATTCTGTCGCTACTGATTACGGTG
CTGCTATCGATGGTTTCATTGGTGACGTTTCCGGCCTTGCTAATGGTAA
TGGTGCTACTGGTGATTTTGCTGGCTCTAATTCCCAAATGGCTCAAGTC
GGTGACGGTGATAATTCACCTTTAATGAATAATTTCCGTCAATATTTAC
CTTCCCTCCCTCAATCGGTTGAATGTCGCCCTTTTGTCTTTAGCGCTGG
TAAACCATATGAATTTTCTATTGATTGTGACAAAATAAACTTATTCCGT
GGTGTCTTTGCGTTTCTTTTATATGTTGCCACCTTTATGTATGTATTTT
CTACGTTTGCTAACATACTGCGTAATAAGGAGTCTTAATCATGCCAGTT
CTTTTGGGTATTCCGTTATTATTGCGTTTCCTCGGTTTCCTTCTGGTAA
CTTTGTTCGGCTATCTGCTTACTTTTCTTAAAAAGGGCTTCGGTAAGAT
AGCTATTGCTATTTCATTGTTTCTTGCTCTTATTATTGGGCTTAACTCA
ATTCTTGTGGGTTATCTCTCTGATATTAGCGCTCAATTACCCTCTGACT
TTGTTCAGGGTGTTCAGTTAATTCTCCCGTCTAATGCGCTTCCCTGTTT
TTATGTTATTCTCTCTGTAAAGGCTGCTATTTTCATTTTTGACGTTAAA
CAAAAAATCGTTTCTTATTTGGATTGGGATAAATAATATGGCTGTTTAT
TTTGTAACTGGCAAATTAGGCTCTGGAAAGACGCTCGTTAGCGTTGGTA
AGATTCAGGATAAAATTGTAGCTGGGTGCAAAATAGCAACTAATCTTGA
TTTAAGGCTTCAAAACCTCCCGCAAGTCGGGAGGTTCGCTAAAACGCCT
CGCGTTCTTAGAATACCGGATAAGCCTTCTATATCTGATTTGCTTGCTA
TTGGGCGCGGTAATGATTCCTACGATGAAAATAAAAACGGCTTGCTTGT
TCTCGATGAGTGCGGTACTTGGTTTAATACCCGTTCTTGGAATGATAAG
GAAAGACAGCCGATTATTGATTGGTTTCTACATGCTCGTAAATTAGGAT
GGGATATTATTTTTCTTGTTCAGGACTTATCTATTGTTGATAAACAGGC
GCGTTCTGCATTAGCTGAACATGTTGTTTATTGTCGTCGTCTGGACAGA
ATTACTTTACCTTTTGTCGGTACTTTATATTCTCTTATTACTGGCTCGA
AAATGCCTCTGCCTAAATTACATGTTGGCGTTGTTAAATATGGCGATTC
TCAATTAAGCCCTACTGTTGAGCGTTGGCTTTATACTGGTAAGAATTTG
TATAACGCATATGATACTAAACAGGCTTTTTCTAGTAATTATGATTCCG
GTGTTTATTCTTATTTAACGCCTTATTTATCACACGGTCGGTATTTCAA
ACCATTAAATTTAGGTCAGAAGATGAAATTAACTAAAATATATTTGAAA
AAGTTTTCTCGCGTTCTTTGTCTTGCGATTGGATTTGCATCAGCATTTA
CATATAGTTATATAACCCAACCTAAGCCGGAGGTTAAAAAGGTAGTCTC
TCAGACCTATGATTTTGATAAATTCACTATTGACTCTTCTCAGCGTCTT
AATCTAAGCTATCGCTATGTTTTCAAGGATTCTAAGGGAAAATTAATTA
ATAGCGACGATTTACAGAAGCAAGGTTATTCACTCACATATATTGATTT
ATGTACTGTTTCCATTAAAAAAGGTAATTCAAATGAAATTGTTAAATGT
AATTAATTTTGTTTTCTTGATGTTTGTTTCATCATCTTCTTTTGCTCAG
GTAATTGAAATGAATAATTCGCCTCTGCGCGATTTTGTAACTTGGTATT
CAAAGCAATCAGGCGAATCCGTTATTGTTTCTCCCGATGTAAAAGGTAC
TGTTACTGTATATTCATCTGACGTTAAACCTGAAAATCTACGCAATTTC
TTTATTTCTGTTTTACGTGCTAATAATTTTGATATGGTTGGTTCAATTC
CTTCCATAATTCAGAAGTATAATCCAAACAATCAGGATTATATTGATGA
ATTGCCATCATCTGATAATCAGGAATATGATGATAATTCCGCTCCTTCT
GGTGGTTTCTTTGTTCCGCAAAATGATAATGTTACTCAAACTTTTAAAA
TTAATAACGTTCGGGCAAAGGATTTAATACGAGTTGTCGAATTGTTTGT
AAAGTCTAATACTTCTAAATCCTCAAATGTATTATCTATTGACGGCTCT
AATCTATTAGTTGTTAGTGCACCTAAAGATATTTTAGATAACCTTCCTC
AATTCCTTTCTACTGTTGATTTGCCAACTGACCAGATATTGATTGAGGG
TTTGATATTTGAGGTTCAGCAAGGTGATGCTTTAGATTTTTCATTTGCT
GCTGGCTCTCAGCGTGGCACTGTTGCAGGCGGTGTTAATACTGACCGCC
TCACCTCTGTTTTATCTTCTGCTGGTGGTTCGTTCGGTATTTTTAATGG
CGATGTTTAGGGCTATCAGTTCGCGCATTAAAGACTAATAGCCATTCA
AAAATATTGTCTGTGCCACGTATTCTTACGCTTTCAGGTCAGAAGGGTT
CTATCTCTGTTGGCCAGAATGTCCCTTTTATTACTGGTCGTGTGACTGG
TGAATCTGCCAATGTAAATAATCCATTTCAGACGATTGAGCGTCAAAAT
GTAGGTATTTCCATGAGCGTTTTTCCTGTTGCAATGGCTGGCGGTAATA
TTGTTCTGGATATTACCAGCAAGGCCGATAGTTTGAGTTCTTCTACTCA
GGCAAGTGATGTTATTACTAATCAAAGAAGTATTGCTACAACGGTTAAT
TTGCGTGATGGACAGACTCTTTTACTCGGTGGCCTCACTGATTATAAAA
ACACTTCTCAAGATTCTGGCGTACCGTTCCTGTCTAAAATCCCTTTAAT

```
CGGCCTCCTGTTTAGCTCCCGCTCTGATTCCAACGAGGAAAGCACGTTA

TACGTGCTCGTCAAAGCAACCATAGTACGCGCCCTGTAGCGGCGCATTA

AGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGG

TTCCGATTTAGTGCTTTACGGCACCTCGACCCCAAAAAACTTGATTTGG

GTGATGGTTCACGTAGTGGGCCATCGCCCTGATAGACGGTTTTTCGCCC

TTTGACGTTGGAGTCCACGTTCTTTAATAGTGGACTCTTGTTCCAAACT

GGAACAACACTCAACCCTATCTCGGGACGGATCGCTTCATGTGGCAGGA

GAAAAAAGGCTGCACCGGTGCGTCAGCAGAATATGTGATACAGGATATA

TTCCGCTTCCTCGCTCACTGACTCGCTACGCTCGGTCGTTCGACTGCGG

CGAGCGGAAATGGCTTACGAACGGGGCGGAGATTTCCTGGAAGATGCCA

GGAAGATACTTAACAGGGAAGTGAGAGGGCCGCGGCAAAGCCGTTTTC

CATAGGCTCCGCCCCCCTGACAAGCATCACGAAATCTGACGCTCAAATC

AGTGGTGGCGAAACCCGACAGGACTATAAAGATACCAGGCGTTTCCCCC

TGGCGGCTCCCTCGTGCGCTCTCCTGTTCCTGCCTTTCGGTTTACCGGT

GTCATTCCGCTGTTATGGCCGCGTTTGTCTCATTCCACGCCTGACACTC

AGTTCCGGGTAGGCAGTTCGCTCCAAGCTGGACTGTATGCACGAACCCC

CCGTTCAGTCCGACCGCTGCGCCTTATCCGGTAACTATCGTCTTGAGTC

CAACCCGGAAAGACATGCAAAAGCACCACTGGCAGCAGCCACTGGTAAT

TGATTTAGAGGAGTTAGTCTTGAAGTCATGCGCCGGTTAAGGCTAAACT

GAAAGGACAAGTTTTGGTGACTGCGCTCCTCCAAGCCAGTTACCTCGGT

TCAAAGAGTTGGTAGCTCAGAGAACCTTCGAAAAACCGCCCTGCAAGGC

GGTTTTTTCGTTTTCAGAGCAAGAGATTACGCGCAGACCAAAACGATCT

CAAGAAGATCATCTTATTAAGGGGTCTGACGCTCAGTGGAACGAAAACT

CACGTTAAGGGATTTTGGTCATGAGATTATCAAAAAGGATCTTCACCTA

GATCCTTTTAAATTAAAAATGAAGTTTTAAATCAATCTAAAGTATATAT

GAGTAAACTTGGTCTGACAGTTACCAATGCTTAATCAGTGAGGCACCTA

TCTCAGCGATCTGTCTATTTCGTTCATCCATAGTTGCCTGACTCCCCGT

CGTGTAGATAACTACGATACGGGAGGGCTTACCATCTGGCCCCAGTGCT

GCAATGATACCGCGAGACCCACGCTCACCGGCTCCAGATTTATCAGCAA

TAAACCAGCCAGCCGATTCGAGCTCGCCCCGGGATCGACCAGTTGGTG

ATTTTGAACTTTTGCTTTGCCACGGAACGGTCTGCGTTGTCGGGAAGAT

GCGTGATCTGATCCTTCAACTCAGCAAAAGTTCGATTTATTCAACAAAG

CCGCCGTCCCGTCAAGTCAGCGTAATGCTCTGCCAGTGTTACAACCAAT

TAACCAATTCTGATTAGAAAAACTCATCGAGCATCAAATGAAACTGCAA

TTTATTCATATCAGGATTATCAATACCATATTTTTGAAAAAGCCGTTTC

TGTAATGAAGGAGAAAACTCACCGAGGCAGTTCCATAGGATGGCAAGAT

CCTGGTATCGGTCTGCGATTCCGACTCGTCCAACATCAATACAACCTAT

TAATTTCCCCTCGTCAAAAATAAGGTTATCAAGTGAGAAATCACCATGA

GTGACGACTGAATCCGGTGAGAATGGCAAAAGCTTATGCATTTCTTTCC

AGACTTGTTCAACAGGCCAGCCATTACGCTCGTCATCAAAATCACTCGC

ATCAACCAAACCGTTATTCATTCGTGATTGCGCCTGAGCGAGACGAAAT

ACGCGATCGCTGTTAAAAGGACAATTACAAACAGGAATCGAATGCAACC

GGCGCAGGAACACTGCCAGCGCATCAACAATATTTTCACCTGAATCAGG

ATATTCTTCTAATACCTGGAATGCTGTTTTCCCGGGGATCGCAGTGGTG

AGTAACCATGCATCATCAGGAGTACGGATAAATGCTTGATGGTCGGAA

GAGGCATAAATTCCGTCAGCCAGTTTAGTCTGACCATCTCATCTGTAAC

ATCATTGGCAACGCTACCTTTGCCATGTTTCAGAAACAACTCTGGCGCA

TCGGGCTTCCCATACAATCGATAGATTGTCGCACCTGATTGCCCGACAT

TATCGCGAGCCCATTTATACCCATATAAATCAGCATCCATGTTGGAATT

TAATCGCGGCCTCGAGCAAGACGTTTCCCGTTGAATATGGCTCATAACA

CCCCTTGTATTACTGTTTATGTAAGCAGACAGTTTTATTGTTCATGATG

ATATATTTTTATCTTGTGCAATGTAACATCAGAGATTTTGAGACACAAC

GTGGCTTTCCCCCCCCCCCCTGCAGGTCTCGGGCTATTCTTTTGATTT

ATAAGGGATTTTGCCGATTTCGGCCTATTGGTTAAAAAATGAGCTGATT

TAACAAAAATTTAACGCGAATTTTAACAAAATATTAACGTTTACAATTT

AAATATTTGCTTATACAATCTTCCTGTTTTTGGGGCTTTTCTGATTATC

AACCGGGGTACATATGATTGACATGCTAGTTTTACGATTACCGTTCATC

GATTCTCTTGTTTGCTCCAGACTCTCAGGCAATGACCTGATAGCCTTTG

TAGACCTCTCAAAAATAGCTACCCTCTCCGGCATGAATTTATCAGCTAG

AACGGTTGAATATCATATTGATGGTGATTTGACTGTCTCCGGCCTTTCT

CACCCTTTTGAATCTTTACCTACACATTACTCAGGCATTGCATTTAAAA

TATATGAGGGTTCTAAAAATTTTTATCCTTGCGTTGAAATAAAGGCTTC

TCCCGCAAAAGTATTACAGGGTCATAATGTTTTTGGTACAACCGATTTA

GCTTTATGCTCTGAGGCTTTATTGCTTAATTTTGCTAATTCTTTGCCTT

GCCTGTATGATTTATTGGATGTT
```

In one preferred embodiment, the second vector (helper phage without RGD sequence) comprises a nucleic acid sequence substantially as set out in SEQ ID No: 11, or a fragment or variant thereof, wherein SEQ ID No: 11 is represented as follows:

[SEQ ID No: 11]
```
AACGCTACTACTATTAGTAGAATTGATGCCACCTTTTCAGCTCGCGCCC

CAAATGAAAATATAGCTAAACAGGTTATTGACCATTTGCGAAATGTATC

TAATGGTCAAACTAAATCTACTCGTTCGCAGAATTGGGAATCAACTGTT

ACATGGAATGAAACTTCCAGACACCGTACTTTAGTTGCATATTTAAAAC

ATGTTGAGCTACAGCACCAGATTCAGCAATTAAGCTCTAAGCCATCCGC

AAAAATGACCTCTTATCAAAAGGAGCAATTAAAGGTACTCTCTAATCCT

GACCTGTTGGAGTTTGCTTCCGGTCTGGTTCGCTTTGAAGCTCGAATTA

AAACGCGATATTTGAAGTCTTTCGGGCTTCCTCTTAATCTTTTTGATGC

AATCCGCTTTGCTTCTGACTATAATAGTCAGGGTAAAGACCTGATTTTT
```

```
GATTTATGGTCATTCTCGTTTTCTGAACTGTTTAAAGCATTTGAGGGGG
ATTCAATGAATATTTATGACGATTCCGCAGTATTGGACGCTATCCAGTC
TAAACATTTTACTATTACCCCCTCTGGCAAAACTTCTTTTGCAAAAGCC
TCTCGCTATTTTGGTTTTTATCGTCGTCTGGTAAACGAGGGTTATGATA
GTGTTGCTCTTACTATGCCTCGTAATTCCTTTTGGCGTTATGTATCTGC
ATTAGTTGAATGTGGTATTCCTAAATCTCAACTGATGAATCTTTCTACC
TGTAATAATGTTGTTCCGTTAGTTCGTTTTATTAACGTAGATTTTTCTT
CCCAACGTCCTGACTGGTATAATGAGCCAGTTCTTAAAATCGCATAAGG
TAATTCACAATGATTAAAGTTGAAATTAAACCATCTCAAGCCCAATTTA
CTACTCGTTCTGGTGTTTCTCGTCAGGGCAAGCCTTATTCACTGAATGA
GCAGCTTTGTTACGTTGATTTGGGTAATGAATATCCGGTTCTTGTCAAG
ATTACTCTTGATGAAGGTCAGCCAGCCTATGCGCCTGGTCTGTACACCG
TTCATCTGTCCTCTTTCAAAGTTGGTCAGTTCGGTTCCCTTATGATTGA
CCGTCTGCGCCTCGTTCCGGCTAAGTAACATGGAGCAGGTCGCGGATTT
CGACACAATTTATCAGGCGATGATACAAATCTCCGTTGTACTTTGTTTC
GCGCTTGGTATAATCGCTGGGGGTCAAAGATGAGTGTTTTAGTGTATTC
TTTCGCCTCTTTCGTTTTAGGTTGGTGCCTTCGTAGTGGCATTACGTAT
TTTACCCGTTTAATGGAAACTTCCTCATGAAAAAGTCTTTAGTCCTCAA
AGCCTCTGTAGCCGTTGCTACCCTCGTTCCGATGCTGTCTTTCGCTGCT
GAGGGTGACGATCCCGCAAAAGCGGCCTTTAACTCCCTGCAAGCCTCAG
CGACCGAATATATCGGTTATGCGTGGGCGATGGTTGTTGTCATTGTCGG
CGCAACTATCGGTATCAAGCTGTTTAAGAAATTCACCTCGAAAGCAAGC
TGATAAACCGATACAATTAAAGGCTCCTTTTGGAGCCTTTTTTTTGGA
GATTTTCAACGTGAAAAAATTATTATTCGCAATTCCTTTAGTTGTTCCT
TTCTATTCTCACTCCGCTGAAACTGTTGAAAGTTGTTTAGCAAAACCCC
ATACAGAAAATTCATTTACTAACGTCTGGAAAGACGACAAAACTTTAGA
TCGTTACGCTAACTATGAGGGTGTCTGTGGAATGCTACAGGCGTTGTA
GTTTGTACTGGTGACGAAACTCAGTGTTACGGTACATGGGTTCCTATTG
GGCTTGCTATCCCTGAAAATGAGGGTGGTGGCTCTGAGGGTGGCGGTTC
TGAGGGTGGCGGTTCTGAGGGTGGCGGTACTAAACCTCCTGAGTACGGT
GATACACCTATTCCGGGCTATACTTATATCAACCCTCTCGACGGCACTT
ATCCGCCTGGTACTGAGCAAAACCCCGCTAATCCTAATCCTTCTCTTGA
GGAGTCTCAGCCTCTTAATACTTTCATGTTTCAGAATAATAGGTTCCGA
AATAGGCAGGGGCATTAACTGTTTATACGGGCACTGTTACTCAAGGCA
CTGACCCCGTTAAAACTTATTACCAGTACACTCCTGTATCATCAAAAGC
CATGTATGACGCTTACTGGAACGGTAAATTCAGAGACTGCGCTTTCCAT
TCTGGCTTTAATGAGGATCCATTCGTTTGTGAATATCAAGGCCAATCGT
CTGACCTGCCTCAACCTCCTGTCAATGCTGGCGGCGGCTCTGGTGGTGG
TTCTGGTGGCGGCTCTGAGGGTGGTGGCTCTGAGGGTGGCGGTTCTGAG
GGTGGCGGCTCTGAGGGAGGCGGTTCCGGTGGTGGCTCTGGTTCCGGTG
```

```
ATTTTGATTATGAAAGATGGCAAACGCTAATAAGGGGCTATGACCGA
AAATGCCGATGAAAACGCGCTACAGTCTGACGCTAAAGGCAAACTTGAT
TCTGTCGCTACTGATTACGGTGCTGCTATCGATGGTTTCATTGGTGACG
TTTCCGGCCTTGCTAATGGTAATGGTGCTACTGGTGATTTTGCTGGCTC
TAATTCCCAAATGGCTCAAGTCGGTGACGGTGATAATTCACCTTTAATG
AATAATTTCCGTCAATATTTACCTTCCCTCCCTCAATCGGTTGAATGTC
GCCCTTTTGTCTTTAGCGCTGGTAAACCATATGAATTTTCTATTGATTG
TGACAAAATAAACTTATTCCGTGGTGTCTTTGCGTTTCTTTTATATGTT
GCCACCTTTATGTATGTATTTTCTACGTTTGCTAACATACTGCGTAATA
AGGAGTCTTAATCATGCCAGTTCTTTTGGGTATTCCGTTATTATTGCGT
TTCCTCGGTTTCCTTCTGGTAACTTTGTTCGGCTATCTGCTTACTTTTC
TTAAAAAGGGCTTCGGTAAGATAGCTATTGCTATTTCATTGTTTCTTGC
TCTTATTATTGGGCTTAACTCAATTCTTGTGGGTTATCTCTCTGATATT
AGCGCTCAATTACCCTCTGACTTTGTTCAGGGTGTTCAGTTAATTCTCC
CGTCTAATGCGCTTCCCTGTTTTTATGTTATTCTCTCTGTAAAGGCTGC
TATTTTCATTTTTGACGTTAAACAAAAAATCGTTTCTTATTTGGATTGG
GATAAATAATATGGCTGTTTATTTTGTAACTGGCAAATTAGGCTCTGGA
AAGACGCTCGTTAGCGTTGGTAAGATTCAGGATAAAATTGTAGCTGGGT
GCAAAATAGCAACTAATCTTGATTTAAGGCTTCAAAACCTCCCGCAAGT
CGGGAGGTTCGCTAAAACGCCTCGCGTTCTTAGAATACCGGATAAGCCT
TCTATATCTGATTTGCTTGCTATTGGGCGCGGTAATGATTCCTACGATG
AAAATAAAAACGGCTTGCTTGTTCTCGATGAGTGCGGTACTTGGTTTAA
TACCCGTTCTTGGAATGATAAGGAAAGACAGCCGATTATTGATTGGTTT
CTACATGCTCGTAAATTAGGATGGGATATTATTTTTCTTGTTCAGGACT
TATCTATTGTTGATAAACAGGCGCGTTCTGCATTAGCTGAACATGTTGT
TTATTGTCGTCGTCTGGACAGAATTACTTTACCTTTTGTCGGTACTTTA
TATTCTCTTATTACTGGCTCGAAAATGCCTCTGCCTAAATTACATGTTG
GCGTTGTTAAATATGGCGATTCTCAATTAAGCCCTACTGTTGAGCGTTG
GCTTTATACTGGTAAGAATTTGTATAACGCATATGATACTAAACAGGCT
TTTTCTAGTAATTATGATTCCGGTGTTTATTCTTATTTAACGCCTTATT
TATCACACGGTCGGTATTTCAAACCATTAAATTTAGGTCAGAAGATGAA
ATTAACTAAAATATATTTGAAAAAGTTTTCTCGCGTTCTTTGTCTTGCG
ATTGGATTTGCATCAGCATTTACATATAGTTATATAACCCAACCTAAGC
CGGAGGTTAAAAAGGTAGTCTCTCAGACCTATGATTTTGATAAATTCAC
TATTGACTCTTCTCAGCGTCTTAATCTAAGCTATCGCTATGTTTTCAAG
GATTCTAAGGGAAAATTAATTAATAGCGACGATTTACAGAAGCAAGGT
ATTCACTCACATATATTGATTTATGTACTGTTTCCATTAAAAAAGGTAA
TTCAAATGAAATTGTTAAATGTAATTAATTTTGTTTTCTTGATGTTTGT
TTCATCATCTTCTTTTGCTCAGGTAATTGAAATGAATAATTCGCCTCTG
CGCGATTTTGTAACTTGGTATTCAAAGCAATCAGGCGAATCCGTTATTG
TTTCTCCCGATGTAAAAGGTACTGTTACTGTATATTCATCTGACGTTAA
```

```
ACCTGAAAATCTACGCAATTTCTTTATTTCTGTTTTACGTGCTAATAAT
TTTGATATGGTTGGTTCAATTCCTTCCATAATTCAGAAGTATAATCCAA
ACAATCAGGATTATATTGATGAATTGCCATCATCTGATAATCAGGAATA
TGATGATAATTCCGCTCCTTCTGGTGGTTTCTTTGTTCCGCAAAATGAT
AATGTTACTCAAACTTTTAAAATTAATAACGTTCGGGCAAAGGATTTAA
TACGAGTTGTCGAATTGTTTGTAAAGTCTAATACTTCTAAATCCTCAAA
TGTATTATCTATTGACGGCTCTAATCTATTAGTTGTTAGTGCACCTAAA
GATATTTTAGATAACCTTCCTCAATTCCTTTCTACTGTTGATTTGCCAA
CTGACCAGATATTGATTGAGGGTTTGATATTTGAGGTTCAGCAAGGTGA
TGCTTTAGATTTTTCATTTGCTGCTGGCTCTCAGCGTGGCACTGTTGCA
GGCGGTGTTAATACTGACCGCCTCACCTCTGTTTTATCTTCTGCTGGTG
GTTCGTTCGGTATTTTTAATGGCGATGTTTTAGGGCTATCAGTTCGCGC
ATTAAAGACTAATAGCCATTCAAAAATATTGTCTGTGCCACGTATTCTT
ACGCTTTCAGGTCAGAAGGGTTCTATCTCTGTTGGCCAGAATGTCCCTT
TTATTACTGGTCGTGTGACTGGTGAATCTGCCAATGTAAATAATCCATT
TCAGACGATTGAGCGTCAAAATGTAGGTATTTCCATGAGCGTTTTTCCT
GTTGCAATGGCTGGCGGTAATATTGTTCTGGATATTACCAGCAAGGCCG
ATAGTTTGAGTTCTTCTACTCAGGCAAGTGATGTTATTACTAATCAAAG
AAGTATTGCTACAACGGTTAATTTGCGTGATGGACAGACTCTTTTACTC
GGTGGCCTCACTGATTATAAAAACACTTCTCAAGATTCTGGCGTACCGT
TCCTGTCTAAAATCCCTTTAATCGGCCTCCTGTTTAGCTCCCGCTCTGA
TTCCAACGAGGAAAGCACGTTATACGTGCTCGTCAAAGCAACCATAGTA
CGCGCCCTGTAGCGGCGCATTAAGCGCGGCGGGTGTGGTGGTTACGCGC
AGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTC
GACCCCAAAAAACTTGATTTGGGTGATGGTTCACGTAGTGGGCCATCGC
CCTGATAGACGGTTTTTCGCCCTTTGACGTTGGAGTCCACGTTCTTTAA
TAGTGGACTCTTGTTCCAAACTGGAACAACACTCAACCCTATCTCGGGA
CGGATCGCTTCATGTGGCAGGAGAAAAAAGGCTGCACCGGTGCGTCAGC
AGAATATGTGATACAGGATATATTCCGCTTCCTCGCTCACTGACTCGCT
ACGCTCGGTCGTTCGACTGCGGCGAGCGGAAATGGCTTACGAACGGGGC
GGAGATTTCCTGGAAGATGCCAGGAAGATACTTAACAGGGAAGTGAGAG
GGCCGCGGCAAAGCCGTTTTTCCATAGGCTCCGCCCCCCTGACAAGCAT
CACGAAATCTGACGCTCAAATCAGTGGTGGCGAAACCCGACAGGACTAT
AAAGATACCAGGCGTTTCCCCCTGGCGGCTCCCTCGTGCGCTCTCCTGT
TCCTGCCTTTCGGTTTACCGGTGTCATTCCGCTGTTATGGCCGCGTTTG
TCTCATTCCACGCCTGACACTCAGTTCCGGGTAGGCAGTTCGCTCCAAG
CTGGACTGTATGCACGAACCCCCCGTTCAGTCCGACCGCTGCGCCTTAT
CCGGTAACTATCGTCTTGAGTCCAACCCGGAAAGACATGCAAAGCACC
```

```
ACTGGCAGCAGCCACTGGTAATTGATTTAGAGGAGTTAGTCTTGAAGTC
ATGCGCCGGTTAAGGCTAAACTGAAAGGACAAGTTTTGGTGACTGCGCT
CCTCCAAGCCAGTTACCTCGGTTCAAAGAGTTGGTAGCTCAGAGAACCT
TCGAAAACCGCCCTGCAAGGCGGTTTTTTCGTTTTCAGAGCAAGAGAT
TACGCGCAGACCAAAACGATCTCAAGAAGATCATCTTATTAAGGGGTCT
GACGCTCAGTGGAACGAAAACTCACGTTAAGGGATTTTGGTCATGAGAT
TATCAAAAGGATCTTCACCTAGATCCTTTTAAATTAAAAATGAAGTTT
TAAATCAATCTAAAGTATATATGAGTAAACTTGGTCTGACAGTTACCAA
TGCTTAATCAGTGAGGCACCTATCTCAGCGATCTGTCTATTTCGTTCAT
CCATAGTTGCCTGACTCCCCGTCGTGTAGATAACTACGATACGGGAGGG
CTTACCATCTGGCCCCAGTGCTGCAATGATACCGCGAGACCCACGCTCA
CCGGCTCCAGATTTATCAGCAATAAACCAGCCAGCCGATTCGAGCTCGC
CCCGGGGATCGACCAGTTGGTGATTTTGAACTTTTGCTTTGCCACGGAA
CGGTCTGCGTTGTCGGGAAGATGCGTGATCTGATCCTTCAACTCAGCAA
AAGTTCGATTTATTCAACAAAGCCGCCGTCCCGTCAAGTCAGCGTAATG
CTCTGCCAGTGTTACAACCAATTAACCAATTCTGATTAGAAAAACTCAT
CGAGCATCAAATGAAACTGCAATTTATTCATATCAGGATTATCAATACC
ATATTTTGAAAAAGCCGTTTCTGTAATGAAGGAGAAAACTCACCGAGG
CAGTTCCATAGGATGGCAAGATCCTGGTATCGGTCTGCGATTCCGACTC
GTCCAACATCAATACAACCTATTAATTTCCCCTCGTCAAAAATAAGGTT
ATCAAGTGAGAAATCACCATGAGTGACGACTGAATCCGGTGAGAATGGC
AAAAGCTTATGCATTTCTTTCCAGACTTGTTCAACAGGCCAGCCATTAC
GCTCGTCATCAAAATCACTCGCATCAACCAAACCGTTATTCATTCGTGA
TTGCGCCTGAGCGAGACGAAATACGCGATCGCTGTTAAAGGACAATTA
CAAACAGGAATCGAATGCAACCGGCGCAGGAACACTGCCAGCGCATCAA
CAATATTTTCACCTGAATCAGGATATTCTTCTAATACCTGGAATGCTGT
TTTCCCGGGGATCGCAGTGGTGAGTAACCATGCATCATCAGGAGTACGG
ATAAAATGCTTGATGGTCGGAAGAGGCATAAATTCCGTCAGCCAGTTTA
GTCTGACCATCTCATCTGTAACATCATTGGCAACGCTACCTTTGCCATG
TTTCAGAAACAACTCTGGCGCATCGGGCTTCCCATACAATCGATAGATT
GTCGCACCTGATTGCCCGACATTATCGCGAGCCCATTTATACCCATATA
AATCAGCATCCATGTTGGAATTTAATCGCGGCCTCGAGCAAGACGTTTC
CCGTTGAATATGGCTCATAACACCCCTTGTATTACTGTTTATGTAAGCA
GACAGTTTTATTGTTCATGATGATATATTTTTATCTTGTGCAATGTAAC
ATCAGAGATTTTGAGACAACGTGGCTTTCCCCCCCCCCCCTGCAGG
TCTCGGGCTATTCTTTTGATTTATAAGGGATTTTGCCGATTTCGGCCTA
TTGGTTAAAAAATGAGCTGATTTAACAAAAATTTAACGCGAATTTTAAC
AAAATATTAACGTTTACAATTTAAATATTTGCTTATACAATCTTCCTGT
TTTTGGGGCTTTTCTGATTATCAACCGGGGTACATATGATTGACATGCT
AGTTTTACGATTACCGTTCATCGATTCTCTTGTTTGCTCCAGACTCTCA
GGCAATGACCTGATAGCCTTTGTAGACCTCTCAAAAATAGCTACCCTCT
```

-continued

```
CCGGCATGAATTTATCAGCTAGAACGGTTGAATATCATATTGATGGTGA

TTTGACTGTCTCCGGCCTTTCTCACCCTTTTGAATCTTTACCTACACAT

TACTCAGGCATTGCATTTAAAATATATGAGGGTTCTAAAAATTTTTATC

CTTGCGTTGAAATAAAGGCTTCTCCCGCAAAAGTATTACAGGGTCATAA

TGTTTTTGGTACAACCGATTTAGCTTTATGCTCTGAGGCTTTATTGCTT

AATTTTGCTAATTCTTTGCCTTGCCTGTATGATTTATTGGATGTT
```

The system according to the nineteenth aspect can be used to produce a particle for use in accordance with any use as disclosed herein. The particle may be for use in accordance with the second, ninth or tenth aspect. In an embodiment, the recombinant phagemid particle produced is for use in treating a subject that has not been exposed to the delivered one or more antigen, for example by prior vaccination.

In an embodiment, the recombinant phagemid particle produced by the system of the nineteenth aspect is for use in a method that further comprises the use of one or more adoptively transferred T cell. Preferably, the adoptively transferred T cell is selected from a group consisting of a chimeric antigen receptor (CAR) T cell; T cell receptor (TCR) transgenic T cell; and tumour infiltrating lymphocyte (TIL). The adoptively transferred T cells may be specific for the one or more antigen introduced by the recombinant phagemid particle into the tumour cell. In a preferred embodiment, the adoptively transferred T cells are CAR T cells.

As described in Example 1, the inventors have devised two alternative approaches (see FIGS. 9 and 10) for producing the recombinant phagemid particle of the invention in a prokaryotic host.

Hence, in a twentieth aspect, there is provided a method for producing a recombinant phagemid particle from a prokaryotic host, the method comprising:—
(i) introducing, into a prokaryotic host cell, a first vector configured to persist inside the prokaryotic host, and comprising at least one transgene expression cassette comprising a nucleic acid sequence encoding one or more cytokine, or one or more antigen that is recognised by one or more adoptively transferred T cell, and a packaging signal for enabling replication of the vector into single-stranded DNA;
(ii) introducing, into the host, a helper phage comprising nucleic acid encoding bacteriophage structural proteins; and
(iii) culturing the host under conditions which result in the single-stranded DNA being packaged by the structural proteins to form and extrude a recombinant phagemid particle from the prokaryotic host.

Advantageously, this method (as shown in FIG. 9) results in very high yields of particles. The first vector (i.e. the phagemid particle's genome) may be introduced into the host cell, for example by infection. The host cell may then be transformed with the helper phage, which results in the production of the recombinant phagemid particle. Preferably, the method comprises a purification step following the culturing step. Purification may comprise centrifugation and/or filtration.

The antigen may be any as disclosed herein. In a preferred embodiment, the or each antigen is a peptide or protein which is expressed on the cell surface of the target tumour cell. Preferably, the or each antigen is a peptide or protein that, when expressed by the tumour cell, would be accessible to a CAR T cell. The peptide or protein may be such that, when expressed by the tumour cell, it is present as a folded peptide protein at or on the cell-surface. The or each antigen may be a known target for existing CAR T cells suitable for use in humans. For example, the or each antigen may be selected from a group consisting of: MUC1; PSMA; CD19; CD20; estrogen-related receptor beta type 2 (ErRB2); or any combination thereof. In an embodiment, the or each antigen may be dengue virus or yellow fever vaccine antigens.

The cytokine may be any as disclosed herein. In particular the cytokine may be IL-4, IL-12, IL-15, TNFα, TRAIL, IFN-γ, or any combination thereof. Preferably, the cytokine is IL-15, Preferably, the cytokine is IL-4. Preferably, the cytokine is IL-12. Preferably, the cytokine is TRAIL. Preferably, the cytokine is IFN-γ.

Preferably, the cytokine is not TNFα. Preferably, the cytokine is TNFα. Preferably, the cytokine is a hybrid TNFα comprising a non-endogenous signal peptide configured to increase expression and/or secretion of TNFα. Preferably, the signal peptide is a cytokine signal peptide other than that of TNFα.

Preferably, the method of the twentieth aspect is used to produce the recombinant phagemid particle of the eighth aspect. Preferably, the first vector therefore comprises the genome of the recombinant phagemid particle. The packaging signal of the first vector may preferably comprise an origin or replication. Preferably, the origin of replication in the first vector comprises an F1 ori, more preferably from an F1 bacteriophage.

The method according to the twentieth aspect can be used to produce a particle for use in accordance with any use as disclosed herein. The particle may be for use in accordance with the second, ninth or tenth aspect. In an embodiment, the recombinant phagemid particle produced is for use in treating a subject that has not been exposed to the delivered one or more antigen, for example by prior vaccination.

In an embodiment, the recombinant phagemid particle produced by the method of the twentieth aspect is for use in a method that further comprises the use of one or more adoptively transferred T cell. Preferably, the adoptively transferred T cell is selected from a group consisting of a chimeric antigen receptor (CAR) T cell; T cell receptor (TCR) transgenic T cell; and tumour infiltrating lymphocyte (TIL). The adoptively transferred T cells may be specific for the one or more antigen introduced by the recombinant phagemid particle into the tumour cell. In a preferred embodiment, the adoptively transferred T cells are CAR T cells.

In a twenty-first aspect, there is provided a method for producing a recombinant phagemid particle from a prokaryotic host, the method comprising:—
(i) introducing into a prokaryotic host cell: (a) a first vector configured to persist inside the prokaryotic host, and comprising at least one transgene expression cassette comprising a nucleic acid sequence encoding one or more cytokine, or one or more antigen that is recognised by one or more adoptively transferred T cell, and a packaging signal for enabling replication of the vector into single-stranded DNA, and (b) a second vector comprising nucleic acid encoding structural proteins required for packaging the single-stranded DNA; and
(ii) culturing the host under conditions which result in the single-stranded DNA being packaged by the structural proteins to form and extrude a recombinant phagemid particle from the prokaryotic host.

Advantageously, this method (as shown in FIG. 10) results in improved safety. The second vector (i.e. the helper phage) may be introduced into the host cell, for example by infection. The host cell may then be transformed with the first vector (i.e. the phagemid particle's genome), which results in the production of the recombinant phagemid particle. Preferably, the method comprises a purification step following the culturing step. Purification may comprise centrifugation and/or filtration.

The antigen may be any as disclosed herein. In a preferred embodiment, the or each antigen is a peptide or protein which is expressed on the cell surface of the target tumour cell. Preferably, the or each antigen is a peptide or protein that, when expressed by the tumour cell, would be accessible to a CAR T cell. The peptide or protein may be such that, when expressed by the tumour cell, it is present as a folded peptide protein at or on the cell-surface. The or each antigen may be a known target for existing CAR T cells suitable for use in humans. For example, the or each antigen may be selected from a group consisting of: MUC1; PSMA; CD19; CD20; estrogen-related receptor beta type 2 (ErRB2); or any combination thereof. In an embodiment, the or each antigen may be dengue virus or yellow fever vaccine antigens.

The cytokine may be any as disclosed herein. In particular the cytokine may be IL-4, IL-12, IL-15, TNFα, TRAIL, IFN-γ, or any combination thereof. Preferably, the cytokine is IL-15. Preferably, the cytokine is IL-4. Preferably, the cytokine is IL-12. Preferably, the cytokine is TRAIL. Preferably, the cytokine is IFN-γ.

Preferably, the cytokine is not TNFα. Preferably, the cytokine is TNFα. Preferably, the cytokine is a hybrid TNFα comprising a non-endogenous signal peptide configured to increase expression and/or secretion of TNFα. Preferably, the signal peptide is a cytokine signal peptide other than that of TNFα.

Preferably, the method of the twenty-first aspect is used to produce the recombinant phagemid particle of the eighth aspect. Preferably, the first vector therefore comprises the genome of the recombinant phagemid particle. The packaging signal of the first vector may preferably comprise an origin of replication. Preferably, the origin of replication in the first vector comprises an F1 ori, more preferably from an F1 bacteriophage.

The method of the twenty-first aspect can be used to produce a recombinant phagemid particle for any use as disclosed herein. The particle may be for use in accordance with the second, ninth or tenth aspect. In an embodiment, the recombinant phagemid particle is for use in treating a subject that has not been exposed to the delivered one or more antigen, for example by prior vaccination.

In an embodiment, the recombinant phagemid particle produced by the method of the twenty-first aspect is for use in a method that further comprises the use of one or more adoptively transferred T cell. Preferably, the adoptively transferred T cells are selected from a group consisting of chimeric antigen receptor (CAR) T cells; T cell receptor (TCR) transgenic T cells; and tumour infiltrating lymphocytes (TILs). The adoptively transferred T cells may be specific for the one or more antigen introduced by the recombinant phagemid particle into the tumour cell. In a preferred embodiment, the adoptively transferred T cells are CAR T cells.

In an twenty-second aspect, there is provided use of a helper phage comprising nucleic acid encoding viral vector structural proteins to produce the recombinant phagemid particle according to the eighth aspect from a prokaryotic host.

There is provided a host cell comprising the first and/or second vector as defined in the twenty-first aspect.

The host cell is preferably prokaryotic, more preferably a bacterial cell. Examples of suitable host cells include: (i) TG1 (Genotype: K-12 supE thi-1 Δ(lac-proAB) Δ(mcrB-hsdSM)5, ($r_K^- m_K^-$), Plasmids: F' [traD36 proAB$^+$ lacI$^q$ lacZΔM15]), (ii) DH5αF' IQ™ (Genotype: F-φ80lacZΔM15 Δ(lacZYA-argF) U169 recA1 endA1 hsdR17 (rk−, mk+) phoA supE44λ-thi-1 gyrA96 relA1, Plasmids: F' proAB+lacIqZΔM15 zzf::Tn5 [KmR]; and (iii) XL1-Blue MRF' (Genotype: Δ(mcrA)183 Δ(mcrCB-hsdSMR-mrr)173 endA1 supE44 thi-1 recA1 gyrA96 relA1 lac, Plasmids: F' proAB lacIqZΔM15 Tn10 (Tetr).

The particle is used therapeutically or in diagnostic methods, preferably in vivo.

The invention may be used for the treatment of a wide variety of cancers due to the target-specific nature and the improved transduction efficiency of the recombinant phagemid particle of the invention. Consequently, the therapeutic opportunities of recombinant bacteriophages used in gene therapy may be significantly increased by the invention due to its ability to carry one or more transgene expression cassettes. The invention may be used prophylactically to prevent cancer, or after the development of a cancer, to ameliorate, manage, and/or treat it.

It will be appreciated that the invention may be used to create a variety of different recombinant phagemid particles that can be used for the treatment and/or diagnosis of a variety of cancers depending on the nature of the particles and the displayed foreign proteins (if an antigen). It will be appreciated that cytokine may not be displayed on the tumour cell. The target cell in the gene therapy technique is preferably eukaryotic, and preferably mammalian.

The gene therapy technique is used to treat, prevent, ameliorate, or manage cancer. The tumour may be a liquid tumour, such as a blood malignancy or a blood-forming tissue, or a haematological malignancy. The tumour may be a solid tumour. Tumours may be in the brain, e.g. medulloblastoma, glioblastoma, or diffuse intrinsic pontine glioma (DIPG). The recombinant phagemid particle may be used in combination with conventional treatments, such as chemotherapeutic drugs (e.g. doxorubicin, temozolomide, lomustine, cisplatin, vincristine), radiation therapy, or other drugs/xenobiotic compound, including but not limited to inhibitors of histone deacetylases (HDAC inhibitors), proteasome inhibiting drugs (e.g. MG132, borzotemib, carfilzomib) and anticancer products from natural and dietary sources (e.g. genistein, Epigallocatechin gallate (EGCG), resveratrol).

The recombinant phagemid particle may also be used to directly display and express the antigen of interest on the major pVIII coat proteins, thus providing an efficient platform for the simultaneous delivery, by a single phage particle, of numerous antigens, or proteins, or proteins with related biological activities. The subject may be mammalian, and is preferably human.

It will be appreciated that the recombinant phagemid particles and systems according to the invention (i.e. referred to hereinafter as "agents") may be used in a medicament to which may be used in a monotherapy, or as an adjunct to, or in combination with, known therapies for treating, ameliorating, managing, or preventing cancer. For example, a combined therapeutic approach using the phagemid particles and systems of the invention with existing chemotherapeutics, such as Temozolamide, cisplatin, Doxorubicin, vincristine, or Genistein, is preferred.

In another preferred embodiment, therapy may comprise the combination of the recombinant phagemid particle and system of the invention with an extracellular matrix degrading agent, such as enzyme or losartan. The inventors believe that extracellular matrix degrading agents should enhance phagemid diffusion in the subject being treated, and especially within a solid tumour.

The agents according to the invention (i.e. the recombinant phagemid particle used in the eighth or any above aspect, or produced by the system according to the nineteenth aspect) may be combined in compositions having a number of different forms depending, in particular, on the manner in which the composition is to be used. Thus, for example, the composition may be in the form of a powder, tablet, capsule, liquid etc. or any other suitable form that may be administered to a person or animal in need of treatment. It will be appreciated that the vehicle of medicaments according to the invention should be one which is well-tolerated by the subject to whom it is given.

Medicaments comprising the agents according to the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally).

Compositions may also be formulated for topical use. For instance, creams or ointments may be applied to the skin.

Agents according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents and compositions according to the invention may be administered to a subject by injection into the blood stream or directly into a site requiring treatment. Injections may be intravenous (bolus or infusion), subcutaneous (bolus or infusion), intradermal (bolus or infusion) or enhanced by convention (convection enhanced delivery—relevant to local injections at disease site).

It will be appreciated that the amount of the agent that is required is determined by its biological activity and bioavailability, which in turn depends on the mode of administration, the physiochemical properties of the agent (i.e. recombinant phagemid viral particle or the system), and whether it is being used as a monotherapy, or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease. Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the agent according to the invention may be used. More preferably, the daily dose is between 0.01 mg/kg of body weight and 400 mg/kg of body weight, and more preferably between 0.1 mg/kg and 200 mg/kg body weight.

As discussed in the Examples, the agent may be administered before, during the or after the onset of disease. For example, the agent may be administered immediately after a subject has developed a disease. Daily doses may be given systemically as a single administration (e.g. a single daily injection). Alternatively, the agent may require administration twice or more times during a day. As an example, the agent may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

Known procedures, such as those conventionally employed by the pharmaceutical industry (e.g. in vivo experimentation, clinical trials, etc.), may be used to form specific formulations comprising the particles or systems according to the invention and precise therapeutic regimes (such as daily doses of the agent and the frequency of administration).

Hence, in a twenty-third aspect of the invention, there is provided a pharmaceutical composition comprising the recombinant phagemid viral particle according to the eighth aspect, produced by the system according to the nineteenth aspect, produced by the methods of the twentieth or twenty-first aspect, or produced according to the use of the twenty-second aspect, and a pharmaceutically acceptable vehicle.

The invention also provides, in an twenty-fourth aspect, a process for making the pharmaceutical composition according to the twenty-third aspect, the process comprising contacting a therapeutically effective amount of the recombinant phagemid particle according to the eighth aspect, produced by the system according to the nineteenth aspect, produced by the methods of the twentieth or twenty-first aspect, or produced according to the use of the twenty-second aspect, and a pharmaceutically acceptable vehicle.

A "subject" may be a vertebrate, mammal, or domestic animal. Hence, agents, compositions and medicaments according to the invention may be used to treat any mammal, for example livestock (e.g. a horse), pets, or may be used in other veterinary applications. Most preferably, however, the subject is a human being.

A "therapeutically effective amount" of agent (i.e. recombinant phagemid viral particle) is any amount which, when administered to a subject, is the amount of drug that is needed to treat the target disease, or produce the desired effect, e.g. result in effective delivery of the transgene to a target cell or tissue, such as result in tumour killing.

For example, the therapeutically effective amount of agent used may be from about 0.01 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the particle or system of the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The particles or system according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The particles or system (i.e. hybrid vector) may be prepared as a sterile solid composition that may be dissolved or suspended at the time of administration using sterile water, saline, or other appropriate sterile injectable medium.

The recombinant phagemid particle, system and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The particles and system according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that adeno-associated virus (AAV) is often the vector of choice for gene therapy. As a gene delivery vector, lentiviral vectors also have key several advantages over other systems. They have a large packaging capacity of at least 8 Kb of DNA, which is an important feature when packaging sizeable expression cassettes of tissue-specific promoters and transgenes. In addition, lentiviral vectors have reduced immunogenicity compared to adenoviral vectors, making it possible to consider systemic delivery routes. However, barrier of using AAV or lentivirus for laboratory and clinical research include their extremely high production cost and low yields.

The inventors have shown that in addition to exhibiting useful applications in gene therapy, the recombinant phagemid particle of the invention can also be used to produce recombinant viral vectors, such as AAV or lentivirus, in vitro or in vivo (including in situ). Phage-guided AAV production utilizes the ability of the phagemid particles to package large amounts of single-stranded ssDNA. A typical AAV production system consists of three major elements: rAAV, rep-cap and adenohelper genes, which function together to produce rAAV particles.

Thus, in a twenty-fifth aspect, there is provided a recombinant phagemid particle according to the eighth aspect, produced according to the system of the nineteenth aspect, produced by the methods of the twentieth or twenty-first aspect, or produced according to the use of the twenty-second aspect, wherein the recombinant phagemid particle is for production of a recombinant viral vector comprising or derived from the viral genome within the genome of the phagemid particle, wherein the recombinant viral vector is used for delivering the nucleic acid sequence encoding one or more antigen or cytokine, to at least adjacent to the tumour cell, when the sequence encodes one or more antigen, the one or more antigen is expressed, and recognisable by one or more adoptively transferred T cell.

A recombinant phagemid particle which can produce a recombinant viral vector which, in turn, encodes an antigen for recognition by an adoptively transferred T cell (such as a CAR T cell) can be advantageous. FIG. 16 illustrates the delivery of a nucleic acid sequence to a malignant tumour; the production of the viral vector enables autoinfection of the tumour, such that the nucleic acid sequence is delivered throughout the tumour. This can be advantageous as this enables an antigen for recognition by an adoptively transferred T cell to be delivered throughout a tumour. This synergises with any subsequent adoptive transfer therapy, such as CAR T cell therapy, as it provides a suitable target for the CAR T cells. Furthermore, it may allow a lower concentration of the introduced vector (i.e. the recombinant phagemid particle) to be used.

In a preferred embodiment, the or each antigen is a peptide or protein which is expressed on the cell surface of the target tumour cell. Preferably, the or each antigen is a peptide or protein that, when expressed by the tumour cell, would be accessible to a CAR T cell. The peptide or protein may be such that, when expressed by the tumour cell, it is present as a folded peptide protein at or on the cell-surface. The or each antigen may be a known target for existing CAR T cells suitable for use in humans. For example, the or each antigen may be selected from a group consisting of: MUC1; PSMA; CD19; CD20; estrogen-related receptor beta type 2 (ErRB2); or any combination thereof. In an embodiment, the or each antigen may be dengue virus or yellow fever vaccine antigens.

The recombinant phagemid particle according to the twenty-fifth aspect can be for any use as disclosed herein. The particle may be for use in accordance with the second, ninth or tenth aspect. In an embodiment, the recombinant phagemid particle is for use in treating a subject that has not been exposed to the delivered one or more antigen, for example by prior vaccination.

In an embodiment, the recombinant phagemid particle of the twenty-fifth aspect is for use in a method that further comprises the use of one or more adoptively transferred T cell. Preferably, the adoptively transferred T cells are selected from a group consisting of chimeric antigen receptor (CAR) T cells; T cell receptor (TCR) transgenic T cells; and tumour infiltrating lymphocytes (TILs). The adoptively transferred T cells may be specific for the one or more antigen introduced by the recombinant phagemid particle into the tumour cell. In a preferred embodiment, the adoptively transferred T cells are CAR T cells.

There is also provided a method for producing recombinant viral vector, the method comprising introducing into, a eukaryotic host cell, the recombinant phagemid particle according to the eighth aspect, or the system according to the nineteenth aspect, and allowing the host cell to produce recombinant viral vector.

Preferably, the recombinant virus product is a recombinant mammalian virus, such as AAV or lentivirus. Preferably, the viral vector product is rAAV. Preferably, the phagemid viral particle according to the eighth aspect, or the system according to the nineteenth aspect is used in cis and/or trans together with the delivery and/or presence of other genetic elements required for the production of mammalian viruses, as determined by the phagemid particle's genome, inside the eukaryotic host cell. The method used to assist or enhance gene transfer to the host cell by the phagemid particle includes those described in WO 2014/184528 (i.e. multifunctional) and WO 2014/184529 (i.e. combination with a cationic polymer to form a complex having a net positive charge).

The eukaryotic host cell may be mammalian. The host cell may comprise or be derived from Human Embryonic Kidney Cells (HEK293), *Spodoptera frugiperda* pupal ovarian tissue (Sf9), or Chinese Hamster Ovary (CHO). Insect cells are also envisaged.

In one example, the host cell may be transformed with one or more phagemid particle genome carrying genes selected from the group consisting of: rAAV, lentivirus, capsid, replication, helper protein encoding genes, and any other genes required for the expression and packaging of mammalian viruses.

For example, in hybrid phagemid particle-guided rAAV production, the rAAV gene may be carried by the recombinant phagemid viral particle according to the eighth aspect, as shown in FIG. 3, and the adenohelper and rep-cap genes may be carried on separate vectors, or be integrated into the eukaryotic host genome. For example, FIG. 12 shows the adenohelper genes on one vector, and FIG. 13 shows the rep-cap on a separate vector. Any combinations of the rAAV, rep-cap and adenohelper genes may be carried on one or more vectors, i.e. in cis or trans configurations. Alternatively, rep-cap or adenohelper proteins, in the context of rAAV production, could also be integrated or introduced into the eukaryotic host as a stably expressed accessory DNA (e.g. a plasmid), whereby the hybrid phagemid particle supplies the recombinant viral genome for packaging into a recombinant virus, as determined by the transgene cassette inside the phagemid particle's genome.

In one preferred embodiment, rAAV, rep-cap and adenohelper genes are carried on a single vector, as shown in FIGS. 14 and 15. The inventors believe that this is the first time that all three sets of genes have been harboured on the same vector.

Hence, in a twenty-sixth aspect, there is provided a recombinant vector comprising rAAV, rep-cap, adenohelper genes, and a nucleic acid sequence encoding one or more cytokine, or one or more antigen for recognition by one or more adoptively transferred T cell, for use in the treatment, prevention, or amelioration of cancer.

The recombinant vector can be for any use or method disclosed herein.

In a twenty-seventh aspect, there is provided a recombinant phagemid particle comprising the vector of the twelfth aspect, for use in a method for the treatment, prevention, or amelioration of cancer.

The recombinant phagemid particle can be for any use or method disclosed herein.

There is provided use of the vector according to the twenty-sixth aspect or the particle of the twenty-seventh aspect, to produce a recombinant AAV viral vector comprising or derived from the viral genome of the phagemid particle.

There is provided a method for producing recombinant AAV viral vector, the method comprising introducing into, a eukaryotic host cell, the vector according to the twenty-sixth aspect or the particle of the twenty-seventh aspect, and allowing the host cell to produce recombinant viral vector.

When introduced into the same eukaryotic host cell (see FIGS. 11 and 14), the rep-cap and adenohelper genes on the vector behave as trans-acting or cis-acting or a combination of both elements that facilitate packaging of the rAAV genome in the AAV virus capsid, in the context of rAAV production. This production process is comparable to transient co-transfection of multiple plasmids, and usually involving three plasmids. However, in this embodiment, the plasmids are replaced with the recombinant phagemid particles of the invention, which are targeted to eukaryotic cells (preferably mammalian cells), which also carry the same elements.

The method may be carried out in vivo, in vitro, ex vivo, or in situ. For in situ production, the recombinant phagemid particles preferably comprise a targeting moiety for the target eukaryotic cell that is the designated eukaryotic host. Preferably, in the context of in situ, ex vivo and in vivo virus production, the designated eukaryotic host cell type is a diseased cell. Preferably, the diseased cell is a malignant or benign tumour. In the context of in vitro virus production, preferably the eukaryotic host is a derivative of any of the eukaryotic hosts listed above. The application of the recombinant phagemid particles and genetic elements required for the production of recombinant virus (as determined by the transgene cassette in the hybrid phagemid particle), could be in any fashion as indicated earlier, either in cis-acting or trans-acting combinations, inside the eukaryotic host cell.

In a twenty-eighth aspect, there is provided a recombinant phagemid particle for expressing a transgene in a target tumour cell transduced with the particle, for use in a method for treating, preventing or ameliorating cancer, wherein the phagemid particle comprises at least one transgene expression cassette comprising a nucleic acid sequence encoding one or more cytokine, or antigen recognisable by one or more adoptively transferred T cell, and comprises a genome which lacks at least 50% of its bacteriophage genome, and wherein the method comprises delivering the nucleic acid sequence to at least adjacent to the tumour cell, when the nucleic encodes an one or more antigen, the one or more antigen is expressed, and recognisable by one or more adoptively transferred T cell.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the nucleic acids identified herein.

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating relative percentage identity between two sequences comprises (i) preparing a sequence alignment using the ClustalW program using a suitable set of parameters, for example, as set out above; and (ii) inserting the values of N and T into the following formula:—

$$\text{Sequence Identity} = (N/T)*100.$$

Alternative methods for identifying similar sequences will be known to those skilled in the art. For example, a substantially similar nucleotide sequence will be encoded by a sequence which hybridizes to a nucleic acid sequence described herein, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive. For the avoidance of doubt, reference to cytokine may preferably relate to IL-4, IL-12, IL-15, TNFα, TRAIL, IFN-γ, or any combination thereof. Preferably, the cytokine is IL-15, Preferably, the cytokine is IL-4. Preferably, the cytokine is IL-12. Preferably, the cytokine is TRAIL. Preferably, the cytokine is IFN-γ.

However, in another preferred embodiment, the cytokine is TNFα. Preferably, the cytokine is a hybrid TNFα comprising a non-endogenous signal peptide configured to increase expression and/or secretion of TNFα. Preferably, the signal peptide is a cytokine signal peptide other than that of TNFα. For example, the signal peptide is preferably the IL-2 signal peptide.

For a better understanding of the invention, and to show how embodiments of the same may be carried into effect, reference will now be made, by way of example, to the accompanying Figures, in which:—

FIG. 1 is a table showing features of the phagemid-AAV (PAAV) virus particle according to the invention compared to prior art AAVP virus particles;

FIG. 2 shows schematic illustrations of embodiments of a Helper Phage and a Phagemid genome (PAAV) according to the invention, and a phagemid-AAV (PAAV) particle that is created by the Helper and phagemid. Structural genes are integral to packaging of DNA in to virus particles, and are supplied by the replication Helper phage. The phagemid genome is extremely parasitic to the Helper phage. Ultimately, the PAAV particles are produced at yields that far surpass prior art systems;

Figure 3:
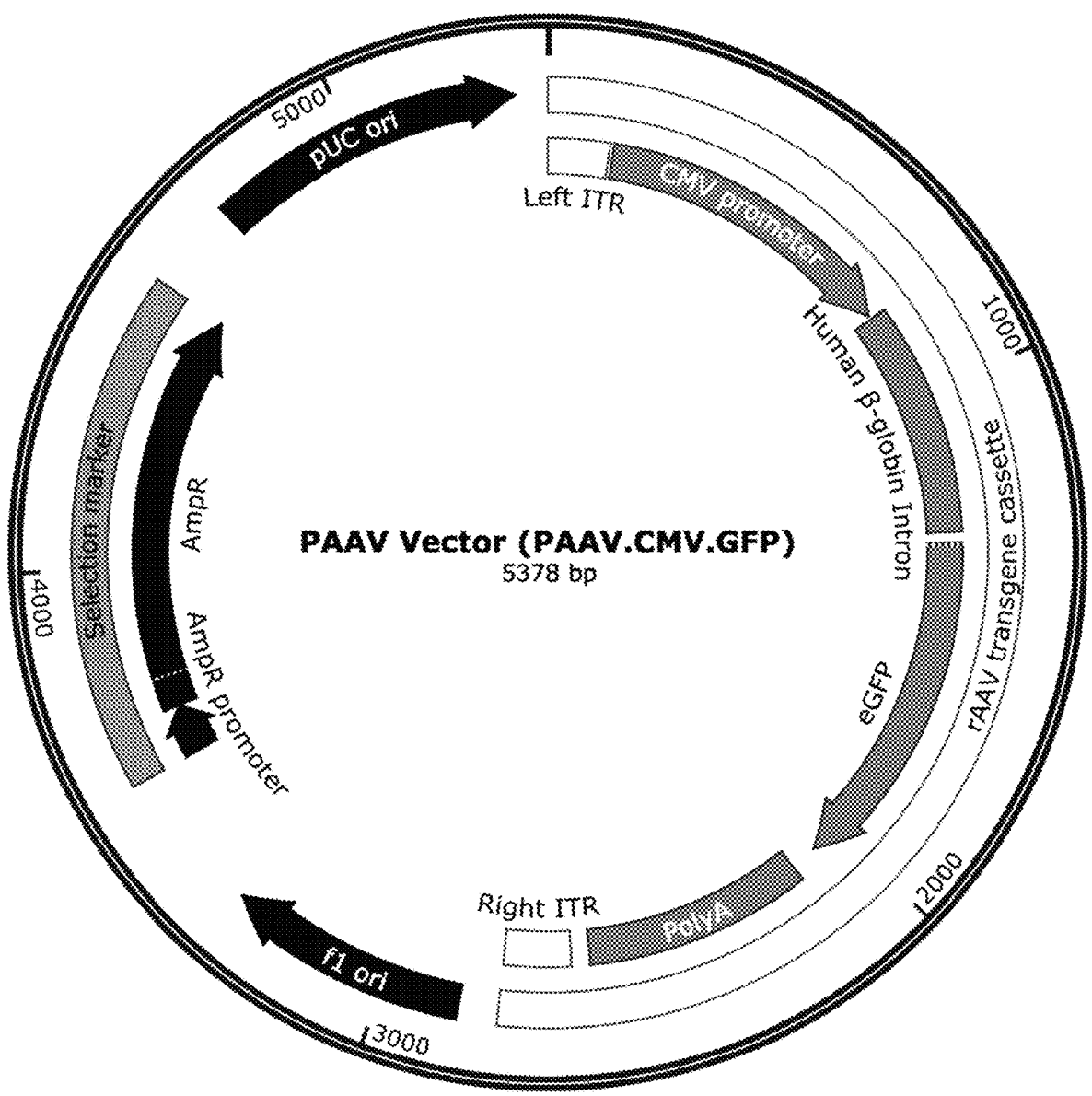
FIG. 3 is a schematic representation of one embodiment of a phagemid genome (PAAV)
Figure 5:
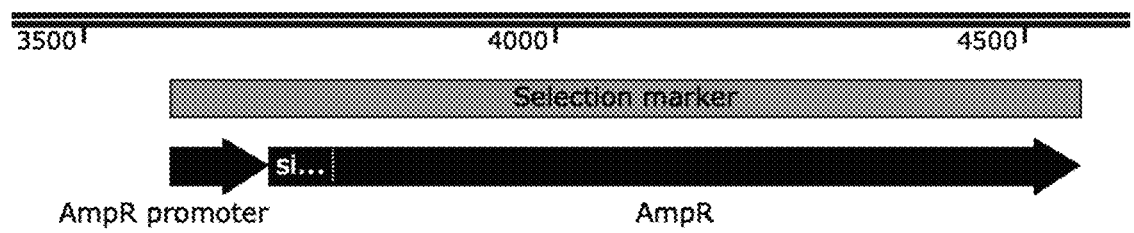
FIG. 5 shows the location of a selection marker gene (AmpR) on a recombinant adeno-associated virus (rAAV) transgene cassette on the phagemid genome shown in FIG. 3.
Figure 6:
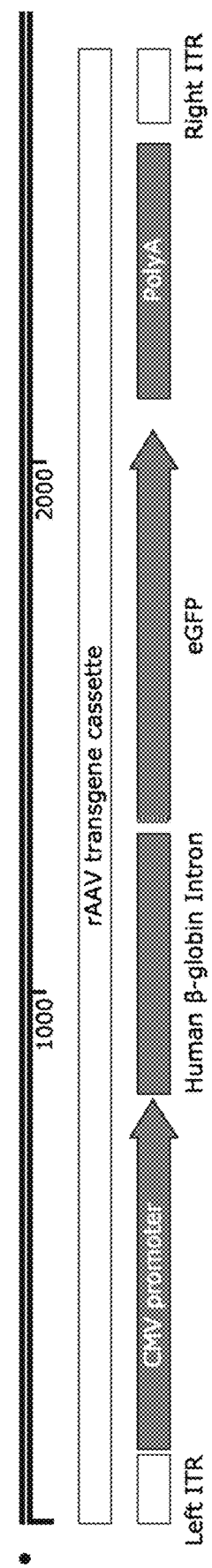
Figure 7:
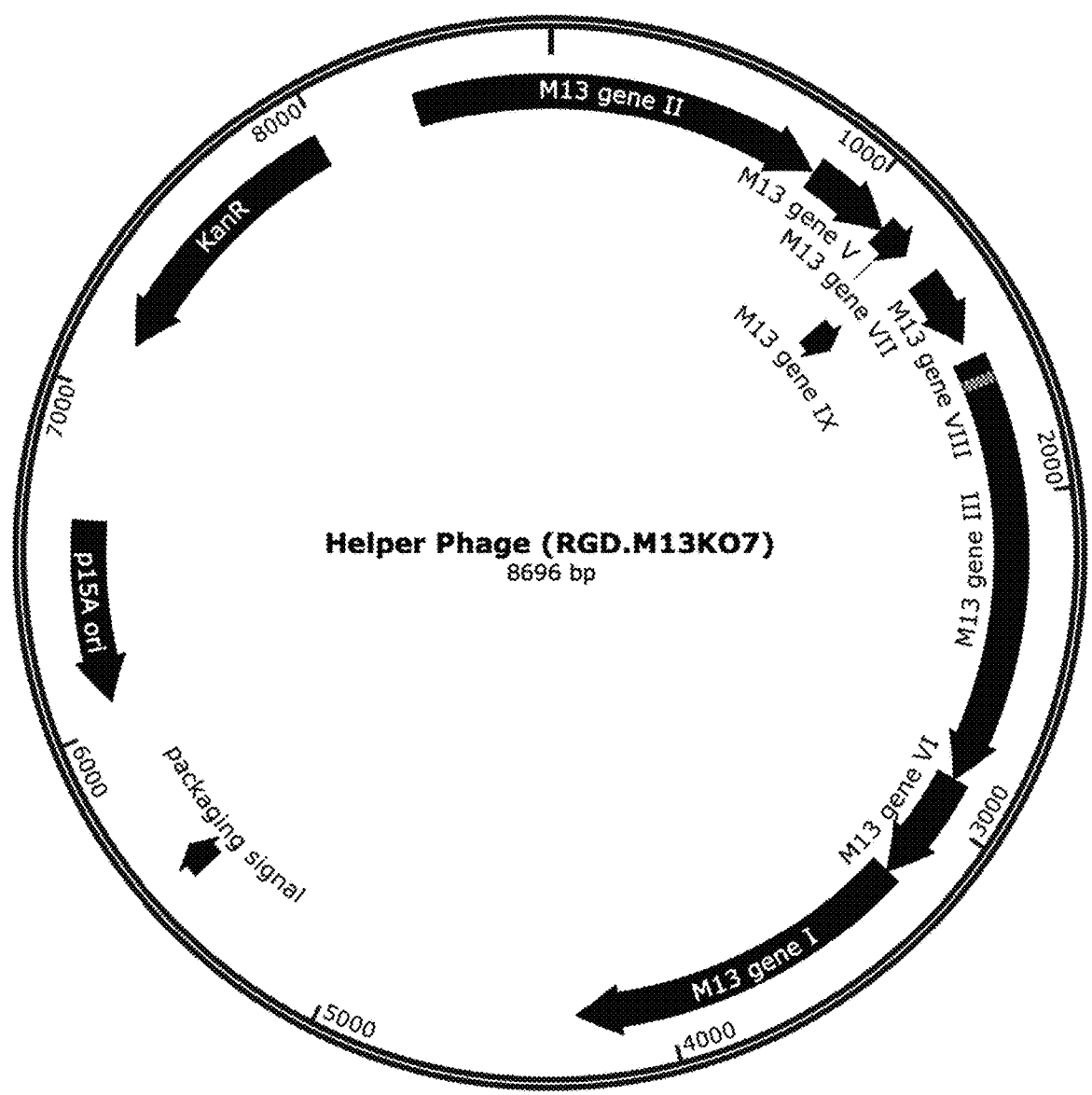
Figure 9:
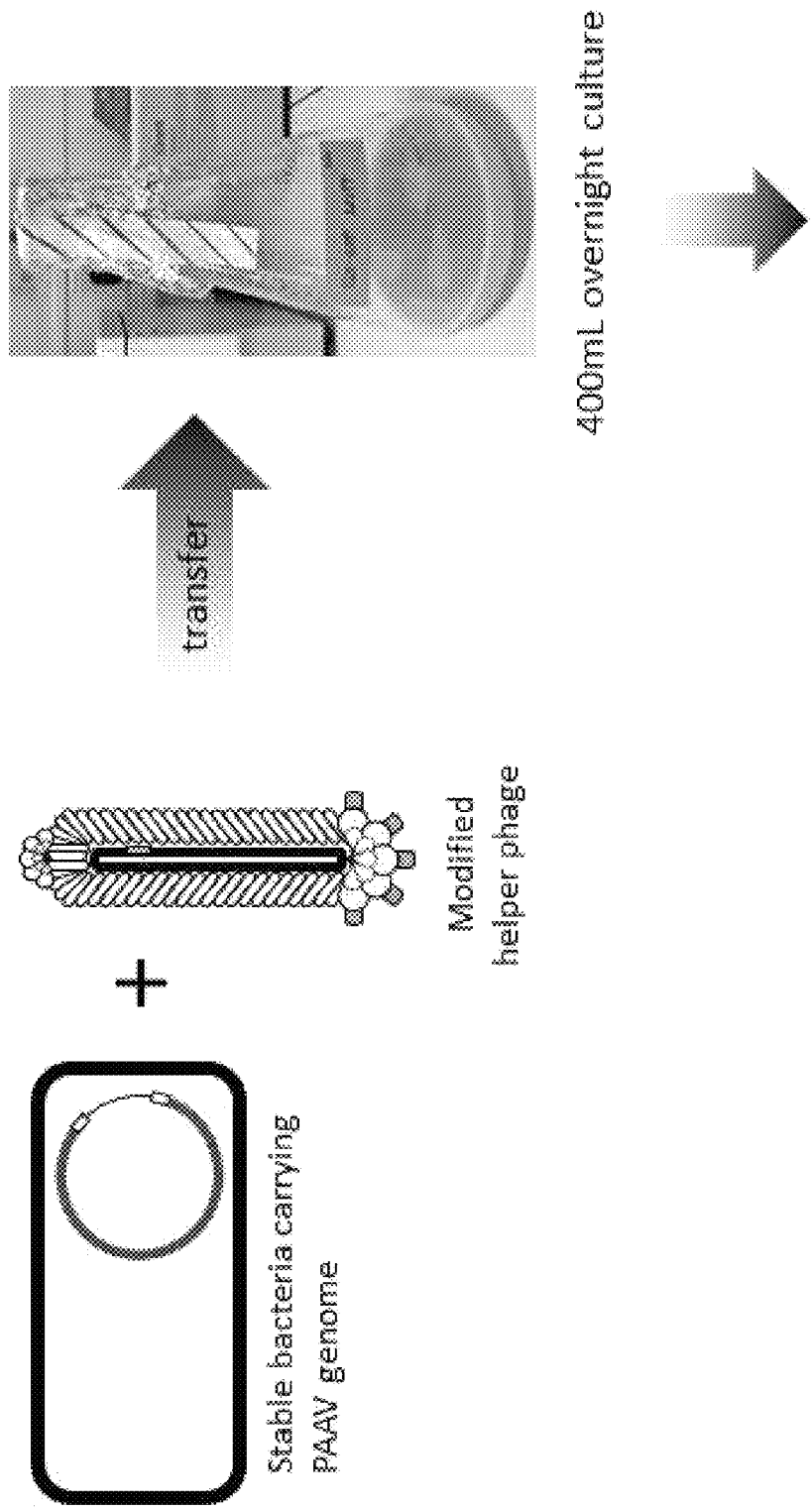
Figure 9:
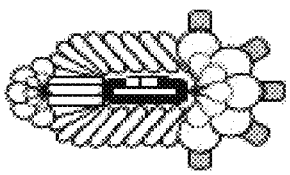
Figure 10:
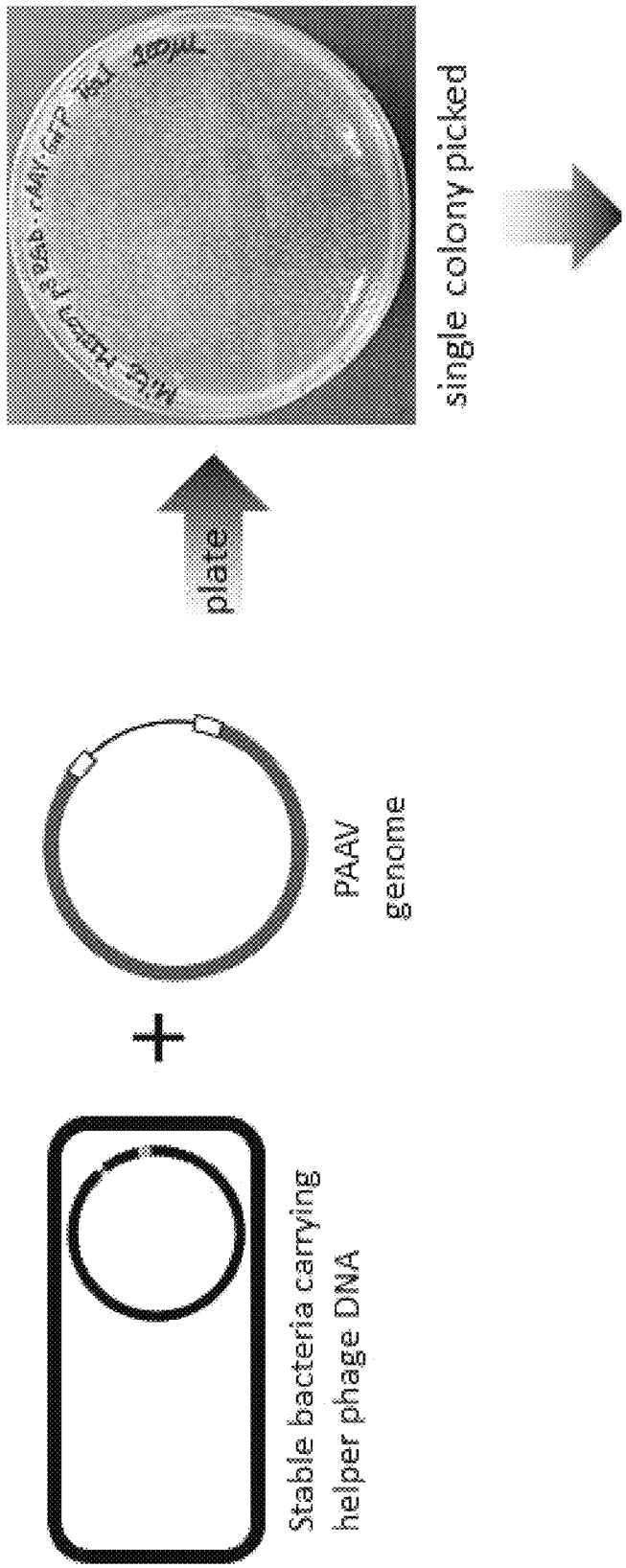
Figure 10:
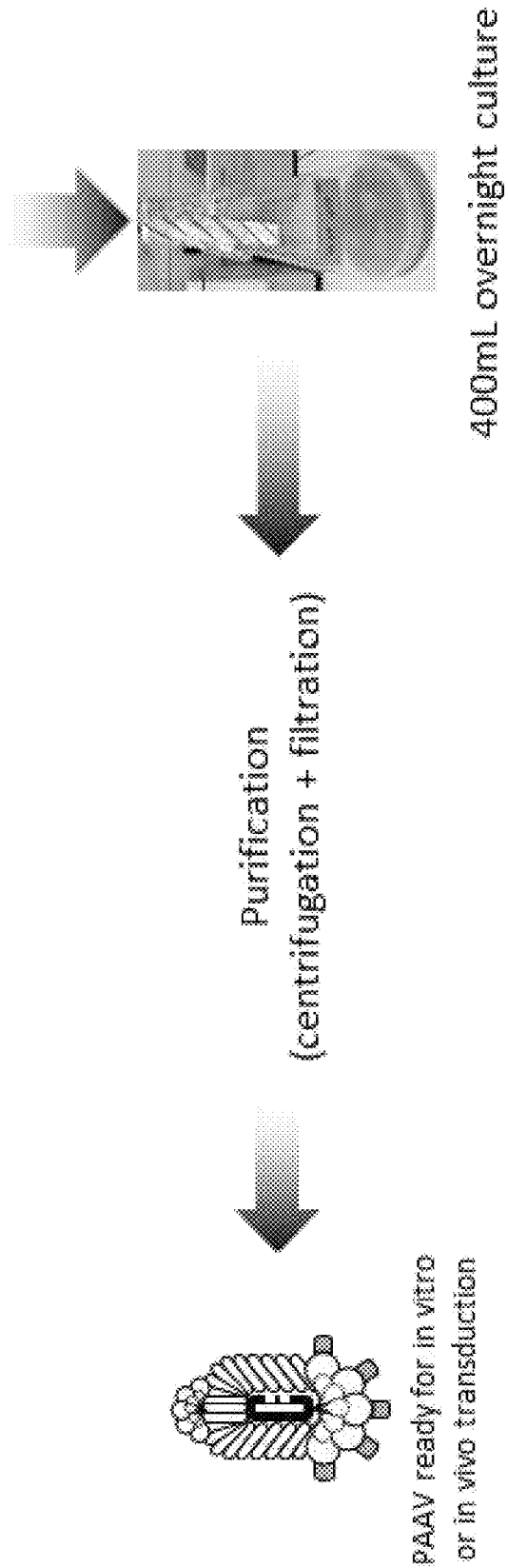
Figure 11:
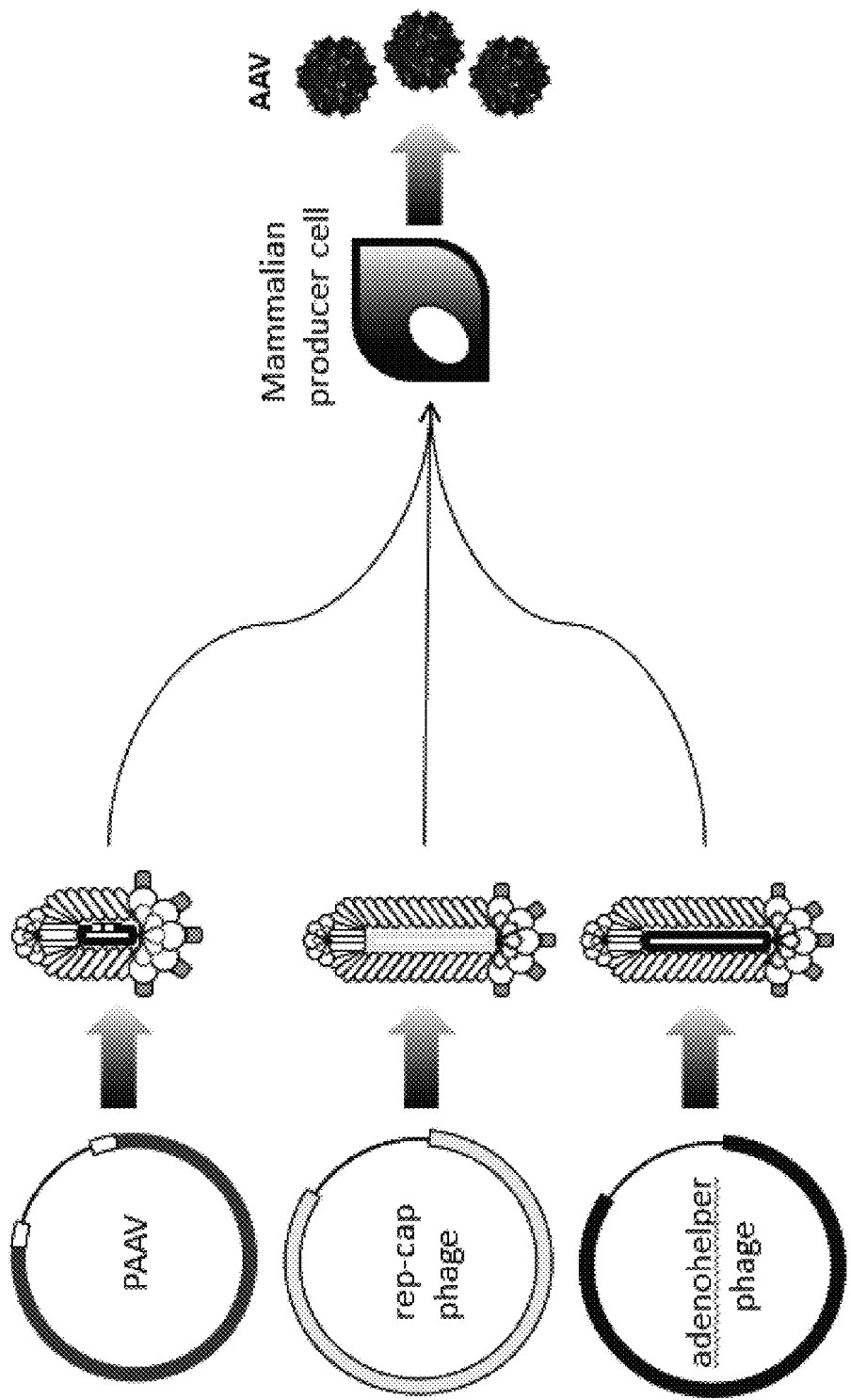
Figure 12:
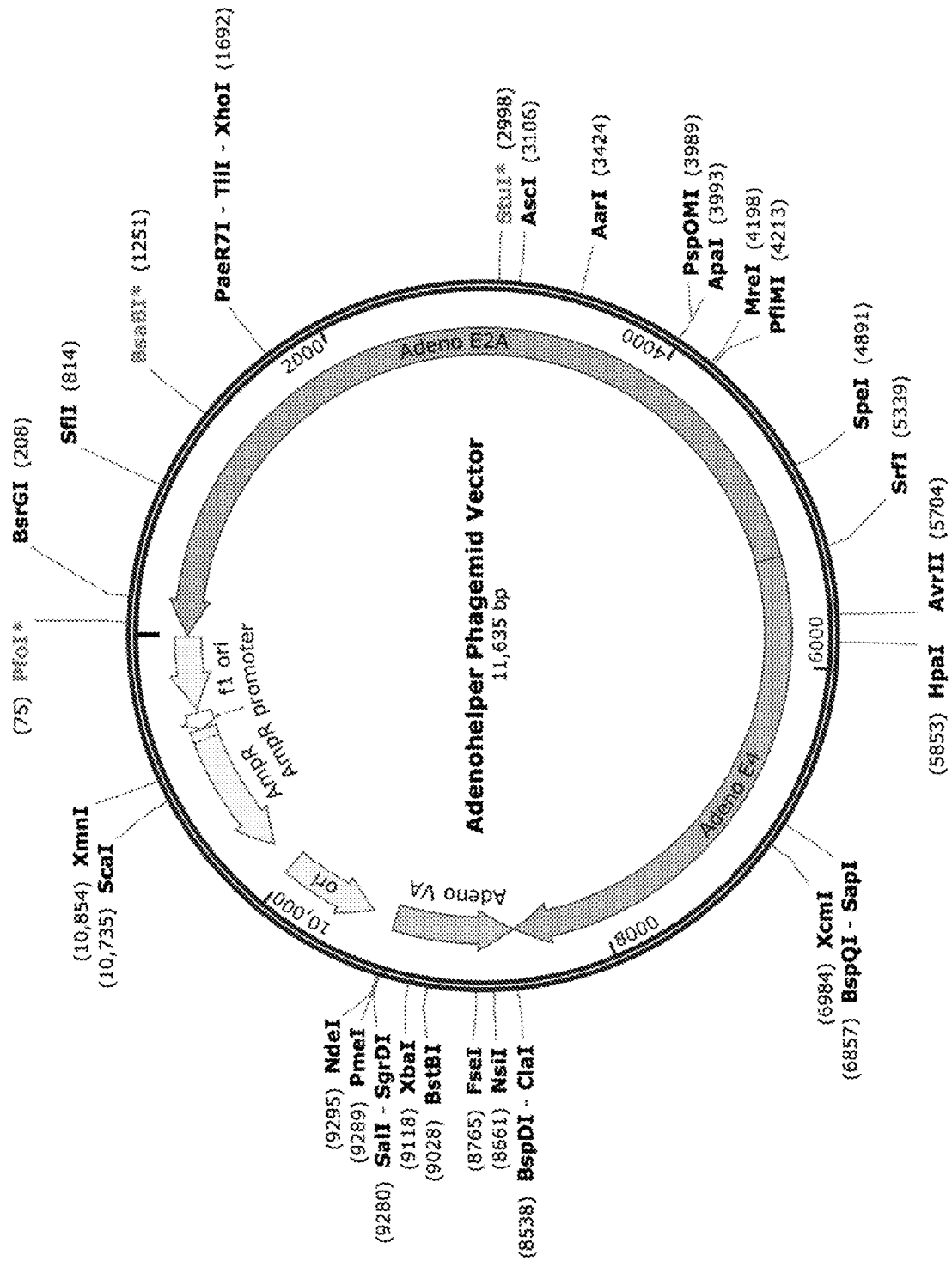
Figure 13:
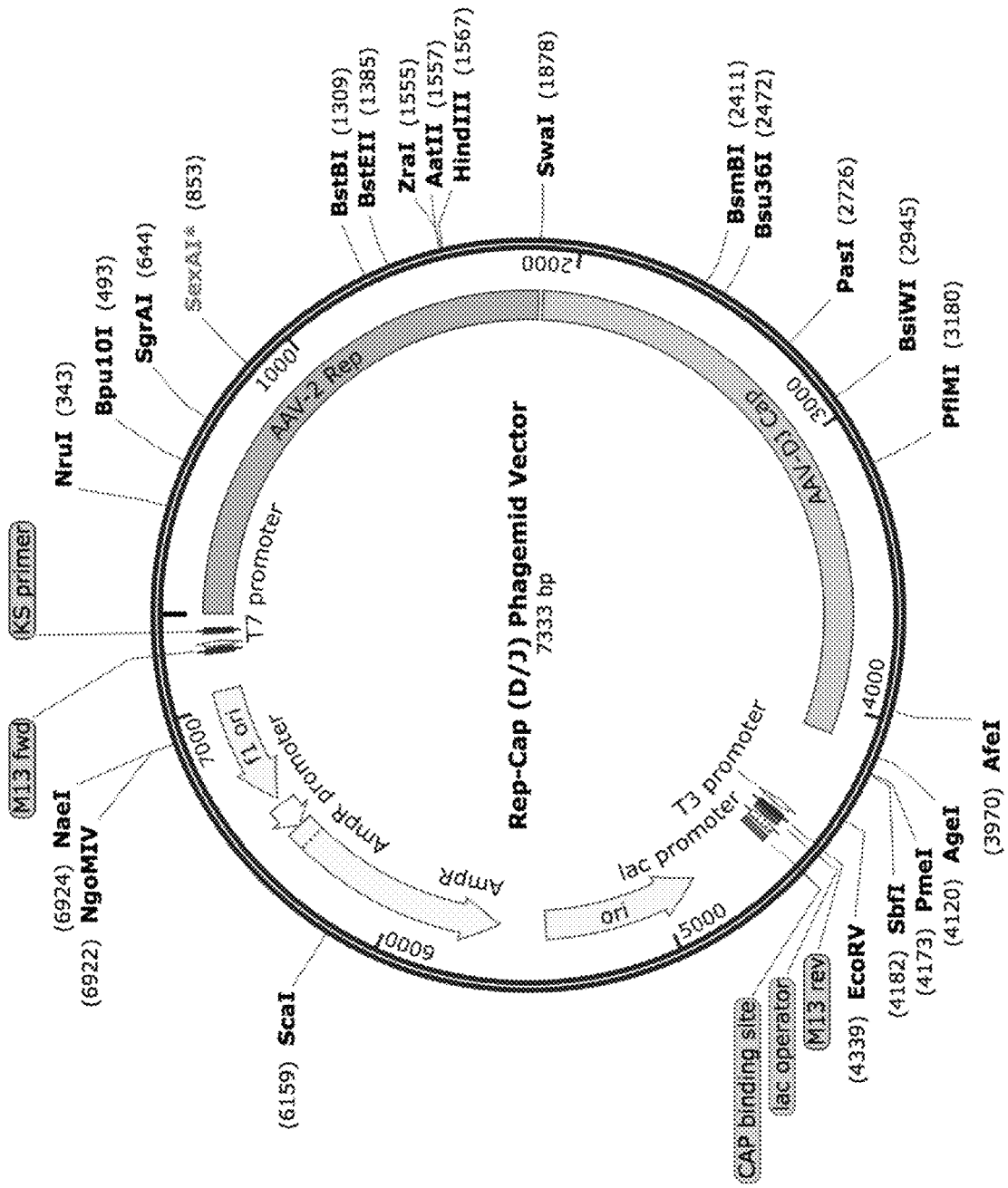
Figure 14:
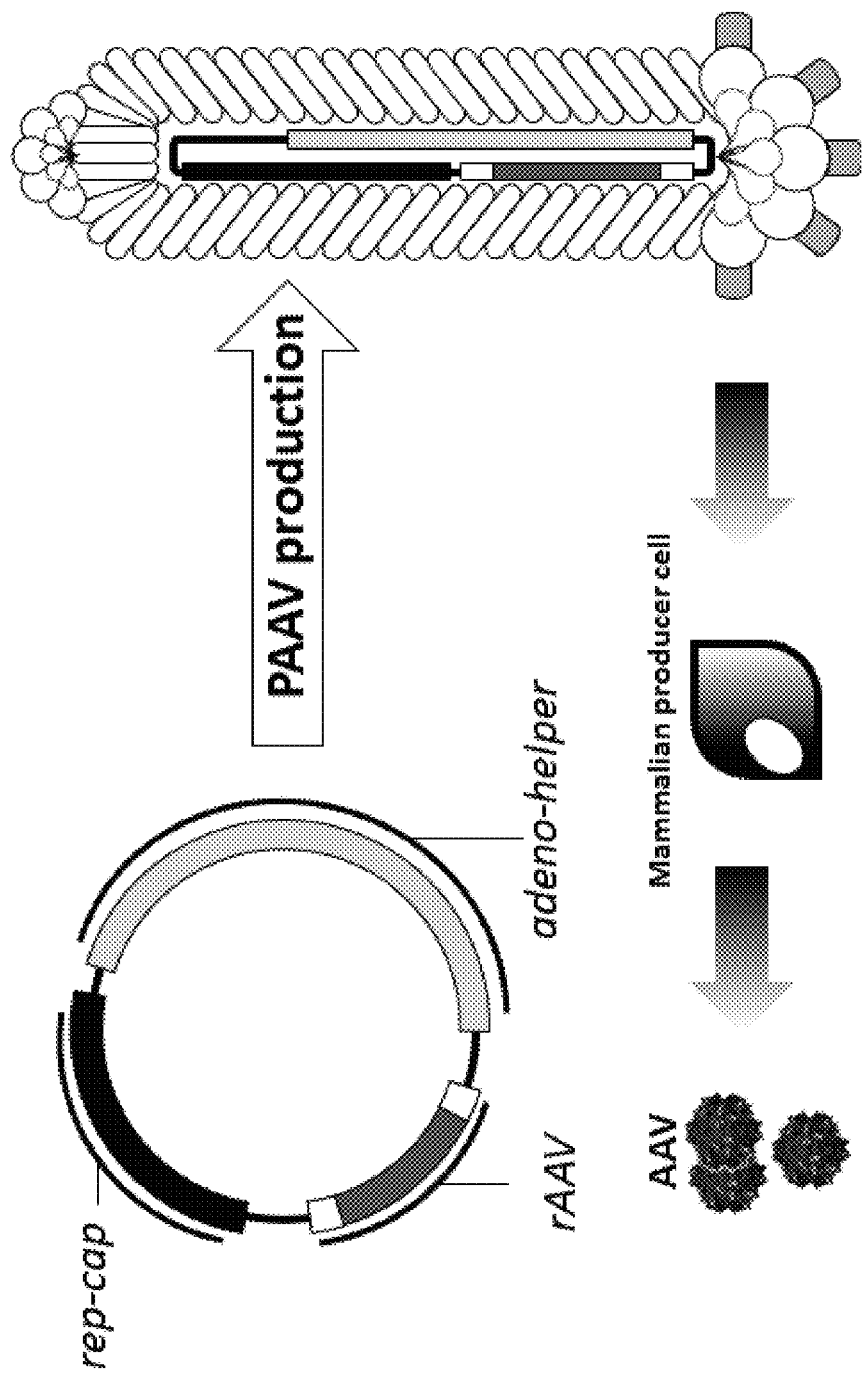
Figure 15:
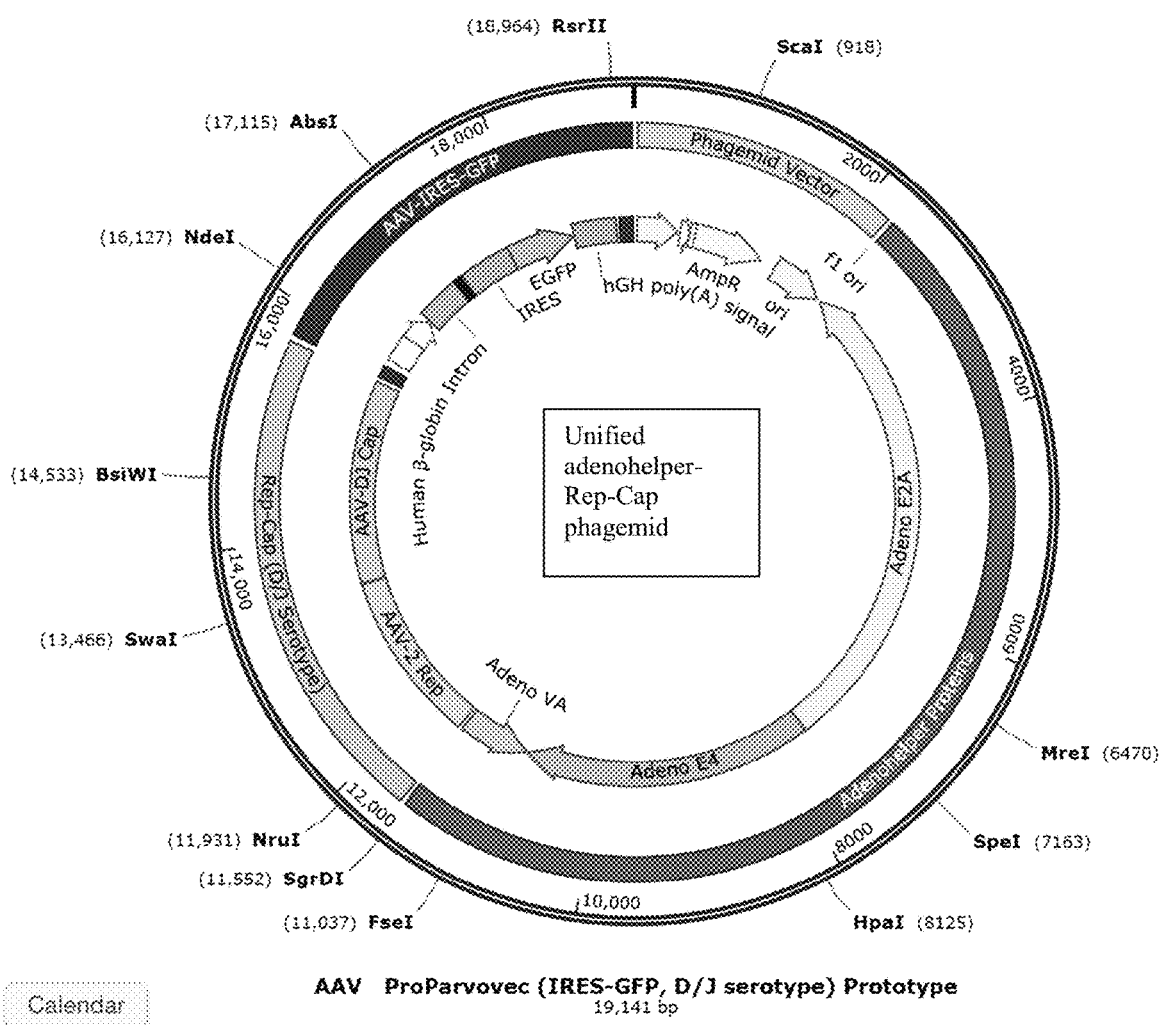
Figure 16:
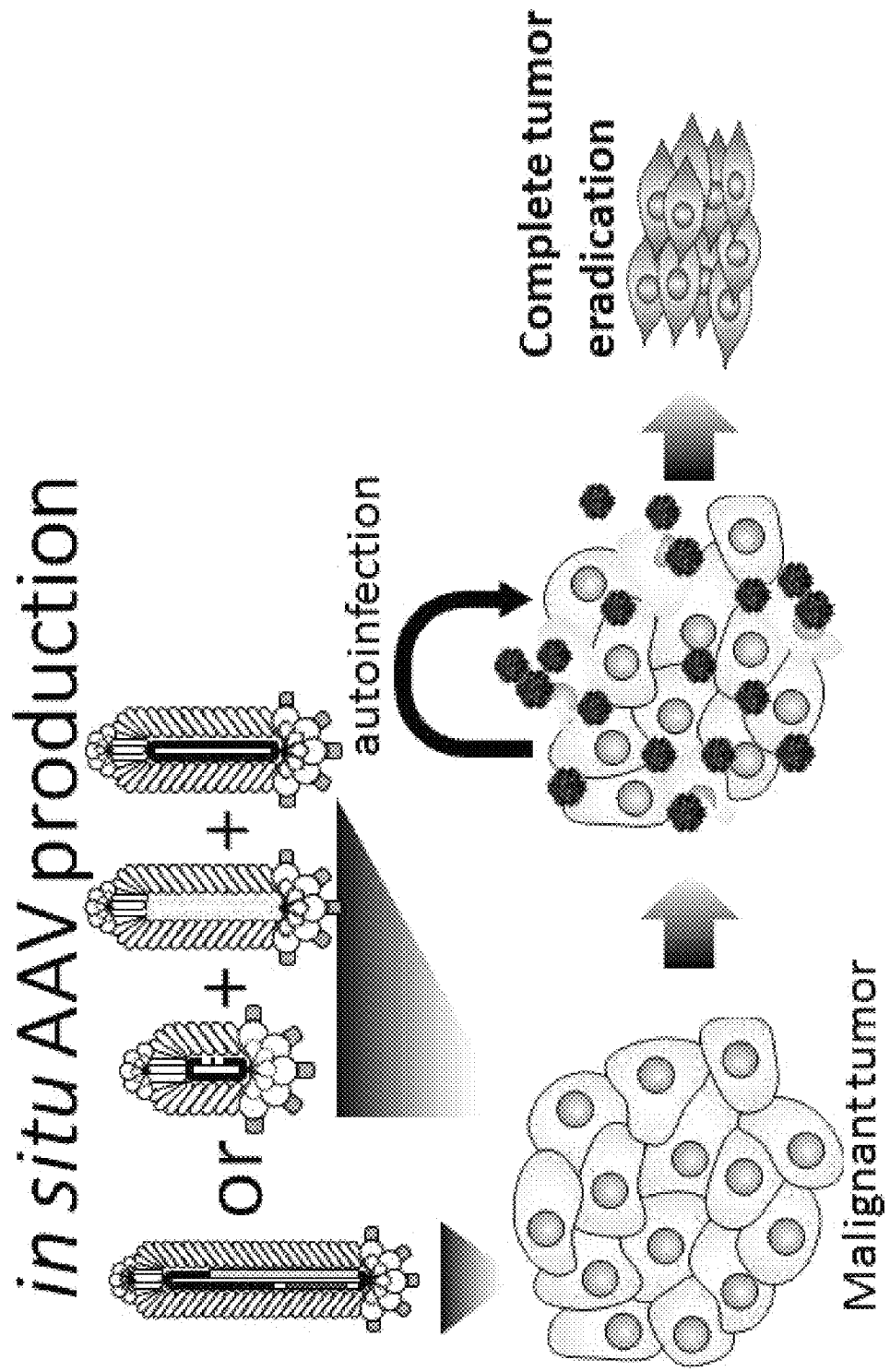
Figure 17:
Figure 18:
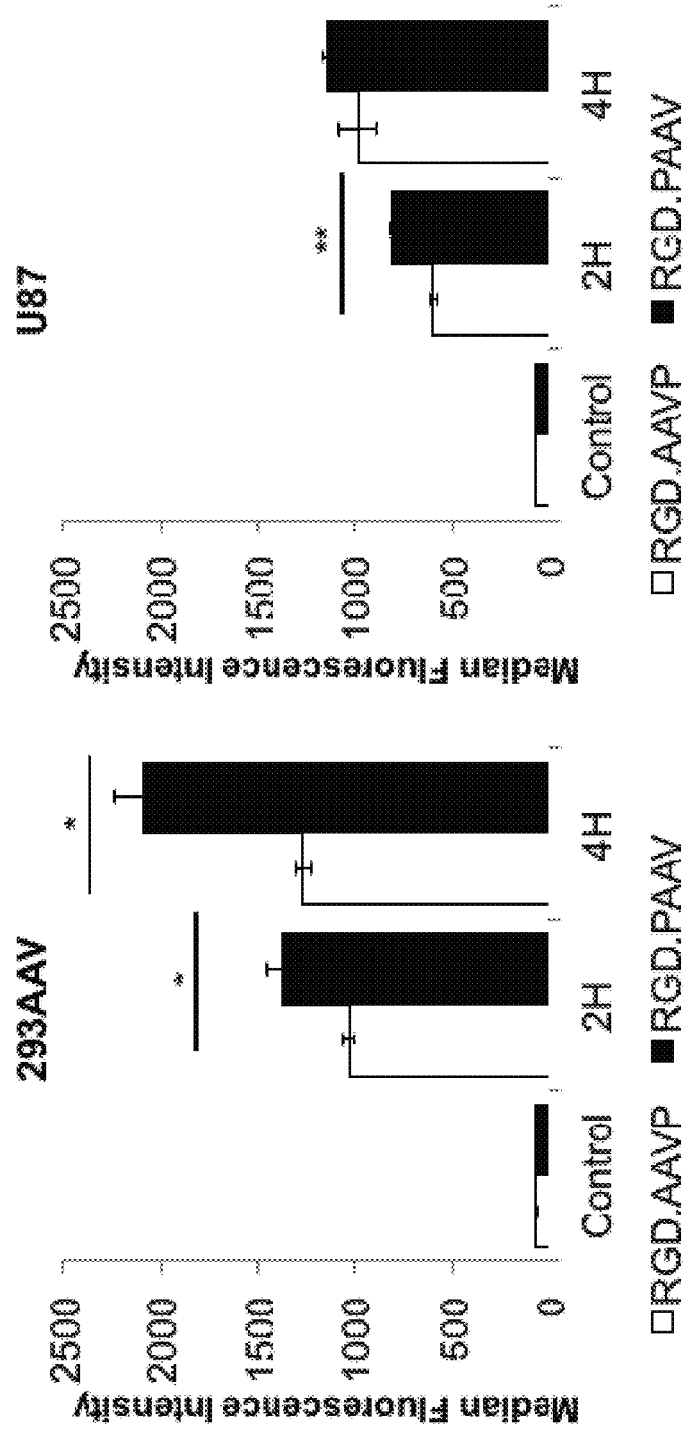
Figure 19:
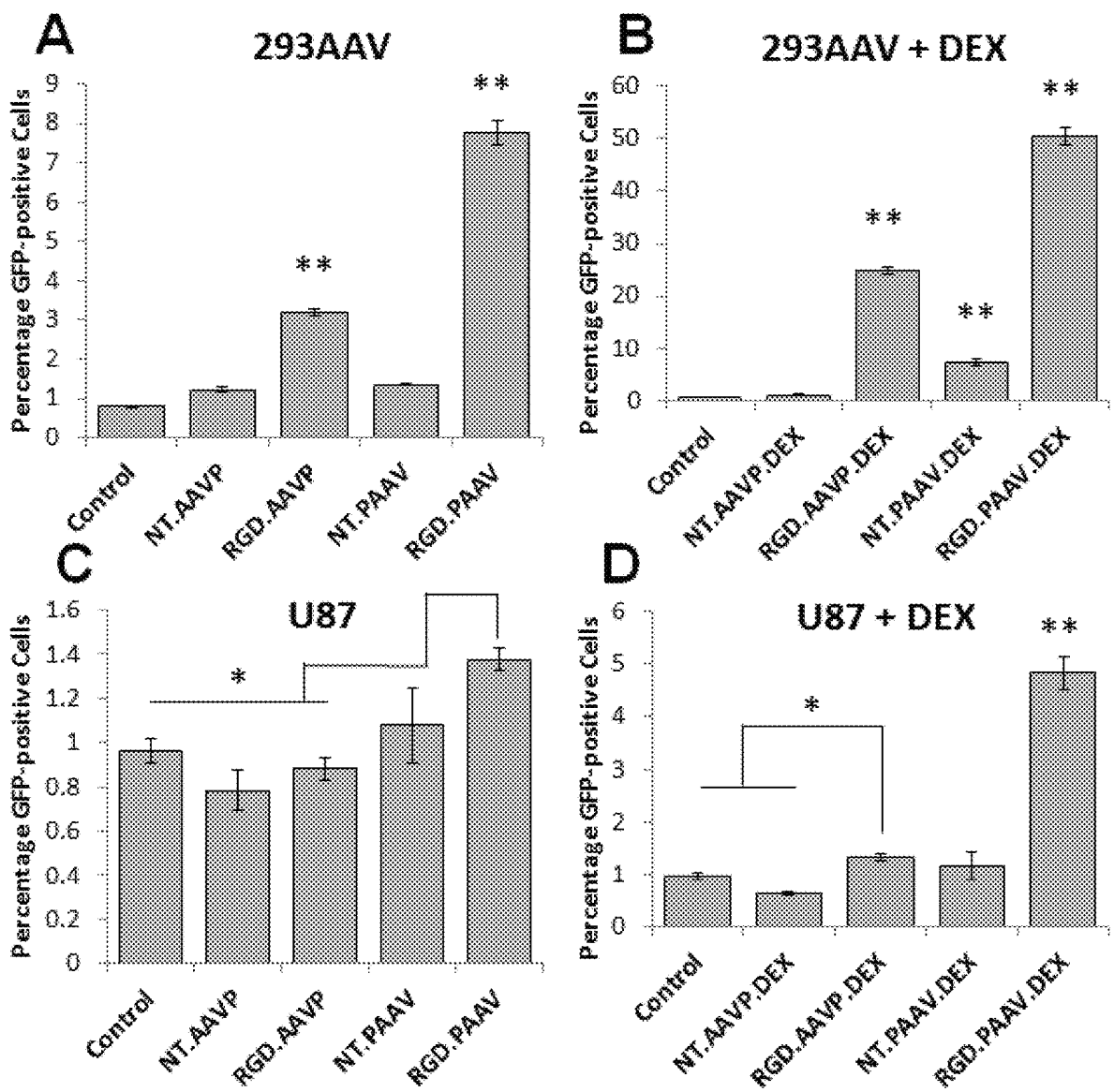
Figure 20:
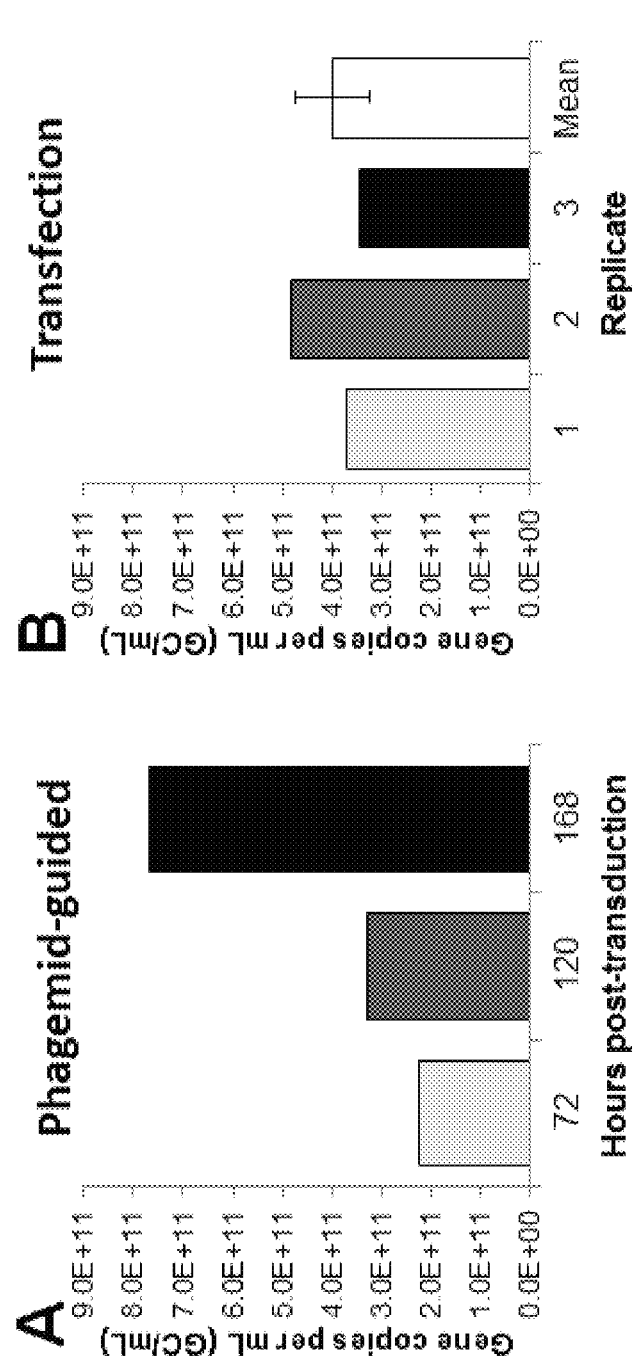
Figure 21:
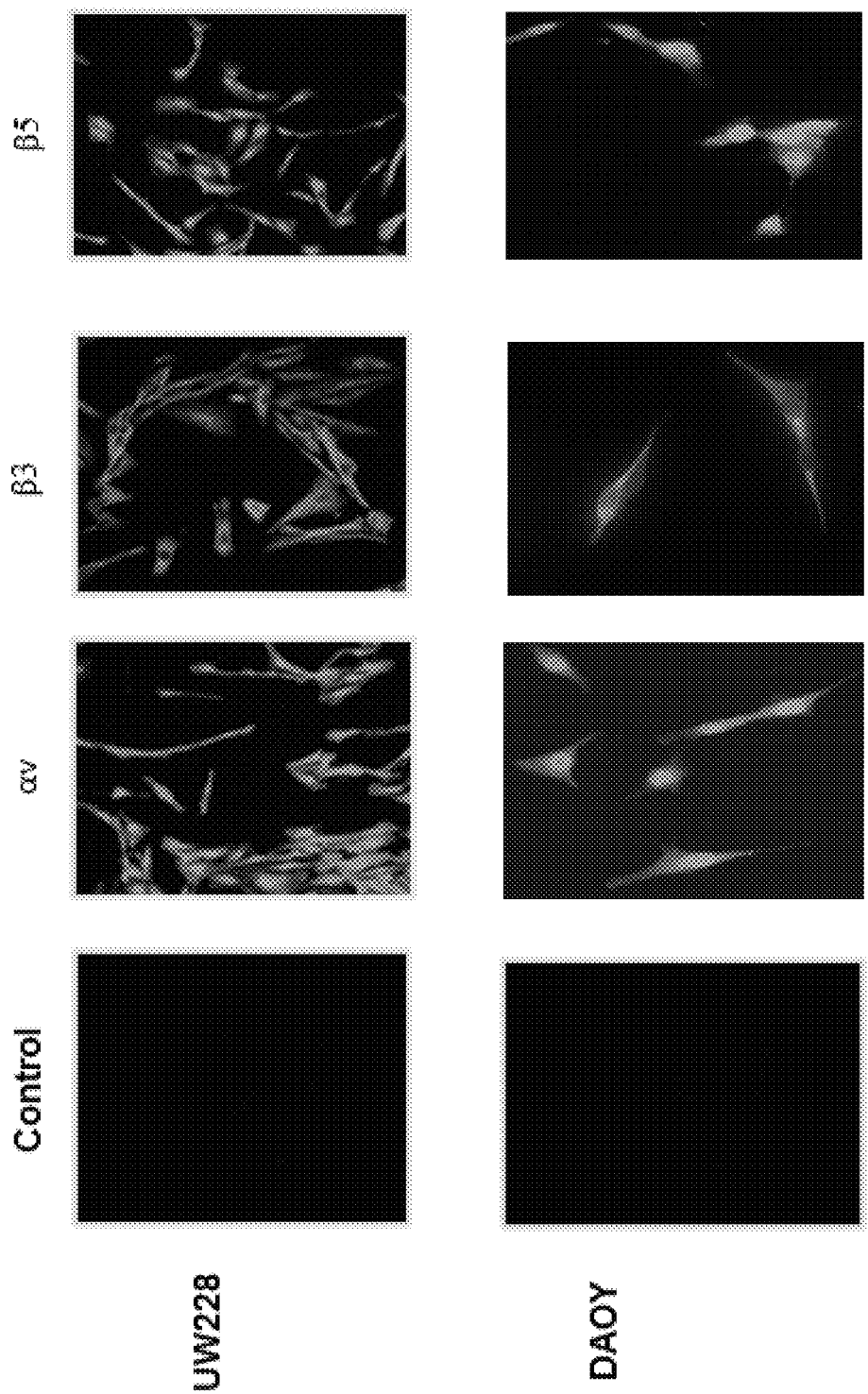
Figure 22:
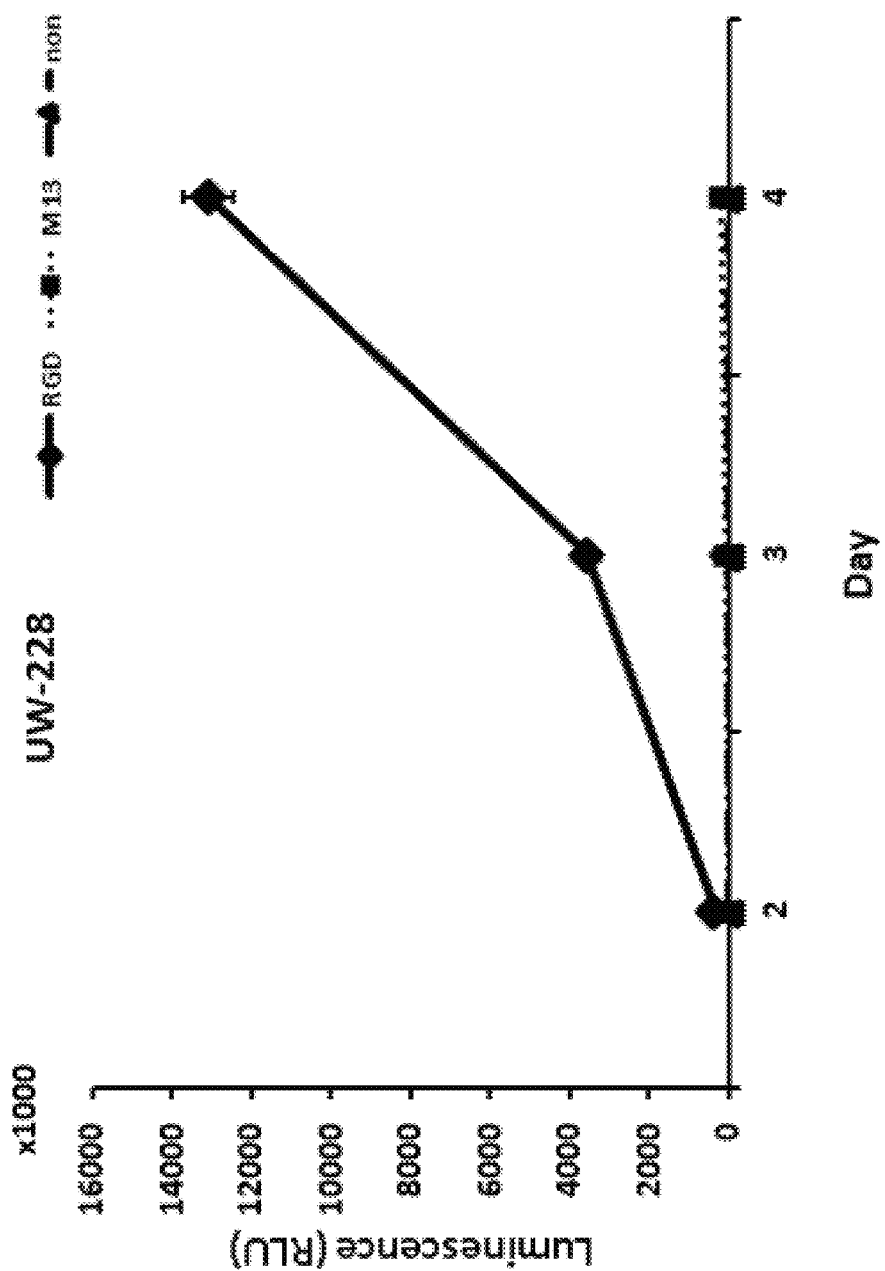
Figure 24:
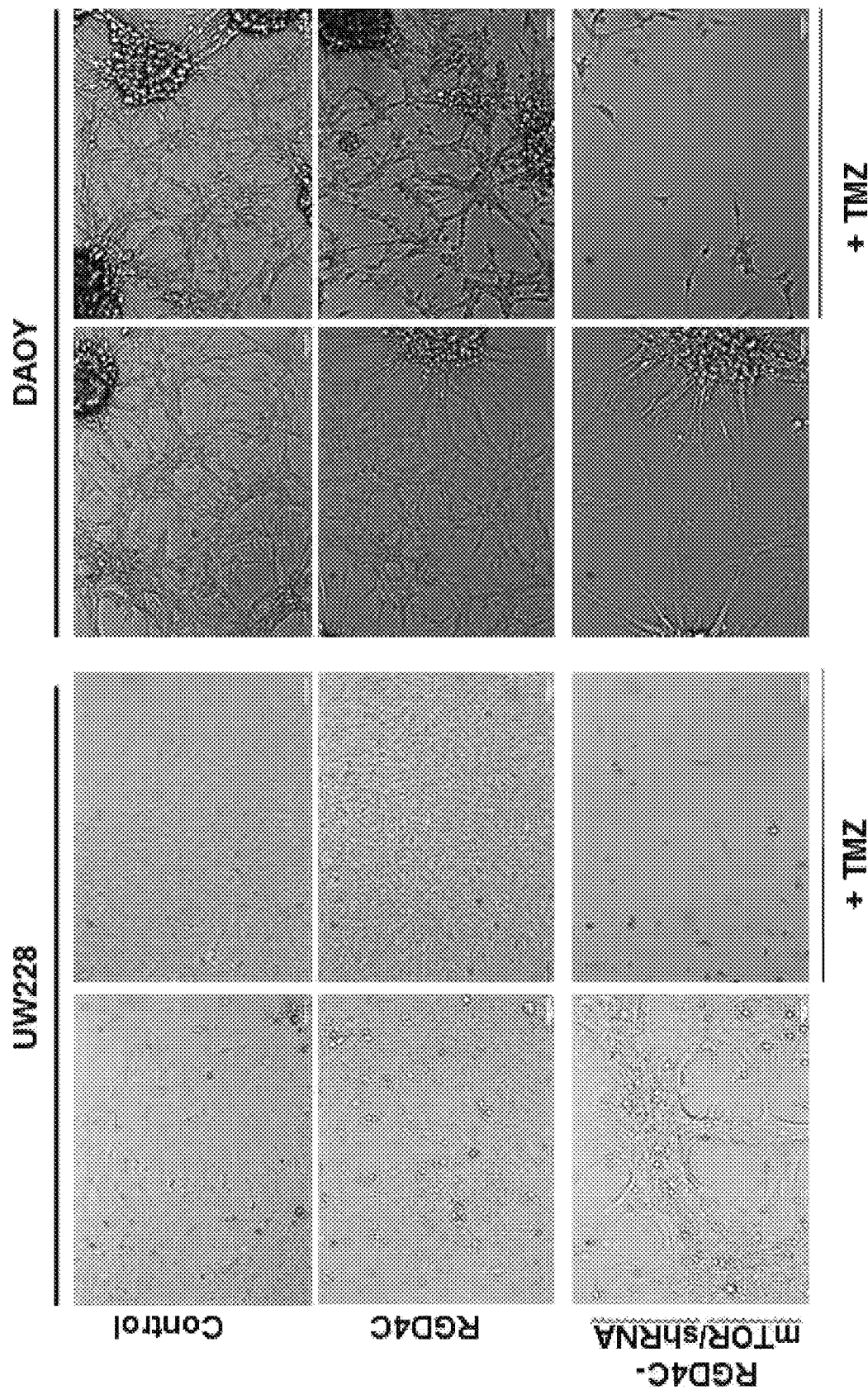
Figure 25:
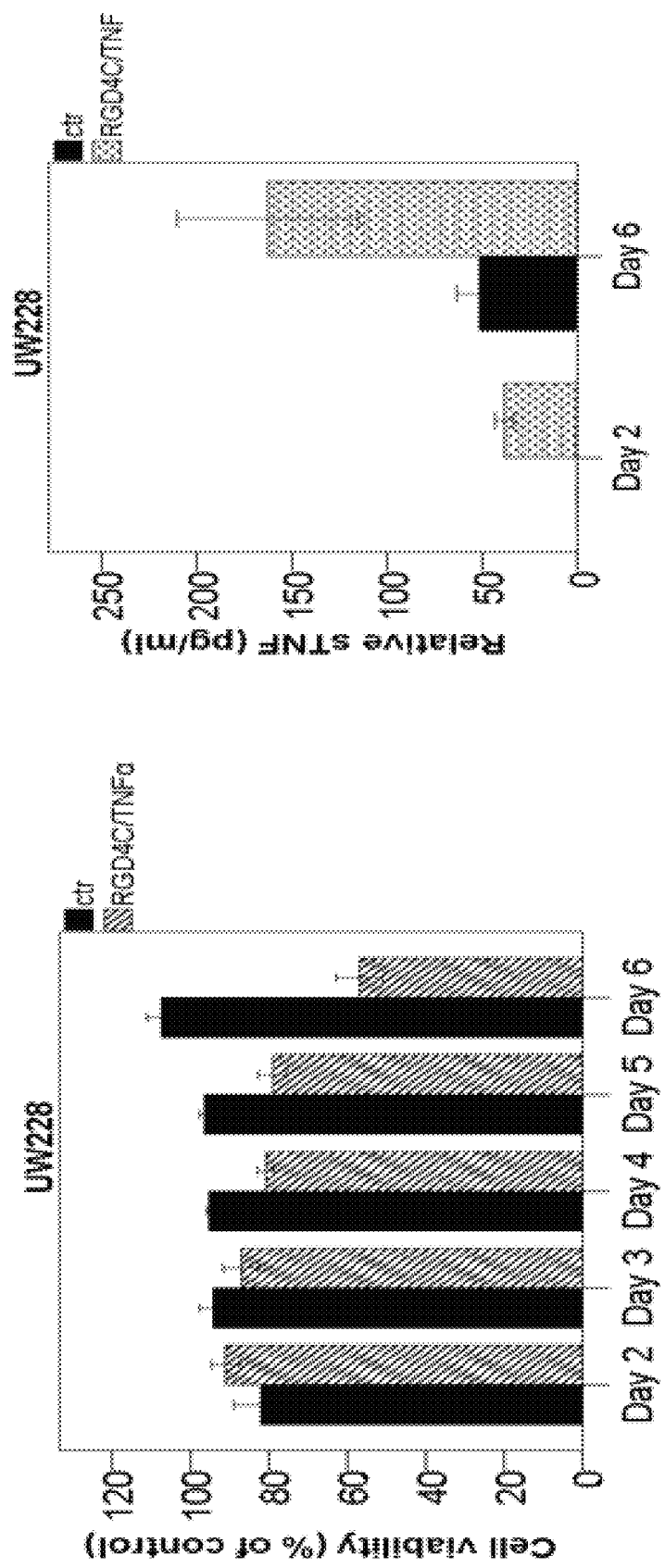
Figure 26:
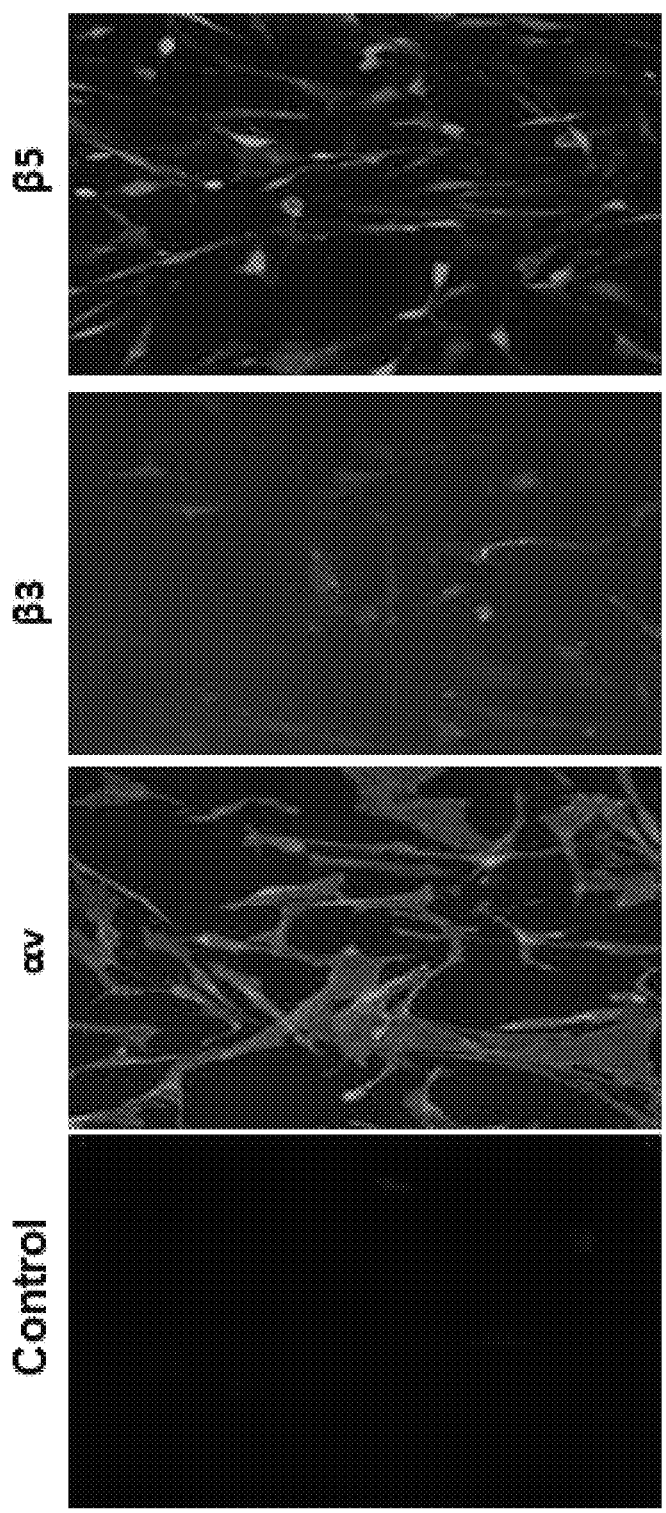
Figure 27B:
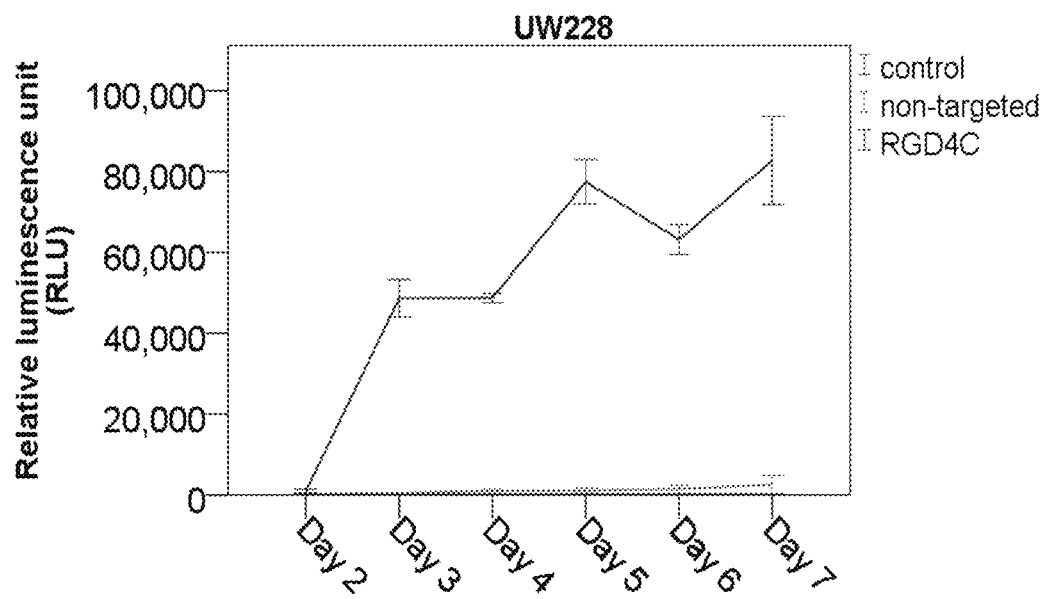
Figure 27C:
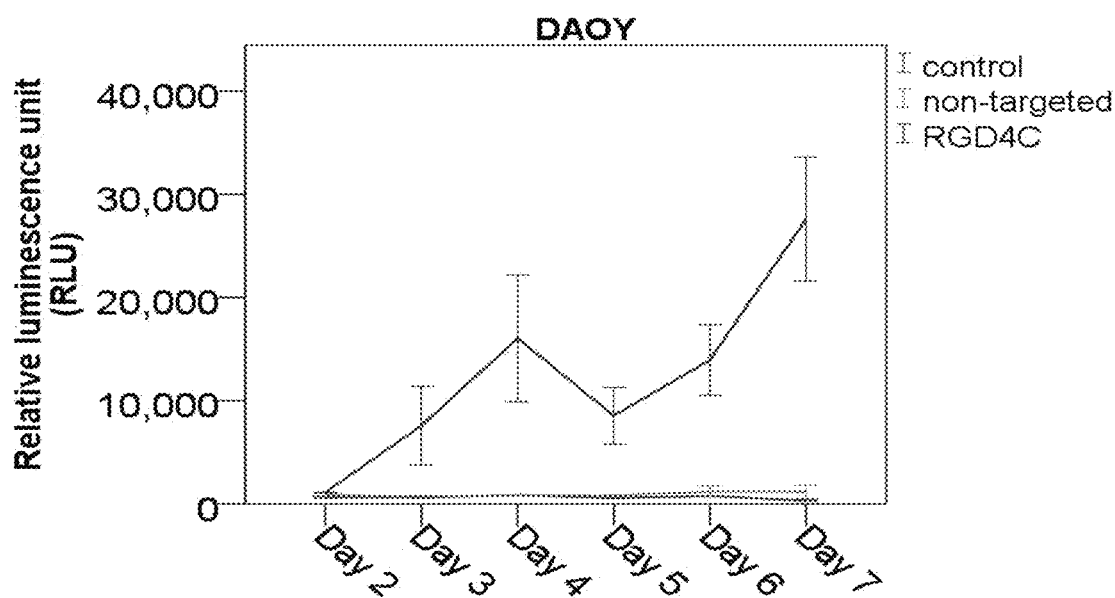
Figure 28:
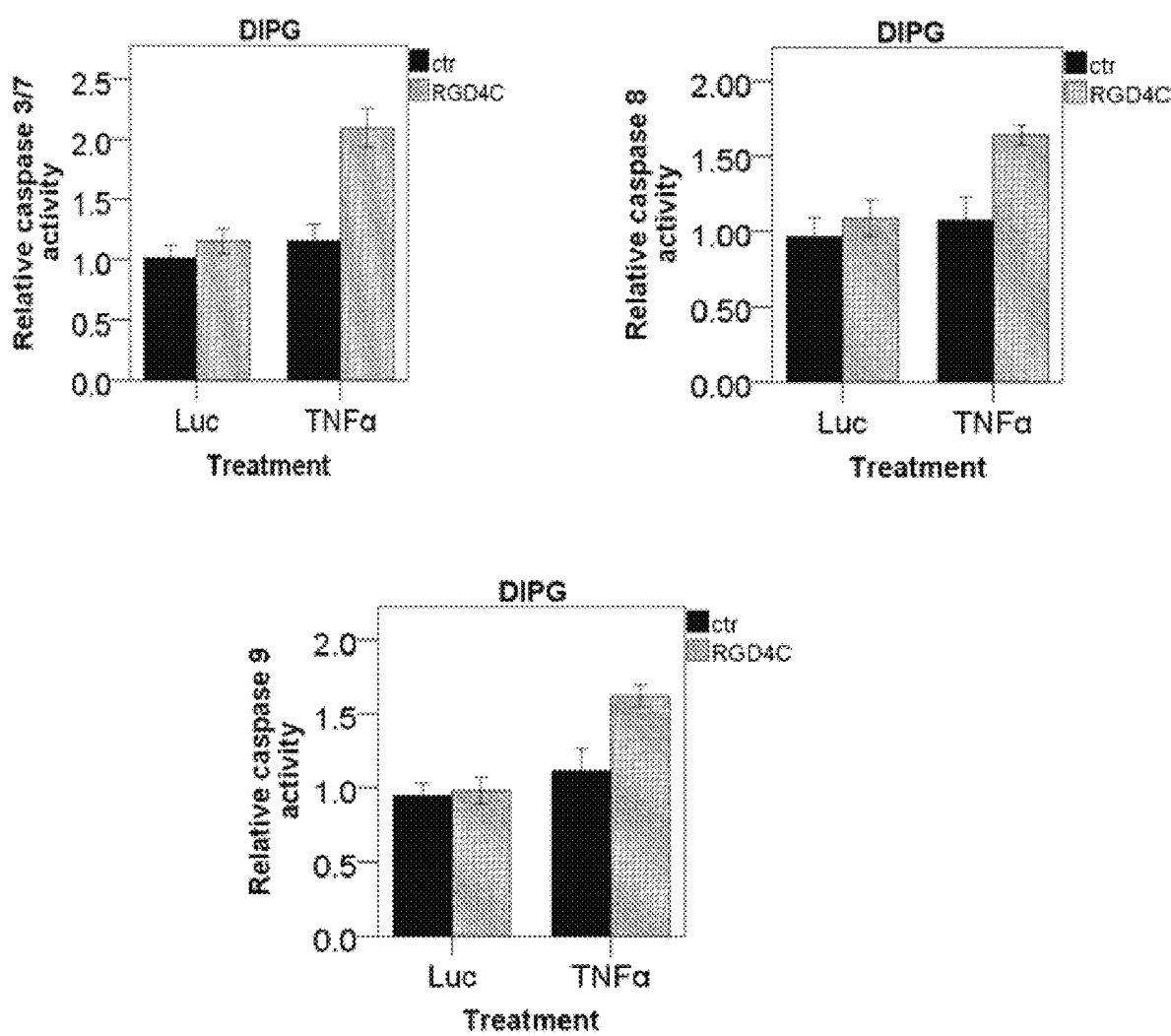
Figure 29:
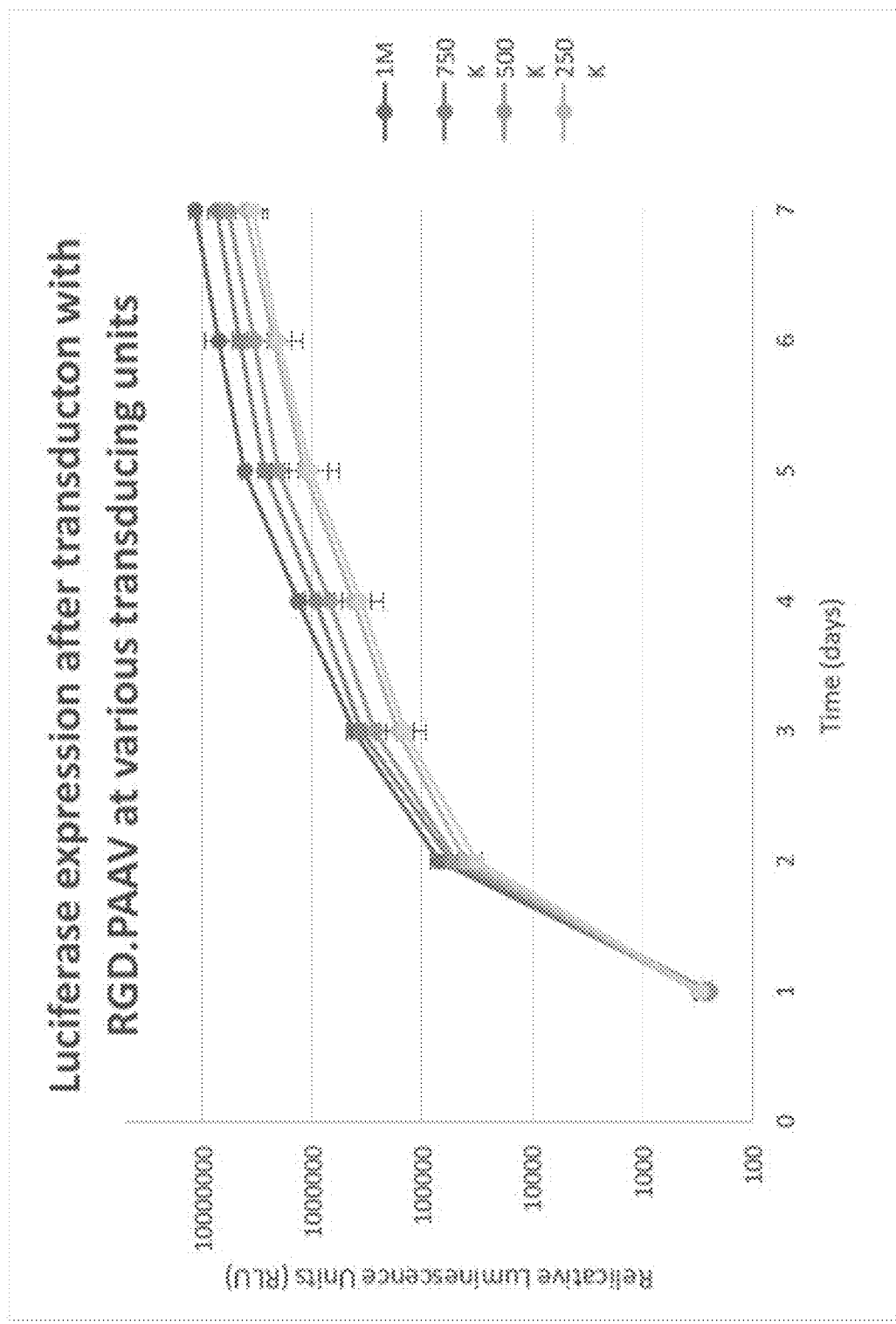
Figure 30:
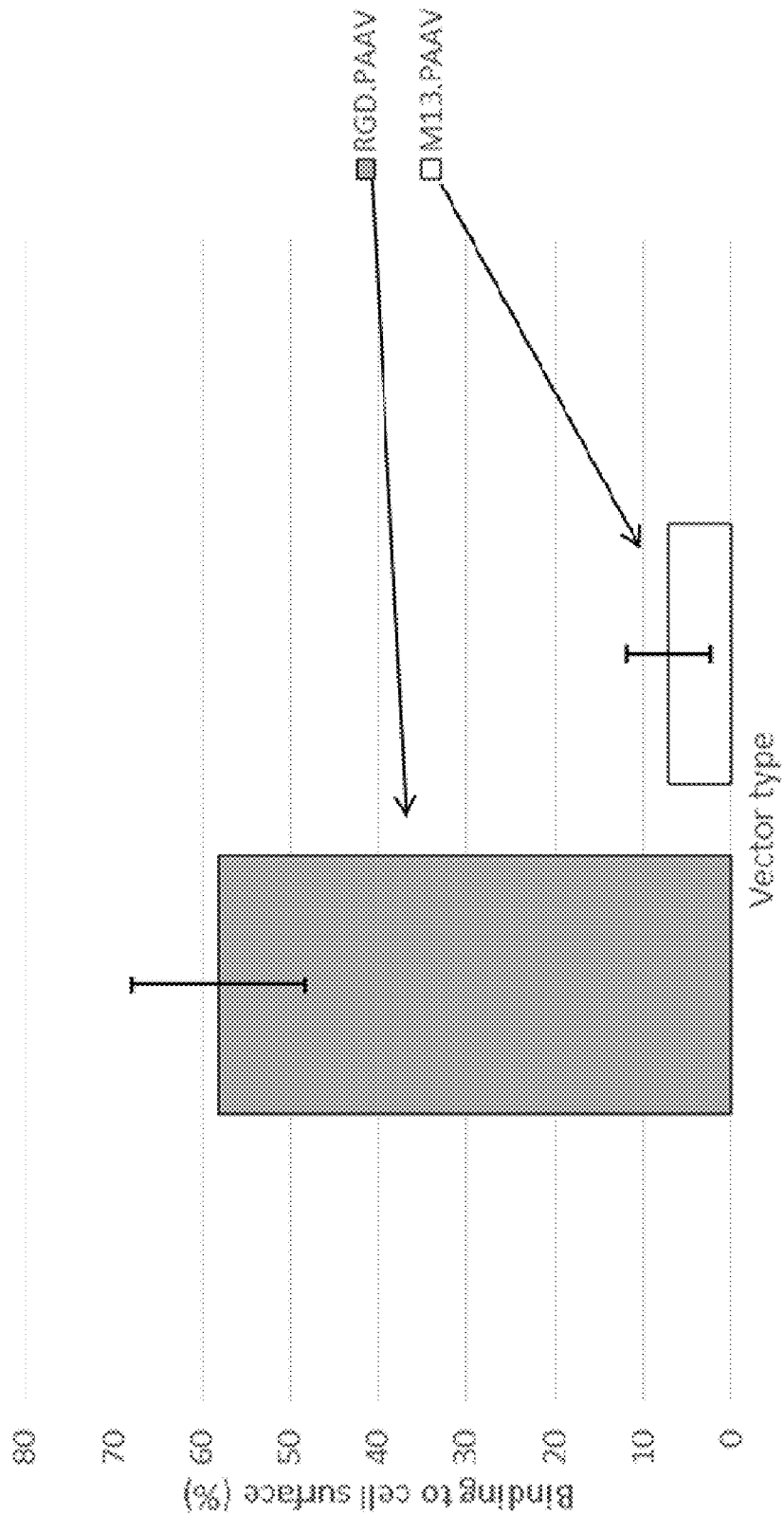
Figure 31A:
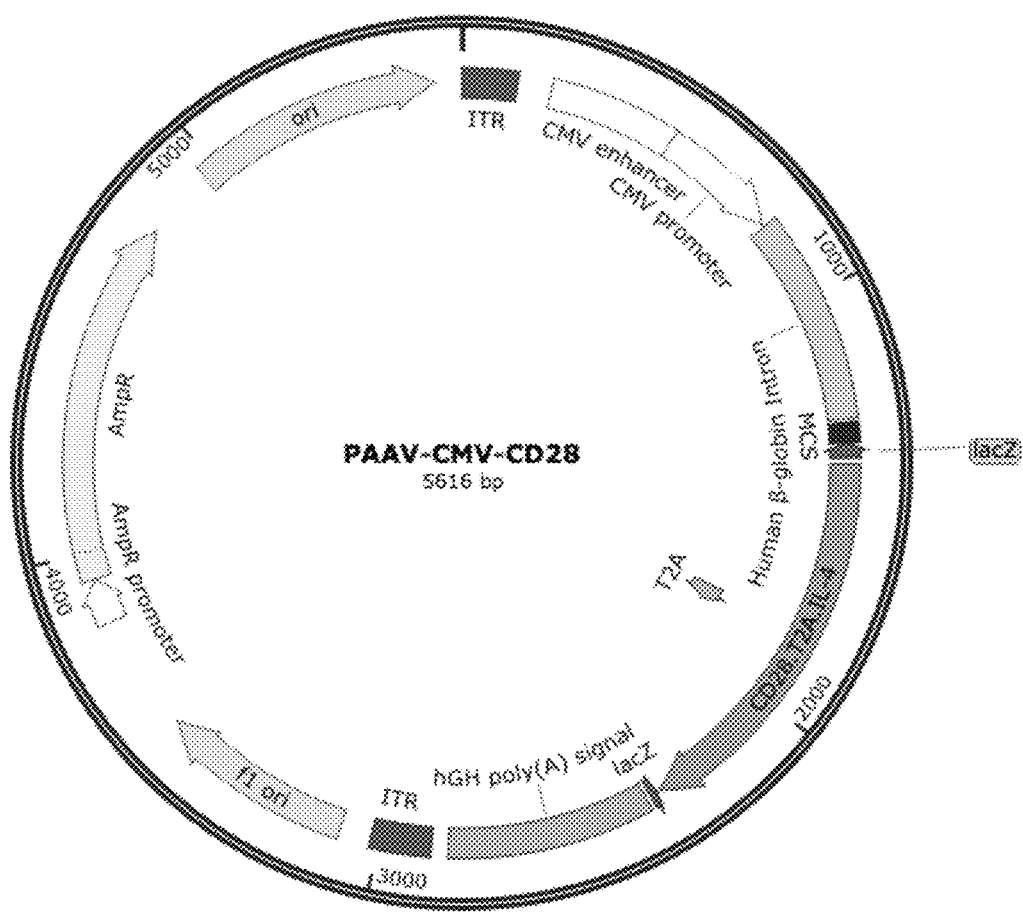
Figure 31B:
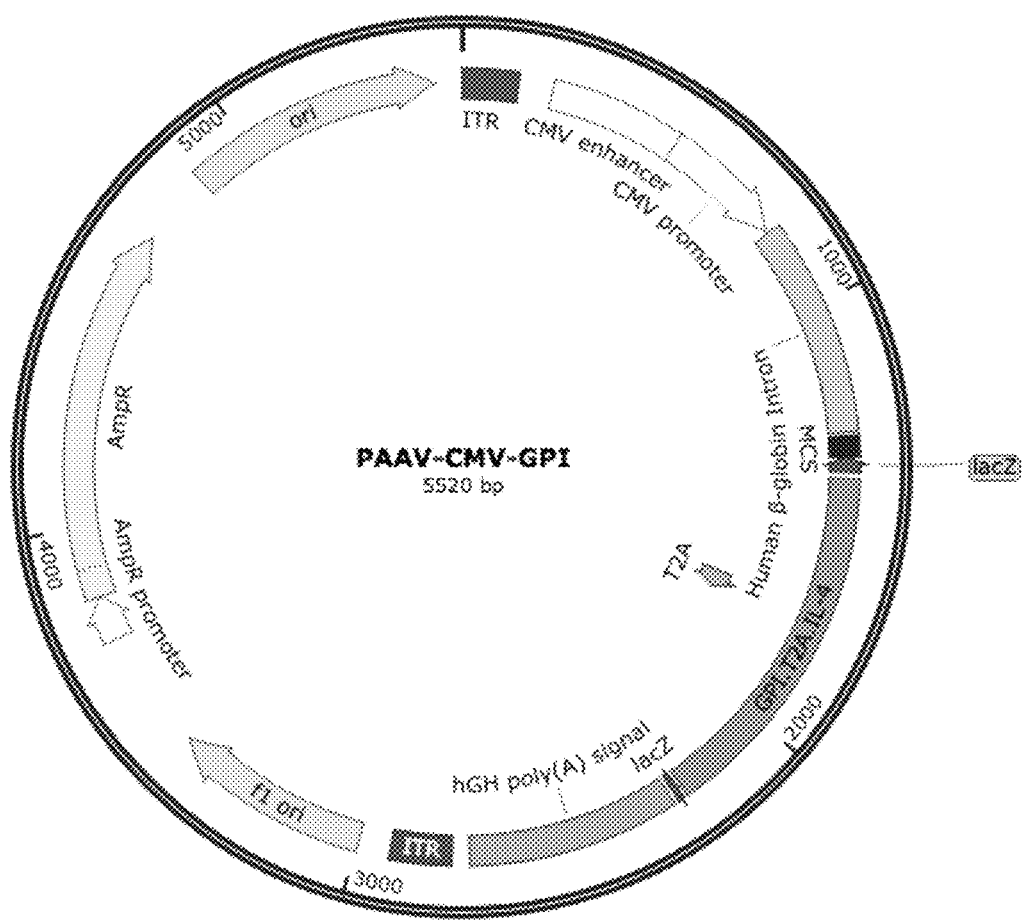
Figure 31C:
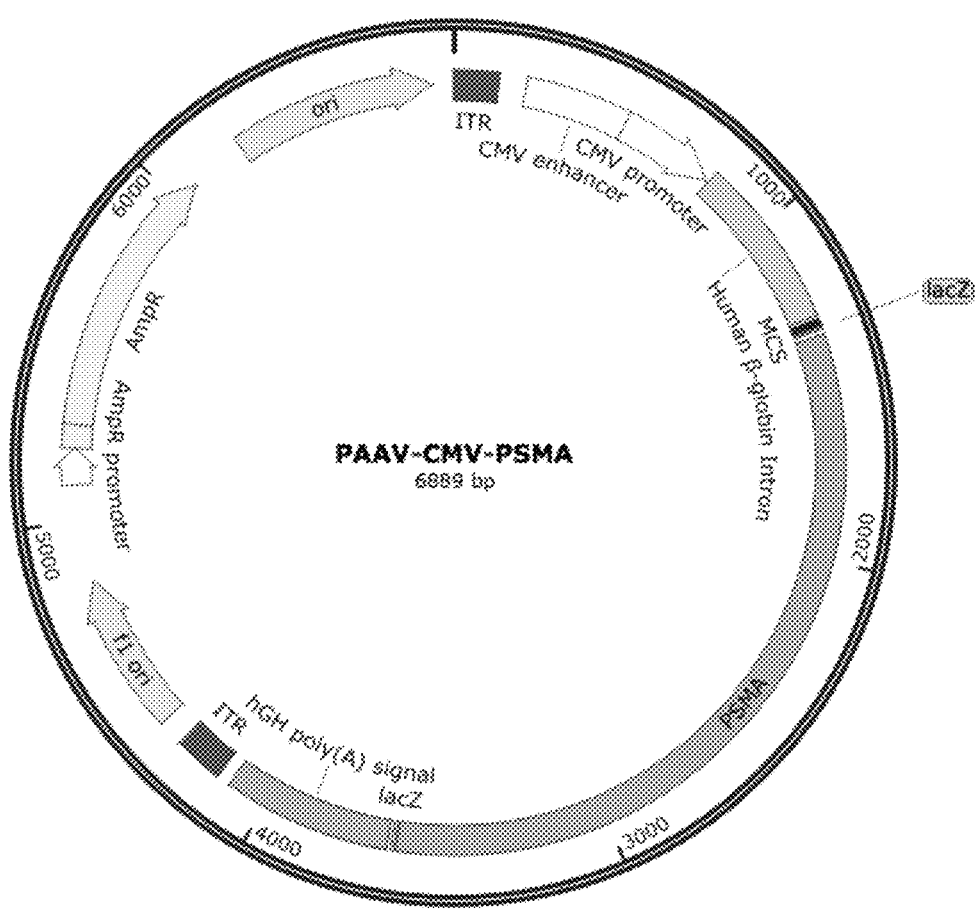
Figure 31D:
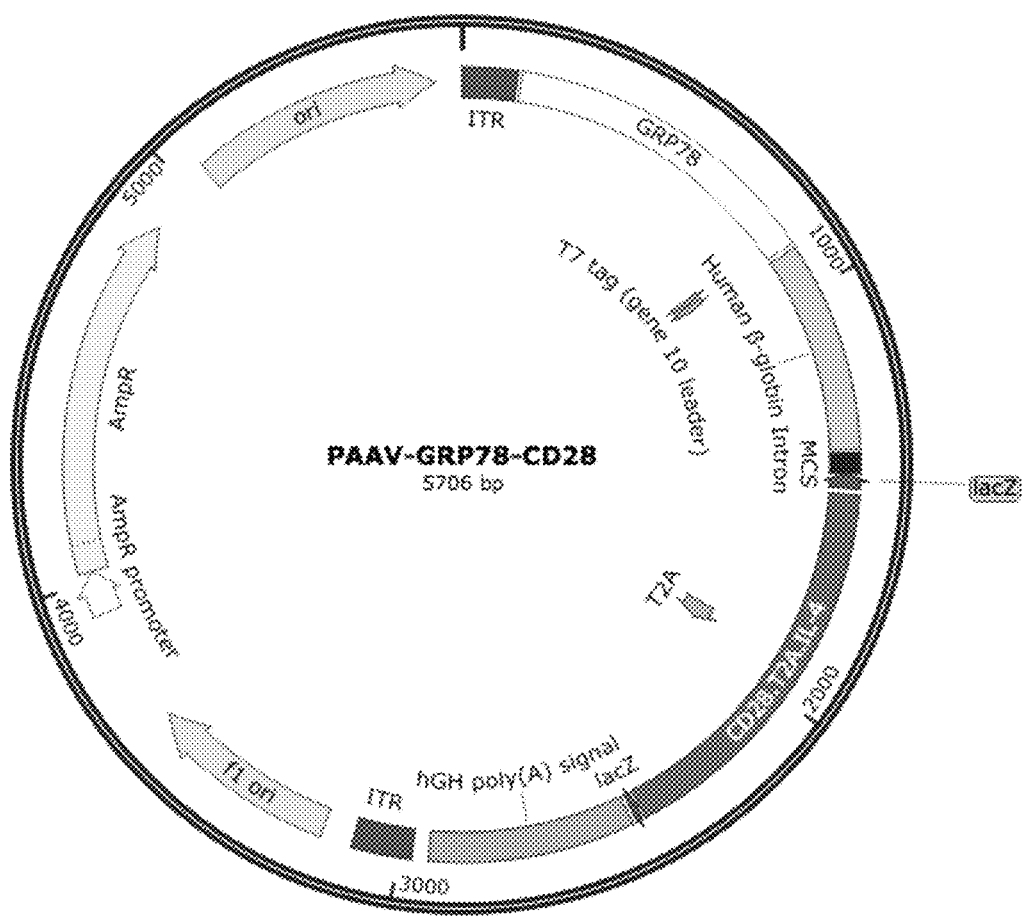
Figure 31E:
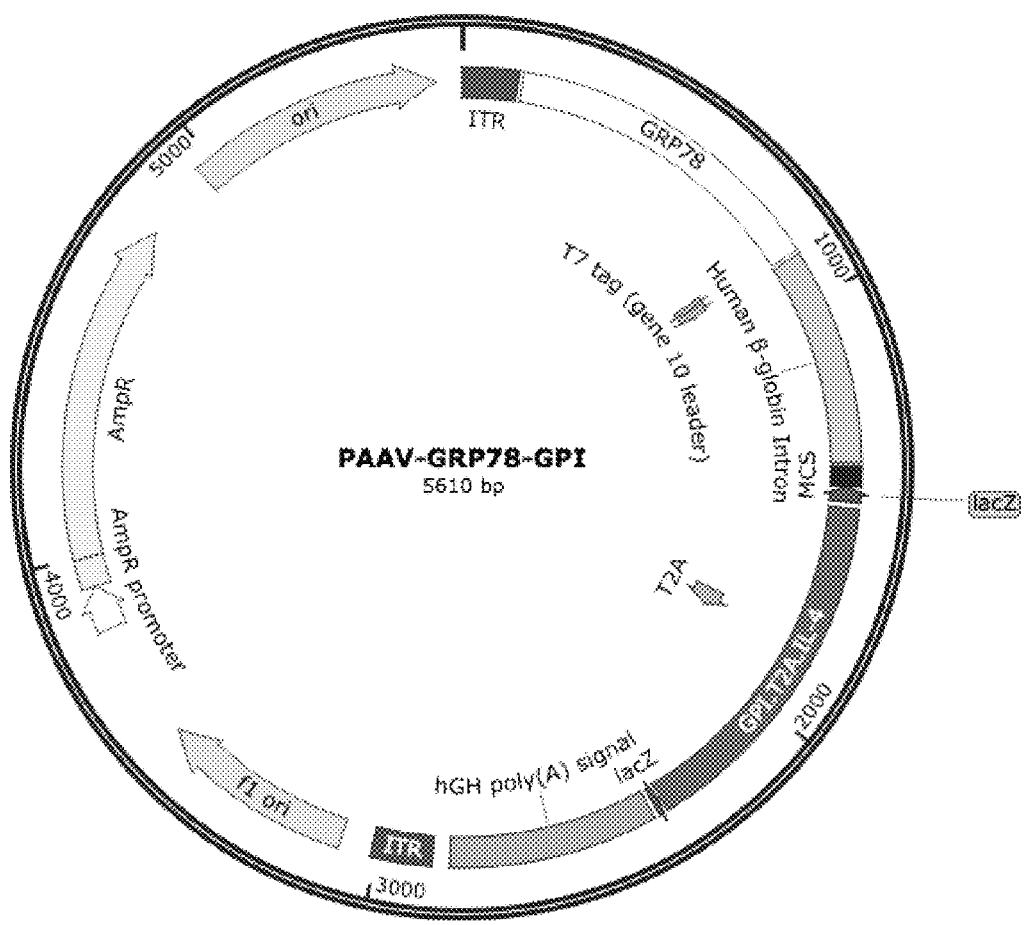
Figure 31F:
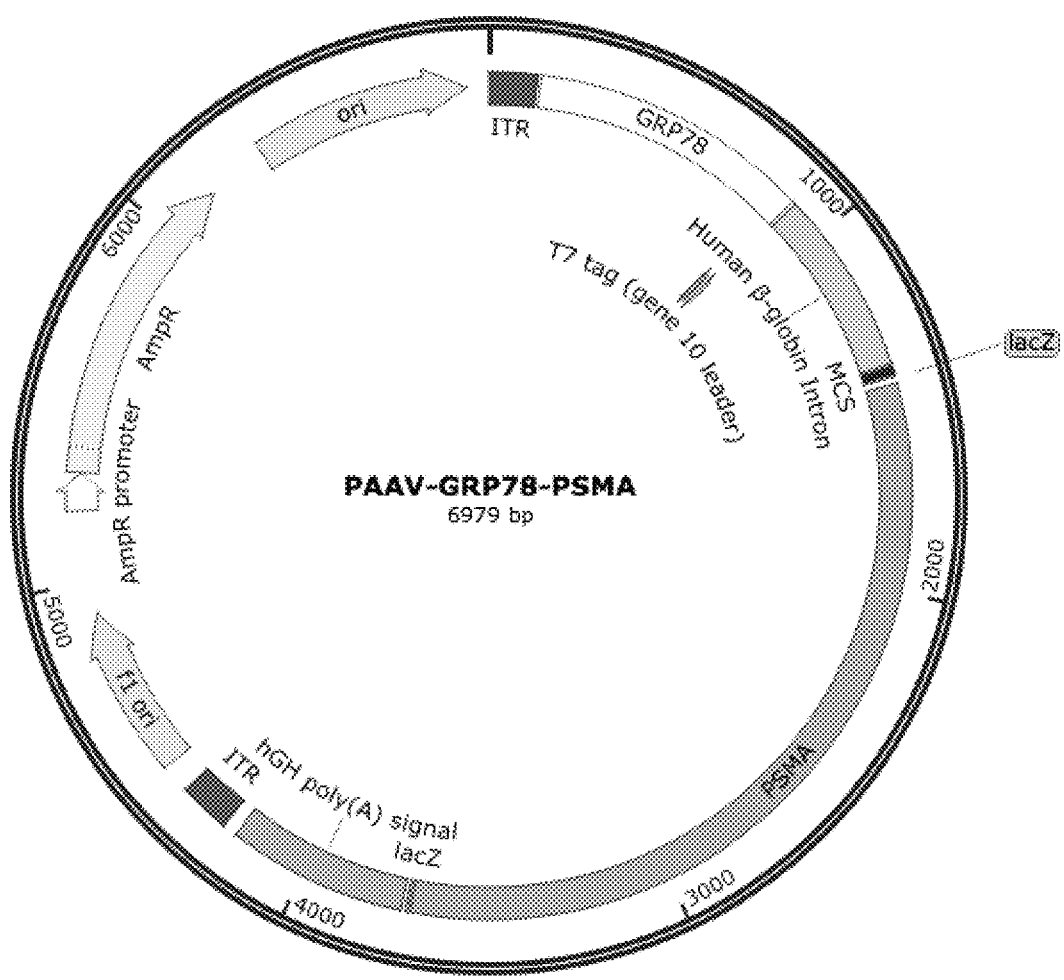

FIG. 6 shows the rAAV transgene cassette on the phagemid genome shown in FIG. 3, which contains a gene of interest (e.g. GFP), the expression of which is driven by a CMV promoter and/or enhancer sequences, and tailed with a polyA signal. The entire transgene cassette is flanked by Inverted Terminal Repeat sequences (ITRs) from AAV;

FIG. 7 shows an embodiment of the Helper phage which is a bacteriophage engineered for rescuing phagemid particles from prokaryotic hosts carrying a phagemid genome, such as that shown in FIG. 3;

FIG. 8 shows a section of the genome of the helper phage shown in FIG. 5 comprising the RGD4C targeting peptide in the pIII minor coat protein, and as shown in SEQ ID Nos 26 and 27;

FIG. 9 shows a first embodiment of a method for producing phagemid-AAV (PAAV) particles;

FIG. 10 shows a second embodiment of a method for producing phagemid-AAV (PAAV) particles;

FIG. 11 shows one embodiment of a phage-based approach for in vitro AAV production showing the three vectors, (i) phagemid-AAV (PAAV), (ii) Rep-Cap phagemid, and (iii) adenohelper phagemid;

FIG. 12 shows the genome map of an embodiment of the adenohelper phagemid vector shown in FIG. 11;

FIG. 13 shows the genome map of an embodiment of a Rep-Cap phagemid vector shown in FIG. 11;

FIG. 14 shows an embodiment of a unified adenohelper/Rep-cap/phagemid-AAV (PAAV) vector;

FIG. 15 shows the genome map of an embodiment of the unified adenohelper-Rep-Cap phagemid vector shown in FIG. 11;

FIG. 16 shows an embodiment of in situ AAV production using either the three phagemid vectors shown in FIGS. 11-13, or the unified adenohelper-Rep-Cap-AAV phagemid vector shown in FIGS. 14 and 15;

FIG. 17 shows Transmission Electron Microscopy (TEM) of known AAVP vectors and PAAV vectors according to the invention. (A) RGD.AAVP.GFP filament (pink) is typically 1455.02 nm in length. (B) RGD.PAAV.GFP filament (blue) is typically 729.96 nm in length; helper phage present in virus sample (green) is typically 1186.03 nm in length;

FIG. 18 shows internalisation of known AAVP vectors and PAAV vectors according to the invention in: (A) 293AAV and (B) U87 cells after 2 and 4 hours. Flow cytometric analysis was used with gating threshold set at 20000 events of total cell population. (n=3) *=p<0.05, **=p<0.01;

FIG. 19 shows quantification of GFP-positive cells 9 days post-transduction in (A) 293AAV, (B) 293AAV with the addition of DEAE.DEXTRAN, (C) U87 and (D) U87 with the addition of DEAE.DEXTRAN. Flow cytometric analysis was used with gating threshold set at 20000 events of total cell population. (n=3) *=p<0.05, **=p<0.01;

FIG. 20 shows quantification of genome copy numbers of rAAV-GFP from cell lysates following phagemid-guided gene transfer (A) or transfection (B) of rAAV expression elements. (Experiment A: n=1; Experiment B: n=3);

FIG. 21 shows immunofluorescence staining of UW228 and DAOY human medulloblastoma cells to demonstrate expression of $\alpha_v$, $\beta_3$ and $\beta_5$ integrin subunits, receptor for RGD4C-phagemid. Tumour cells were stained using primary rabbit anti-$\alpha_v$, $\beta_3$ or $\beta_5$ antibodies (diluted 1:50 in PBS-1% BSA), then with goat anti-rabbit AlexaFluor-488 secondary antibody (showed in green) and counterstained with 0.05 µg/ml DAPI (in blue). Images were taken using a confocal microscope;

FIG. 22 shows targeted gene delivery to paediatric medulloblastoma cells by RGD4C-phagemid. Medulloblastoma cells (UW228) were grown on 96 well-plates, then transduced with RGD4C-phagemid vector carrying the Luciferase gene (RGD). Untreated cells or cells treated with the non-targeted vector (M13) were used as negative controls. Luciferase expression was monitored over a time course from day 2 to 4 after transduction;

FIG. 23 shows Western blot analyses showing down regulation of mTOR expression in paediatric UW228 and DAOY medulloblastoma cells following treatment with RGD4C-phagemid carrying a sequence encoding the mTOR/shRNA (RGD4C-mTOR/shRNA)). Cell lysates were collected at day 4 post vector treatment, and total proteins were measured by BCA assay. Western blot was probed with a monoclonal antibody to human mTOR (Cell Signalling). Untreated cells (CTR) and cells treated with RGD4C-phagemid, lacking mTOR/shRNA, (RGD4C) were used as negative controls;

FIG. 24 shows combination treatment of temozolomide (TMZ) and RGD4C-phagemid carrying a sequence encoding shRNA for mTOR in medulloblastoma. Medulloblastoma cells (UW228 and DAOY) were transduced with RGD4C-phagemid (RGD4C) or RGD4C-phagemid carrying a sequence encoding mTOR/shRNA (RGD4C-mTOR/shRNA). Untreated cells were also used as controls. At day 7 post vector treatment, temozolamide (TMZ, 100 uM) was added in a few treated wells to assess effect of combination of vectors with chemotherapy. Images were taken at day 8 after vector treatment;

FIG. 25 shows treatment of medulloblastoma cells with TNFα phagemid vectors. UW228 cells were treated with RGD4C-phagemid-TNFα (RGD4C/TNF) and non-targeted (ctr). A) Cell viability, using MTT assay, following expression of TNFα. B) Expression of TNFα in the medium of vector-treated cells, measured using human TNFα ELISA Max. Error bars: mean±SEM;

FIG. 26 shows immunofluorescence staining of DIPG cells to demonstrate expression of $\alpha_v$, $\beta_3$ and $\beta_5$ integrin subunits, receptor for RGD4C-phagemid. Cells were stained using primary rabbit antibodies then with goat anti-rabbit AlexaFluor-488 secondary antibody. Control cells received secondary antibody alone. Images were taken using a confocal microscope;

FIG. 27 shows selective and dose dependent delivery of gene expression to UW228, DAOY, and DIPG cells by RGD4C-phagemid/AAV. Increasing vector dose 1×10$^6$ or 2×10$^6$ TU/cell of RGD4C-phagemid-Luc (RGD4C) carrying the reporter Luc (luciferase) gene was used to treat the cells. Luc expression was measured daily. Non-targeted vector lacking RGD4C (ctr) was used as negative control for targeting. Error bars: mean±SEM. (A) shows treatment of DIPG cells, (B) shows treatment of UW228, (C) shows treatment of DAOY cells;

FIG. 28 shows treatment with RGD4C-phagemid-TNFα of UW288, DAOY, or DIPG cells. DIPG were transduced with $2\times10^6$ TU/cell RGD4C-phagemid-TNFα (RGD4C) and non-targeted vector as negative control (ctr). UW288 or DAOY cells were transduced with $1\times10^6$ TU/cell with or without DEAE dextran. Apoptotic activity was measured at day 9 post-vector treatment by measuring the percentage of viable cells or using caspase-Glo assay (caspase 3/7, caspase 8, and caspase9). Error bars: mean±SEM. *P≤0.05, P≤0.01, *P≤0.001;

FIG. 29 shows luciferase expression after transduction with RGD.PAAV at various transducing units of RGD-.PAAV;

FIG. 30 shows the percentage of PAAV vectors bound to the cell surface of 293 AAV cells. RGD.PAAV vectors had 58.2% binding efficiency, whereas M13.PAAV vectors had 7.1% binding efficiency relative to their respective controls;

FIG. 31 shows schematic diagrams of embodiments of the expression plasmid constructs for bacteriophage-guided CAR T cell therapy; 31a represents MUC1-CD28.IL4 expression plasmid driven by CMV promoter, 31b represents MUC1-GPI.IL4 expression plasmid driven by CMV promoter, 31c represents PSMA expression plasmid driven by CMV promoter, 31d represents MUC1-CD28.IL4 expression plasmid driven by Grp78 promoter, 31e represents MUC1-GPI.IL4 expression plasmid driven by Grp78 promoter and 31f represents PSMA expression plasmid driven by Grp78 promoter.

Figure 32:
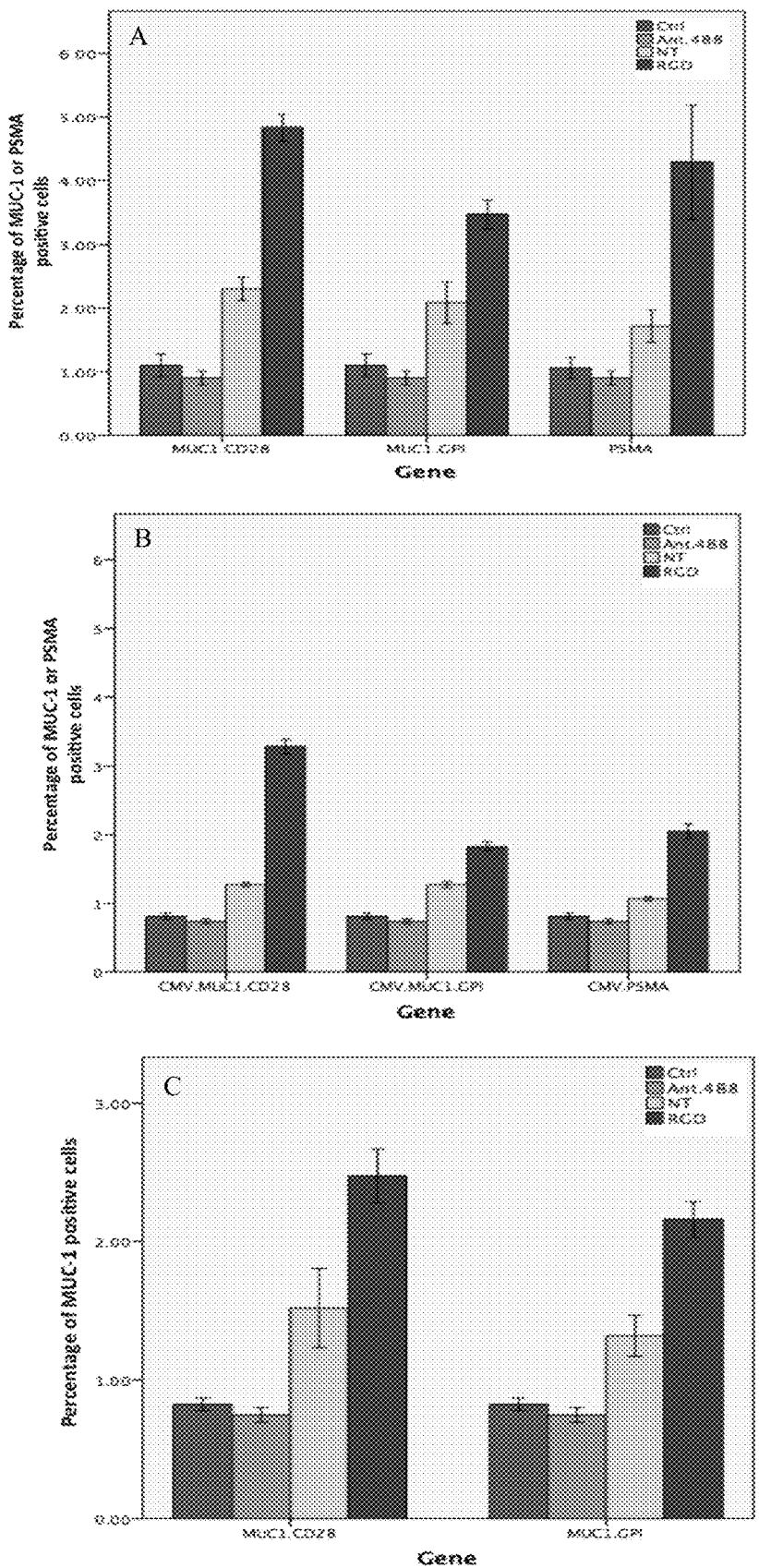
Figure 33A:
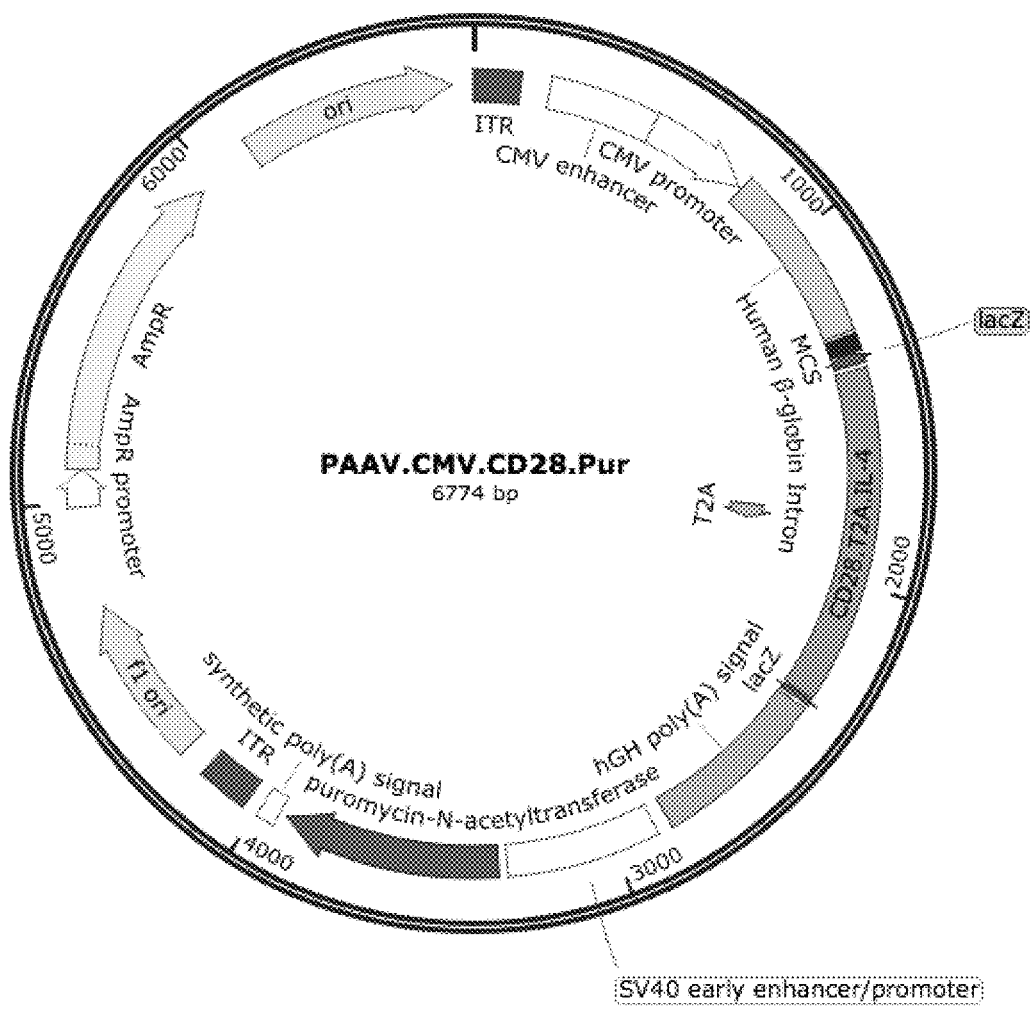
Figure 33B:
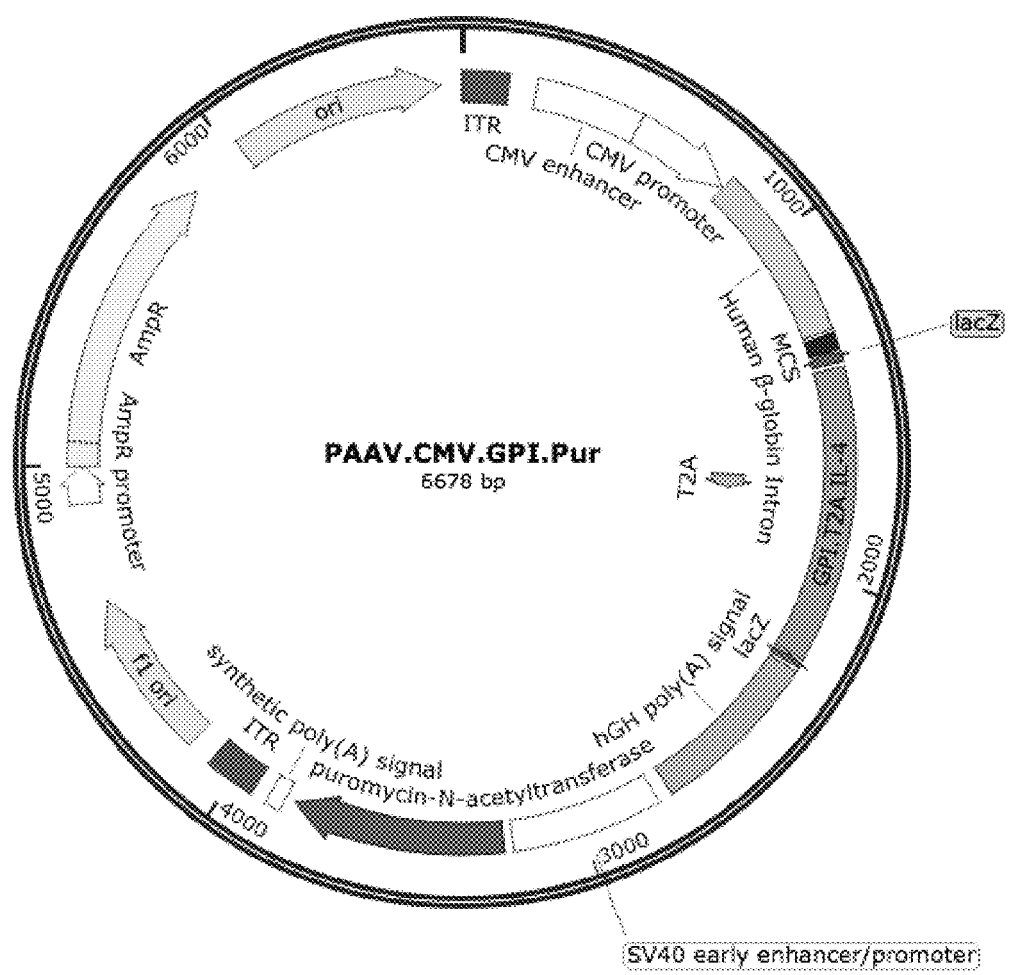
Figure 33C:
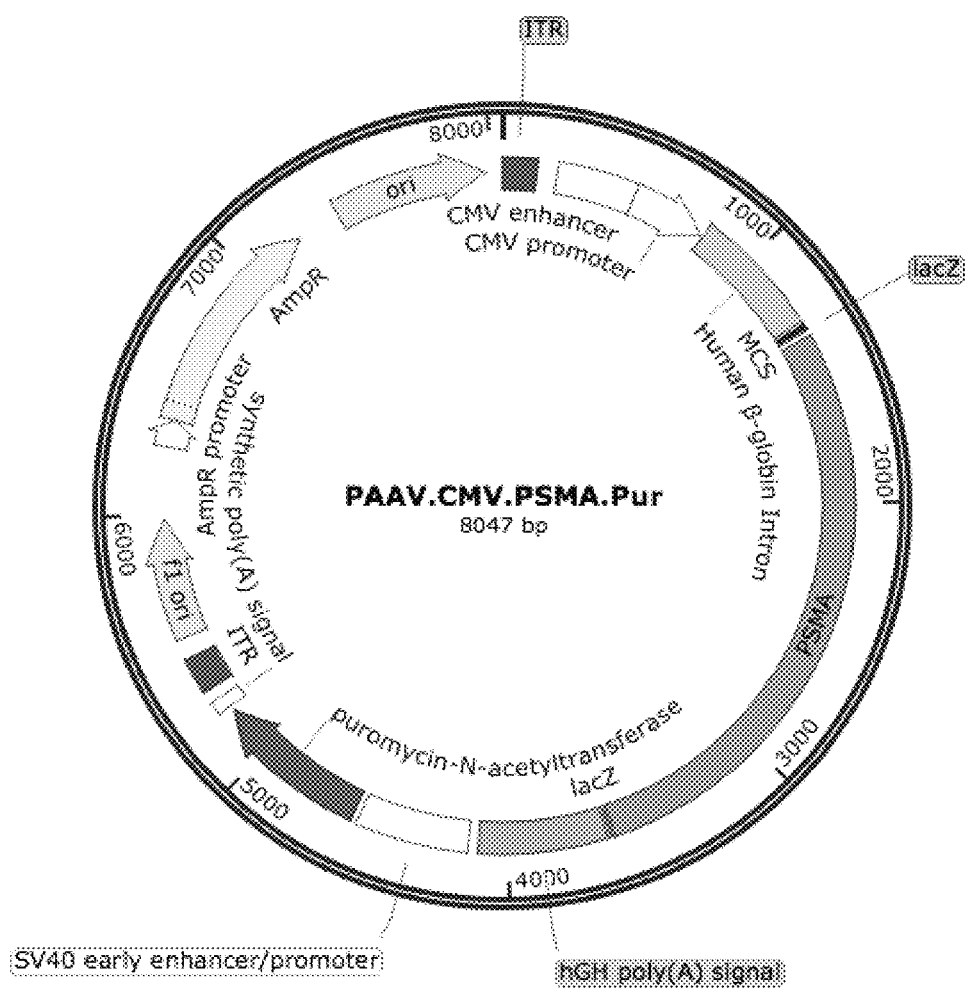
Figure 33D:
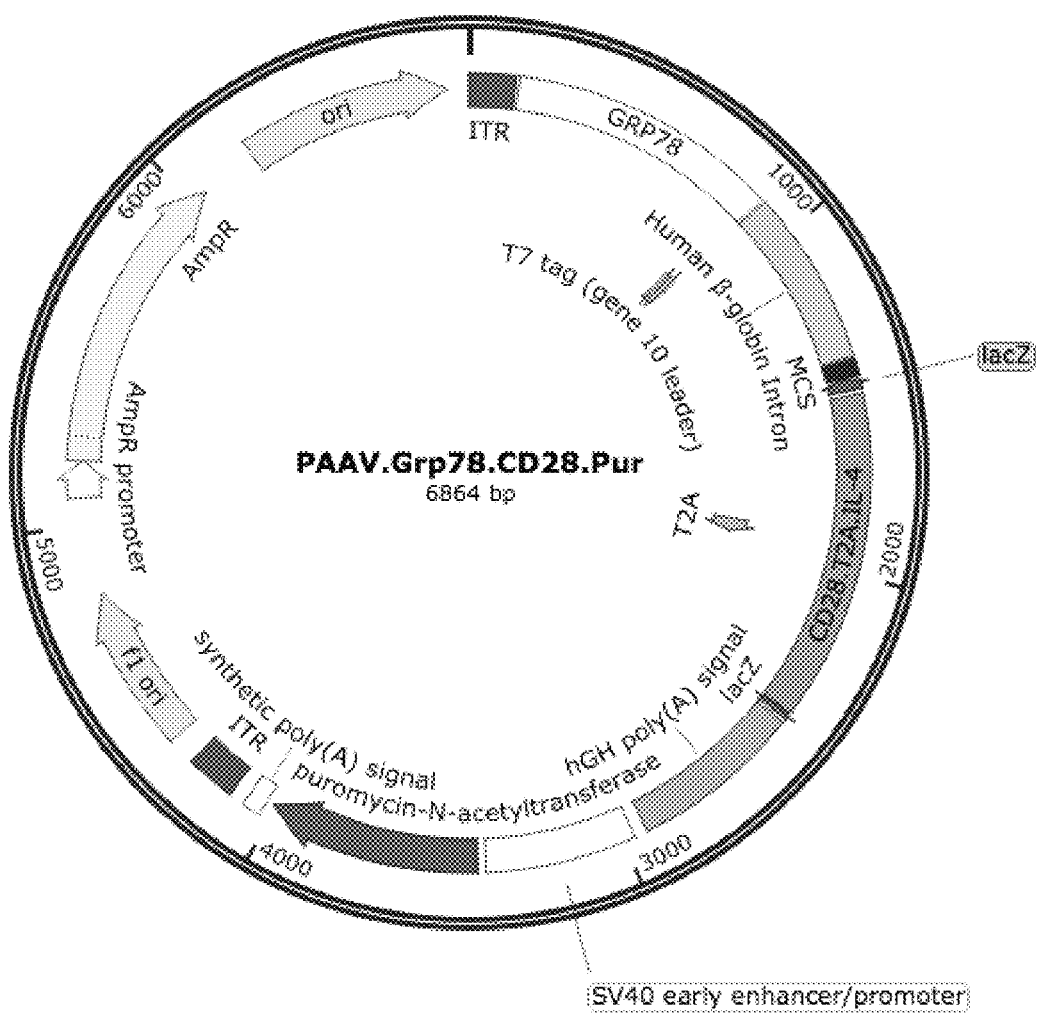
Figure 33E:
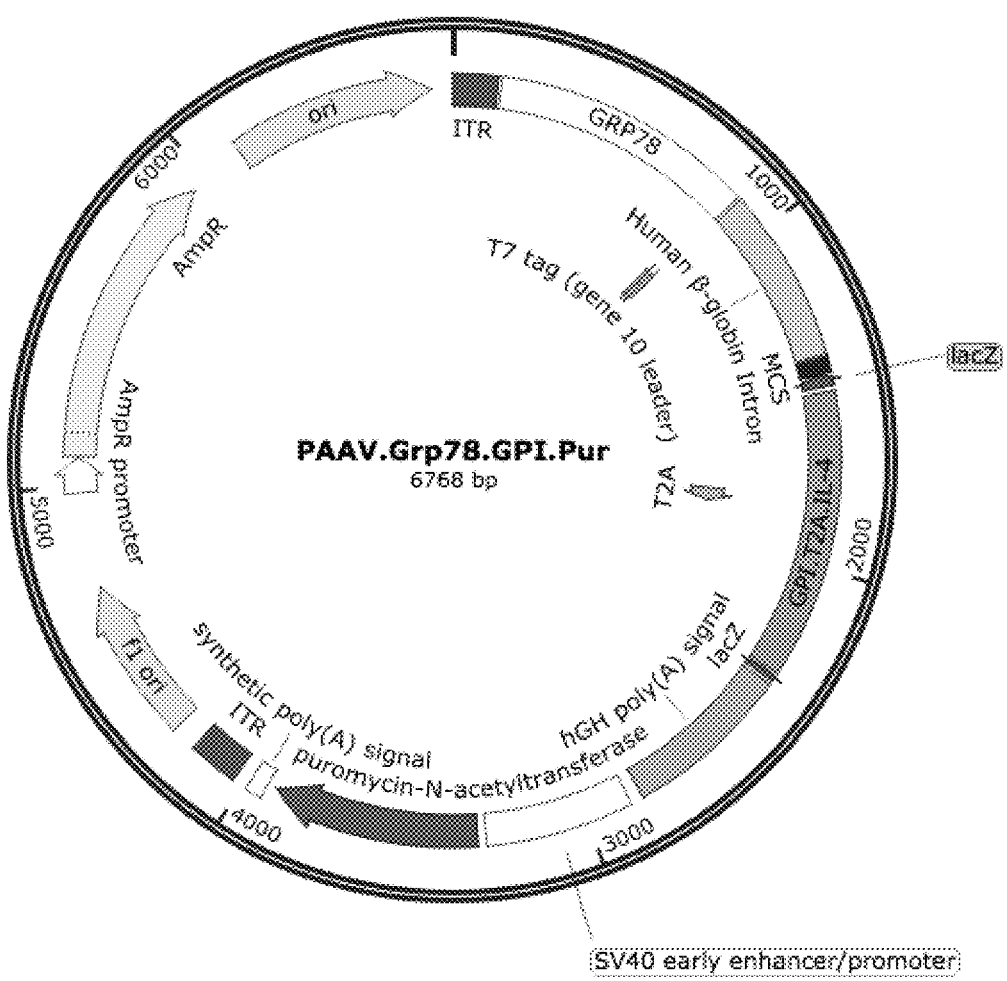
Figure 33F:
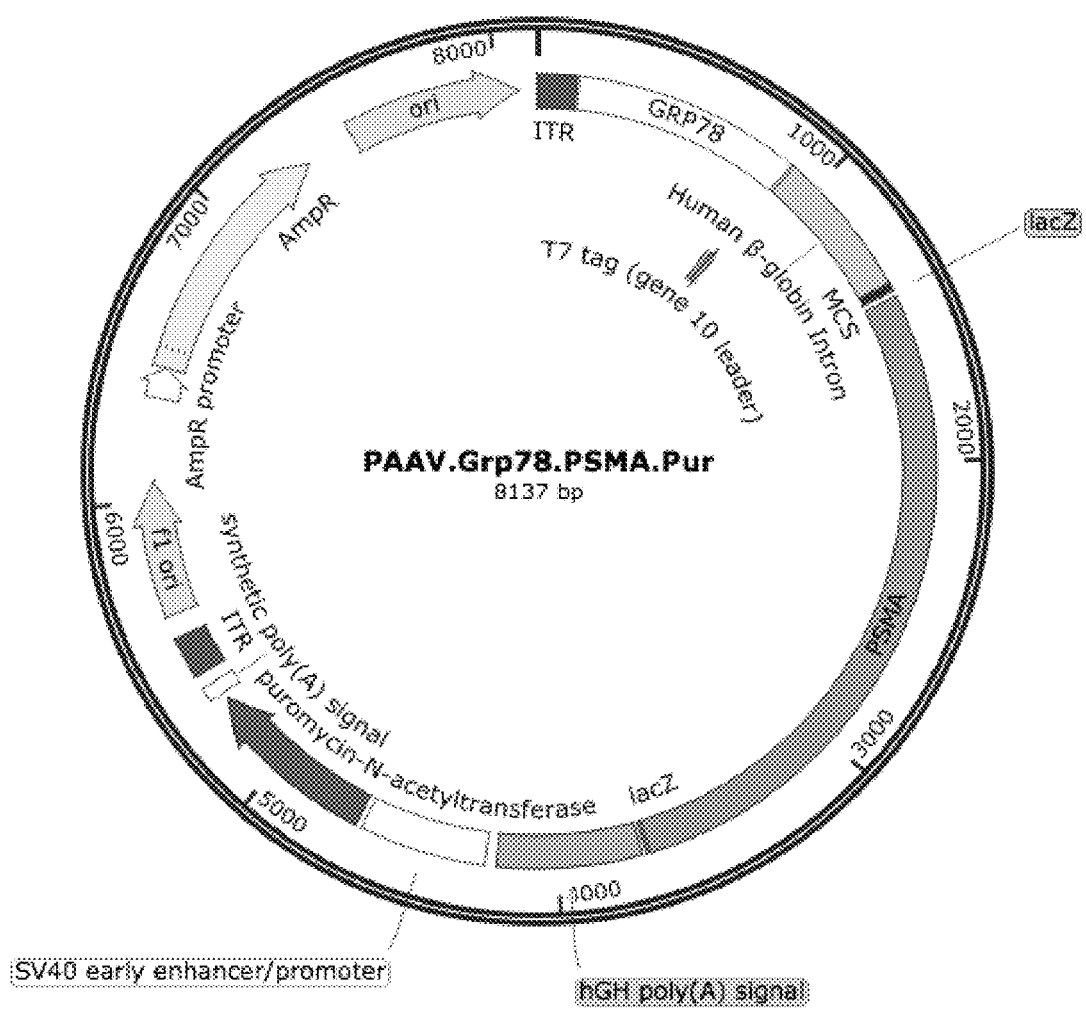
Figure 34:
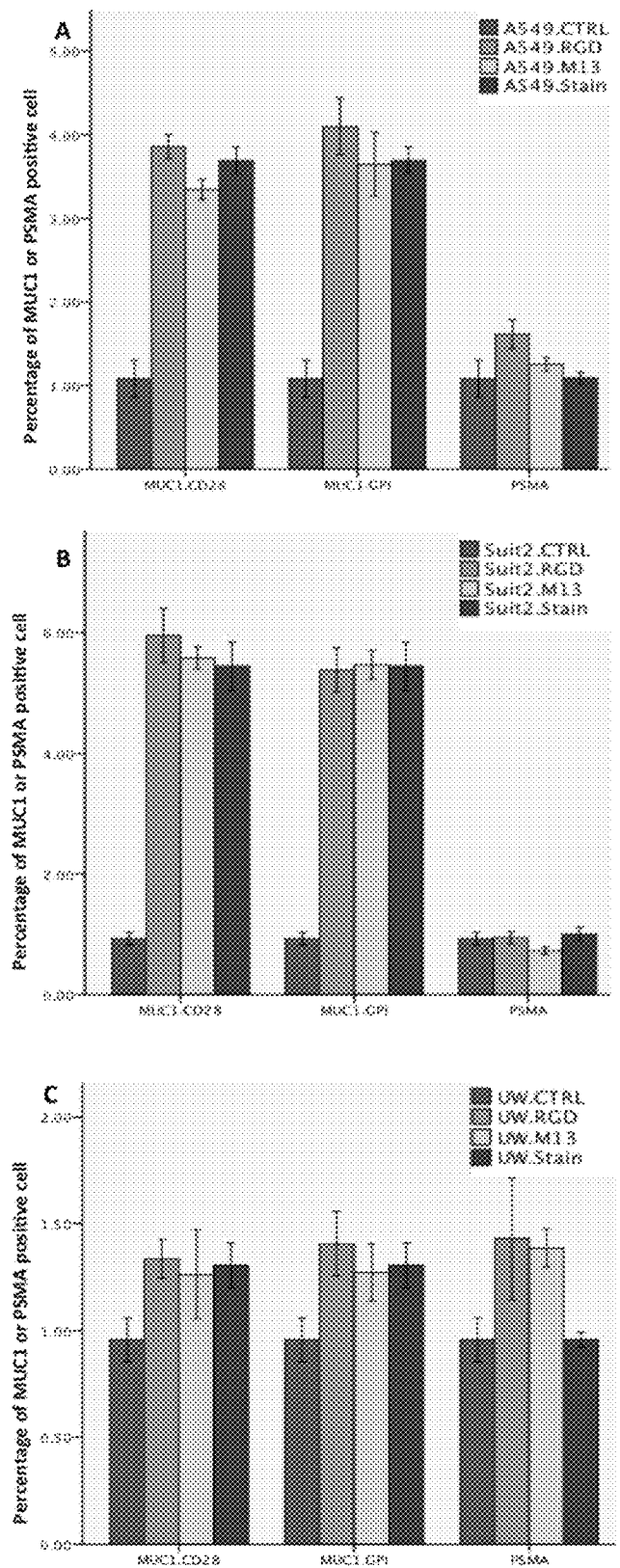
Figure 35:
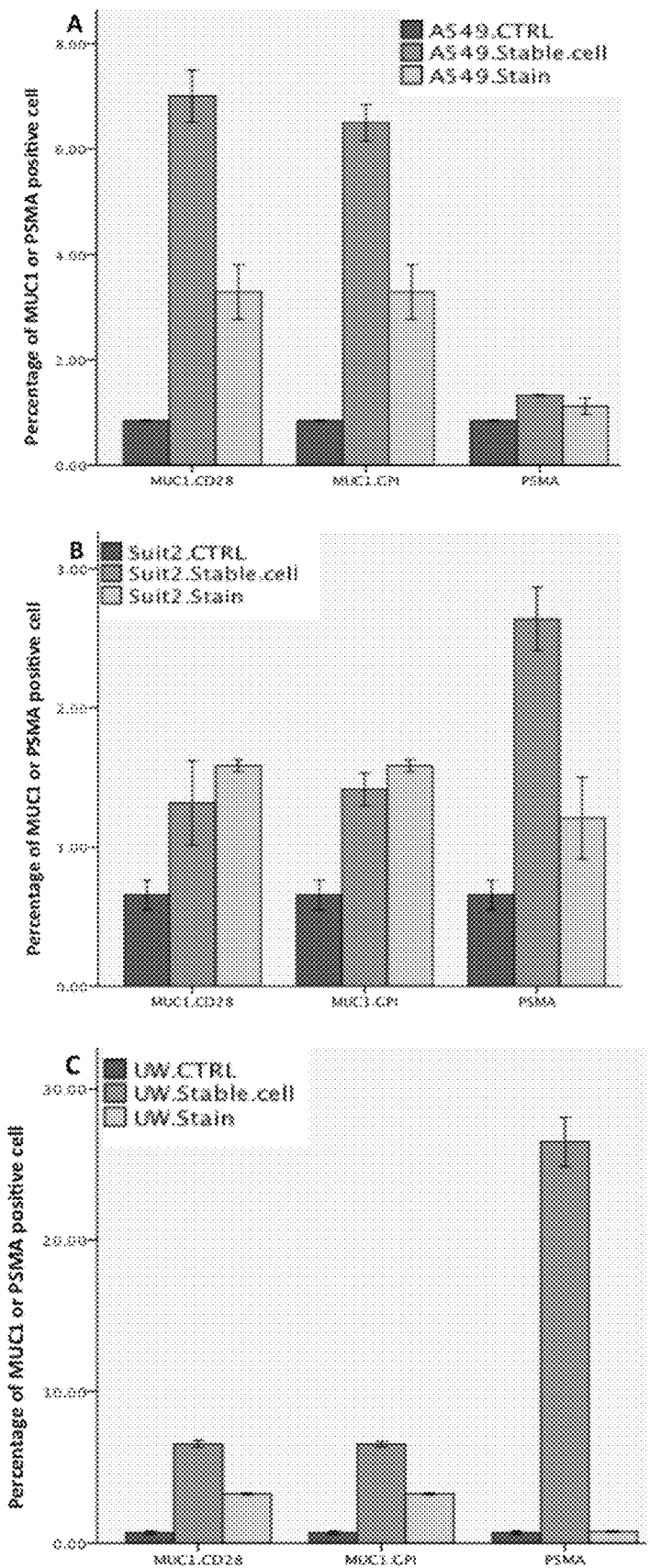
Figure 37:
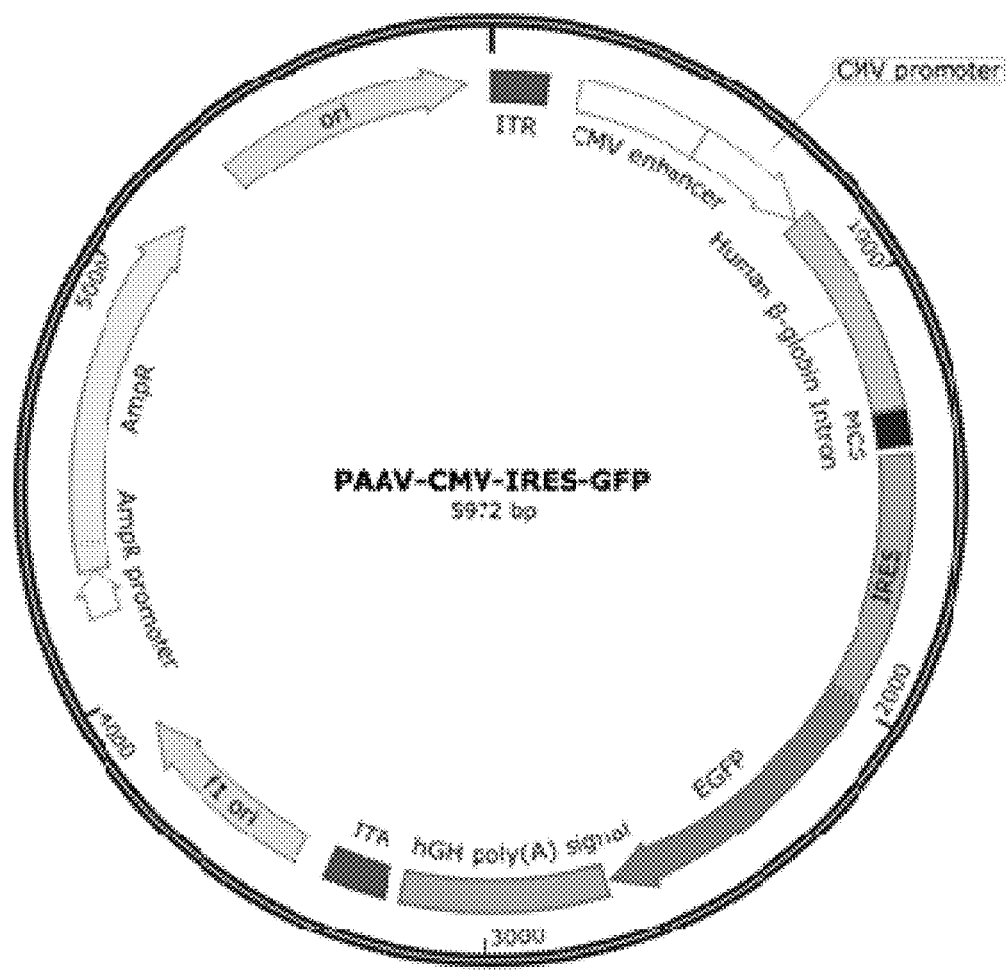
Figure 37:
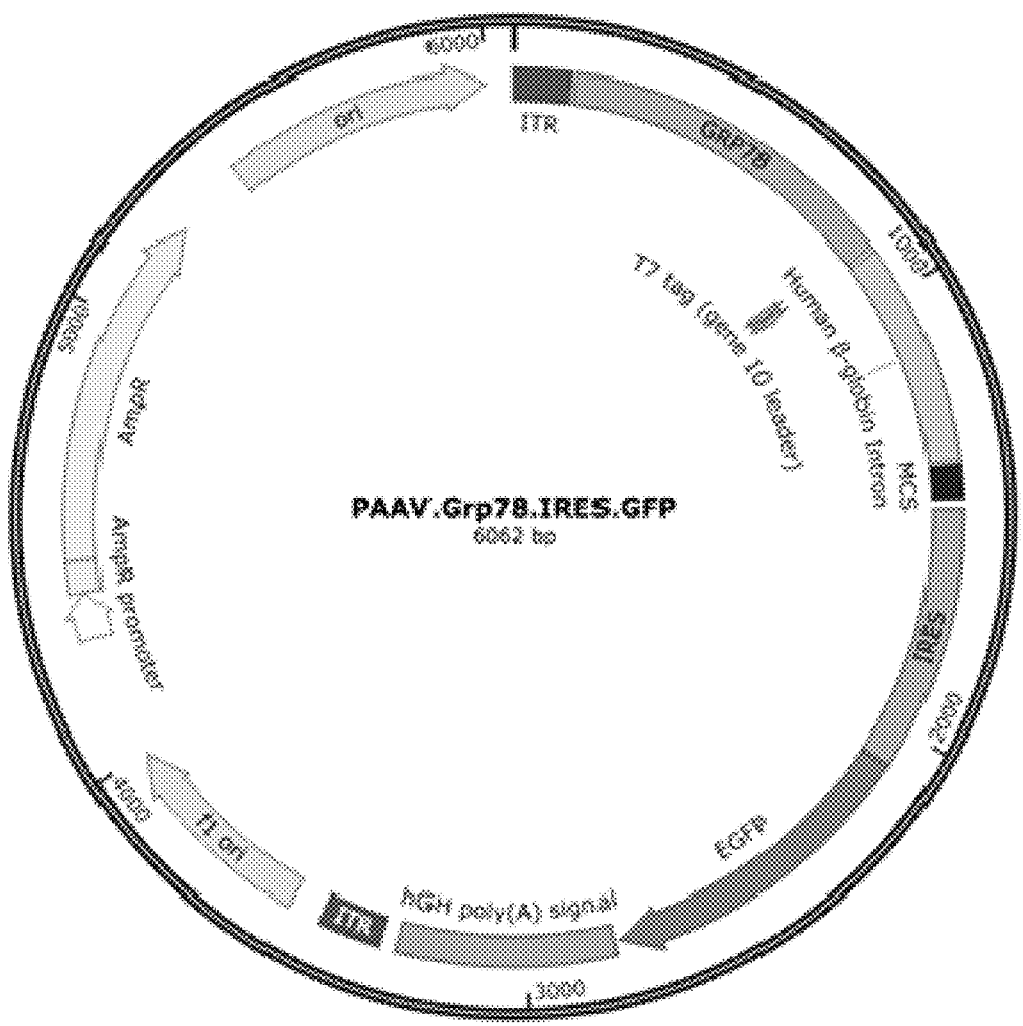

FIG. 32 shows MUC-1.CD28, MUC-1.GPI and PSMA antigen expression on day 6 post-transduction. HEK 293 cells were transduced by either $10^6$ TU/cell of RGD targeted PAAV (RGD) or non-targeted PAAV (NT). Untreated HEK 293 cells (Ctrl) and, targeted PAAV transduced-HEK 293 cells with only 488 secondary antibody staining (Ant.488) were shown as control. A represents the MUC-1 or PSMA expression of HEK 293 cells transduced by CMV promoter-driven PAAV vector (construct in FIGS. 31a, 31b and 31c). DEAE-dextran was added. B represents the MUC-1 or PSMA expression of HEK 293 cells transduced by CMV promoter-driven PAAV vector (construct in FIGS. 31a, 31b and 31c) without DEAE dextran added. C represents the MUC-1 expression of HEK 293 cells transduced by Grp78 promoter-driven PAAV vector (construct in FIGS. 31d and 31e) without DEAE dextran added;

FIG. 33 shows schematic diagrams of the expression plasmid constructs with puromycin resistance gene for stable cell line selection bacteriophage-guided CAR T cell therapy; 33a represents MUC1-CD28.IL4 expression plasmid driven by CMV promoter, 33b represents MUC1-GPI.IL4 expression plasmid driven by CMV promoter, 33c represents PSMA expression plasmid driven by CMV promoter, 33d represents MUC1-CD28.IL4 expression plasmid driven by Grp78 promoter, 33e represents MUC1-GPI.IL4 expression plasmid driven by Grp78 promoter and 33f represents PSMA expression plasmid driven by Grp78 promoter;

FIG. 34 shows MUC-1.CD28, MUC-1.GPI and PSMA antigen expression of cancer cells on day 6 post-transduction. Cancer cells were transduced by either 106 TU/cell of RGD targeted PAAV (RGD) or non-targeted PAAV (M13). Untreated cells without any antibody staining (CTRL) were shown as control while untreated cells were stained with primary and secondary antibody (Stain) to checked internal expression of the antigen by FACS. A represents the MUC-1 or PSMA expression of A549 cells transduced by CMV promoter-driven PAAV vector. B represents the MUC-1 or PSMA expression of Suit2 cells transduced by CMV promoter-driven PAAV vector. C represents the MUC-1 expression of UW 228 cells transduced by CMV promoter-driven PAAV vector;

FIG. 35 shows MUC-1.CD28, MUC-1.GPI and PSMA antigen expression in stable cancer cells. RGD4C-PAAV-Stably transduced cancer cells expressing MUC1 or PSMA antigen (Stable cell) were selected with puromycin antibiotic, then used to perform FACS analyses for MUC-1 or PSMA expression. Untreated cells without any antibody staining (CTRL) were shown as control while untreated cells were stained with primary and secondary antibody (Stain) to checked internal expression of the antigen. A represents the MUC-1 or PSMA expression of A549 cells. B represents the MUC-1 or PSMA expression of Suit2 cells. C represents the MUC-1 expression of UW 228 cells;

FIG. 36 shows treatment and comparison of DIPG cell killing in vitro between PAAV carrying either the transmembrane tmTNFα or secreted sTNFα. DIPG cells were treated with either RGD4C-PAAV-tmTNFα or RGD4C-PAAV-sTNFα (RGD4C and non-targeted M13 [ctr]) and cell viability was measured at day 7 post-vector treatment. The RGD4C-PAAV-sTNFα particle carrying the secreted sTNFα was more potent in inducing DIPG cell killing than the RGD4C-PAAV-tmTNFα, even in a transient transduction context where only a small population of cells are transduced by the vector;

FIG. 37 shows schematic diagrams of embodiments of the plasmid constructs used by the presently disclosed methods; 37a represents PAAV-CMV-IRES GFP plasmid, 37b represents PAAV.Grp78.IRES.GFP;

FIG. 38 includes parts A and B, each of which shows expression of TNFα after PAAV-tm.TNFα transduction. Part (A), UW228, and Part (B), Daoy, were seeded in 96-well plate and transduced with $1\times10^6$ TU/cell with DEAE dextran, the supernatant was collected at day 6 and TNFα in the supernatant was determined by ELISA. Data are represented as mean±SEM.

Figure 39:
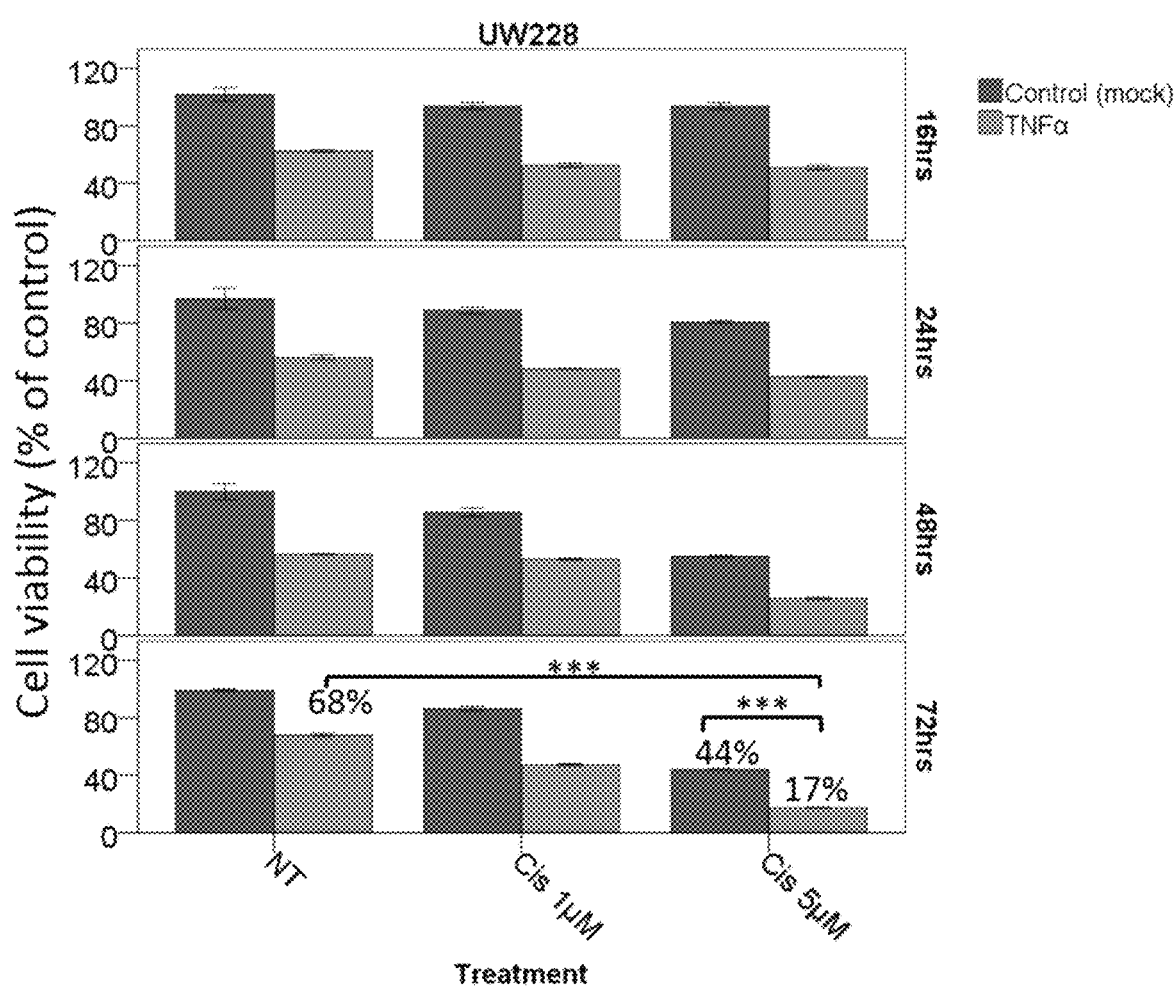
Figure 40:
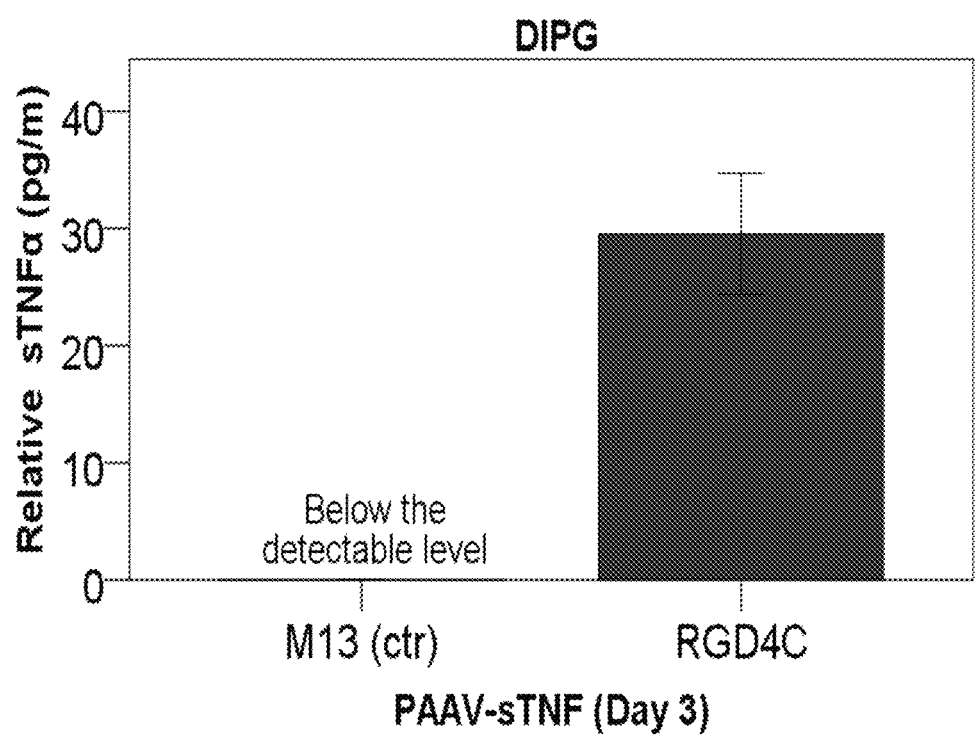
Figure 41:
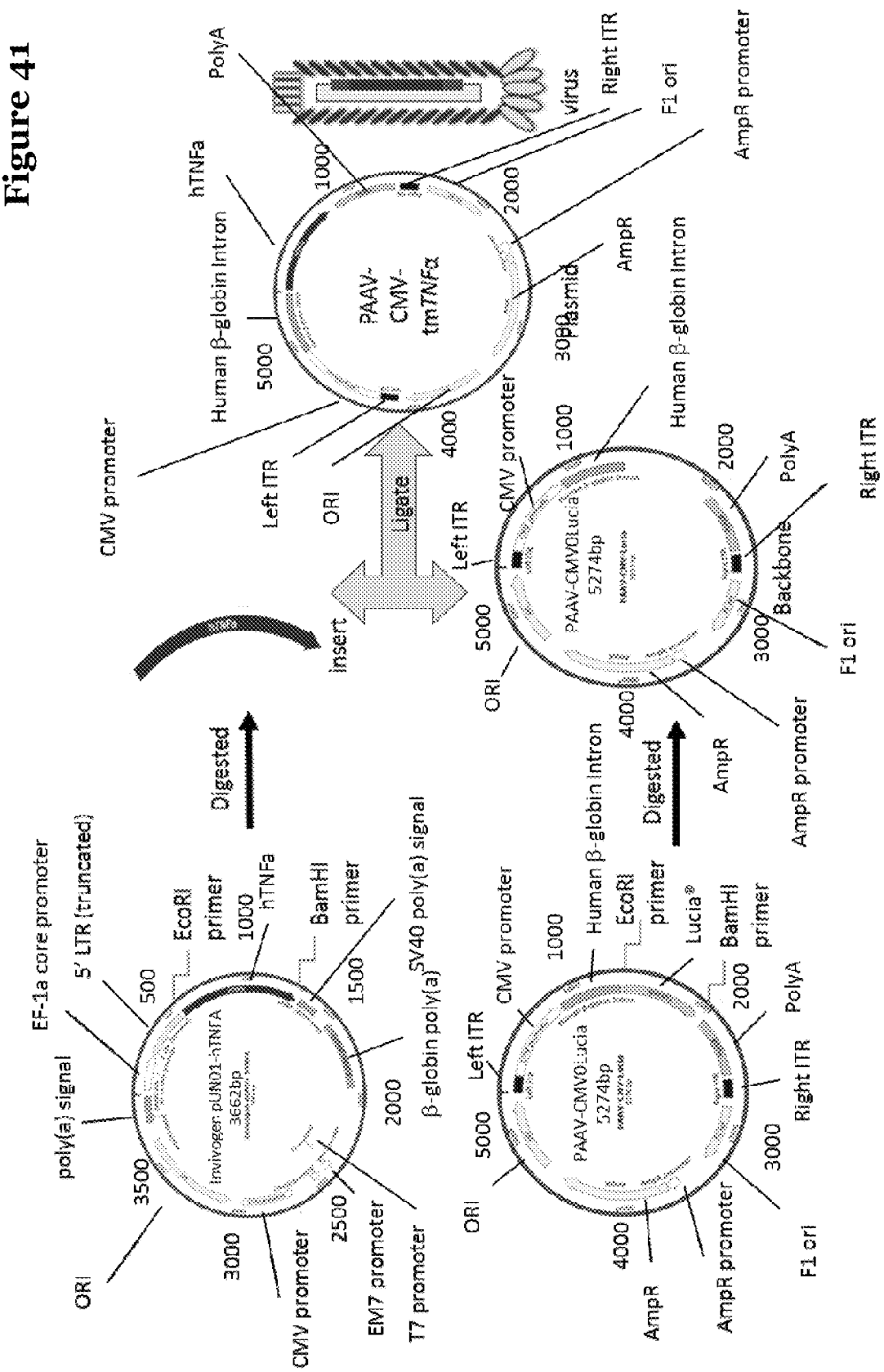
Figure 42:
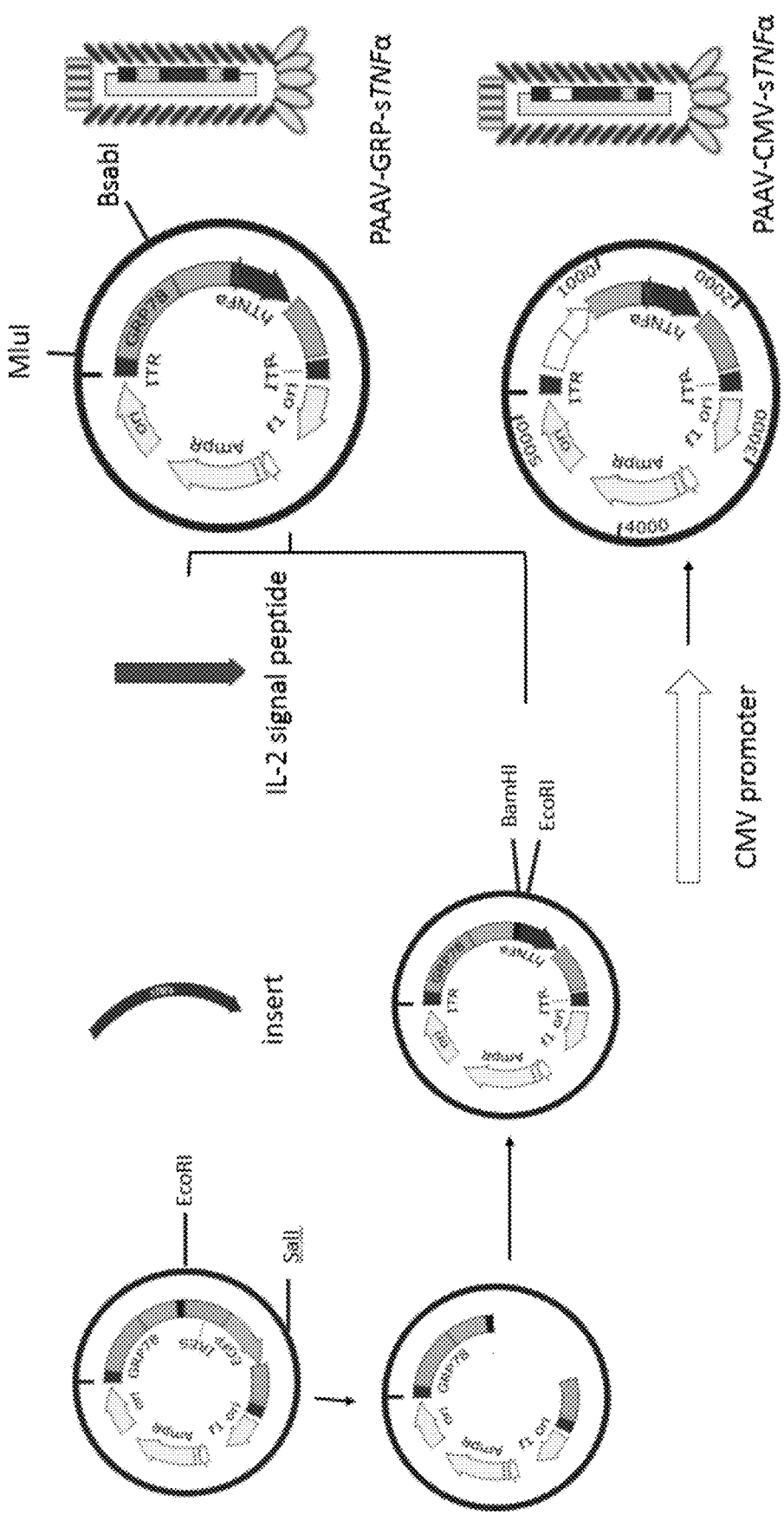
Figure 44:
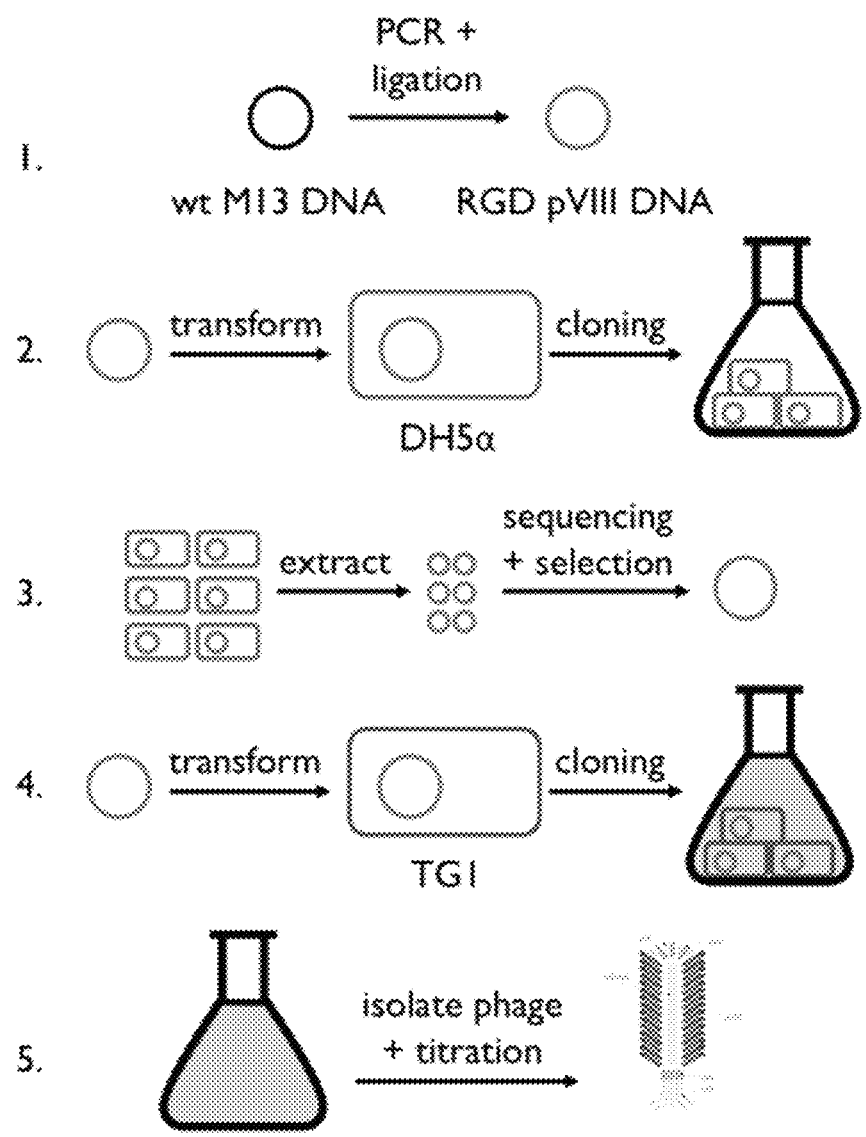
Figure 45:
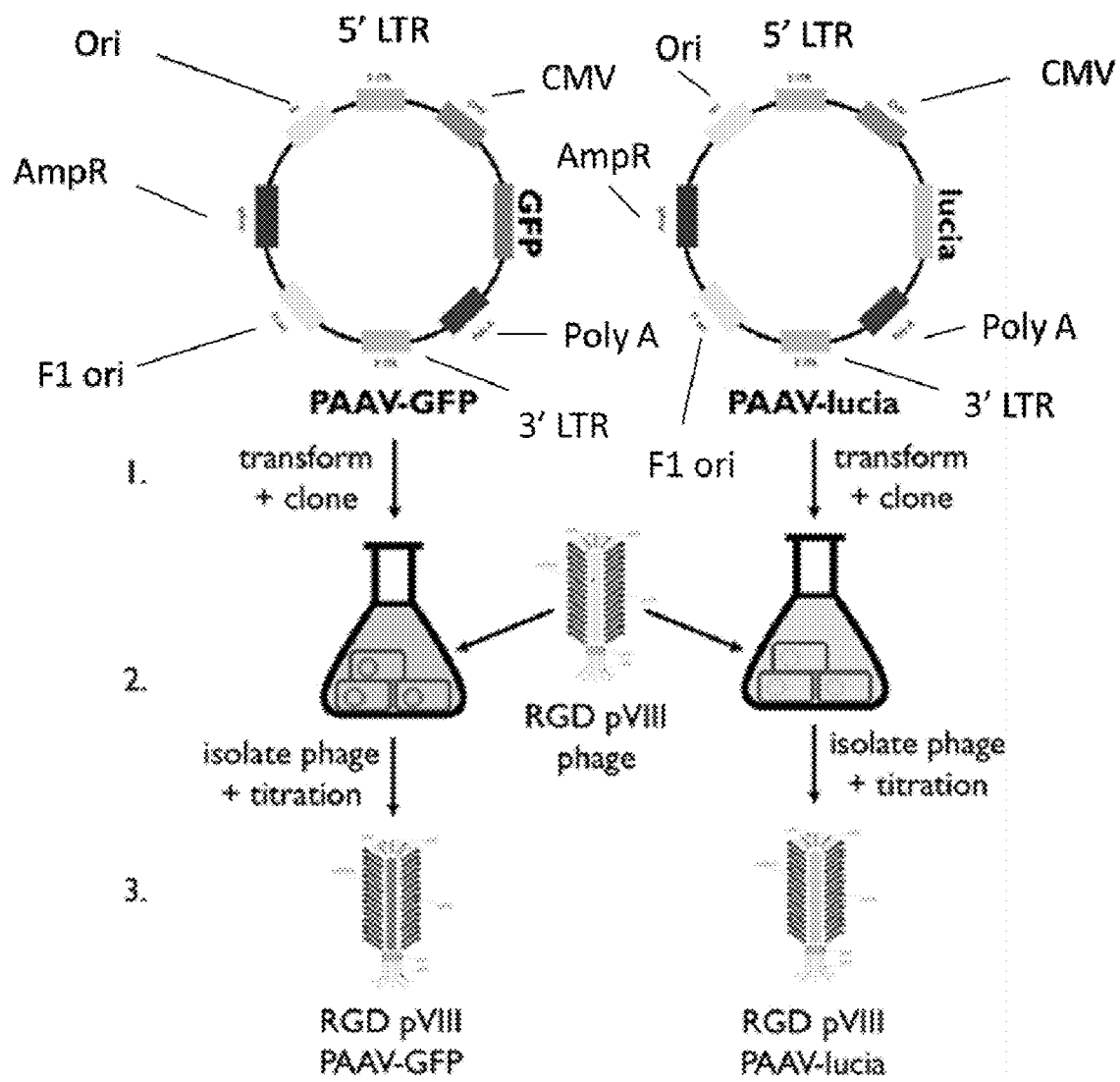
Figure 46:
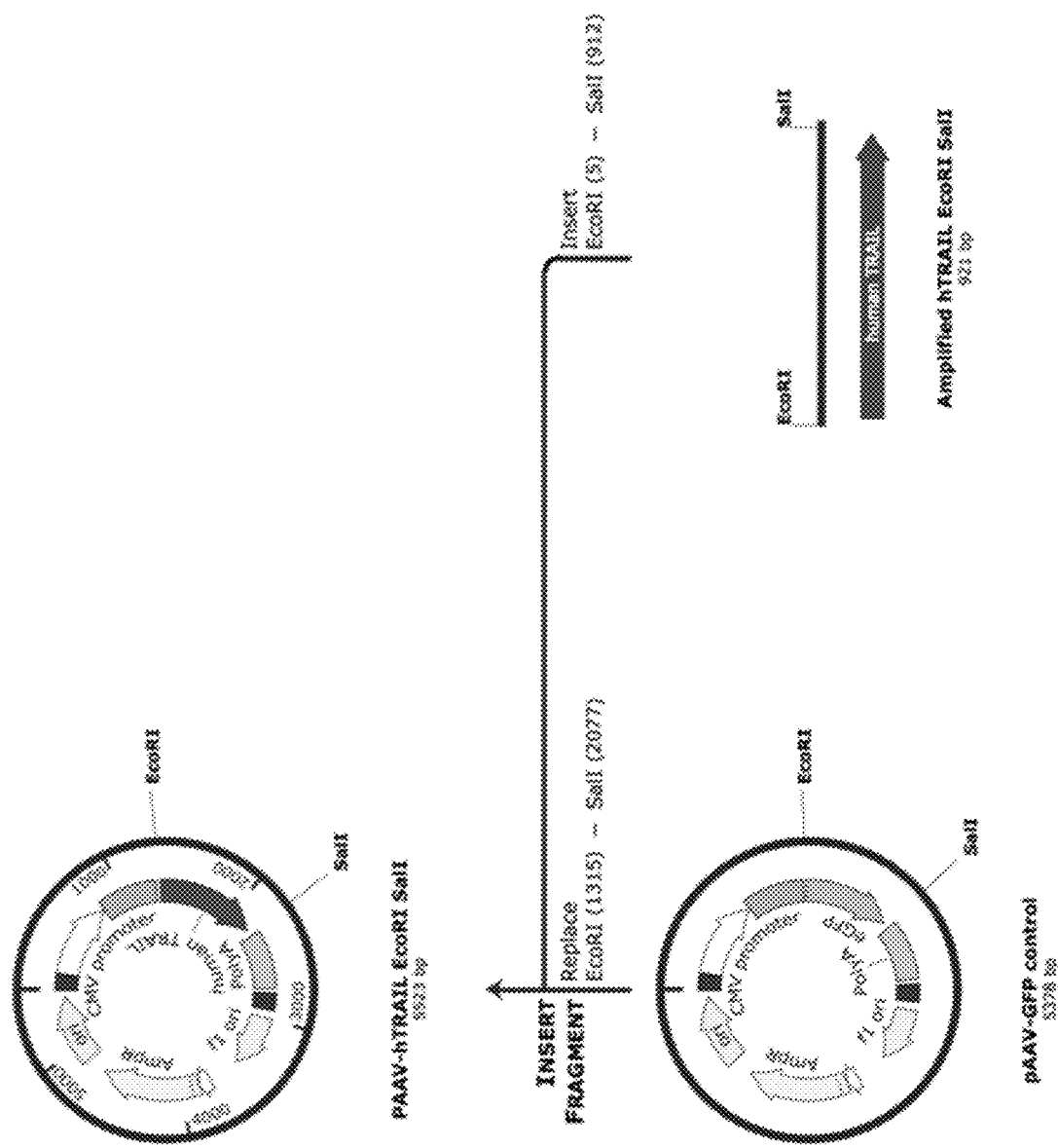
Figure 47:
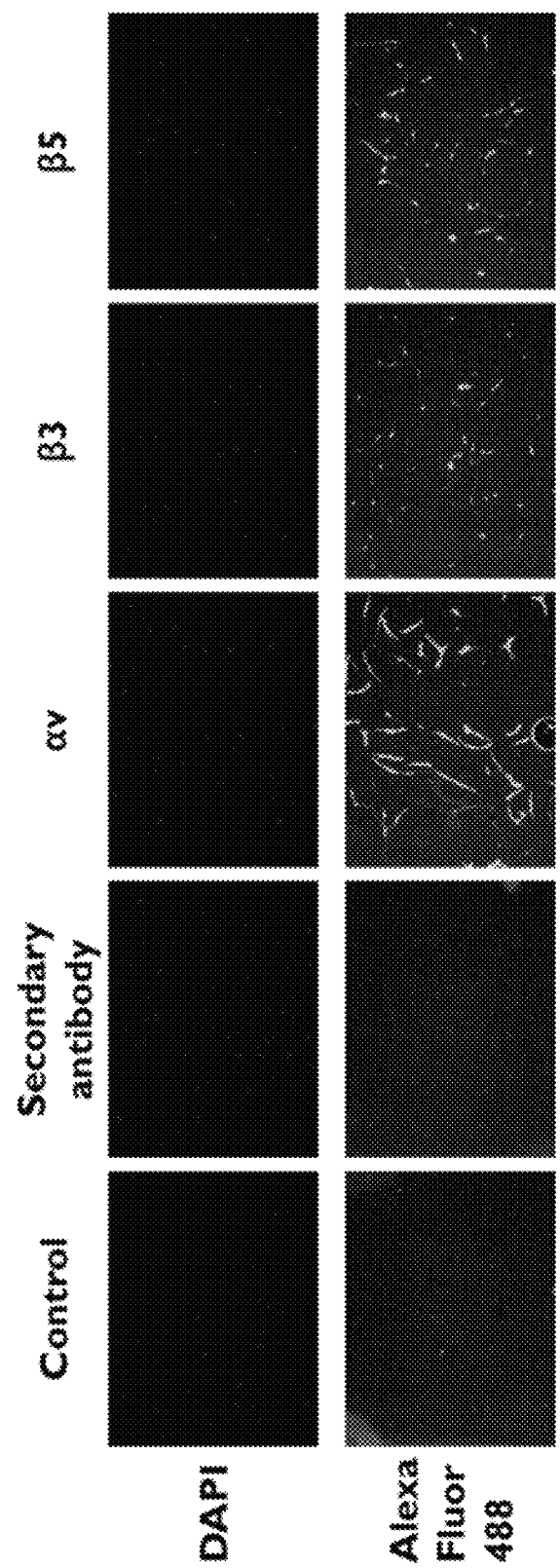
Figure 48:
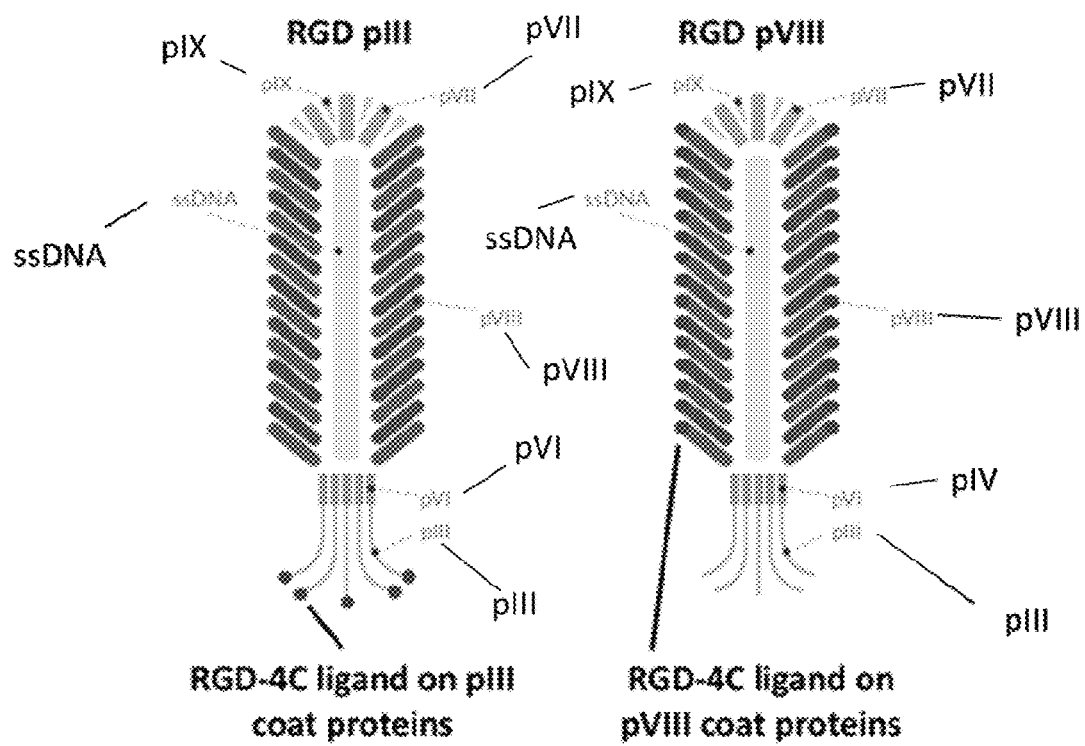
Figure 49:
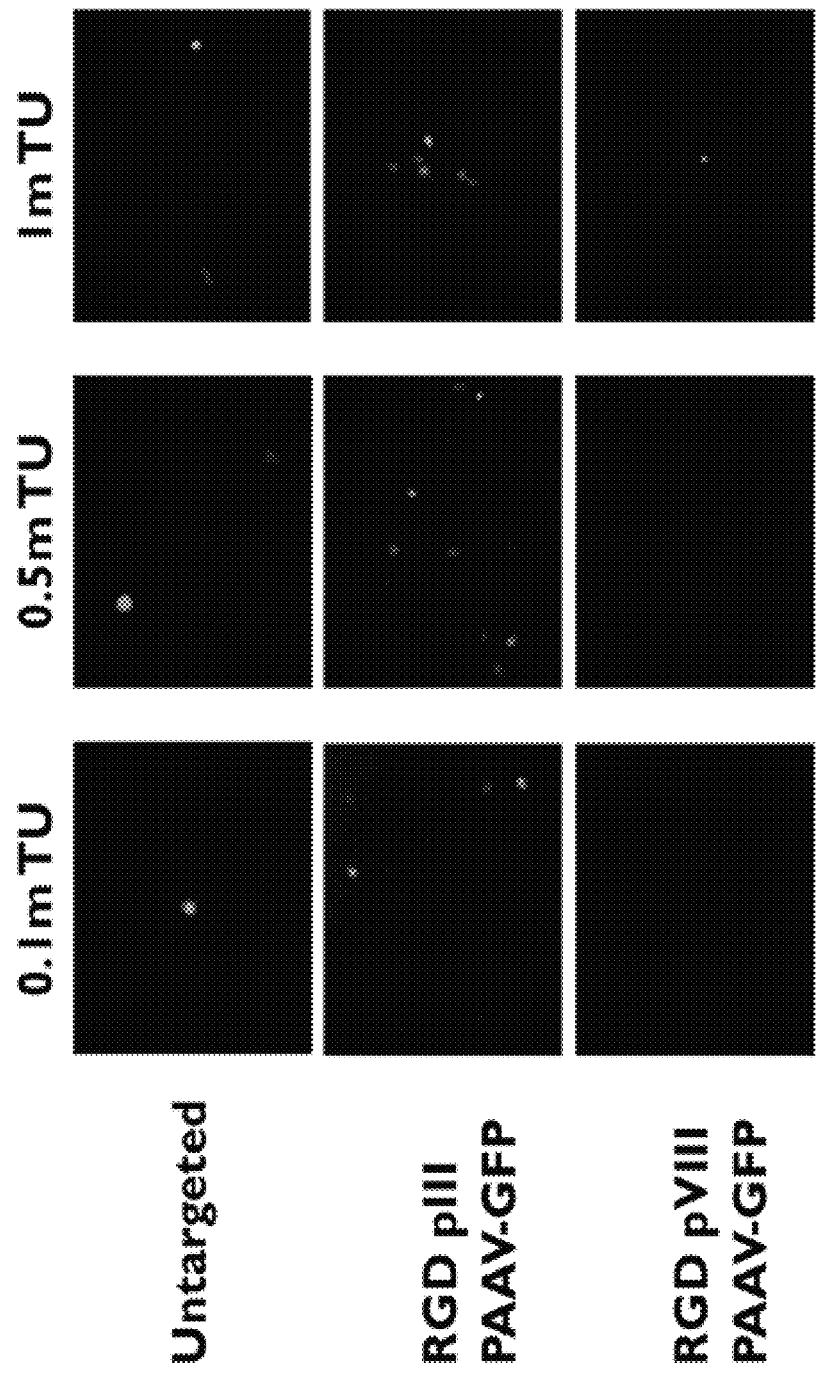
Figure 50:
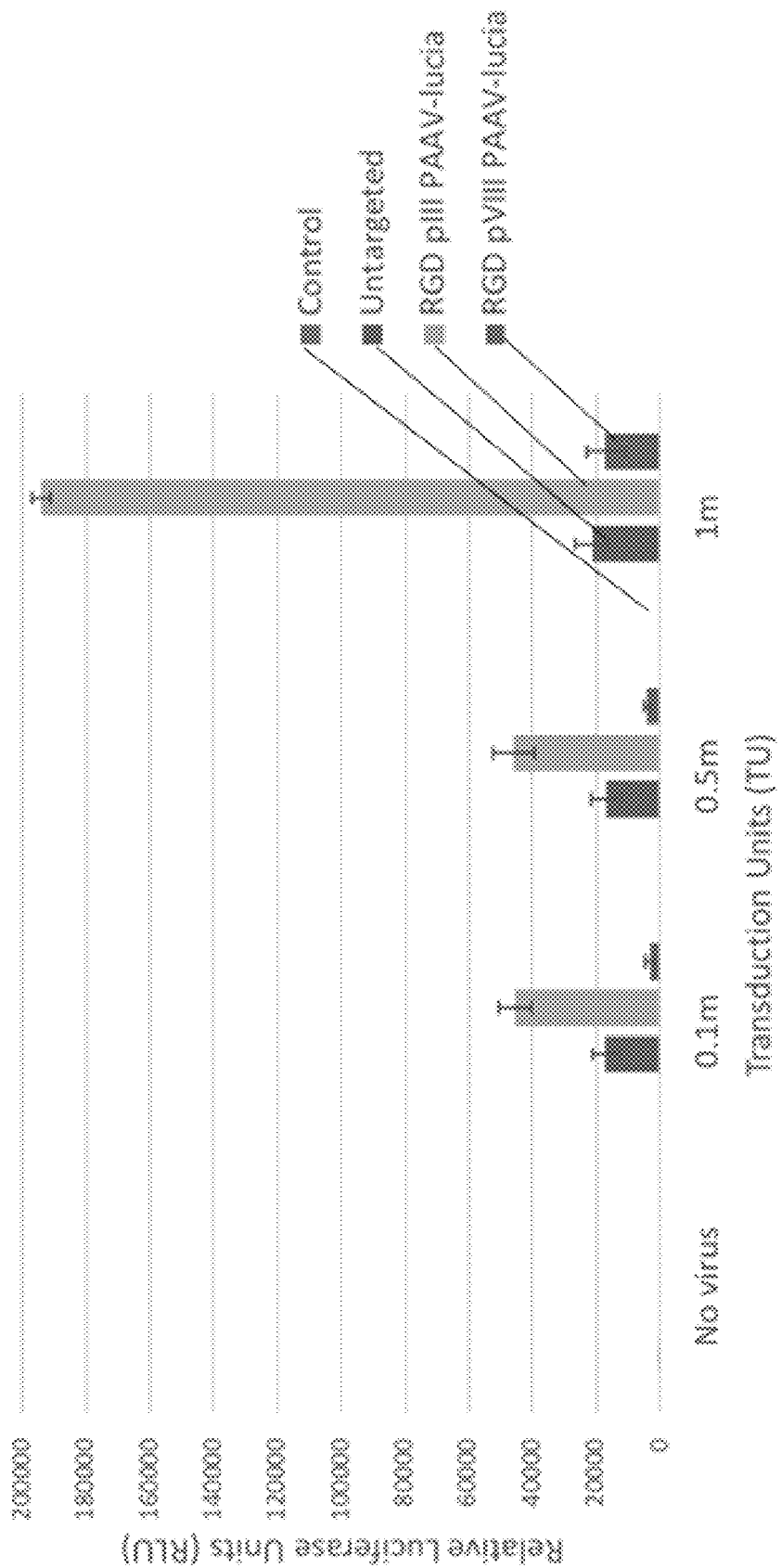
Figure 51:
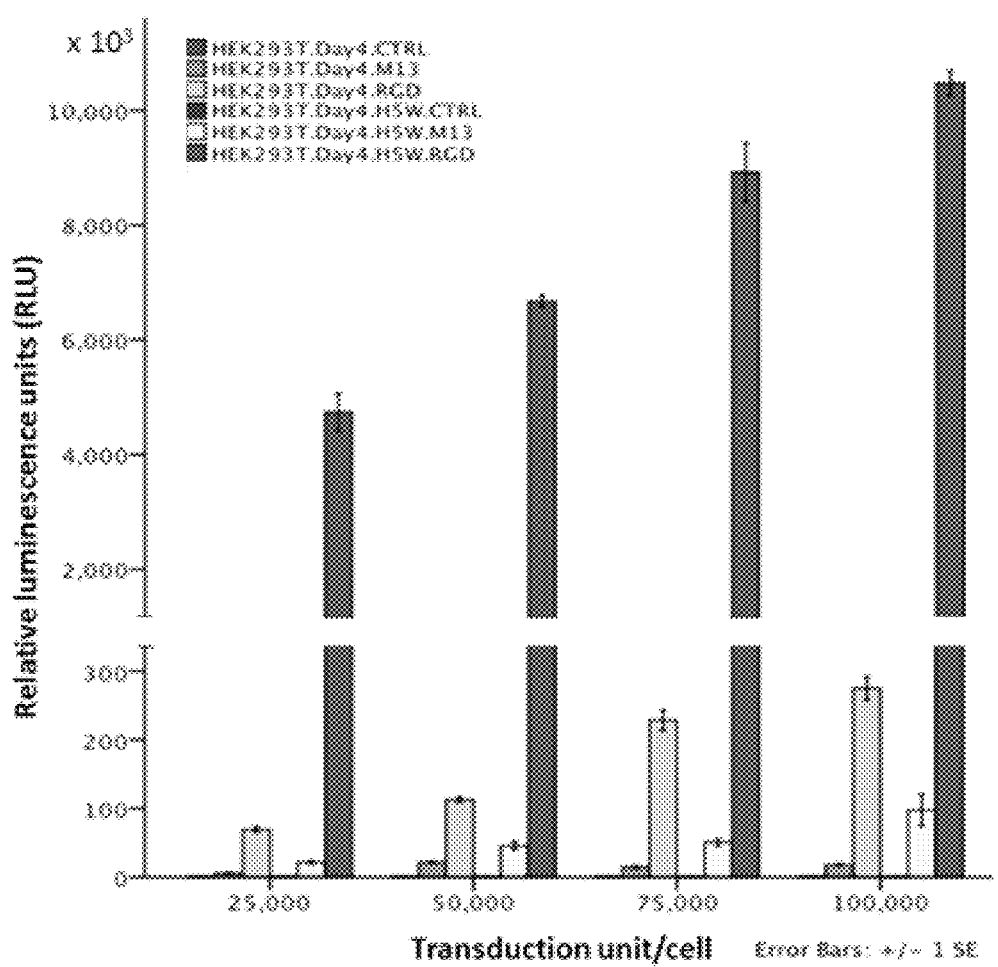
Figure 52:
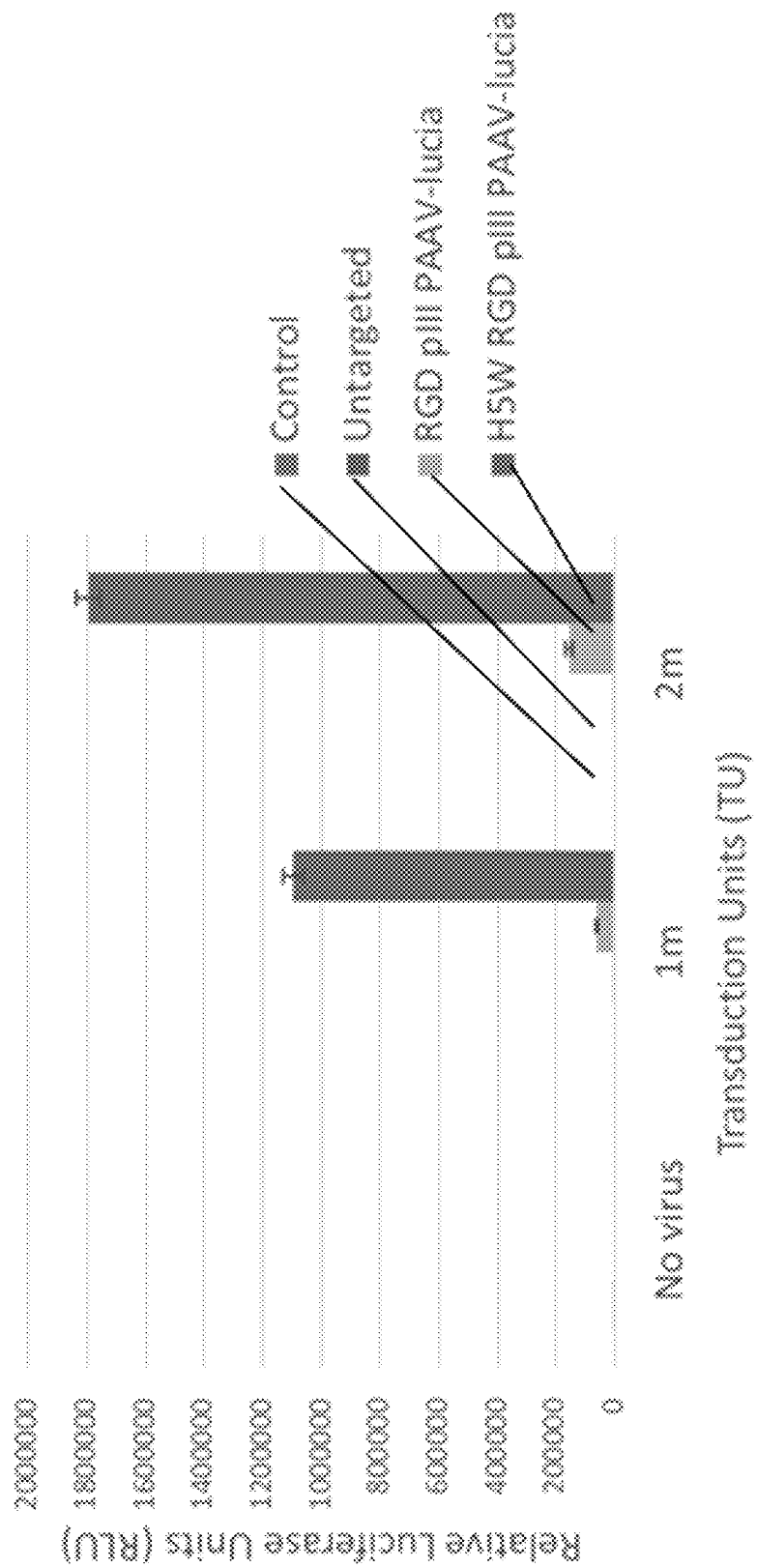
Figure 53:
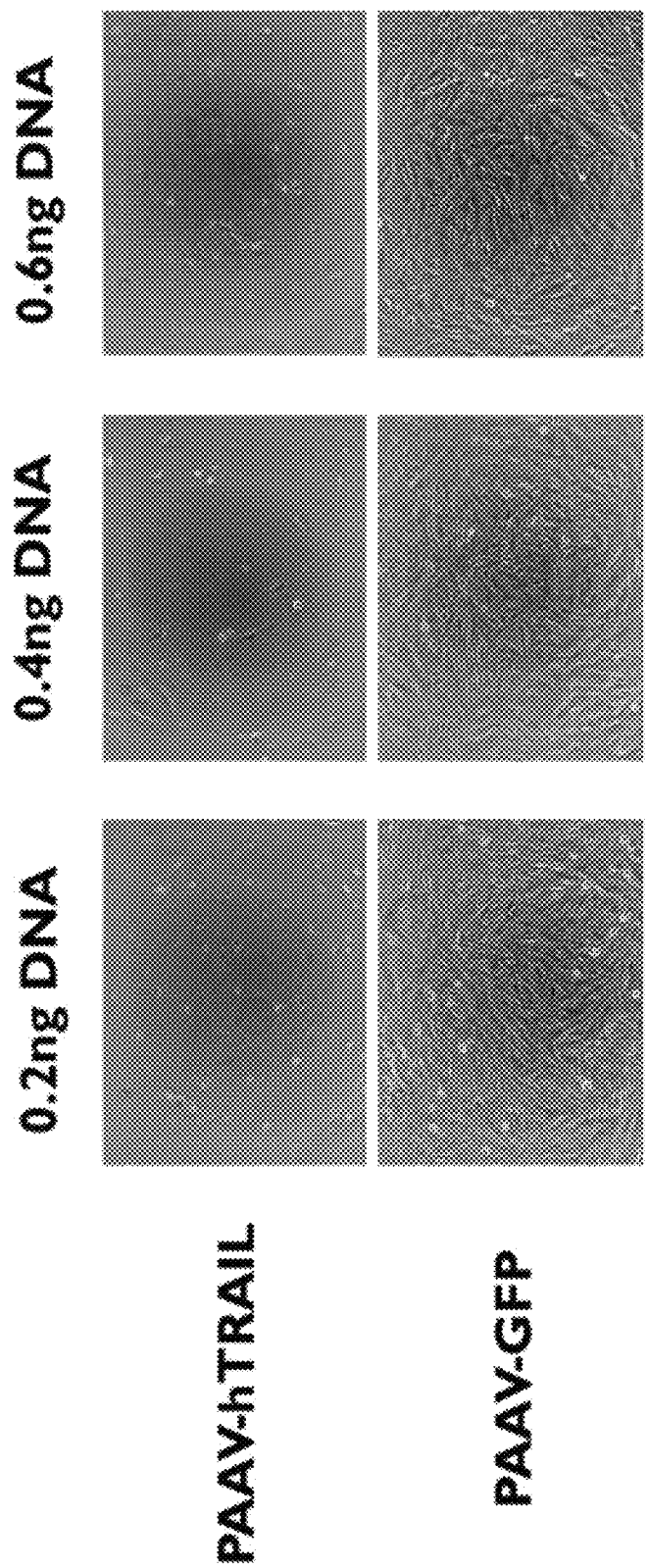
Figure 54:
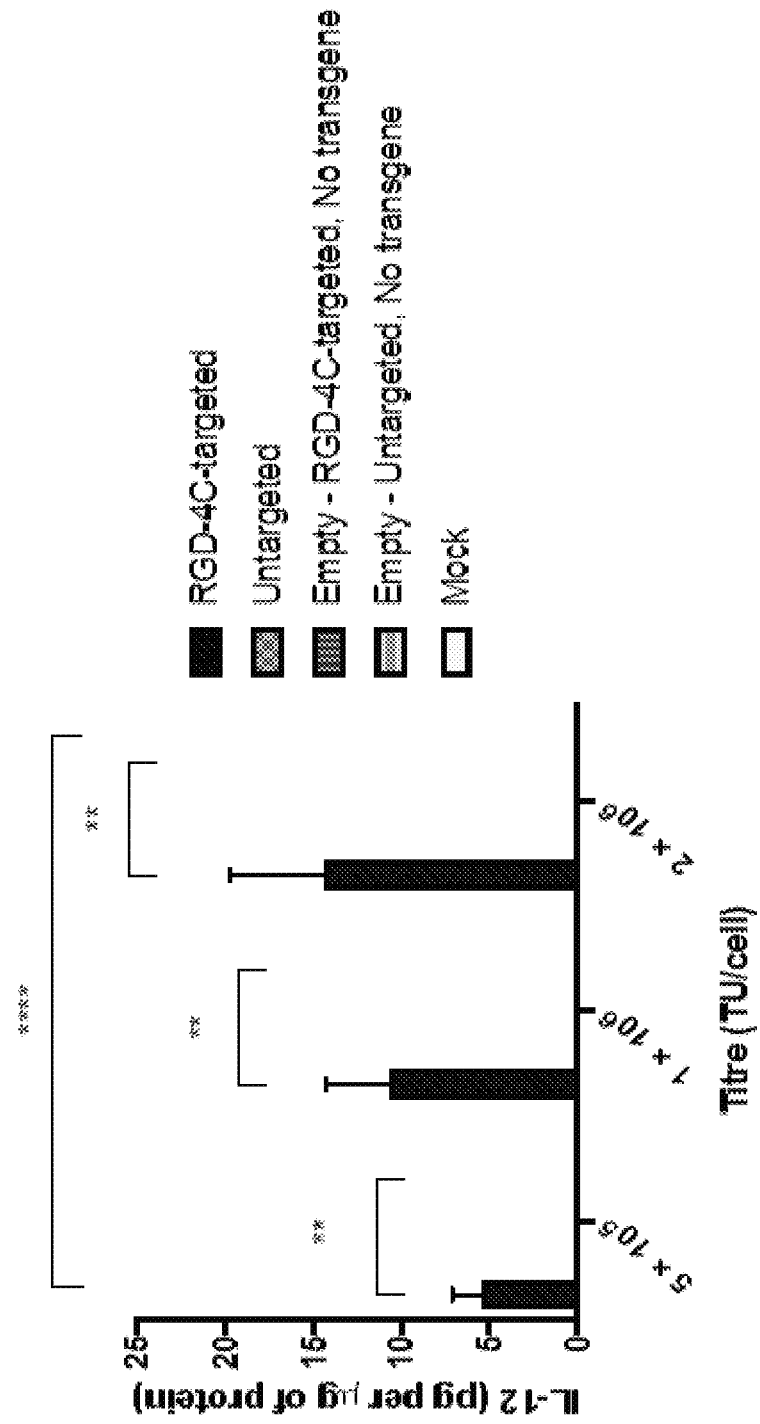
Figure 55:
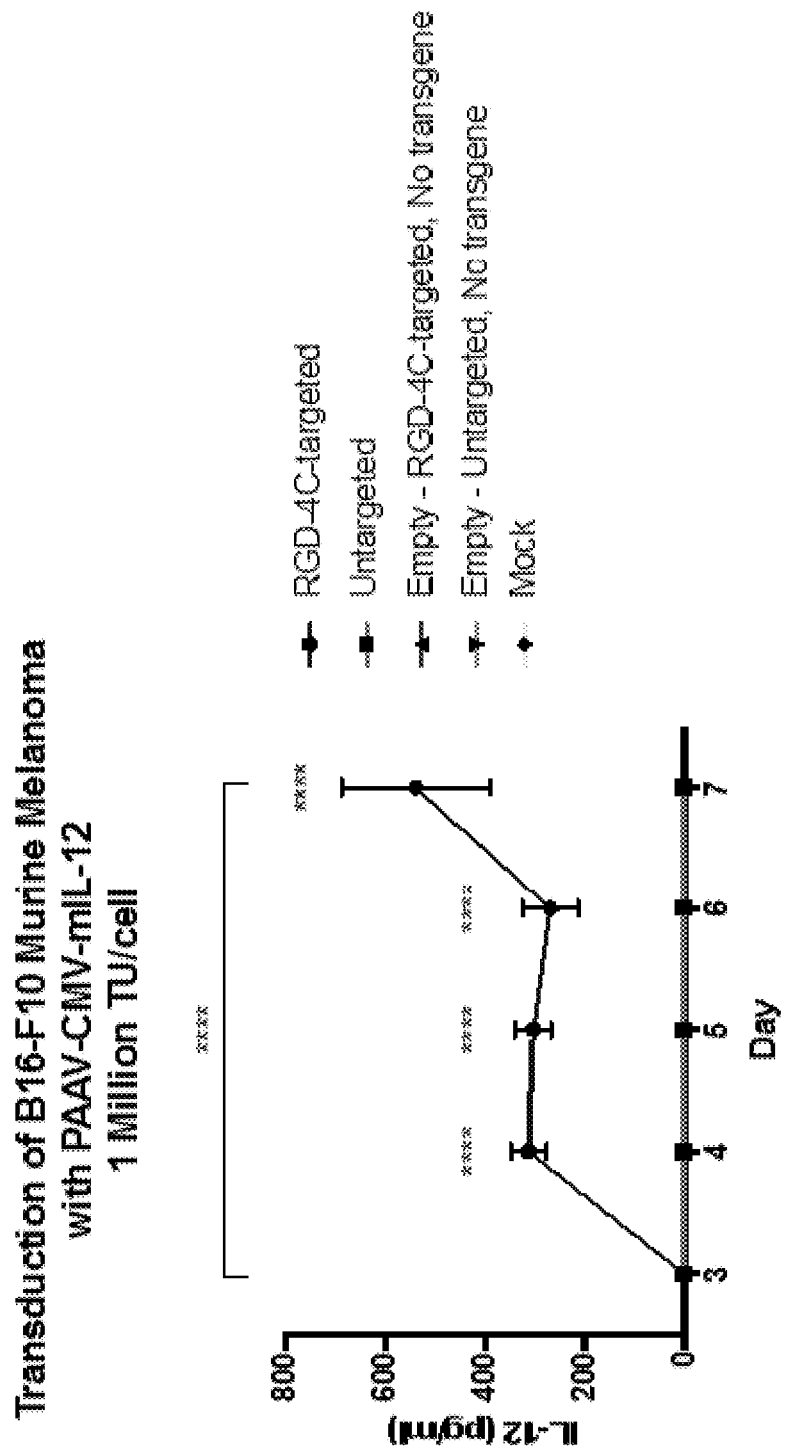
Figure 56:
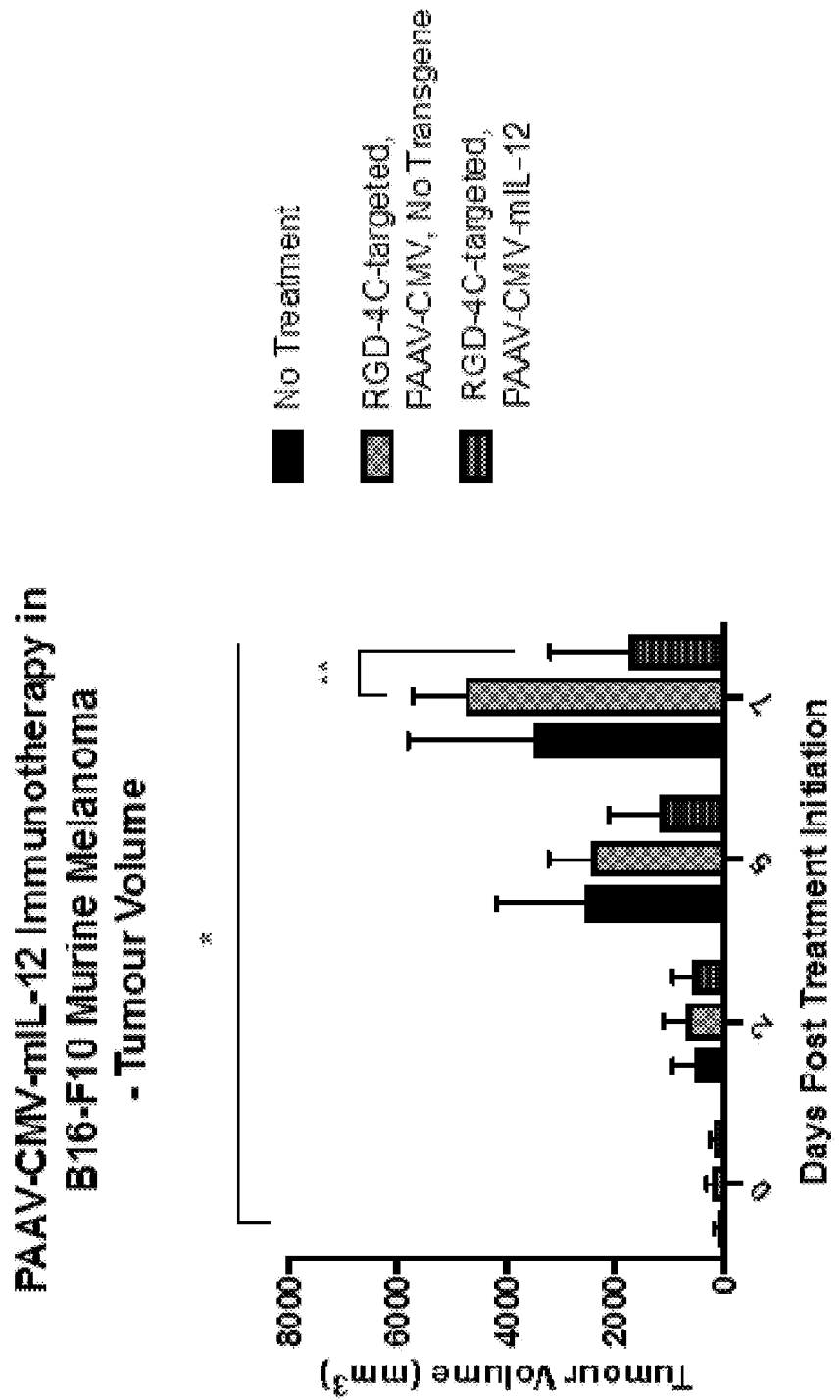
Figure 57:
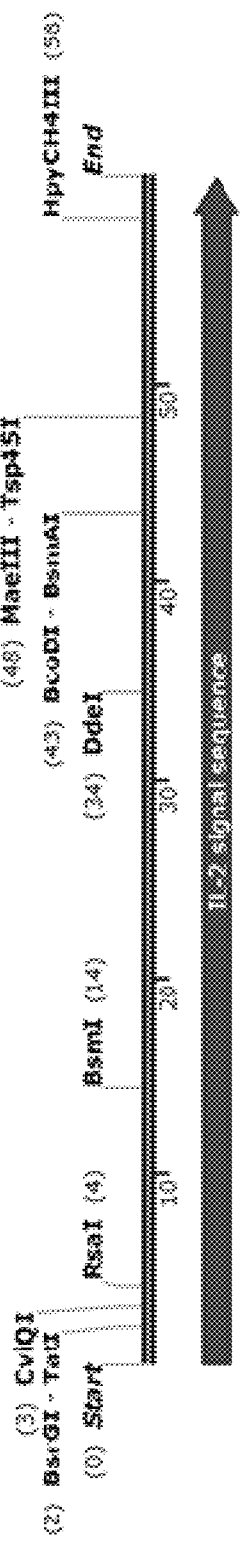
Figure 58:
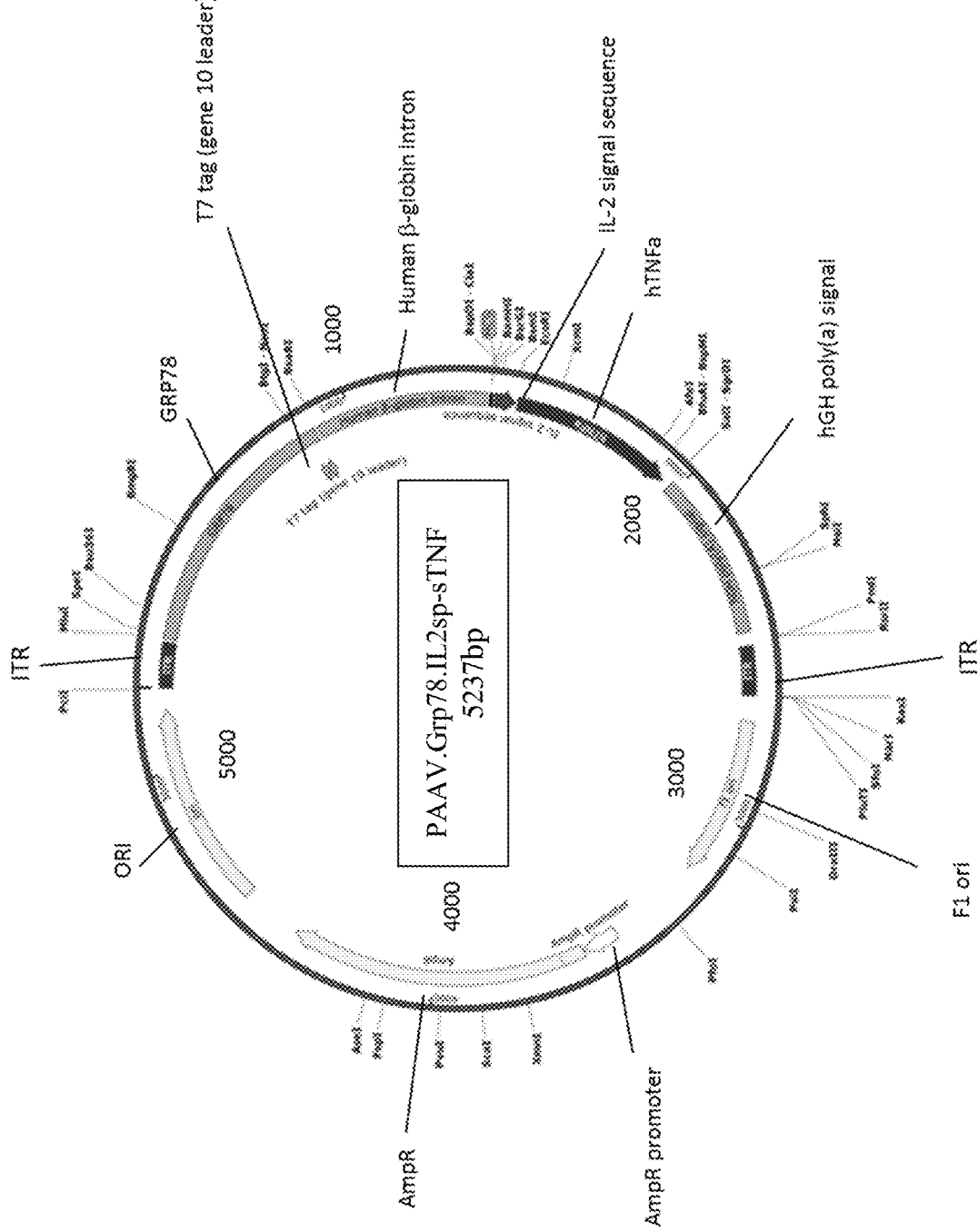
Figure 59:
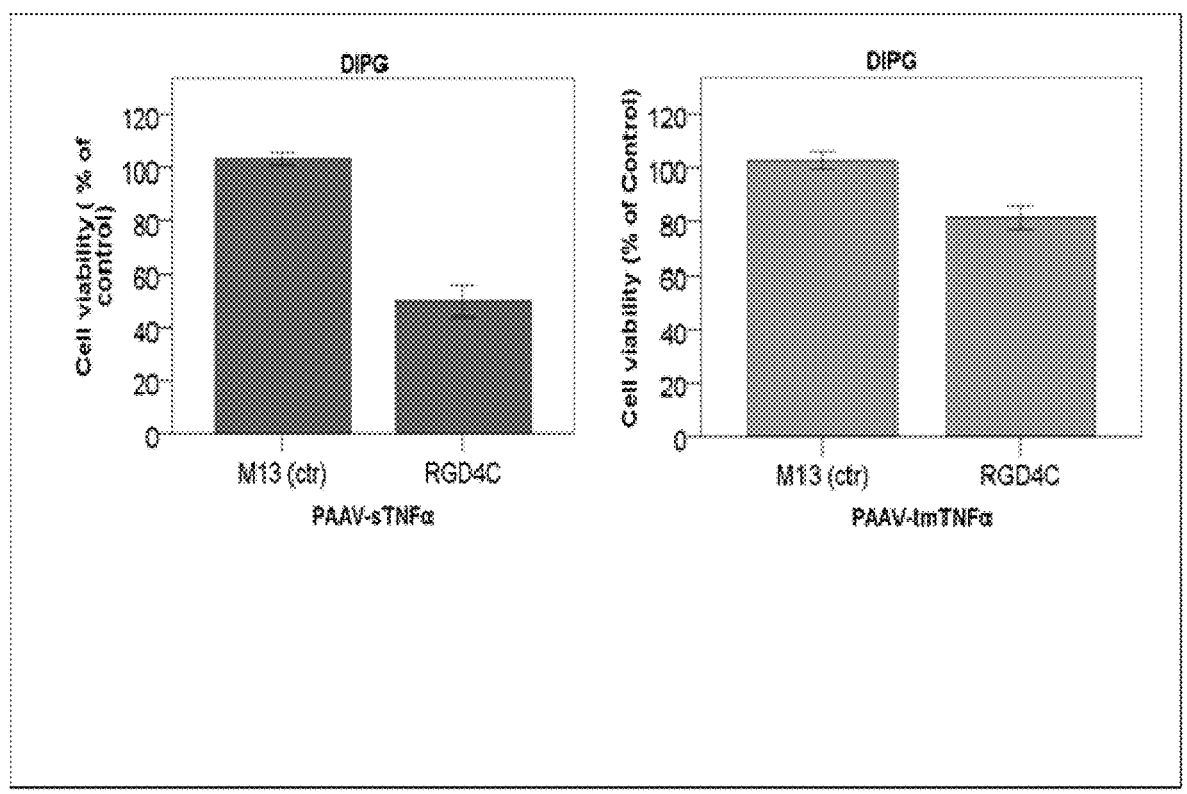
Figure 60:
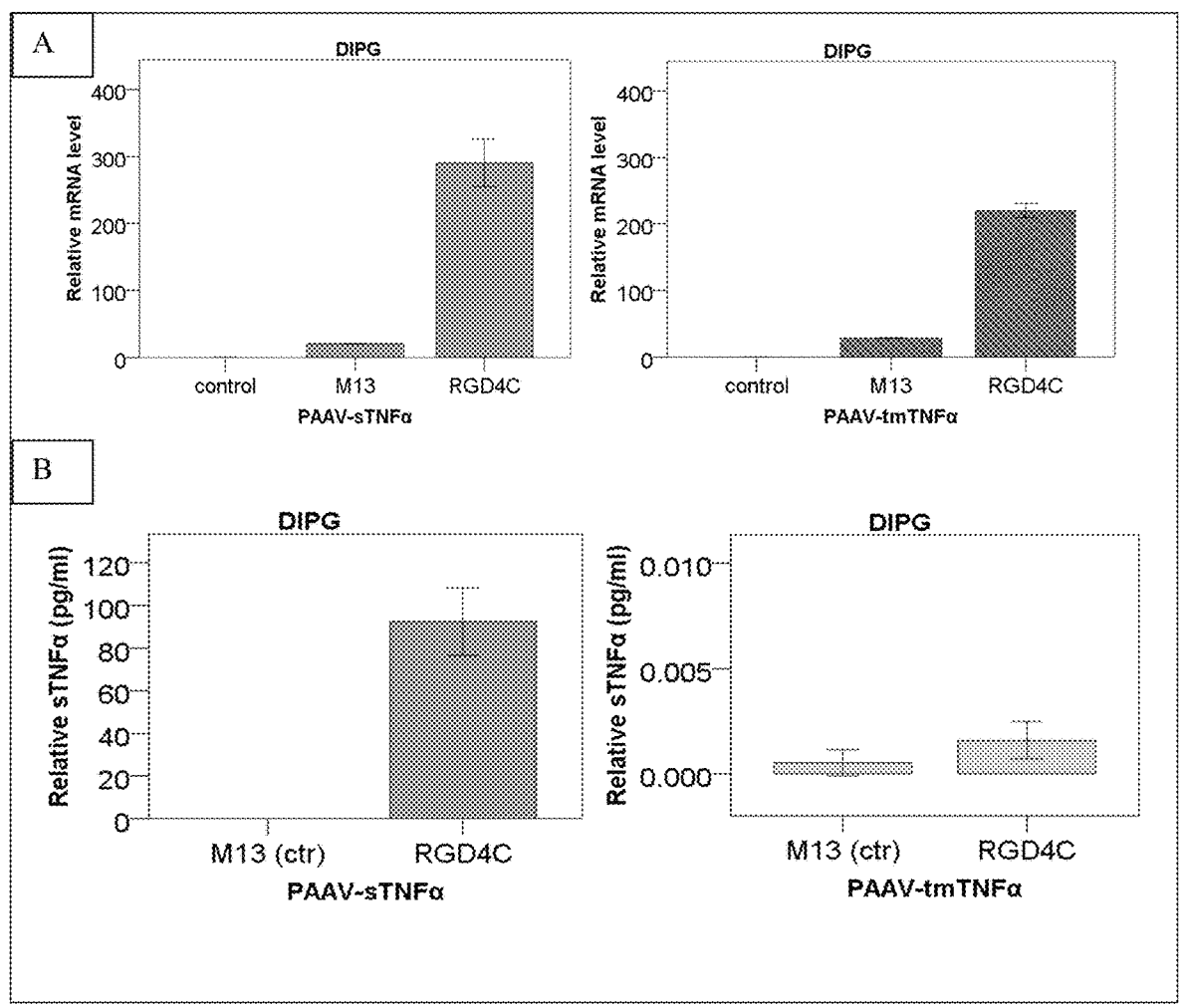

FIG. 39 shows the effect of TNFα and cisplatin combination treatment in UW228 cells. Cell viability was measured at different time points using sulphorodamine B assay. Stably transduced UW228 were treated with 1 μM and 5 μM cisplatin chemotherapy 48 hrs after seeding the cells. Data are represented as mean±SEM.***P≤0.001. The figure shows that a combination with cisplatin (cis) chemotherapy increases tmTNFα cytokine gene therapy against medulloblastoma;

FIG. 40 shows expression of TNF after PAAV-sTNF transduction. DIPG were seeded in 96-well plate and transduced with $2\times10^6$ TU/cell with DEAE dextran, the supernatant was collected at day 3 and TNFα in the supernatant was determined by ELISA;

FIG. 41 shows the generation of PAAV-CMV-tmTNFα;

FIG. 42 shows the generation of PAAV-sTNFα;

FIG. 43 shows a targeted PAAV vector, showing RGD-4C ligand displayed on pIII coat proteins of the M13 filamentous phage. The hybrid genome shows important gene fragments that are necessary for expression of the desired gene;

FIG. 44 shows a schematic for producing RGD pVIII helper viruses;

FIG. 45 shows a schematic for producing RGD pVIII PAAV-GFP and RGD pVIII PAAV-lucia, which are used in in vitro transduction experiments to assess efficiency of vector and level of gene expression;

FIG. 46 shows a schematic for producing PAAV-hTRAIL (image from SnapGene);

FIG. 47 shows fluorescent microscopic images of DIPG cells incubated with a primary anti-phage antibody and Alexa Fluor-488 labelled secondary antibody (green) to assess integrin ($\alpha_v/\beta_3/\beta_5$) expression. Images of control cells with no antibodies or secondary antibodies only were taken to account for background fluorescence. Nuclei were stained with DAPI (blue);

FIG. 48 shows theorised constructs of RGD-4C ligands as displayed on pIII (left) or pVIII (right) coat proteins of the M13 filamentous phage;

FIG. 49 shows fluorescent microscopic images of HEK293T cells incubated with un-targeted, RGD pIII PAAV-GFP or RGD pVIII PAAV-GFP vectors at 0.1 m TU, 0.5 m TU and 1 m TU at day 6 post-transduction. GFP expression is highest in RGD pIII PAAV-GFP at all Tus;

FIG. 50 shows RLU of HEK293T cells incubated with un-targeted, RGD pIII PAAV-lucia or RGD pVIII PAAV-lucia vectors at 0.1 m TU, 0.5 m TU and 1 m TU at Day 6 post-transduction. RLU is highest in RGD pIII PAAV-lucia at all TUs. Error bars are +/−1 standard error;

FIG. 51 shows RLU of HEK293T cells incubated with vectors at Day 4 post-transduction. RLU is highest in H5W RGD pIII PAAV-lucia at all TUs. Error bars are +/−1 standard error. (Sajee Waramit, unpublished data);

FIG. 52 shows RLU of DIPG cells incubated with un-targeted, RGD pIII PAAV-lucia or H5W RGD pIII PAAV-lucia vectors at 1 m TU and 2 m TU at Day 3 post-transduction. RLU is highest in H5W RGD pIII PAAV-lucia at all TUs. Error bars are +/−1 standard error;

FIG. 53 Microscopic images of DIPG cells transfected with PAAV-hTRAIL and control PAAV-GFP plasmids at 0.2 ng, 0.4 ng and 0.6 ng DNA. Images were taken at 18 hours post-transfection. Cell viability is lower in cells transfected with PAAV-hTRAIL at all DNA concentrations;

FIG. 54 shows a Bar graph showing IL-12 concentration of media collected on day 6 post transduction with PAAV-CMV-IL-12 normalised to 1 µg of protein. Controls of transduction with a targeted and untargeted empty vector with a CMV promoter and mock transduction are shown. The outer selection bar designates analysis of IL-12 production data of all vector titres and controls by 2-way ANOVA. The inner selection bars designate comparison between vectors and controls at each titre by unpaired t-test. The experiment was performed in triplicate;

FIG. 55 shows a line graph showing mouse IL-12 concentration of media sampled at various days post transduction with PAAV-CMV-mIL-12. Controls of transduction with a targeted and untargeted empty vector with a CMV promoter and mock transduction are shown. The outer selection bar designates analysis of mouse IL-12 production data from all sampled days for vectors and controls by 2-way ANOVA. The asterisks over specific data points designate comparison between vectors and controls at each specified day by unpaired t-test;

FIG. 56 shows a bar graph showing the mean tumour size in mm3 of B16-F10 murine melanoma tumours in C57BL/6 mice over seven days after treatment with RGD-4C-targeted PAAV-CMV-mIL-12 (n=4) with RGD-4C-targeted PAAV-CMV with no transgene (n=4) and no treatment controls (n=4). Three doses of $5\times10^{10}$ TU vector were administered intravenously on days 0, 2 and 5. Data were analysed by 2-way ANOVA with a Tukey's multiple comparisons test;

FIG. 57 shows the IL2 signal sequence;

FIG. 58 shows the Il-2/TNFα construct;

FIG. 59 shows cell killing efficiency of RGD4C-sTNFα and RGD4C-tmTNFα in DIPG. DIPG cells were transduced with PAAV targeted (RGD4C) or non-targeted (M13) carrying either secreted or transmembrane TNFα (sTNFα) transgene. The cells were seeded in 96-well plate. Two day later, the cells were transduced with 2×[10]^6 TU/cell with 40 ng/µg of protein DEAE dextran. The viability was measured with sulforhodamine B (SRB) assay. Statistical significance was determined by student's t-test Data are represented as mean±SEM. *P00.05, **P≤0.01;

FIG. 60 shows expression of TNFα after transduction with PAAV-sTNFα and PAAV-tmTNFα. DIPG cells were seeded in 6-well plate and transduced with RGD4C and M13 carrying either secreted or transmembrane form of TNFα transgene. A) RNA was extracted and expression of TNFα was determined by qRT-PCR. B) The supernatant was collected and TNFα in the supernatant was determined by ELISA. Data are represented as mean±SEM. P≤0.01*P≤0.001. Statistical significance was determined by student's t-test;

BACKGROUND

The development of gene delivery technologies is instrumental to successful translation of basic research to the society. In the past decade, a number of viral and non-viral vectors have emerged as potential delivery vectors for industrial and therapeutic applications. An important property of vectors, in addition to being efficient at delivering genes, is that it must also be easily produced and commercially viable. In 2006, Hajitou et al. attempted to fulfil the need for such vectors by creating a hybrid between recombinant adeno-associated virus (rAAV) and filamentous bacteriophage (phage), called the adeno-associated Virus/Phage (AAVP) (*Nature protocols* 2, 523-531 (2007); *Cell* 125, 385-398 (2006)). The resulting AAVP vector possesses favourable characteristics of mammalian and prokaryotic viruses, but does not suffer from the disadvantages that those individual vectors normally carry. However, there are certain aspects of the AAVP vector that still leaves room for significant improvement. Above all, this includes the genetic design of the vector, which carries ramifications in its production and therapeutic properties. Ultimately, this leads to AAVP's relatively low gene transduction efficacy when compared to mammalian viruses.

The research described herein relates to the design of the most advanced version of phage gene delivery vectors and their superiority to the known and existing phage vector, AAVP, by using a so-called "phagemid system", with the new phagemid vector being referred to as Phagemid/Adeno-associated Virion Phagemid (i.e. PAAV). Unlike the AAVP genome, which consists of a rAAV cassette inserted in to the filamentous phage genome, the PAAV genome does not contain any structural phage genes—a prokaryotic helper virus is required to facilitate vector assembly (*Mol Ther* 3, 476-484; *Pharmaceutical research* 27, 400-420 (2010)). Separating the reproductive and therapeutic elements of the virus in to a therapeutic vector carrying the transgene and a separate helper virus carrying the structural genes substantially decreases the genome/vector size and thereby significantly increases transgene capacity, a useful advantage for gene therapy applications of the new system. Consequently, this results in the encapsidation of a eukaryotic virus genome into the capsid of a prokaryotic virus, resulting in a vector as hybrid between eukaryotic genome and prokaryotic capsid with enhanced production yield, gene transduction efficiency and flexibility of the vector system for other applications.

As described in the Examples below, the inventors have:—
1. Designed and constructed a hybrid Phagemid—AAV Vector (PAAV) particle expression system;
2. Characterised and determined whether the phagemid/ AAV vector (PAAV) is more efficient at gene transduction than the known AAVP system at various stages, including but not limited to:
   a. Binding to the cell surface,
   b. Internalisation of the vector from the cell surface,
   c. Recombinant transgene expression.
3. Determined whether the hybrid phagemid PAAV vector system is capable of producing rAAV from a mammalian producer cell-line.
4. Demonstrated that the system can be used in CAR-T therapy for cancer treatment.
5. Demonstrated that the system can be used to deliver the cytokines IL-12, TRAIL and hybrid TNFα to target cells for cancer treatment.
6. Designed and constructed a phagemid particle comprising a hybrid TNFα construct.
7. Demonstrated that a hybrid TNFα constructs show increased expression, secretion and cell killing efficiency when compared to full length TNFα.

Figure 1:
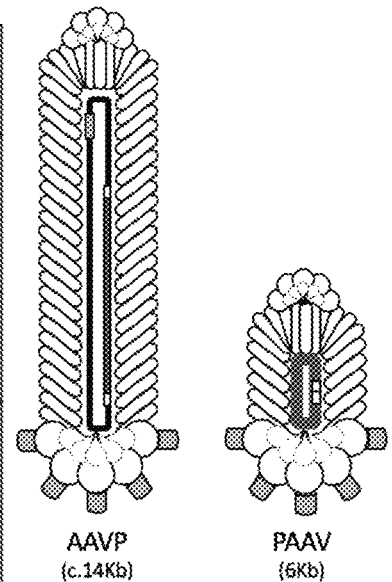

Referring first to FIG. 1, there is shown a table comparing features of the phagemid-AAV (PAAV) particles according to the invention (i.e. virions) with the prior art AAVP viral particles. As can be seen, the PAAV particles (6 kb) of the invention are much smaller than the known AAVP particles (14 kb), i.e. 42% less DNA, and 50% shorter viral particles, and the PAAV particles are produced at yields that far surpass prior art systems (100×) the yield of AAVP). As a result, PAAV particles of the invention can carry larger payloads, which is very useful for delivering multiple transgenes in gene therapy approaches. The inventors have therefore demonstrated that the modified bacteriophage expression system (PAAV) can be used as a highly viral vector for gene therapy, or for large-scale production of viral vectors.

Example 1—Phagemid—AAV Vector (PAAV) Construction

Figure 2:
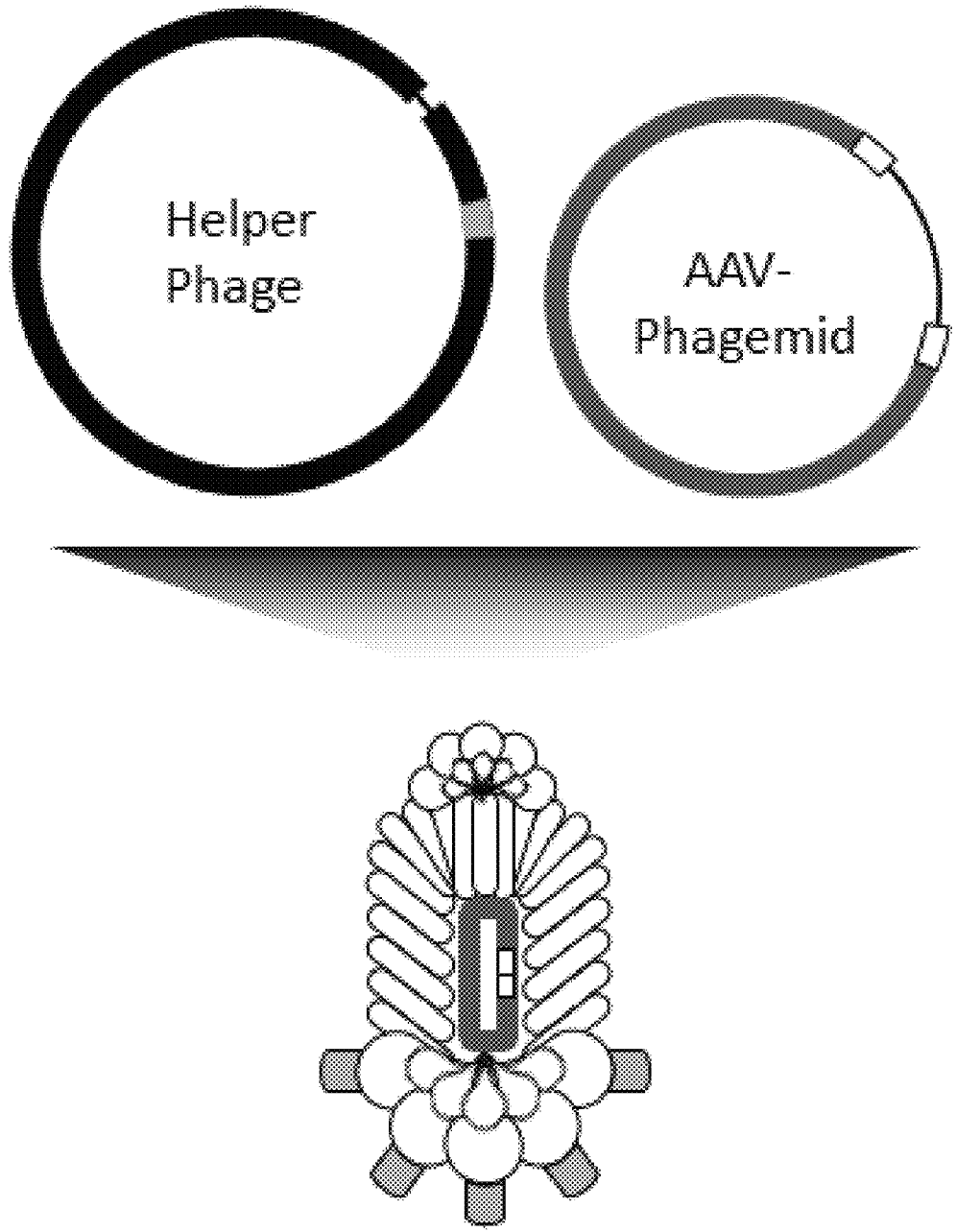

Referring to FIG. 2, there is shown an embodiment of a Helper Phage genome and a Phagemid genome (PAAV DNA) according to the invention, which are used together upon expression in a prokaryote to produce the phagemid-AAV (PAAV) particle, also shown in FIG. 1. Structural genes are integral to packaging of DNA in to virus particles, and are supplied by the replication-defective Helper phage, which is discussed in detail below. The phagemid genome is extremely parasitic to the Helper phage, meaning it outcompetes the replication-defective helper phage in both replication and packaging.

A) Phagemid/AAV Vector

Referring now to FIG. 3, there is shown one embodiment of the phagemid genome which is a plasmid containing two origins of replication and two other genetic elements. Phagemid genomes require two origins of replication to facilitate both its replication inside the prokaryotic (e.g. bacterial) host and packaging into phagemid particles when rescued by a helper virus.

Figure 4:
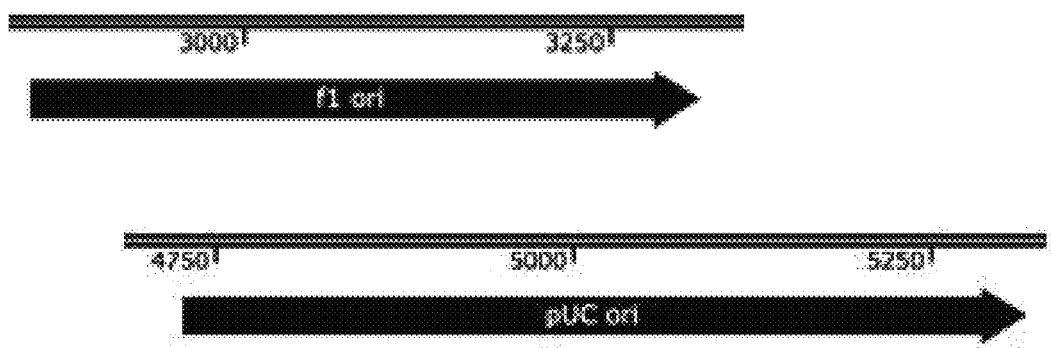
FIG. 4 shows the respective locations of f1 ori and pUC ori on the phagemid genome shown in FIG. 3.

Referring to FIG. 4, the first origin of replication (ori) is a high-copy number origin of replication (pUC ori) that enables replication of the double-stranded phagemid (dsDNA) inside the prokaryotic host at large quantities. The second origin of replication is a phage origin of replication (f1 ori) that enables replication of the plasmid into single-stranded DNA, which can subsequently be packaged into a phagemid vector particle (PAAV).

Referring to FIG. 5, the phagemid genome includes a selection marker gene. In order for the phagemid genome to replicate efficiently inside the prokaryotic host, a selection marker (e.g. ampicillin resistance) is used to ensure expression and provides selective pressure to prevent loss of the phagemid genome in the form of an antibiotic resistance gene (with its own promoter). This ensures expression (and replication) of the phagemid genome when the prokaryotic host is cultured in the presence of the antibiotic that the selection marker confers resistance to.

Referring to FIG. 6, the phagemid genome further includes a recombinant (adeno-associated virus, AAV) transgene cassette which contains a transgene of interest. This can include, but is not limited to, polypeptides/proteins, short hairpin/small interfering/short guiding RNAs, or a combination of both. By way of example only, the transgene shown in FIG. 6 encodes GFP and human Beta-globin. Expression of the transgene is driven by a viral promoter (e.g. CMV) and/or enhancer sequences, and tailed with a polyA signal. The promoter can also be a mammalian and tumour specific promoter in cancer gene therapy applications (i.e. promoter of the Glucose Regulated Protein [grp78]). The entire transgene cassette is flanked by Inverted Terminal Repeat sequences (ITRs) from AAV, which form a protective hairpin structure allowing the transgene cassette to be stably maintained as concatameric episomal (extrachromosomal) DNA in the mammalian cell nucleus transduced by the phagemid particle. The ITRs allow concatemer formation of AAV and subsequently enable AAV transgene cassettes to be stably expressed over a long period of time.

The phagemid is unable to package itself into particles as it lacks structural phage genes. As a result, it requires "rescuing" by a helper virus, as shown in FIG. 7, which provides structural (i.e. capsid) proteins required for formation and extrusion of particles from the prokaryotic host. Conventionally speaking, genetic elements in the vector are generic and used widely in genetic engineering.

B) Helper Phage

Referring to FIG. 7, the helper phage (referred to herein as M13KO7) is a bacteriophage engineered specifically for rescuing phagemid particles (i.e. PAAV) from prokaryotic hosts carrying and/or containing the phagemid genome shown in FIG. 3. The helper phage contains a disrupted origin of replication (p15a, medium copy number) and packaging signal, which significantly deters its ability to package itself into phage particles. Consequently, the phagemid genome will outcompete the helper phage in both replication and packaging.

In order to give the phagemid targeting properties (or multifunctional properties as described in WO 2014/184528), the genome of the helper phage must be engineered to do so, as it provides the structural capsid proteins for phagemid particle assembly. For example, the helper genome may encode a pIII capsid minor coat protein that is configured to display a cell-targeting ligand for enabling delivery of the resultant PAAVP particle to a desired target cell (e.g. tumour). It can also encode at least one pVIII major coat protein that is configured to display a foreign peptide on the resultant PAAV particle. In one embodiment, therefore, it is desired to induce a 9-amino acid mutation in the pIII minor coat protein to confer specificity to tumour cells and angiogenic tumour-associated endothelial cells that express $\alpha_v\beta_3$ and $\alpha_v\beta_5$ integrin receptors. Thus, referring to FIG. 8, the genome of the helper phage comprises the RGD4C peptide (CDCRGDCFC—SEQ ID No: 7) targeting these $\alpha_v\beta_3$ and $\alpha_v\beta_5$ integrins.

Once the PAAV phagemid genome and the Helper phage have been constructed, they are used together to produce, in a prokaryotic host, the Phagemid—AAV Vector (PAAV) particle, as discussed below.

Example 2—Phagemid—AAV Vector (PAAV) Production

The inventors have devised two different methods (Methods 1 and 2) for producing the Phagemid—AAV Vector (PAAV) particle, and these are illustrated in FIGS. 9 and 10.

Notes:
TG1: a strain of *E. coli* that carries the fertility factor (F' pilus).
2×YT: liquid broth used to culture TG1 *E. coli*.
Kanamycin: antibiotic resistance selection marker present on the helper phage.
Ampicillin: antibiotic resistance selection marker present on the phagemid vector.
TYE top agar: solid media used to culture TG1 *E. coli*, adapted from 2×TY by the addition of 1.25% bacteriological agar.

Phagemid/AAV Vector (PAAV) Production Method 1: Infective Rescue

With reference to FIG. 9:
1. Add 4-5 ml of TG1 *E. coli* carrying PAAV genome pre-culture (overnight) to 60 ml 2×YT (100 µg/mL Ampicillin) supplemented with 1% glucose.
2. Incubate culture at 37° in shaker (250 RPM).
3. Once $OD_{600}$ is in the range of 0.5 to 0.8 (log phase), add at least
   $1\times10^{10}$ transducing units of helper phage (M13KO7) to culture.
4. Invert to mix. Incubate at 37° for 30 minutes.
5. Pour the infected starter culture from step 3 in to a 2 L flask with 2×YT (100 µg/mL Ampicillin+25 µg/mL Kanamycin) supplemented with 1% glucose to a final volume of 400-450 mL.
6. Incubate overnight in an orbital shaker at 37°, 250 rpm for 16-20 hours.
7. Purify phagemid (PAAV) particles from culture supernatant.

The benefits of Method 1 are its very high yields.

Phagemid/AAV Vector (PAAV) Production Method 2: Stable Producer Cell-Line

With reference to FIG. 10:
Part 1: Competent Producer Cell-Line Production
1. Transform and plate TG1 competent *E. coli* (Zymo Research, USA) with ssDNA genome from helper hage M13KO7 in TYE top agar (50 µg/mL Kanamycin)
1. Pick individual colonies and inoculate 5 mL 2×YT media (50 µg/mL Kanamycin) supplemented with 1% glucose.
2. Incubate overnight in an orbital shaker at 37°, 250 rpm for 16-20 hours
3. Check for true positive transformants by extracting DNA from the 5 mL overnight cultures using a commercial extraction kit (QIAGEN, Netherlands) and run on 1% agarose gel (100 volts, 2.5 mA) against a DNA ladder.
4. Prepare chemically competent cells from the correct transformant identified in step 4 using a published protocol (adapted from that published by Krantz et al., UC Berkeley)

Part 2: PAAV Phagemid Particle Production
1. Transform competent cell-line created in Part 1 with a Phagemid/AAV genome and plate on TYE top agar (100 µg/mL Ampicillin+50 µg/mL Kanamycin)
2. Pick a colony and inoculate 5 mL 2×YT (100 g/mL Ampicillin+50 µg/mL Kanamycin) supplemented with 1% glucose.
3. Incubate in an orbital shaker at 37°, 250 rpm for 4 hours
4. Pour the infected starter culture from step 3 in to a 2 L flask with 2×YT (100 µg/mL Ampicillin+25 µg/mL Kanamycin) supplemented with 1% glucose to a final volume of 400-450 mL
5. Incubate overnight in an orbital shaker at 37°, 250 rpm for 16-20 hours
6. Purify phagemid particles from culture supernatant PAAV Phagemid Particle Purification
1. Transfer the warm overnight culture to centrifuge bottles and pellet the bacteria by centrifugation at 3300 G, 4° for 30 minutes.
2. Discard the pellet and transfer supernatant to a clean centrifuge bottle.
3. Add 30% volume of supernatant in each bottle with ice-cold 20% PEG-800/2.5M NaCl and swirl to mix.
4. Incubate on ice for 4-24 hours
5. Precipitate phagemid particles by centrifugation at 10000 G, 4° for 30 minutes. Discard the supernatant.
6. Dry the phagemid particle pellet by centrifugation at 10000 G, 4° for 1 minute.
7. Remove remaining supernatant with PEG/NaCl
8. Resuspend the phagemid particle pellet in 0.5-2 mL PBS
9. Filter the resuspended phagemid particle preparation using a 0.45 micron filter.
10. Keep the preparation at 4°. The preparation is stable for up to 2 years 4°. A 25% glycerol stock can be stored indefinitely at −80°.

Example 3—Use of Phagemid—AAV Vector (PAAV) for Gene Therapy Techniques

Examples 1 and 2 describe the components of the invention (i.e. phagemid genome shown in FIG. 3 and helper phage shown in FIG. 7) required to produce the Phagemid—AAV Vector (PAAV) particle and two methods of production. Once produced and purified, the PAAV particles can have a range of uses, such as in gene therapy.

As an example, the PAAV particles described herein carry the GFP transgene, as it is readily detectable in known assays to show successful delivery to a target cell. In therapy, any transgene may be selected and engineered into the phagemid genome shown in FIG. 3, to be carried in the resultant PAAV particles. For example, the transgene may be any gene encoding a protein, which may have therapeutic or industrial utility. For example, the transgene may encode one or more antigen for recognition by adoptively transferred T cells, such as CAR T cells. The transgene may also encode a short hairpin/small interfering/short guiding RNA molecule using in RNAi therapy. The transgene may encode multiple polypeptides, nucleic acids, or a combination of both, fused together using an internal ribosomal entry site (IRES) or a viral fusion peptide (T2A peptides for in-frame fusion).

Example 4—Use of Phagemid—AAV Vector (PAAV) for In Vitro AAV Production

In addition to gene therapy, the PAAV particles described herein can be used in novel methods for producing adeno-associated virus (AAV). Phage-guided AAV production utilizes the ability of the phagemid particles to package large amounts of dsDNA. A typical AAV production system consists of three major elements: rAAV, rep-cap and adeno-helper genes, which function together to production recombinant AAV particles. The inventors have devised two different strategies.

With reference to FIG. 11, the first strategy employed is to produce three different phagemid vectors that carry the rAAV-producing elements. These are the Phagemid—AAV Vector (PAAV) (see FIG. 3), the adenohelper phagemid particle (see FIG. 12), and the rep-cap phagemid particle (see FIG. 13). The basic structures of these particles are similar, as they contain two origins of replication and a selection marker, as described in the phagemid/AAV construction section. The key difference, however, is the transgene cassette. While the Phagemid—AAV (PAAV) genome contains an AAV transgene cassette, as shown in FIG. 3, the adenohelper and rep-cap particles contain the adenohelper transgene or rep-cap transgene, as shown in FIGS. 12 and 13, respectively.

In another embodiment, the inventors have genetically engineered a so-called "unified construct" that contains all of the required elements inside a single vector genome, as shown in FIGS. 14 and 15.

When introduced into the same mammalian producer cell (see FIGS. 11 and 14), either on separate vectors or on the same unified vector, the rep-cap and adenohelper genes behave as trans-acting elements that facilitate packaging of the rAAV genome in the phagemid/AAV vector. This production process is comparable to transient co-transfection of three plasmids. However, in this case, the plasmids are replaced with phagemid vectors carrying the very same elements.

Below is described a protocol for PAAV phagemid-guided production of adeno-associated virus (AAV).

Notes:
DMEM: Dulbecco's Modified Eagle Medium.
FBS: Foetal Bovine Serum, a growth supplement.
Complete media: DMEM+10% FBS.
EDTA: Ethyl-diamine tetra-acetic acid, an ion chelator used to dissociate cells by sequestering calcium ions required for tight junction formation.
GlutaMax: a growth supplement, analogue of L-Glutamine.

Protocol for Phagemid-Guided AAV Production:
1. Seed and grow HEK293 cells in complete media (DMEM supplemented with 10% FBS, 20 mM GlutaMax, Penicillin/Streptomycin and Non-Essential Amino Acids) in a 15 cm tissue culture plate for a minimum of 48 hours until 80% confluence is achieved.
2. Mix Phagemid/AAV, rep-cap phagemid and adenohelper phagemid to achieve a 1:1:1 transducing unit ratio under 5 mL total volume OR Aliquot a unified vector (single vector containing all three elements in a single particle) to achieve 1 million transducing units per cell.
3. Add an equal volume of serum-free DMEM (supplemented with 20 mM GlutaMax) to the transduction mixture made in step 3.
4. Invert to mix. Incubate at room temperature for 15 minutes.
5. Wash the HEK293 cells plated in step 1 with PBS, repeat 3 times.
6. Add the transduction mixture and swirl gently to distribute the mixture evenly.
7. Incubate at 37°, 5% CO2 in a cell culture incubator for 72 hours
   a. After 6 hours of incubation with the transduction mixture, supplement with an equal volume of complete media (DMEM supplemented with 10% FBS, 20 mM GlutaMax, Penicillin/Streptomycin and Non-Essential Amino Acids).
   b. After 24 hours, replace media with complete media (DMEM supplemented with 10% FBS, 20 mM GlutaMax, Penicillin/Streptomycin and Non-Essential Amino Acids).

rAAV Purification:
1. Add 0.5M EDTA solution to the medium in the tissue culture plate to a final concentration of 0.010M, incubate for 5 minutes at room temperature.
2. Collect the cells and media by aspiration and trituration and transfer to a 50 mL centrifuge tube.
3. Pellet the cells by centrifugation at 1500 RPM, 5 minutes, Room temperature.
   a. Optional: collect the supernatant for further AAV purification.
4. Resuspend the cell pellet in 2-5 mL serum-free DMEM.
5. Lyse the cells in the suspension by subjecting to 4 freeze-thaw cycles in an ethanol-dry ice bath and a water bath set to 37°.
6. Centrifuge the cell lysate at 10000 G, 10 minutes at Room temperature.
   a. Aliquot the supernatant for quantification/further purification/concentration.
   b. Discard the pellet (debris).

Example 5—Use of Phagemid—AAV Vector (PAAV) for In Situ AAV Production

Referring to FIG. 16, the inventors have devised a method for the in situ production of AAV particles using the PAAV.

Firstly, an optimal dose (or multiple doses) of the three phagemid vectors or the unified vector are introduced in vivo through intravenous/thecal/peritoneal or intramuscular/subcutaneous (or any of the aforementioned routes of administration). The diseased tissue is a tumour displaying the relevant integrins and so the targeting moiety on the phagemid PAAV particles is the RGD4C sequence. The tumour should start to produce rAAV containing the viral transgene encoded in the hybrid phagemid particle and not wild-type AAV. These AAV therapeutic particles should autoinfect nearby sites, as they naturally have high affinity to mammalian tissue, and eradicate the tumour over a given time.

Example 6—Engineering Pseudovirions for Large-Scale Targeted Gene Transfer and Recombinant Adeno-Associated Virus Production Transmission Electron Microscopy In characterising the particles, the inventors imaged PAAV particles to show that vector size is substantially reduced when using the phagemid-based vector system. Using Transmission Electron Microscopy, the inventors imaged and measured the length of PAAV of the invention and known AAVP particles on mesh copper TEM grids after negative staining with uranyl acetate (see FIG. 17). It was found that the average AAVP particle was 1455.02 nm in length (FIG. 17A), while a typical PAAV particle according to the invention is only 729.96 nm in length (FIG. 17B)—which equates to approximately 50% reduction in particle size. Compared to the helper phage that is used to produce PAAV particles (typically 1186.03 nm, FIG. 17B), the relative vector size is approximately 38% shorter than the helper virus.

The difference in vector size forms the basis of the theory that PAAV may be more efficient as a gene delivery vector than the AAVP, not only in terms of production yield, but also in subsequent infection processes when entering and expressing genes in mammalian cells. As such, the inventors probed vector efficiency at various stages of infection, including binding, internalisation, and gene expression in 293AAV (a derivative of Human Embryonic Kidney 293) and U87 glioblastoma cell lines.

Vector Internalisation

Following binding, vectors undergo receptor-mediated endocytosis by the target cell. To investigate potential differences in vector internalisation, the inventors assayed the number of internalised vectors in target cells at two time-points (2 hours, 2H; 4 hours, 4H) using flow cytometry (see FIG. 18). It was found that PAAV vectors were internalised more efficiently at 2 hours (Median Fluorescence Intensity (MFI)=1031.7, 335 higher than AAVP, p<0.05) and to a greater overall extent at 4 hours when compared to AAVP in both cell lines. The MFI at 2 hours for PAAV was significantly higher than AAVP by 335 for 293AAV and 207 for U87 cells (p<0.05). At 4 hours post-transduction, this difference became substantially greater for 293AAV (829 MFI, p<0.05), but less so for U87 (157 MFI, non-significant). Overall, the MFI peaked at 2092 (293AAV, p<0.05, FIG. 18A) and 1137 (U87, FIG. 18B) for PAAV1-treated cells, which was significantly higher than AAVP, which respectively peaked at 1063 (293AAV) and 980 (U87). The data demonstrates that PAAV performed consistently better than AAVP in rate and extent of internalisation for both time-points in both cell-lines.

Green Fluorescent Protein Expression Following AAVP and PAAV-Mediated Gene Transfer To investigate whether the differences in vector internalisation translates to increased gene expression, the inventors performed a GFP-expression assay using RGD and NT PAAV.GFP and AAVP.GFP vectors (see FIG. 19). In this experiment, they also tested whether addition of the cationic polymer DEAE.DEXTRAN (Dex) could enhance gene transfer by increasing the bioavailability and endosome-escape of PAAV vectors, as described in WO2014/184529. Nine days post-transduction, cells were trypsinised, and counted and analysed using a flow cytometer. It was found that transgene expression was generally higher in 293AAV cells than U87, regardless of whether Dex was used to assist vector transduction. When vector alone is used, the targeted RGD.PAAV.GFP vector transduces target cells with higher efficacy (7.7%, p<0.01 and 1.4%, p<0.05 GFP+ve cells in 293AAV and U87 cells, respectively)—compared to AAVP, this translates to a 2.44 and 1.56 fold increase respectively in 293AAV and U87 cells (FIG. 19A, C).

When Dex is added however, gene expression increases dramatically for RGD.AAVP and RGD.PAAV vectors. In 293AAV cells, GFP expression in RGD.AAVP.GFP treated cells increased to 25% while RGD. PAAV.GFP treated cells experience a substantial increase to 50% (all p<0.01); addition of Dex resulted in an increase in gene expression of 7.9-fold for RGD.AAVP and 6.5-fold for RGD. PAAVP (FIG. 19B, D). In U87 cells, which is regarded as highly resilient to transduction, Dex was able to augment gene expression by over 3.6-fold in RGD.PAAV.GFP to 4.8% GFP+ve cells (p<0.01)—this was not the case for RGD-.PAAV.GFP, as Dex increased gene expression by only 1.5-fold to 1.3% GFP+ve cells (p<0.05). Interestingly, Dex enabled transduction by NT. PAAV (non-targeted) vectors in 293AAV cells (7.34%), but not with U87.

Phagemid-Guided Recombinant Adeno-Associated Virus Production

To assess whether PAAV and phagemid-derived vectors could be used to produce rAAV in a commercial producer cell-line, the inventors transduced 293AAV cells with three targeted vectors, which are normally plasmids that require transfection for gene transfer. They were able to harvest rAAV particles from the cell lysate and quantify the rAAV gene copy number (GC) per mL over three time-points after phagemid-guided transduction (FIG. 20A). When compared to conventional transfection with FuGene6 (transfection reagent, 3.99e11 GC/mL, FIG. 20B), phagemid-guided rAAV production provides over 1.9-fold increase at 168 hours (7.69e11 GC/mL, FIG. 21A) in rAAV yield. Because phagemid-guided gene transfer requires extensive intracellular processing (unlike transfection), it requires a longer time for viral genes to be expressed and packaged in to functional particles. When yields are compared at the same 72-hour time-point however, transfection produced 1.76e11 GC/mL higher than phage-guided rAAV production. The rAAV yield per mL culture supernatant from transfection or phagemid-guided production dishes at all time points were approx. 8-9e10 GC/mL with no observable trends (data not shown).

Example 7—Construction and Uses of RGD4C-Phagemid

The tripeptide, RGD, is found in proteins of the extracellular matrix, including fibronectin. The integrins act as receptors for fibronectin by binding to the RGD motif located in fibronectin in the site of cell attachment to $\alpha_v\beta_3$ integrin, and so the inventors induced a 9-amino acid mutation in the pIII minor coat protein of the recombinant phagemid particle in order to confer its specificity to tumour cells and angiogenic tumour-associated endothelial cells that express $\alpha_v\beta_3$ and $\alpha_v\beta_5$ integrins. Thus, the genome of the second vector comprises the RGD4C targeting peptide (CDCRGDCFC—SEQ ID No: 7).

Referring to FIG. 21, there is shown immunofluorescence staining of UW228 and DAOY human medulloblastoma cells, which demonstrates the expression of $\alpha_v$, $\beta_3$ and $\beta_5$ integrin subunits, receptor for RGD4C-phagemid. These data demonstrate that the phagemid vector containing the RGD4C targeting peptide can be used for targeted gene delivery and gene therapy in the paediatric brain tumor, medulloblastoma.

Referring to FIG. 22, there is shown targeted gene delivery to paediatric medulloblastoma cells by the RGD4C-phagemid, over a time course of 4 days. The data show that RGD4C-phagemid mediated efficient and selective gene delivery that increased overtime in medulloblastoma.

FIG. 23 shows Western blot analyses showing downregulation of the mammalian target of rapamycin (mTOR) expression in paediatric UW228 and DAOY medulloblastoma cells following treatment with RGD4C-phagemid carrying a sequence encoding the mTOR/shRNA (RGD4C-mTOR/shRNA)). These data demonstrate that the RGD4C-phagemid can be successfully used to deliver shRNA in tumour cells to knock down expression of the therapeutic target mTOR in a selective and efficient way.

FIG. 24 shows combination treatment of temozolomide (TMZ) and RGD4C-phagemid carrying a sequence encoding shRNA for mTOR in medulloblastoma cells, known for their resistance to temozolomide. The data demonstrate that targeted the RGD4C-mTOR/shRNA can re-sensitize medulloblastoma cells to TMZ and achieve complete tumour cell eradication. Therefore, targeted knockdown of mTOR expression by the RGD4C-phagemid is an efficient strategy to use in combination with temozolomide against chemoresistant tumour cells, such as medulloblastoma.

FIG. 25 shows treatment of medulloblastoma cells with TNFα vectors. Therefore, RGD4C/TNFα has therapeutic potential for use in targeted tumour killing such as medulloblastoma. FIG. 26 shows immunofluorescence staining of DIPG cells to demonstrate expression of $α_v$, $β_3$ and $β_5$ integrin subunits, receptor for RGD4C-phagemid. These data demonstrate that the phagemid vector containing the RGD4C targeting peptide can be used for targeted gene delivery and gene therapy in the paediatric brain tumours, DIPG.

FIG. 27 shows selective and dose dependent delivery of gene expression to UW288, DAOY, or DIPG cells by RGD4C-phagemid/AAV. These data prove that RGD4C-phagemid can successfully deliver gene expression to DIPG in a dose-dependent and selective way. These data also indicate that RGD4C-PAAV shows efficient gene transfer to medulloblastoma in vitro that increased over time. There was no non-specific uptake in the cells transduced with the control (non-targeted PAAV-Luc). The transduction efficiency was enhanced with the cationic polymer DEAE dextran for medulloblastoma cell lines.

FIG. 28 shows treatment with RGD4C-phagemid-TNFα. These data demonstrate that RGD4C-phagemid can successfully deliver TNFα to DIPG in a selective manner, resulting in apoptosis induction. Therefore, RGD4C-phagemid-TNFα has therapeutic potential for use in targeted therapy against DIPG. FIG. 28 also shows that medulloblastoma is a good candidate for treatment with RGD4C-phagemid-TNFα, as the treatment resulted in tumour cell killing when tested with either of the cell lines UW288 or DAOY. For instance, UW288 showed about 60% cell death on day 6 relative to the control. Tumour cell killing was further enhanced with the cationic polymer DEAE dextran.

Example 8—Luciferase Expression of RGD4C-Phagemid

Protocol:
HEK cells were plated in a 48-well plate in complete media (DMEM, 10% FBS, 1% glutamine, 1% penicillin/streptomycin) and incubated for at least 48 hours until 70-80% confluence was reached. Cells were then washed with PBS and transduced with hybrid phage/phagemid vectors suspended in serum-free media (DMEM) for 12 hours before the media was supplemented with complete media. Luciferase expression was measured by adding 10 uL of culture media to 50 uL of prepared Quanti-luc (InvivoGen, USA) reagent. The emission of photos was measured using a plate reader equipped to with a luminometer (promega, USA).

FIG. 29 shows luciferase expression after transduction with RGD.PAAV at various concentrations of transducing units. The graph demonstrates a dose-dependent exponential relationship between time and expression of luciferase after incubation with hybrid phage/phagemid vectors at various concentrations. The figure demonstrates that quantifiable gene expression can be achieved by phagemid vectors via an assay for secreted luciferase.

Example 9—Binding of RGD.PAAV Vector to 29. AAV Cells

Protocol:
293AAV cells were seeded on 24-well plates in complete media (DMEM+10% FBS, 1% Glutamine, 1% Penicillin/Streptomycin), and were left to reach 70-90% confluence for a minimum of 48 hours. The cells were washed twice with 500 uL PBS and placed on ice before being transduced with 200000 TU/cell (transducing units/cell) of PAAV vectors suspended in 200 uL of serum-free DMEM. After 1 hour of incubation on ice, the media was recovered from the wells and the amount of phagemid particles were titrated on TG1 E. coli and quantified by colony-counting.

Referring to FIG. 30, there is shown the percentage of PAAV vectors bound to the cell surface of 293 AAV cells. RGD.PAAV vectors had 58.2% binding efficiency, whereas M13. PAAV vectors had 7.1% binding efficiency relative to their respective controls.

Example 10—Transduction of Tumour Cells by PAAV to Express Either MUC1 or PSMA Antigen on their Cell Surface, Such that they can be Targeted by Specific CAR T Cells The conventional treatment for cancer currently consists of one or more of the following three options: surgery, chemotherapy and radiotherapy. Although the disease can sometimes be cured by these interventions, in many cases the cancer cells are not completely eliminated, and so the recurrence rate is high. To make matters worse, chemotherapy and radiotherapy are associated with unpleasant side effects. As a result, there is a great interest in the development of alternative approaches for cancer treatment. One of the most promising of these new therapeutic techniques is cancer immunotherapy, which aims to harness the power and specificity of patients' own immune system to eliminate cancer cells. Cancer immunotherapy is an evolving avenue of treatment. Two main strategies involve active immunotherapy targeting tumour-associated antigens (TAAs) and passive immunotherapies that enhance existing anti-tumour responses.

Examples of cancers include paediatric brain tumours, such as medulloblastoma and Diffuse Intrinsic Pontine Glioma (DIPG). Medulloblastoma is the most common brain tumour and originates in the cerebellum with a five years survival rate following the current therapeutic strategy that consists of surgical resection, radiotherapy, and chemotherapy (Rudin et al., 2009). However, the survivors often have long term endocrinological and neurocognitive side effects. Therefore, development of novel therapeutic approaches that are non-invasive, tumour specific, safer, cost-effective and efficient is urgently needed to avoid the long-term side-effects from current treatment. On the other hand, diffuse intrinsic pontine glioma (DIPG) is the most aggressive brain tumour that arises exclusively in children with poor survival of only 6-10% beyond two years. Due to its diffuse nature, there is no effective therapeutic strategy for this type of cancer (Jansen et al., 2012, Mueller and Chang, 2009).

Due to the immune system's unique properties and its central and universal role in the organism, immunotherapy possesses the great potential to treat cancer and offers long-term protection while potentially providing fewer side effects than other treatments. One particular approach, adoptive cell therapy (ACT), involves the transfer of immune cells that have anti-tumour activity. These cells can be T cells that already exist in a tumour, known as tumour-infiltrating lymphocytes (TIL), some of which will be specific for TAAs. These cells can be isolated from excised tumour tissue, cultivated, activated and expanded ex vivo, then re-infused into patients. Other types of cells that are useful for ACT include genetically engineered T cells that express either a modified T cell receptor (TCR) or a chimeric antigen receptor (CAR). These artificial receptors specifically direct the T cells to target antigens expressed by tumour cells (Blankenstein T, et al. The determinants of tumour immunogenicity. Nat Rev Cancer. 2012; 12(4):307-13; Sharpe M and Mount N. Genetically modified T cells in cancer therapy: opportunities and challenges. Dis Model Mech. 2015; 8(4):337-50).

CAR proteins are expressed on the surface of T cells, and contain extracellular binding domains which bind strongly to specific tumour antigens, a hinge region linking between extracellular domains and transmembrane domains, a transmembrane domain, and intracellular signalling domains (also called co-stimulatory domains) such as CD28 and OX40 (a tumour necrosis factor receptor). Co-stimulatory signals mediated by those domains enable efficiency and prolong the anti-tumour activity of the T cells (Sharpe M and Mount N. Genetically modified T cells in cancer therapy: opportunities and challenges. Dis Model Mech. 2015; 8(4): 337-50; Till B G, et al. CD20-specific adoptive immunotherapy for lymphoma using a chimeric antigen receptor with both CD28 and 4-1BB domains: pilot clinical trial results. Blood. 2012; 119(17):3940-50; Koehler H, et al. CD28 co-stimulation overcomes transforming growth factor-beta-mediated repression of proliferation of redirected human CD4+ and CD8+ T cells in an antitumor cell attack. Cancer Res. 2007; 67(5):2265-73). CAR T cells can be designed to recognise broad types of antigen, which may be expressed on tumour's cell surface. Potential target antigens include proteins, carbohydrates, and glycolipids. CAR T cells do not need the antigen to be processed and presented by MHC, unlike conventional T cells and transgenic TCR T cells. Therefore, the same CAR-based strategy can be applied in all patients expressing the same tumour antigen regardless of the patient's MHC haplotype (Sharpe M and Mount N. Genetically modified T cells in cancer therapy: opportunities and challenges. Dis Model Mech. 2015; 8(4): 337-50, Haji-Fatahaliha M, et al. CAR-modified T-cell therapy for cancer: an updated review. Artif Cells Nanomed Biotechnol. 2015:1-11).

Despite having many advantages, CAR T cell therapy has some limitations. For instance, the tumour may not express a suitable target antigen. This may occur for a variety of reasons such as the neo-antigens being unknown, expressed at inappropriate levels, expressed only on a sub-population of tumour cells, also expressed on non-tumour tissues, not expressed in a manner that is suitable for the targeting of CAR T cells to the tissue, or if expression of the antigen by the tumour is likely to be reduced or lost during treatment.

For example, it has been reported that some CAR T cell therapies have unwanted toxicity in both animal models and in clinical trials. The problem can occur when the antigen recognised by the CAR T cell is not merely expressed on tumour cells but also presented on normal cells leading to damage of healthy tissue (Palmer D C, et al. Effective tumour treatment targeting a melanoma/melanocyte-associated antigen triggers severe ocular autoimmunity (Proc Natl Acad Sci USA. 2008; 105(23):8061-6; Morgan R A, et al. Case report of a serious adverse event following the administration of T cells transduced with a chimeric antigen receptor recognizing ERBB2. Mol Ther. 2010; 18(4):843-51; Lamers C H J, et al. Treatment of Metastatic Renal Cell Carcinoma With Autologous T-Lymphocytes Genetically Retargeted Against Carbonic Anhydrase IX: First Clinical Experience. Journal of Clinical Oncology. 2006; 24(13): e20-e2; Grupp S A, et al. Chimeric antigen receptor-modified T cells for acute lymphoid leukemia. N Engl J Med. 2013; 368(16):1509-18). Therefore, the availability and selection of the target antigen are challenging. Ideally, the antigen presented exclusively by the tumour cells or alternatively by normal cells that is not essential for survival (Rosenberg S A, Restifo N P. Adoptive cell transfer as personalized immunotherapy for human cancer. Science. 2015; 348(6230):62-8). At present, many CAR T cells have successfully been developed against various tumour antigens, such as mucin 1 (MUC1) for the treatment of prostate cancer and breast cancer (Sanchez C, et al. Combining T-cell immunotherapy and anti-androgen therapy for prostate cancer. Prostate Cancer Prostatic Dis. 2013; 16(2):123-31, Si; Wilkie S, et al. Retargeting of Human T Cells to Tumor-Associated MUC1: The Evolution of a Chimeric Antigen Receptor. The Journal of Immunology. 2008; 180(7):4901-9), prostate-specific membrane antigen (PSMA) for the treatment of prostate cancer (Maher J, et al. Human T-lymphocyte cytotoxicity and proliferation directed by a single chimeric TCR[zeta]/CD28 receptor. Nat Biotech. 2002; 20(1):70-5), CD19 and CD20 for the treatment of B-cell malignancies (Brentjens R J, et al. Safety and persistence of adoptively transferred autologous CD19-targeted T cells in patients with relapsed or chemotherapy refractory B-cell leukemias. Blood. 2011; 118(18):4817-28) and estrogen-related receptor beta type 2 (ErRB2) for the treatment of prostate and breast cancer (Pinthus J H, et al. Immuno-Gene Therapy of Established Prostate Tumors Using Chimeric Receptor-redirected Human Lymphocytes. Cancer Research. 2003; 63(10):2470-6). Furthermore, to pursue a higher selectivity on tumour cell, T cells have been developed through several strategies including dual-CARs T cells that are modified to express two CARs targeting specifically two different antigens expressed on the same tumour cell (Kloss C C, et al. Combinatorial antigen recognition with balanced signalling promotes selective tumor eradication by engineered T cells. Nat Biotechnol. 2013; 31(1):71-5; Wilkie S, et al. Dual targeting of ErbB2 and MUC1 in breast cancer using chimeric antigen receptors engineered to provide complementary signalling. J Clin Immunol. 2012; 32(5):1059-70).

Molecular Cloning and Genetic Engineering

Each PAAV-CMV-CD28-IL4, PAAV-CMV-GPI-IL4 and PAAV-CMV-PSMA (FIG. 32f) were constructed by combining PAAV-CMV-GFP plasmid (FIG. 3) with either pUC57-CD28-IL4 plasmid, pUC57-GPI-IL4 or pUC57-PSMA plasmid while PAAV-Grp78-GFP plasmid was combined with either pUC57-CD28-IL4 plasmid, pUC57-GPI-IL4 or pUC57-PSMA plasmid to construct PAAV-Grp78-CD28-IL4, PAAV-Grp78-GPI-IL4 and PAAV-Grp78-PSMA.

The new plasmids; PAAV.CMV.MUC1.CD28.IL4, PAAV.CMV.MUC1.GPI.IL4, PAAV.CMV.PSMA, PAAV.Grp78.MUC1.CD28.IL4, PAAV.Grp78.MUC1.GPI.IL4 and PAAV.Grp78.PSMA, were conducted by restriction enzyme digestion and ligation, transformed into TG1 competent E. coli and plated on 2×YT top agar with ampicillin. All constructs were validated firstly by restriction digestion and gel electrophoresis, and secondly by DNA sequencing (MRC CSC Genomics Core Laboratory, UK).

FIG. 31 shows schematic diagrams of embodiments of the expression plasmid constructs for bacteriophage-guided CAR T cell therapy; 32a represents MUC1-CD28.IL4 expression plasmid driven by CMV promoter, 32b represents MUC1-GPI.IL4 expression plasmid driven by CMV promoter, 32c represents PSMA expression plasmid driven by CMV promoter, 32d represents MUC1-CD28.IL4 expression plasmid driven by Grp78 promoter, 32e represents MUC1-GPI.IL4 expression plasmid driven by Grp78 promoter and 32f represents PSMA expression plasmid driven by Grp78 promoter.

CD28, GPI and PSMA Antigen Expression

HEK 293 cells at approximately 60% confluent in 12-well plate were incubated 24 hours with each vector (1,000,000 TU/cell) in complete media consisting of Dulbecco's Modified Eagle's Medium (DMEM) supplemented with 10% Fetal Bovine Serum (FBS), L-Glutamine (2 mM, Sigma), penicillin (100 units/ml, Sigma), and streptomycin (100 mg/ml, Sigma). Untreated cells were used as a negative control. Next day, all vectors was removed from the culture and the cells were maintained in a humidified incubator at 37° C. in 5% C02 as monolayers in complete medium. The medium was renewed every two days.

At day 6 post-transduction, the cells were harvested with cell dissociation buffer (Invitrogen), washed in washing buffer (PBS containing 2% FBS and 0.1% NaN3) and incubated in Clear Back (human Fc receptor blocking agent, MBL) for 20 minutes at room temperature. The cells were subsequently incubated with either HMFG2 antibody provided by Dr. John Maher (King's College London, UK) or PSMA antibody (MBL) diluted in washing buffer at 4° C. overnight. Next day, the cells were washed in washing buffer and incubated for 30 minutes at room temperature with anti-mouse IgG Alexa fluor 488 conjugated secondary antibodies (Invitrogen). The cells were finally washed in washing buffer and subjected to FACs calibur Flow cytometer (BD Biosciences). The mean fluorescence intensity was measured for at least 20,000 gated cells per triplicate well. Results were analyzed using Flowjo (TreeStar) software.

MUC-1.CD28, MUC-1.GPI and PSMA Antigen Expression on Day 6 Post-Transduction

HEK 293 cells were transduced by either $10^6$ TU/cell of RGD targeted PAAV (RGD) or non-targeted PAAV (NT). FIG. 33 shows the resultant data. Untreated HEK 293 cells (Ctrl) and, targeted PAAV transduced-HEK 293 cells with only 488 secondary antibody staining (Ant.488) were shown as control. (A) represents the MUC-1 or PSMA expression of HEK 293 cells transduced by CMV promoter-driven PAAV vector. DEAE-dextran was added. (B) represents the MUC-1 or PSMA expression of HEK 293 cells transduced by CMV promoter-driven PAAV vector without DEAE dextran added. (C) represents the MUC-1 expression of HEK 293 cells transduced by Grp78 promoter-driven PAAV vector without DEAE dextran added.

Stable Cell Line Selection

To select the stable cell line expressing MUC-1.CD28, MUC-1.GPI or PSMA antigen on their cell surfaces', puromycin resistant sequence was inserted in PAAV-CMV-CD28-IL4, PAAV-CMV-GPI-IL4, PAAV-CMV-PSMA, PAAV-Grp78-CD28-IL4, PAAV-Grp78-GPI-IL4 and PAAV-Grp78-PSMA plasmids.

FIG. 34 shows schematic diagrams of the expression plasmid constructs with puromycin resistant gene for stable cell line selection bacteriophage-guided CAR T cell therapy; 34a represents MUC1-CD28.IL4 expression plasmid driven by CMV promoter, 34b represents MUC1-GPI.IL4 expression plasmid driven by CMV promoter, 34c represents PSMA expression plasmid driven by CMV promoter, 34d represents MUC1-CD28.IL4 expression plasmid driven by Grp78 promoter, 34e represents MUC1-GPI.IL4 expression plasmid driven by Grp78 promoter and 34f represents PSMA expression plasmid driven by Grp78 promoter.

The new plasmid was conducted by restriction enzyme digestion and ligation, transformed into TG1 competent *E. coli* and plated on 2×YT top agar with ampicillin. All construct was validated firstly by restriction digestion and gel electrophoresis, and secondly by DNA sequencing (MRC CSC Genomics Core Laboratory, UK)

Results

PAAV vectors encoding either MUC1 or PSMA transgene were produced using the helper phage system. These transgene products are subjected to display on tumour cell surface after being transduced by PAAV. MUC1 and PSMA antigens are specifically recognised by MUC1-CAR T cells and PSMA-CAR T cells.

Presented herein are data showing that the phagemid particles of the invention can be used to transduce cancer cells, and that the cancer cells subsequently stably display the delivered antigens in a manner suitable for use as the target of an adoptively transferred T cell.

Discussion

There is strong evidence to suggest that targeted PAAV vectors are more efficient than AAVP vectors at gene transduction in both commercial and disease cell lines. Both internalisation and gene expression data concordantly indicate that PAAV are more efficient than AAVP. Evidence is also provided to suggest a strong synergistic effect between DEAE-Dex and PAAV vectors on gene transduction that surpasses that of AAVP. Although these data suggest that PAAV are superior to AAVP, it must also be considered that PAAV vector samples contain helper phage contamination. Despite efforts in optimising experimental conditions during vector production, helper phage contamination (in this case, approx. 1/10) is unavoidable and will competitively inhibit transduction as it too displays the RGD targeting sequence on its minor coat protein. Taking this into account, the internalisation and gene expression data may very well be underestimating the 'true' efficacy of RGD.PAAV. Additionally, because the internalisation assay utilises staining of intracellular phage capsid for signal detection, the smaller overall size (and available capsid protein per particle) of the PAAV means that the proportional number of particles internalised cannot be compared directly to that of AAVP, which we have shown using TEM is twice in length compared to PAAV particles. Accordingly, methods of the invention involve a purification step (e.g. FPLC) to remove the helper phage.

It is essential that in addition to providing mechanistic insight, future work must encompass replication of all experiments using pure PAAV samples. In particular, phagemid-guided rAAV production may benefit greatly from decreased competitive inhibition by helper phage contamination and yield multiple fold higher rAAV particles compared to conventional transfection protocols.

Summary

Hybrid phagemid vectors that are highly efficient at gene transfer to mammalian cells are described. These phagemid/AAV (PAAV) vectors have very large cloning capacities and are targeted to mammalian cells, meaning transfection reagents are not required. This platform allows the production of vectors that are suitable for therapeutic gene therapy. Evidence is provided that this platform can deliver genes, including antigens suitable for targeting by adoptive T cell transfer therapy or CAR T cell therapy, to tumour cells.

Example 11—Superior Phagemid/AAV Hybrid Vector for Guided Delivery of TRAIL Gene to Paediatric DIPG Cells The use of cytokines in gene therapy was investigated as they serve diverse functions as differentiation, proliferation, activation or induction of cell death by apoptosis. The tumour necrosis factor (TNF) superfamily is one such group of molecules that are of interest because of their ability to induce death of tumour cells. Members of the TNF superfamily including Fas ligand (FasL), CD95 ligand (CD95 L) and TNFα have been identified as important therapeutic agents for cancer biological therapy. Their administration can induce apoptosis in different cancer cells but also cause severe toxicity to liver, preventing their application in the clinic.

Given the dilemma of systemic toxicity, another member of the TNF superfamily, TRAIL, is rising as a promising cancer therapeutic agent. Preclinical and early clinical trials using recombinant TRAIL and antibodies against TRAIL receptors have shown that TRAIL has preferential toxicity toward tumour cells with generally little or no toxicity to normal tissues while retaining its anti-tumour properties. TRAIL is constitutively present in many tissues at the level of mRNA, most predominately in spleen, lung and prostate, and is expressed mainly by cells of the immune system such as natural killer (NK) cells and macrophages.

TRAIL is synthesized as a Type II transmembrane protein that can also be proteolytically cleaved by a cysteine protease to generate a secretedform7. The membrane-bound conformation appears to be more potent, as TRAIL is biologically active as a homotrimer and this specific conformation presumably facilitates cross-linking of ligand-receptor complexes, thereby increasing signalling strength. The secreted form is less potent, but effects can be enhanced by engineering an extracellular domain fused to motifs such as a leucine zipper, which helps with stabilisation and formation of homotrimers.

Like other TNF superfamily members, TRAIL induces apoptosis through interacting with cross-linked receptor molecules on the surface of the target cells5,10. There are 5 receptors that have been identified: TRAIL R-1 and R-2 are death receptors that contain a cytoplasmic sequence death domain (DD) which triggers apoptosis, while TRAIL R-3, R-4 and osteoprotegerin are decoy receptors that prevent apoptosis5,6,10.

When homotrimer TRAIL binds to death receptors, the receptors form a trimer and recruit adaptor protein Fas-associated death domain (FADD). FADD recruits initiator caspases 8 or 10, forming the death inducing signal complex (DISC), where initiator caspases are auto-activated by proteolysis. Activated caspase 8 or 10 then cleave the effector caspase 3, causing cleavage of death substrates and cell death. If TRAIL binds to the decoy receptors instead, FADD is not recruited and apoptosis is not triggered. Even in cells resistant to TRAIL-induced apoptosis, TRAIL can induce necroptosis11. The TRAIL-receptor system can induce direct killing of tumour-supportive immune cells and its expression on NK cells is an important mechanism used by the immune system to kill cancer cells.

Current clinical trials to deliver agonists of those in the TNF superfamily, including recombinant TRAIL or agonist antibodies against TRAIL receptors, have unfortunately failed to produce a clinical benefit in cancer patients, partly due to insufficient agonistic activity and short half-life of the drugs. Additionally, often these drugs are limited in their efficacy from design due to concerns that systemic delivery of stronger agents can induce lethal adverse effects. In order to ensure the delivery of TRAIL at optimal concentrations to produce clinical results, a suitable vector is required to selectively target and transport TRAIL to cancer cells.

Using phage display-based technology, viral vectors that display ligands that target and bind receptors selectively expressed in tumour tissues can be used to deliver TRAIL. Most research has focused on the use of eukaryotic viruses such as retrovirus and adenovirus as vectors as they provide superior transgene delivery. However, they have had limited success in systemic gene therapy due to their wide tropism for mammalian cell-membrane receptors, leading to undesired uptake by the liver, reticuloendothelial system and unwanted tissues, as well as immunogenicity. In contrast, prokaryotic viruses are advantageous, as they do not require ablation of native tropism for use in mammalian cells, are cost effective and readily produced in high titres. As they lack tropism, they are inherently poor vehicles for mammalian cell transduction13. However, by altering their coat proteins to display selective ligand peptide motifs, phages can be internalised into cells.

Effective administration of treatment solely to the tumour for prolonged effects without systemic toxicity can be achieved using vectors based on bacterial viruses, bacteriophage or phage. These bacteriophage-based vectors can be engineered to display selective ligand peptide motifs on its coat proteins to allow viral binding to targeted cells and subsequent internalisation for ligand-directed delivery of genes19. By combining the favourable biological attributes of eukaryotic and prokaryotic viruses, a chimeric virus vector was constructed comprising of recombinant adeno-associated virus (AAV) and M13-derived filamentous phage, named AAV/Phage or AAVP13. The pIII coat protein of the phage was engineered to display the double-cyclic peptide CDCRGDCFC (RGD-4C, SEQ ID NO: 7), which binds to specific $\alpha_v$ integrin receptors ($\alpha_v\beta_3$ or $\alpha_v\beta_5$) that are overexpressed in both tumour and supporting angiogenic vaculature. This allows for superior ligand-directed delivery and cellular transduction of therapeutic transgenes as a targeted platform and these functional attributes have been confirmed in preclinical models of several cancers including prostate, breast cancer and soft-tissue sarcomas.

The inventors have improved known vector platforms by using the phagemid system to produce the next-generation vector known as Phagemid-AAV (PAAV) (FIG. 43). PAAV vector is a chimeric virus—a M13 filamentous phage containing a hybrid genome constructed using DNA sequences from the AAV serotype 2. The gene of interest is regulated by the constitutively active cytomegalovirus, CMV promoter and flanked by full-length inverted terminal repeats (ITRs). The phagemid contains an f1 origin of replication, which is used for single stranded replication and packaging into phage particles; as well as an origin of replication for double stranded replication once it enters the target cell. It can be selected with ampicillin during cloning and production of virus vector.

In this hybrid vector model, most of the phage genome is removed which allows for longer DNA sequences to be accommodated, but necessitates the use of helper viruses to provide the capsid and other phage components. RGD-4C peptide motif is first displayed on the pIII coat protein of the M13 bacteriophage to produce a targeted backbone helper virus. The helper virus is then used to transduce TG1 *E. coli* bacteria containing the engineered phagemid, and selection of the targeted vectors containing phagemid can be conducted using selection pressure with antibiotics. The new model was able to accommodate longer DNA sequences, had higher transduction efficiency and could be produced at higher titre over the original AAVP.

Without wishing to be bound to any particular theory, further improvements to transduction efficiency can be achieved via two methods. First, by engineering the RGD-4C peptide to display on pVIII instead of pIII coat protein. pVIII, being the major coat protein, is expressed in up to 2700 copies while pIII is only expressed up to 5 copies. A greater number of RGD-4C ligands that are available for targeting and binding integrins are therefore thought to be have higher efficiency at binding and transducing cells.

Without wishing to be bound to any particular theory, another strategy to enhance efficiency is by displaying the histidine rich H5W ligand, an endosomal escape peptide on the recombinant pVIII coat proteins. Intracellular barriers such as endosomes can limit the rate of gene expression even if the efficiency of internalisation is high, by trapping vectors and preventing it from exerting its therapeutic effects. The histidine side chain can form zwitterions, allowing it to act as a proton sponge and buffer the low pH in the endosome following ligand-directed endocytosis of the phage vector. When protons enter the endosome, water is drawn into the endosome via a vacuolar membrane proton pump, causing pores to form on the endosome and thereby releasing the phage vector.

The aim of this study was to develop a superior PAAV vector with optimal transduction efficiency of DIPG cells, by altering the peptides displayed on the vector's coat proteins. Next, the most suitable PAAV vector was used to deliver the TRAIL transgene to assess the effectiveness of TRAIL as a therapeutic gene in the treatment of DIPG.

Without being bound to any particular theory, the inventors hypothesised that:

1. Specificity of targeting and efficacy of genetic transfer can be enhanced by displaying the RGD-4C ligand on pVIII coat proteins or H5W peptide on the recombinant pVIII coat proteins
2. TRAIL is an effective therapeutic gene to specifically induce DIPG cell death in in vitro experiments and in an in vivo orthotopic DIPG animal model Aims of Study 1. Design and produce a viral vector for specific targeting of DIPG cells with optimal expression of the desired gene.
2. Assess and investigate the killing potential of therapeutic gene TRAIL against DIPG
3. To assess the specificity of targeting TRAIL expression to DIPG in vivo and investigate the therapeutic efficacy following intravenous administration of vector to immunodeficient mice with established orthotopic human DIPG.

Protocol

Cell Culture

HEK293T cell lines were maintained in Dulbecco's Modified Eagle's Medium (DMEM) supplemented with 10% foetal bovine serum (FBS) and 1% penicillin and streptomycin. DIPG tumour cell lines were obtained from Hospital Saint Joan de Déu Barcelona. They were maintained in Tumour Stem Medium (TSM) Base supplemented with 10% FBS. TSM is made according the recipe provided (Table XXX).

Integrin Staining

DIPG cells were seeded on poly-D-lysine coated coverslips in 24-well plates and grown until 60-70% confluent. 5 wells were used to stain for: control, secondary antibody only, $\alpha_v$, $\beta_3$ and $\beta_5$ integrins. Cells were washed and fixed in 4% formaldehyde for 10 minutes at room temperature (RT). Cells were washed three times in PBS and incubated with 50 mM ammonium chloride for 5 minutes. Cell were washed again with PBS for three times and blocked for 30 minutes in 2% bovine serum album (BSA-PBS). Subsequently, cells were incubated with primary antibodies anti-$\alpha v$ (1:100), anti-$\beta_3$ (1:50) and anti-$\beta_5$ integrins (1:100) diluted in 1% BSA-PBS for one day and kept in a moist chamber at 4° C. Following which, cells were washed with three times with 1% BSA-PBS and incubated for 1 hour with secondary Alex Fluor 488-conjugated antibodies (1:750) and 4',6-diamidino-2-phenylindole (DAPI, 1:2000). Coverslips were washed three times with 1% BSA-PBS, three times with PBS and once with sterile water. After air-drying, coverslips were mounted in Mowiol mounting medium. Cells were viewed and images were taken with a fluorescence microscope.

Production, Purification and Titration of Helper Phage with RGD-4C Ligand Displayed on pVIII Coat Proteins (FIG. 44)

Wild-type M13 phage DNA was modified to express RGD-4C on pVIII coat proteins by polymerase chain reaction (PCR). The primers used in the PCR were designed by a colleague (Sajee Waramit) prior to the start of this project. PCR product was ligated using T4 DNA ligase (NEB) and transformed into DH5a bacteria for cloning. Plasmids are extracted by Miniprep (QIAGEN), validated by restriction digestion and gel electrophoresis and then sent for sequencing to ensure integrity of DNA sequences (MRC CSC Genomics Core). The selected clone was then transformed into TG1 competent E. coli (Zymo research) and plated on 2×YT (Sigma) agar with 50 g/ml kanamycin overnight in an incubator at 37° C.

After colonies form, a single colony is selected and grown in 1 L of 2×YT media with kanamycin in a shaking incubator (32° C., 220 rpm) for 18 hours. The overnight culture was centrifuged at 6000 g for 30 minutes at 4° C. Phage supernatant was collected and 20% v/v PEG/NaCl (20% PEG 6000, 2.5M NaCl) was added and mixed thoroughly. After incubation in the cold room overnight, the supernatant was centrifuged again at 10000 g for 30 minutes at 4° C. Phage pellet was re-suspended in 16 mL phosphate buffer saline (PBS) and 20% v/v PEG/NaCl and kept in the cold room overnight. The final phage suspension was centrifuged at 10,000 g for 30 minutes at 4° C. and the supernatant discarded. The purified phage pellet was re-suspended in 1-2 mL of PBS (depending on the pellet size) and sterile-filtered through a 0.45 µm filter cartridge.

Titration was carried out using serial dilutions of 10-fold increments. 5 µL of each dilution of phage was used to infect 500 µL of naïve TG1 E. coli that has been grown to log phase (OD600=0.45–0.50) by incubating them for 30 minutes at 37° C. Following incubation, 100 µL of the bacteria was plated on 2×YT agar with kanamycin overnight in an incubator at 37° C. Colonies were counted on the following morning after 18 hours of incubation and virus titre estimated and expressed as bacterial transducing units (TU).

Production, Purification and Titration of RGD pVIII Vectors Containing Reporter Genes (Green Fluorescent Protein [GFP] and Lucia Luciferase [Lucia]) (FIG. 45)

To assess efficiency in transduction of DIPG cells, vectors were constructed containing phagemids with the reporter genes green fluorescent protein (GFP) and lucia (InvivoGen). GFP expression can be detected via fluorescent microscopy, while lucia is a secreted luciferase that can be quantified with its substrate Quanti-Luc by measuring to Relative Luciferase Units (RLUs). The following protocol uses PAAV-GFP plasmid or PAAV-lucia plasmids.

Plasmids were first transformed into TG1 competent *E. coli* (Zymo research) and plated on 2×YT (Sigma) agar with 50 µg/ml ampicillin overnight in an incubator at 37° C. After colonies form, a single colony is selected and grown in 2×YT media with ampicillin in a shaking incubator (32° C., 220 rpm). 100 mL of the bacteria is grown to log phase (OD600=0.45-0.50), following which 15-20 µL of the RGD pVIII helper phage is added and incubated in a shaking incubator (32° C., 150 rpm). The bacteria are then grown in 1 L of 2×YT media containing kanamycin and ampicillin in a shaking incubator (32° C., 150 rpm) for 18 hours. Purification was carried out as per previous investigation. Titration was carried out by growing bacteria on 2×YT with ampicillin only and on another plate with kanamycin only, in order to estimate titre of reporter gene vector and helper phage respectively.

Production, Purification and Titration of H5W Peptide RGD pIII Vectors Containing Reporter Gene (Lucia)

H5W RGD pIII helper phage was produced by a colleague (Sajee Waramit) prior to the start of this project. Production was largely similar to previous stated protocol, with the exception that 1 mM isopropyl β-D-1-thiogalactopyranoside (IPTG) was also added to select for H5W RGD pIII vectors. Purification and titration of vectors were carried out as per previous investigation.

Transduction of Vector into Cells

Cells used in transduction (HEK293T or DIPG) were seeded in plates until 60-70% confluent. The media is then removed and cells were incubated overnight with vectors diluted in OptiMEM, the amount of which is derived based on the virus titre obtained from titration. The transduction media is then removed and replaced with complete media. For cells transduced with GFP, at indicated time points the cell is viewed under fluorescence and images taken to look for cells expressing GFP. For cells transduced with lucia, at indicated time points 10 µl of cell media and 25 µl of Quanti-Luc (InvivoGen), the substrate for the lucia, were mixed in a white polystyrene 96-well plate then incubated for 5 minutes at RT. Luciferase expression was quantified using a Promega Glomax microplate reader.

Assess and Investigate the Killing Potential of Therapeutic Gene TRAIL Against DIPG Production of PAAV-human TRAIL (hTRAIL) plasmid for transfection (FIG. 46) The GFP sequence in a PAAV-GFP plasmid was replaced by the hTRAIL gene sequence by PCR. hTRAIL gene was amplified and designed to contain restriction sites for EcoRI and SalI at the ends by cloning pUNO1-hTRAIL (InvivoGen) using specific primers (Table 1). Molecular cloning, plasmid extraction and DNA sequence validation were carried out as per previous investigation. The selected clone was then transformed into TG1 bacteria for amplification, then extracted via Maxiprep (QIAGEN).

TABLE 1

| Primer sequences (Invitrogen) used to produce hTRAIL fragment with restrictions sites (EcoRI/SalI) using pUNO1-hTRAIL and PCR. |
| --- |
| Forward primer 5'-3' |
| GAG TGA ATT CGC TGT GAC CGG CGC CTA C-SEQ ID NO: 24 |
| Reverse primer 5'-3' |
| GCT CGT CGA CTC ATG TCT GGC CAG CTA GCT TAG CC-SEQ ID NO: 25 |

Transfection of Plasmids into Cells

DIPG cells were seeded in 48 well-plates until 60-70% confluent. Prior to start of experiment, cells were incubated in OptiMEM low serum media for 1-2 hours. For 48-well plates, the FuGENE HD transfection protocol (Promega) the protocol advises to aim for a media volume of 0.5-2.0 ml, FuGENE volume of 0.6-1.81 µl and DNA amount of 0.2-0.6 µg. Transfection efficiency depends on the ration of FuGENE to DNA, in this case a ratio of 3:1 is used.

Eppendorf tubes were prepared and labelled for use in the experiment. OptiMEM was added to each tube up to 20 µl, depending on the volume of FuGENE to be used. FuGENE is then directly added into the medium without contact with the walls of the plastic tube, and the mixture is incubated for 5 minutes at RT. Plasmid DNA is added to the tubes and the transfection reagent:DNA complex is incubated for 15 minutes at RT. The complex is then added to DIPG cells in a drop-wise manner and the plate swirled to ensure even distribution. Cells were incubated at 37° C. for 6 hours, following which the transfection media is changed TSM media supplemented with FBS without antibiotic. Cells are replaced in the incubator and observed for cell viability in the next 24-48 hours.

Results

DIPG Cells Express Integrin Receptors for RGD-4C Ligand Binding

To establish the suitability of this vector model in this cell line for targeted gene delivery, cells were first investigated for expression of the integrins αvβ3 and αvβ5, by means of fluorescence microscopy. As shown in FIG. 47, DIPG cells tested were positive for expression for αv, β3 and β5 units, with no fluorescence observed in cells incubated without antibodies or secondary antibody alone.

RGD-4C Ligand as Displayed on PIll Coat Protein Produced Higher Transduction Efficiency and Gene Expression Levels than pVIII Coat Protein Previous data from the inventor's lab has shown that targeted RGD-4C pIII vector mediated gene delivery and expression was selective and efficient as compared to un-targeted vector. In order to optimise transduction, one of the hypotheses was to display the RGD-4C on the pVIII coat protein in order to increase the number of copies of ligand per phage (FIG. 48).

Using reporter gene vectors (GFP or lucia), transduction efficiency was compared using human kidney embryonic cells, HEK293T, a cellular model that was continuously used to characterise phage vectors. Cells were incubated with un-targeted vector (control lacking RGD-4C), targeted RGD pIII PAAV-GFP or RGD pVIII PAAV-GFP vectors and viewed under fluorescent microscopy (FIG. 49). Across all TUs, the highest GFP expression was seen in cells transduced with RGD pIII PAAV-GFP.

Similarly, in HEK293T cells transduced with un-targeted, RGD pIII PAAV-lucia or RGD pVIII PAAV-lucia vectors, the highest RLU is observed in RGD pIII PAAV-lucia (FIG. 50). This suggested that RGD displayed on pIII was superior to pVIII in transduction and gene expression.

H5W Peptide as Displayed on Recombinant pVIII Coat Protein Improves Transduction Efficiency and Gene Expression An alternative strategy to optimise the vector was to display H5W peptide on recombinant pVIII coat protein. Previous data from the lab showed that in a transduction experiment using vectors containing reporter gene lucia (Sajee Waramit, unpublished data), display of H5W peptide increases luciferase expression in HEK293T cells as compared to RGD pIII alone (FIG. 51).

To investigate if this finding could be applied to DIPG cells, DIPG cells were incubated with un-targeted, RGD pIII PAAV-lucia or H5W RGD pIII PAAV-lucia vectors. Consistent with that of HEK293T data, the highest RLU in DIPG cells is observed in H5W RGD pIII PAAV-lucia (FIG. 52). This suggested that H5W peptide was able to improve vector efficiency in DIPG cells and should be used in the final vector construct.

Transfection of PAAV-hTRAIL Plasmid into DIPG Cells Induced Cell Death

Following optimisation of vector and before further experiments were conducted, it was essential to determine if the selected gene of interest, human TRAIL (hTRAIL), was able to induce cell death in DIPG cells via transfection.

DIPG cells were transfected with either PAAV-hTRAIL or control PAAV-GFP plasmid. There was significantly more cell death in cells transfected with PAAV-hTRAIL according to microscopic images taken 18 hours post-transfection at all DNA concentrations (FIG. 53).

Discussion

Without wishing to be being bound to any given theory, the data thus far show that vectors expressing H5W and RGD-4C on pIII coat proteins were most optimal in targeting and inducing expression of desired genes in DIPG cells. Data from transfection experiments also suggests that the therapeutic gene TRAIL is able to induce DIPG cell death, which warrants further investigation.

Example 12—Hybrid IL2-TNFa

To increase targeted loco-regional production of TNFa within the tumour site, the inventors constructed a phagemid encoding a secreted TNFa by inserting a signal peptide from IL-2 to precede the TNFa sequence lacking the transmembrane domain. To the inventor's knowledge this is the first time that a hybrid IL2-TNFa was designed and their data suggest that preceding TNFa gene with the IL2 signal peptide sequence significantly enhanced expression and secretion of TNFa in cancer cells. Such modifications represent a significant advance in the technique available for targeted production and release of TNFa in the tumour microenvironment and should be considered for increasing the therapeutic levels of TNFa.

Protocol

PAAV.Grp78.IL-2SP.hTNFa Construction

The coding therapeutic sequence inserted in the phagemid is a hybrid sequence that contained a tumour specific promoter of the Glucose Regulated protein (Grp78), signal peptide (SP) sequence from IL-2 (FIG. 57) and human sequence of TNFa. The Grp78 promoter is stress-inducible and is strongly activated by conditions of glucose deprivation, chronic anoxia, and acidic pH that persist within aggressive and poorly perfused tumours. Moreover, the Grp78 promoter is induced in a wide variety of tumours and thus makes it an attractive candidate for use in gene therapy. Previous studies have demonstrated several advantages of this promoter over viral promoters. The safety and tumour specificity of this promoter have also been elegantly reported in transgenic mice carrying a LacZ transgene. High LacZ expression was shown in tumours established in these transgenic mice, while no promoter activity was detected in major normal tissues. Furthermore, unlike viral promoters used in gene therapy vectors, mammalian promoters such as Grp78 are not silenced in eukaryotic cells. In the inventor's previously published work, they reported that the double-targeted RGD4C/phage-Grp78 provides persistent transgene expression over RGD4C/Phage-CMV carrying the cytomegalovirus CMV promoter. Inclusion of both RGD4C ligand and Grp78 promoter generates a vector with dual tumour targeting at both cell entry and transcriptional levels.

The TNFα is transmembrane, to generate a secreted TNFα with better availability for its receptor on the cell surface of tumour cells, we generated a secreted form of TNFα, by removing the transmembrane domain of TNFα and replacing it with the signal peptide of interleukin-2 (IL-2). The IL-2 was previously used as an effective signal peptide tested in various studies to enhance the secretion of other cytokines or growth factors into the extracellular milieu and subsequently increased their efficacy and availability for their corresponding receptors. IL-2 signal peptide sequence flanked by BamHI and EcoRI restriction sites (Thermoscientific, UK) was ligated to PAAV.Grp78 backbone. hTNFα sequence flanked by EcoRI and SalI restriction sites was provided from pUNO1-hTNFα plasmid (Invivogen, France) by polymerase chain reaction (PCR), then ligated to PAAV.Grp78.IL-2 backbone. Molecular cloning steps were conducted using restriction enzyme digestion (NEB, UK) and quick T4 DNA ligase for ligation (NEB, UK). The modified plasmid was transformed into TG1 competent *E. coli* (Zymo research, USA). The bacteria carrying the plasmid were then selected by ampicillin selection on 2×YT agar plate. The construct was validated by restriction digestion and gel electrophoresis, and DNA sequencing (MRC CSC Genomics Core Laboratory, UK) see FIG. 58.

Example 13—Application of PAAV-Delivered TNFα Cytokine Gene Therapy in DIPG

Introduction

Diffuse intrinsic pontine glioma (DIPG) is the most aggressive brain tumour that arise exclusively in children with poor survival of only 6-10% beyond two years. Due to its diffuse nature and its sensitive location in the brainstem, surgical removal is not feasible and there is no effective therapeutic strategy for this type of cancer. The current standard treatment for DIPG is radiotherapy, which is not showing any success, as all children relapse afterwards, even in combination with radio-sensitizers. Many clinical trials have tested the effect of chemotherapy in combination with the conventional radiotherapy, yet no improvement on increasing the overall survival even when combining high doses of chemotherapeutic drugs. This resistance to chemotherapy is due to the intact blood brain barrier as well as the anatomical location of DIPG in the pons makes it more difficult for any drug to reach the targeted location. To overcome this issue, a clinical trial has applied the use of convection-enhanced delivery (CED) to deliver the chemodrug, topotecan, for the treatment of DIPG in 2 children. In this pilot study, both patients died after treatment although initially there was a reduction in tumour size. CED is a technique that directs the delivery of chemotherapeutic drugs to the brain tumours through sustained flow. This technique is being used lately by clinical trials to overcome the drug delivery challenges by bypassing the blood brain barrier.

Targeted therapy for DIPG seems to be the best solution due to its diffuse nature and sensitive location. In an attempt to target DIPG tumour, an ongoing clinical trial applying the concept of targeted radiation through labelling a radioactive substance, 124I, with 8H9 antibody, which is known to bind selectively to cancer cells sparing the healthy brain cells (clinicaltrials.gov ID NCT01502917) [8]. Another candidate to target brain tumours, as suggested by our group (Hajitou's lab) and showed high selectivity in glioblastoma, are the integrins αvβ3 and αvβ5 through the binding of RGD4C peptide as discussed in chapter 3. In fact, RGD4C targeting DIPG is currently being used in an ongoing phase I clinical trial (clinicaltrials.gov ID NCT03178032). In this trial an oncolytic adenovirus, DNX2401, is used to target tumour cells and induce cell death. Among thirty ongoing clinical trials for DIPG, the majority are focused on testing different drugs and radiotherapy, other treatments including gene therapy has not yet been applied. TNFα is an inflammatory cytokine that is known for its anticancer properties by mediating apoptosis, necrosis, and immune cell activation. Depending on the cell context, it can also induce cell proliferation and angiogenesis. Its anti-tumour activity has been studied in many solid tumours including colon cancer, oesophageal adenocarcinoma, melanoma, pancreatic cancer and many others. Yet, the efficiency as a therapeutic agent was very limited due to its significant toxicities when introduced systemically. This limited the clinical use of TNFα in the clinic as a therapeutic agent for cancer to be used for soft tissue sarcoma, melanoma and other irresectable tumours confined to the limb in the form of isolated limb perfusion (ILP) to avoid limb amputation. Indeed, TNFα works synergistically with chemotherapeutic drugs in vivo through targeting tumour vasculature disrupting the VE-cadherins and thus increase the penetration of the chemotherapeutic drugs to tumour environment. Thus, efforts to overcome the limitation of systemic toxicity are required to enhance therapeutic efficacy of TNFα. One strategy was made to decrease TNFα toxicity and yet retain its anti-tumour activity by making a mutant form of TNFα. This mutated TNFα was further targeted to the tumour environment by the signalling peptide RGD4C and enhanced the efficiency of the chemotherapeutic drugs in hepatoma and sarcoma allografts.

In vitro studies for DIPG are very limited with little human tissue available for study, restricting the understanding of this devastating type of brain cancer. Therapeutic applications, other than chemotherapeutic drugs and radiotherapy, are also hindered due to the lack of in vitro applications and understanding. Thus, in the inventors investigated the therapeutic effect of two forms of TNFα, transmembrane (tmTNFα) and secreted (sTNFα), against DIPG. TNFα was used in the form of gene therapy to be expressed and delivered to the cells using PAAV targeted by the signalling peptide RGD4C. Without wishing to be bound to any particular theory, the use of RGD4C-targeted PAAV as a therapeutic gene delivery vehicle to the tumour site will ensure safer, selective and efficient gene transfer for the treatment of DIPG.

In order to understand the mechanism of cell death induced by TNFα, the inventors studied the viability and apoptotic activity in response to transduction of PAAV carrying two different forms of TNFα, tmTNFα and sTNFα. The apoptotic activity was determined by measuring the activity of caspase3/7, caspase 8, and caspase 9.

Finally, the effect of chemotherapeutic drug, cisplatin, in enhancing gene therapy was studied. Thus, two different promoters, GRP78 and CMV, upstream of TNFα were used to understand the synergistic effect of gene therapy with cisplatin. Lucia reporter gene under the control of GRP78 and CMV promoters was used for quantitative analysis for gene expression after cisplatin treatment and further understand the role of cisplatin in enhancing gene expression.

Results

Transduction of DIPG with PAAV Carrying the Transmembrane tmTNFα and Secreted sTNFα Transgene:

Transmembrane TNFα gene and secreted TNFα were cloned into PAAV vector, PAAV-tmTNFα and PAAV-sTNFα (comprising the vector as shown in example 12), followed by the production of targeted (RGD4C) and non-targeted (M13/control) viruses. DIPG cells were transduced and cell viability was measured at day 7 post-transduction. The transduction efficiency was further enhanced with 40 ng/μg of phage protein DEAE dextran. DIPG cells showed better response to PAAV-sTNFα in inducing cell death compared to PAAV-tmTNFα, where the former shows about 50% cell death on day 7 compared to only 20% cell death that was induced by the transmembrane form as shown in FIG. 59. Together, these data suggest that sTNFα is a good candidate for the treatment of DIPG.

Gene delivery and TNFα expression after transduction with PAAV: The efficiency of PAAV gene delivery was assessed by measuring mRNA levels after transduction. Both forms of TNFα were expressed in the transduced cells with high specificity as the non-targeted (M13) form shows negligible mRNA expression of TNFα compared to the targeted PAAV (RGD4C) as shown in FIG. 60A. At the protein level, Transduction of PAAV-tmTNFα did not lead to the secretion of TNFα in the medium as was detected by ELISA (FIG. 60B). Although transduction with both forms shows TNFα expression at the mRNA level, only the secreted form was related to the level of TNFα protein. This further confirms that the transduction of the transgene was efficient and may suggest that the inefficiency of inducing cell death by the transmembrane form is due to the lack of soluble secreted protein. As the release of sTNFα from the initial membrane bound form requires the enzymatic activity or expression of TNFα converting enzyme (TACE). Thus, TACE enzyme expression was measured by western blot and compared with other paediatric brain tumour cells (medulloblastoma). DIPG expression of TACE enzyme was 4× lower than the expression level of UW228 and 2× lower than the expression level of Daoy cells.

The invention claimed is:

1. A method of expressing one or more cytokines in a cell, the method comprising transducing the cell with a recombinant phagemid particle comprising M13 phage coat proteins and a phagemid particle genome that expresses a transgene expression cassette in the cell,
   wherein the transgene expression cassette comprises a promoter and a nucleic acid sequence encoding the one or more cytokines, and wherein the genome comprises no more than 50% of a bacteriophage genome and encodes neither a pIII capsid minor coat protein nor a p VIII capsid major coat protein, and the one or more cytokines are expressed in the cell.

2. The method according to claim 1, wherein the one or more cytokines are selected from IL-4, IL-12, IL-15, TNFα, TRAIL, IFN-γ.

3. The method according to claim 1, wherein the one or more cytokines are one or more hybrid cytokines comprising a signal peptide that is not endogenous to the cytokine.

4. The method according to claim 3, wherein the signal peptide is an IL-2 signal peptide.

5. The method according to claim 4, wherein the one or more hybrid cytokines comprise a hybrid TNFα comprising a IL-2 signal peptide configured to precede the TNFα sequence and thereby increase expression and/or secretion of TNFα.

6. The method according to claim 5, wherein the hybrid TNFα comprises an amino acid sequence substantially as set out in SEQ ID No: 22 or a fragment or variant thereof.

7. The method according to claim 5, wherein the hybrid TNFα is encoded by a nucleic acid sequence comprising SEQ ID No: 23 or a fragment or variant thereof.

8. The method according to claim 1, wherein the genome of the recombinant phagemid particle comprises a packaging signal for enabling replication of the phagemid genome into single-stranded DNA, which can subsequently be packaged into the phagemid particle inside a prokaryotic host.

9. The method according to claim 1, wherein the genome of the recombinant phagemid particle comprises an origin of replication for enabling replication of double-stranded vector inside a prokaryotic host.

10. The method according to claim 1, wherein the genome of the recombinant phagemid particle comprises one or more DNA sequences, which favours targeted integration into a host genome.

11. The method according to claim 1, wherein the at least one transgene expression cassette comprises a viral transgene expression cassette, or wherein the particle comprises multiple transgene expression cassettes.

12. The method according to claim 1, wherein the at least one transgene expression cassette comprises a mammalian viral transgene expression cassette.

13. The method according to claim 1, wherein the transgene expression cassette comprises one or more functional elements required that expresses the nucleic acid in the target cell selected from the groups consisting of: a nucleic acid encoding a polyA tail operable linked to the one or more cytokine coding sequences, and either left and/or right Inverted Terminal Repeat sequences (ITRs) or left and/or right Long Terminal repeat sequences (LTRs).

14. The method according to claim 1 wherein the at least one transgene expression cassette comprises a lentivirus transgene expression cassette or an adeno-associated virus (AAV) transgene expression cassette.

* * * * *